US012630534B2

(12) United States Patent
Hasui et al.

(10) Patent No.: US 12,630,534 B2
(45) Date of Patent: May 19, 2026

(54) 1-((1H-PYRAZOL-4-YL)METHYL)-3-(PHENYL)-1,3-DIHYDRO-2H-IMIDAZOL-2-ONE DERIVATIVES AND RELATED COMPOUNDS AS GPR139 ANTAGONISTS FOR THE TREATMENT OF E.G. DEPRESSION

(71) Applicant: TAKEDA PHARMACEUTICAL COMPANY LIMITED, Osaka (JP)

(72) Inventors: Tomoaki Hasui, Fujisawa (JP); Satoshi Mikami, Fujisawa (JP); Toru Yamashita, Fujisawa (JP); Shinji Nakamura, Fujisawa (JP); Shinji Morimoto, Fujisawa (JP); Toshihiro Imaeda, Fujisawa (JP); Kazuaki Takami, Fujisawa (JP); Masaki Daini, Fujisawa (JP); Hiroyuki Kakei, Fujisawa (JP); Minoru Nakamura, Fujisawa (JP); Fumie Yamaguchi, Fujisawa (JP); Chunxiang Wang, Fujisawa (JP); Sachie Takashima, Fujisawa (JP); Shogo Hashizume, Fujisawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 684 days.

(21) Appl. No.: 17/999,505

(22) PCT Filed: May 20, 2021

(86) PCT No.: PCT/IB2021/000336

§ 371 (c)(1),
(2) Date: Nov. 21, 2022

(87) PCT Pub. No.: WO2021/234450

PCT Pub. Date: Nov. 25, 2021

(65) Prior Publication Data

US 2023/0348435 A1 Nov. 2, 2023

(30) Foreign Application Priority Data

May 22, 2020 (JP) ................................ 2020-090110

(51) Int. Cl.

*C07D 403/06* (2006.01)
*A61K 45/06* (2006.01)
*C07D 401/14* (2006.01)
*C07D 403/14* (2006.01)
*C07D 405/14* (2006.01)
*C07D 413/14* (2006.01)

(52) U.S. Cl.

CPC ............ *C07D 403/06* (2013.01); *A61K 45/06* (2013.01); *C07D 401/14* (2013.01); *C07D 403/14* (2013.01); *C07D 405/14* (2013.01); *C07D 413/14* (2013.01)

(58) Field of Classification Search

CPC .. C07D 403/06; C07D 401/14; C07D 403/14; C07D 405/14; C07D 413/14; A61K 45/06

See application file for complete search history.

(56) References Cited

U.S. PATENT DOCUMENTS 10,123,993 B2 * 11/2018 Glunz .................. C07D 401/14
2023/0357220 A1 11/2023 Hasui et al.

FOREIGN PATENT DOCUMENTS

WO WO 2008/089005 A2 7/2008
WO WO 2008/094556 A3 8/2008
WO WO 2020/097609 A1 5/2020

(Continued)

OTHER PUBLICATIONS

Carlson et al., "Neural Correlates of Rapid Antidepressant Response to Ketamine in Treatment-Resistant Unipolar Depression: A Preliminary Positron Emission Tomography Study," *Biol Psychiatry* 2013, 73, pp. 1213-1221.

Castellani et al., "Copy Number Variation Distribution in Six Monozygotic Twin Pairs Discordant for Schizophrenia," *Twin Research and Human Genetics* 2014; 17, pp. 108-120.

Ebejer et al., "Genome-Wide Association Study of Inattention and Hyperactivity-Impulsivity Measured as Quantitative Traits," *Twin Research and Human Genetics* 2013; 16(2), pp. 560-574.

Hu et al., "Identification of Surrogate Agonists and Antagonists for Orphan G-Protein-Coupled Receptor GPR139," *Journal of Biomolecular Screening*, 2009, 14, pp. 789-797.

(Continued)

*Primary Examiner* — Kamal A Saeed
*Assistant Examiner* — Quincy McKoy
(74) *Attorney, Agent, or Firm* — Finnegan, Henderson, Farabow, Garrett & Dunner LLP

(57) ABSTRACT

The present invention refers to compounds of formula (I). The present invention also relates to compounds of formula (I) for use as G Protein coupled Receptor 139 (GPR139) antagonists in methods of medical treatment of e.g. depression, Alzheimer's disease schizophrenia, drug addiction, sleep disorders, pain, and attention deficit hyperactivity disorder. Exemplary compounds are e.g. 1-((1H-pyrazol-4-yl)methyl)-3-(phenyl)-1,3-dihydro-2H-imidazol-2-one derivatives and related compounds. The present description discloses the synthesis and characterisation of exemplary compounds, pharmacological data thereof, as well as exemplary tablet formulations comprising the compounds of the invention (e.g. page 100 to page 143; examples 1 to 167; test examples 1 and 2; tables 1 to 4).

(I)

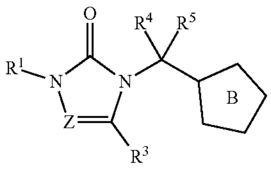

31 Claims, No Drawings

(56) References Cited

FOREIGN PATENT DOCUMENTS

| | | | |
|---|---|---|---|
| WO | WO 2021/234450 | A1 | 11/2021 |
| WO | WO 2021/234451 | A1 | 11/2021 |

OTHER PUBLICATIONS

Liu C et al., "GPR139, an Orphan Receptor Highly Enriched in the Habenula and Septum, Is Activated by the Essential Amino Acids L-Tryptophan and L-Phenylalanine," Mol Pharmacol. 2015 88(5):911-25.
Matsuo et al., "Molecular cloning and characterization of a novel Gq-coupled orphan receptor GPRg1 exclusively expressed in the central nervous system," *Biochemical and Biophysical Research Communications* 331, 2005, pp. 363-369.
O'Roak et al., "Exome sequencing in sporadic autism spectrum disorders identifies severe de novo mutations," *Nature Genetics*, 2011; 43, pp. 585-589.
Patel and Sharma, "New Synthetic Approaches to Substituted Pyridine-2-(1H)-Ones Clubbed with Substituted Aryl Diazo Substituents," Synthetic Communications, 43, 1250-1262, 2013.
Sartorius et al., "Remission of Major Depression Under Deep Brain Stimulation of the Lateral Habenula in a Therapy-Refractory Patient," *Biol Psychiatry*, 2010, 67: pp. e9-e11.
Yang et al, "Ketamine blocks bursting in the lateral habenula to rapidly relieve depression," *Nature* 2018 554, pp. 317-322.
CAplus Registry No. RN 1174845-16-9 (five pages).
Chabchoub, F. et al., "New Method for the Synthesis of Hydrazonates. Reaction of Primary Amines With N-1-Ethoycarbonyl Hydrazonates: Synthesis of 1,2,4-Triazol-5-Ones," Journal De La Societe Chimique De Tunisie, vol. 4, No. 3, 1998, pp. 171-178.
Kattimani, Pramod P. et al., "C 5-Alkyl-1,3,4-Oxadiazol-2-ones Undergo Dealkylation upon Nitrogen Insertion to Form 2H-1,2,4-Triazol-3-ones: Synthesis of 1,2,4-Triazol-3-one Hybrids with Triazolothiadiazoles and Triazolothiadiazines: Synthesis of November 1,2,4-Triazolin-3-one Derivatives," Journal of Heterocyclic Chemistry, vol. 54, No. 4, Feb. 27, 2017, pp. 2258-2265.
Nesaragi, Aravind R. et al., "Microwave assisted regioselective synthesis of quinoline appended triazoles as potent anti-tubercular and antifungal agents via copper (I) catalyzed cycloaddition," Bioorganic & Medicinal Chemistry Letters, Elsevier, Amsterdam, NL, vol. 41, Mar. 22, 2021.
Somagond, Shilpa M. et al., "Click chemistry based on regioselective one-pot synthesis of coumarin-3-yl-methyl-1,2,3-triazolyl-1,2,4-triazol-3(4H)-ones as newer potent antitubercular agents," Archiv Der Pharmazie, vol. 352, No. 10, Aug. 9, 2019, https://doi.org/10.1002/ardp.201900013 (13 pages).
Somagond, Shilpa M. et al., "Microwave-Assisted Synthesis of November Symmetric Bis-1,2,4-triazolin-3-ones as Potent Inhibitors of CYP51: An Antifungal Activity Study", ChemistrySelect, vol. 3, No. 29, pp. 8529-8538, Aug. 6, 2018.

* cited by examiner

1-((1H-PYRAZOL-4-YL)METHYL)-3-(PHENYL)-1,3-DIHYDRO-2H-IMIDAZOL-2-ONE DERIVATIVES AND RELATED COMPOUNDS AS GPR139 ANTAGONISTS FOR THE TREATMENT OF E.G. DEPRESSION

This application is a national stage filing under 35 U.S.C. § 371 of International Application No. PCT/IB2021/000336, filed May 20, 2021, which claims the benefit of priority of Japanese Patent Application No. 2020-090110, filed May 22, 2020, the contents of each of which are incorporated by reference herein in their entirety.

The present disclosure relates to heterocyclic compounds which exhibit G protein-coupled receptor (GPR) 139 receptor antagonist action and are expected to be useful in the treatment or prevention of GPR139-mediated diseases such as depression, Alzheimer's disease, schizophrenia, drug addiction, sleep disorders, pain, and attention deficit hyperactivity disorder.

GPR139 is an orphan G-protein coupled receptor that is coupled with Gs and Gq proteins (Journal of Biomolecular Screen 2009 14:789-797; Biochemical and Biophysical Research Communications 331 (2005) 363-369). The protein sequence of GPR139 is highly conserved among different species. For example, human, mouse, and rat GPR139 protein sequences share more than 94% identity at the amino acid level. Additionally, expression of GPR139 is high in the central nervous system, in particular, the striatum, septal area, hypothalamus, and habenular nucleus, and is low in peripheral tissue. The high degree of sequence homology and predominant expression in the brain across different species suggests that GPR139 plays an important role in physiology.

Variations of the GPR139 gene have been reported in psychiatric disorders such as schizophrenia and in cases with symptoms of autism spectrum disorder or attention deficit hyperactivity disorder (Twin Research and Human Genetics 2014 April; 17(2):108-120; Nature Genetics 2011 June; 43(6):585-589; Twin Research and Human Genetics 2013 April; 16(2):560-574). In addition, the habenular nucleus, which is one of the regions of the brain where GPR139 is highly expressed, is known to regulate stress response and learning; the habenular nuclei of patients with depression are thought to be hyperactive. In cases of patients who also exhibit refractory psychiatric symptoms, the HAMD21 score for evaluating depression symptoms has been reported to improve upon strong stimulation of the habenular nucleus using deep brain stimulation (DBS) (Biol Psychiatry 2010 67:e9-e11). Furthermore, when the regions of the brain where neural activity changes after ketamine administration were investigated by positron emission tomography (PET) in 20 patients with refractory depression, glucose metabolism, which reflects neural activity, was suppressed in regions of the brain such as the habenular nucleus, and depression symptoms improved (Biol Psychiatry 2013 73(12):1213-1221). In animal tests, the neural activity of the habenular nucleus was suppressed by directly administering ketamine into the habenular nucleus, and an improvement in anhedonia-like behavior was observed (Nature 2018 554 (7692):317-322). Together, these results suggest that GPR139 activity affects the neural activity of the habenular nucleus and may dramatically alter central nervous function or neuropsychiatric state.

Antagonists (including inverse agonists) of the GPR139 receptor may be useful for treating CNS disorders such as depression, Alzheimer's disease, schizophrenia, drug addiction, sleep disorders, pain, and attention deficit hyperactivity disorder. Accordingly, there is a need for novel compounds exhibiting GPR139 receptor antagonist action.

Certain heterocyclic compounds may be useful as antagonists of the GPR139 receptor.

PCT International Publication No. WO 2008/094556 describes a compound represented by the following formula:

(I)

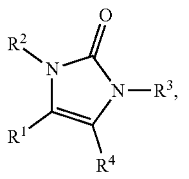

where each symbol is as defined in WO 2008/094556. This compound possesses a TGF3 inhibitory action and may be useful in the treatment of neuronal demyelination in multiple sclerosis, Alzheimer's disease, cerebrovascular disorders, and the like.

Additionally, PCT International Publication No. WO 2008/089005 discloses a compound represented by the following formula:

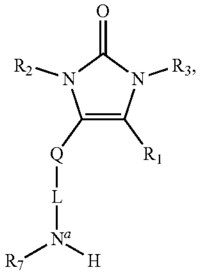

where each symbol is as defined in WO 2008/089005. This compound exhibits a renin inhibitory action and may be useful in the treatment of cardiovascular disease, hypertension, congestive heart failure, myocardial infarction, renoprotection, inflammation, neurological disorders, cancer, and the like.

The following compound is also known in the art as CAS No. 1174845-16-9.

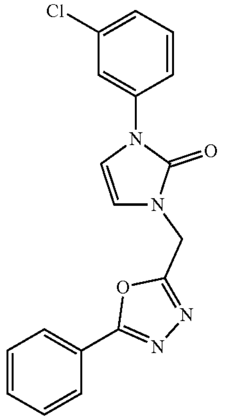 [SMILES: O=c1n(Cc2nnc(-c3ccccc3)o2)ccn1-c1cccc(Cl)c1]

Disclosed herein are compounds exhibiting GPR139 receptor antagonist action, which may be useful in the treatment or prevention of depression, Alzheimer's disease, schizophrenia, drug addiction, sleep disorders, pain, attention deficit hyperactivity disorder, and the like.

Disclosed herein is a compound (also called Compound (I) hereinafter) of Formula (I):

(I)

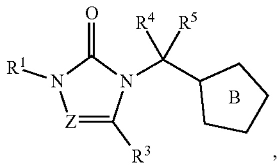, of a salt thereof, wherein:

$R^1$ is a group represented by:

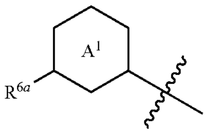 or 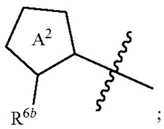;

ring $A^1$ is chosen from optionally further substituted 6-membered aromatic rings;

ring $A^2$ is chosen from optionally further substituted 5-membered monocyclic aromatic heterocyclic rings;

Z is C—$R^2$ or N;

$R^2$ and $R^3$ are each independently chosen from a hydrogen atom, a halogen atom, and optionally halogenated $C_{1-6}$ alkyl groups;

$R^4$ and $R^5$ are each independently chosen from a hydrogen atom and substituents;

$R^{6a}$ and $R^{6b}$ are each independently chosen from substituents; and ring B is chosen from optionally further substituted 5-membered monocyclic aromatic heterocyclic rings, provided that the compound or salt is not 1-(3-chlorophenyl)-3-[(5-phenyl-1,3,4-oxadiazole-2-yl)methyl] 1,3-dihydro-2H-imidazole-2-one or a salt thereof.

In some embodiments, $R^1$ is a group represented by RA

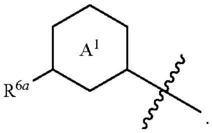.

In some embodiments, $R^1$ is a group represented by

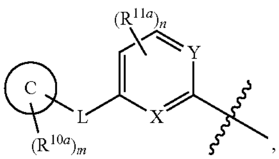, wherein:

X is CH or N;

Y is CH or N;

L is chosen from a bond, —O—, —$OR^{9a}$—*, —NH—, and —$N(R^{9b})R^{9a}$—*, wherein * denotes the connection point to ring C;

ring C is chosen from 6- to 8-membered aromatic rings, 5- to 8-membered monocyclic aromatic heterocyclic rings, $C_{3-8}$ cycloalkyl groups, and 5- to 8-membered heterocyclic groups;

$R^{9a}$ is chosen from $C_{1-3}$ alkyl groups;

$R^{9b}$ is chosen from a hydrogen atom and $C_{1-3}$ alkyl groups;

each $R^{10a}$ is independently chosen from halogen, $C_{1-6}$ alkyl, and $C_{1-6}$ alkoxy groups, wherein the $C_{1-6}$ alkyl and $C_{1-6}$ alkoxy groups are optionally substituted with 1 to 4 halogen atoms;

each $R^{11a}$ is independently chosen from cyano, halogen, $C_{3-6}$ cycloalkyl, $C_{1-6}$ alkyl, and $C_{1-6}$ alkoxy groups, wherein the $C_{3-6}$ cycloalkyl, $C_{1-6}$ alkyl, and $C_{1-6}$ alkoxy groups are optionally substituted with 1 to 4 halogen atoms;

m is 0, 1, 2, or 3; and n is 0, 1, 2, or 3.

In some embodiments, L is chosen from a bond, —O—, —NH—, —$NHCH_2$—*, and —$N(CH_3)CH_2$—*, and all other variables are as defined above.

In some embodiments, L is a bond, and all other variables are as defined above. In some embodiments, L is —O—, and all other variables are as defined above. In some embodiments, L is —NH—, and all other variables are as defined above. In some embodiments, L is —$NHCH_2$—*, and all other variables are as defined above. In some embodiments, L is —$N(CH_3)CH_2$—*, and all other variables are as defined above.

In some embodiments, X is N, Y is CH, and all other variables are as defined above.

In some embodiments, X is N, Y is N, and all other variables are as defined above.

In some embodiments, X is CH, Y is CH, and all other variables are as defined above.

In some embodiments, ring C is chosen from benzene, morpholine, oxane, piperidine, and cyclobutane, and all other variables are as defined above.

In some embodiments, ring C is benzene and all other variables are as defined above. In some embodiments, ring C is morpholine and all other variables are as defined above. In some embodiments, ring C is oxane and all other variables are as defined above. In some embodiments, ring C is piperidine and all other variables are as defined above. In some embodiments, ring C is cyclobutane and all other variables are as defined above.

In some embodiments, $R^1$ is a group represented by

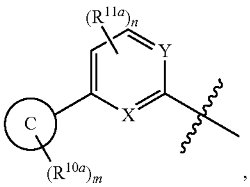, wherein X, Y, ring C, $R^{10a}$, $R^{11a}$, m, and n are as defined above.

In some embodiments, X is N, Y is CH, and all other variables are as defined above.

In some embodiments, X is N, Y is N, and all other variables are as defined above.

In some embodiments, X is CH, Y is CH, and all other variables are as defined above.

In some embodiments, ring C is chosen from benzene, morpholine, oxane, piperidine, and cyclobutane, and all other variables are as defined above.

In some embodiments, ring C is benzene and all other variables are as defined above. In some embodiments, ring C is morpholine and all other variables are as defined above. In some embodiments, ring C is oxane and all other variables are as defined above. In some embodiments, ring C is piperidine and all other variables are as defined above. In some embodiments, ring C is cyclobutane and all other variables are as defined above.

In some embodiments, $R^1$ is a group represented by

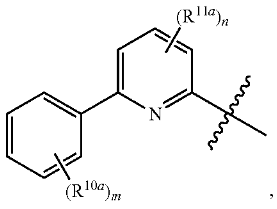

, wherein $R^{10a}$, $R^{11a}$, m, and n are as defined above.

In some embodiments, $R^1$ is a group represented by

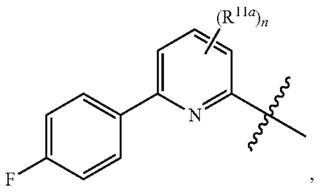

, wherein $R^{11a}$ and n are as defined above.

In some embodiments, $R^1$ is a group represented by

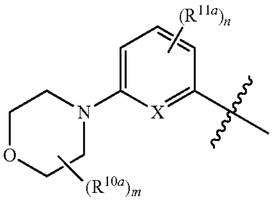

, wherein X, $R^{10a}$, $R^{11a}$, m, and n are as defined above. In some embodiments, X is CH. In some embodiments, X is N.

In some embodiments, $R^1$ is a group represented by

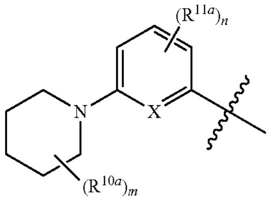

, wherein X, $R^{10a}$, $R^{11a}$, m, and n are as defined above. In some embodiments, X is CH.

In some embodiments, $R^1$ is a group represented by

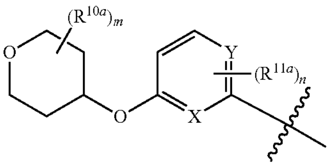

, wherein X, Y, $R^{10a}$, $R^{11a}$, m, and n are as defined above. In some embodiments, X is N and Y is CH.

In some embodiments, $R^1$ is a group represented by

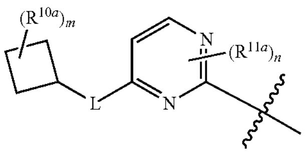

, wherein L, $R^{10a}$, $R^{11a}$, m, and n are as defined above. In some embodiments, L is $-NHCH_2-*$. In some embodiments, L is $-N(CH_3)CH_2-*$.

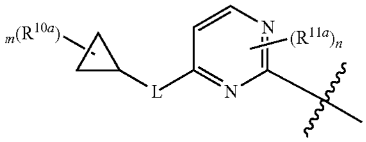

,

In some embodiments, $R^1$ is a group represented by, wherein L, $R^{10a}$, $R^{11a}$, m, and n are as defined above. In some embodiments, L is $-NHCH_2-*$. In some embodiments, L is $-N(CH_3)CH_2-*$.

In some embodiments, $R^1$ is a group represented by

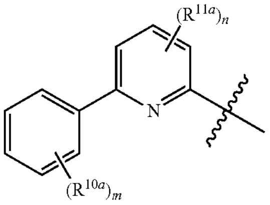

, wherein:

each $R^{10a}$ is independently chosen from halogen atoms, $C_{1-6}$ alkyl, and $C_{1-6}$ alkoxy groups, wherein the $C_{1-6}$ alkyl and $C_{1-6}$ alkoxy groups are optionally substituted with 1 to 4 halogen atoms;

each $R^{11a}$ is independently chosen from cyano, halogen, $C_{3-6}$ cycloalkyl, $C_{1-6}$ alkyl, and $C_{1-6}$ alkoxy groups, wherein the $C_{3-6}$ cycloalkyl, $C_{1-6}$ alkyl, and $C_{1-6}$ alkoxy groups are optionally substituted with 1 to 4 halogen atoms;

m is 0, 1, 2, or 3; and n is 0, 1, 2, or 3.

In some embodiments, each $R^{10a}$ is independently chosen from halogen atoms and $C_{1-6}$ alkyl groups, wherein the $C_{1-6}$ alkyl groups are optionally substituted with 1 to 4 halogen atoms; each $R^{11a}$ is independently chosen from cyano, halogen, $C_{1-6}$ alkyl, and $C_{1-6}$ alkoxy groups, wherein the $C_{1-6}$ alkyl and $C_{1-6}$ alkoxy groups are optionally substituted with 1 to 4 halogen atoms; m is 0, 1, 2, or 3, and n is 0, 1, 2, or 3.

In some embodiments, $R^1$ is a group represented by

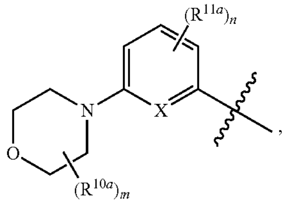

wherein:

X is CH or N;

each $R^{10a}$ is independently chosen from halogen atoms, $C_{1-6}$ alkyl, and $C_{1-6}$ alkoxy groups, wherein the $C_{1-6}$ alkyl and $C_{1-6}$ alkoxy groups are optionally substituted with 1 to 4 halogen atoms;

each $R^{11a}$ is independently chosen from halogen, $C_{3-6}$ cycloalkyl, $C_{1-6}$ alkyl, and $C_{1-6}$ alkoxy groups, wherein the $C_{3-6}$ cycloalkyl, $C_{1-6}$ alkyl, and $C_{1-6}$ alkoxy groups are optionally substituted with 1 to 4 halogen atoms;

m is 0, 1, 2, or 3; and n is 0, 1, 2, or 3.

In some embodiments, $R^1$ is a group represented by

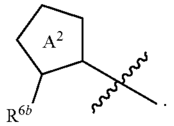

In some embodiments, $R^4$ and $R^5$ are each independently chosen from hydrogen and $C_{1-3}$ alkyl groups. In some embodiments, $R^4$ and $R^5$ are both hydrogen atoms.

In some embodiments, ring B is a group represented by

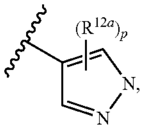

wherein each $R^{12a}$ is independently chosen from $C_{1-3}$ alkyl groups and p is 0, 1, or 2.

In some embodiments, ring B is a group represented by

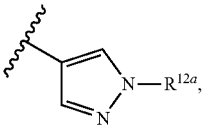

wherein $R^{12a}$ is chosen from $C_{1-3}$ alkyl groups. In some embodiments, $R^{11a}$ is ethyl.

In some embodiments, the compounds of Formula (I) and pharmaceutically acceptable salts thereof are provided for use in the treatment or prevention of a disease chosen from depression, Alzheimer's disease, schizophrenia, drug addiction, sleep disorders, pain, and attention deficit hyperactivity disorder. In some embodiments, a compound chosen from Examples 1-167 and pharmaceutically acceptable salts thereof is provided for use in the treatment or prevention of a disease chosen from depression, Alzheimer's disease, schizophrenia, drug addiction, sleep disorders, pain, and attention deficit hyperactivity disorder.

Also disclosed herein is a pharmaceutical composition comprising at least one compound of Formula (I) or a pharmaceutically acceptable salt thereof. In some embodiments, the pharmaceutical composition comprises: at least one compound of Formula (I) or a pharmaceutically acceptable salt thereof; and at least one pharmaceutically acceptable carrier.

Also disclosed herein is a compound of Formula (I) or a pharmaceutically acceptable salt thereof for use in therapy. In some embodiments, there is provided a compound chosen from Examples 1-167 and pharmaceutically acceptable salts thereof for use in therapy.

In some embodiments, a compound of Formula (I) or a pharmaceutically acceptable salt thereof is combined with at least one combination drug for simultaneous, separate, or sequential use in the treatment or prevention of a disease chosen from depression, Alzheimer's disease, schizophrenia, drug addiction, sleep disorders, pain, and attention deficit hyperactivity disorder. In some embodiments, when the use is simultaneous, the compound or pharmaceutically acceptable salt and the at least one combination drug are in separate pharmaceutical compositions. In some embodiments, when the use is simultaneous, the compound or pharmaceutically acceptable salt and the at least one combination drug are together in the same pharmaceutical composition. In some embodiments, the compound or pharmaceutically acceptable salt is chosen from Examples 1-167 and pharmaceutically acceptable salts thereof.

In some embodiments, a combination of a compound of Formula (I) or a pharmaceutically acceptable salt thereof and a combination drug is provided for use in a method of treating or preventing a disease chosen from depression, Alzheimer's disease, schizophrenia, drug addiction, sleep disorders, pain, and attention deficit hyperactivity disorder. In some embodiments, the compound or pharmaceutically acceptable salt and the combination drug are prepared for administration in the same pharmaceutical composition. In some embodiments, the compound or pharmaceutically acceptable salt and the combination drug are prepared for administration in separate pharmaceutical compositions. In some embodiments, the compound or pharmaceutically acceptable salt and the combination drug are prepared for simultaneous administration. In some embodiments, the compound or pharmaceutically acceptable salt and the combination drug are prepared for sequential administration. In some embodiments, the compound or pharmaceutically acceptable salt is chosen from Examples 1-167 and pharmaceutically acceptable salts thereof.

Also disclosed herein is a pharmaceutical composition comprising a compound of Formula (I) or a pharmaceutically acceptable salt thereof for use in therapy. In some embodiments, there is provided a pharmaceutical composition comprising a compound chosen from Examples 1-167 and pharmaceutically acceptable salts thereof for use in therapy.

Also disclosed herein is a method of treating or preventing a disease chosen from depression, Alzheimer's disease, schizophrenia, drug addiction, sleep disorders, pain, and attention deficit hyperactivity disorder, the method comprising administering at least one compound of Formula (I) or a pharmaceutically acceptable salt thereof.

It should be understood that references herein to methods of treatment or prevention (e.g., methods of treating or preventing a disease chosen from depression, Alzheimer's disease, schizophrenia, drug addiction, sleep disorders, pain, and attention deficit hyperactivity disorder) using one or more compounds (e.g., compounds of Formula (I) and pharmaceutically acceptable salts thereof) should be interpreted as references to:

- one or more compounds for use in methods of treating and/or preventing, for example, depression, Alzheimer's disease, schizophrenia, drug addiction, sleep disorders, pain, or attention deficit hyperactivity disorder; and/or
- the use of one or more compounds in the manufacture of a medicament for treating and/or preventing, for example, depression, Alzheimer's disease, schizophrenia, drug addiction, sleep disorders, pain, or attention deficit hyperactivity disorder.

Non-Limiting Example Embodiments 1

Without limitation, some embodiments of the disclosure include:

1. A compound of Formula (I):

(I)

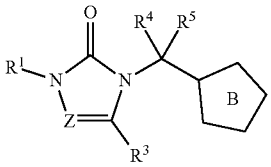, or a salt thereof, wherein:

$R^1$ is a group represented by

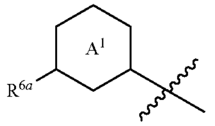

or

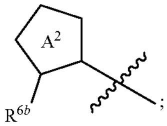;

ring $A^1$ is chosen from optionally further substituted 6-membered aromatic rings;

ring $A^2$ is chosen from optionally further substituted 5-membered monocyclic aromatic heterocyclic rings;

Z is C—$R^2$ or N;

$R^2$ and $R^3$ are each independently chosen from a hydrogen atom, a halogen atom, and optionally halogenated $C_{1-6}$ alkyl groups;

$R^4$ and $R^5$ are each independently chosen from a hydrogen atom and substituents;

$R^{6a}$ and $R^{6b}$ are each independently chosen from substituents; and ring B is chosen from optionally further substituted 5-membered monocyclic aromatic heterocyclic rings, provided that the compound or salt is not 1-(3-chlorophenyl)-3-[(5-phenyl-1,3,4-oxadiazole-2-yl)methyl]1,3-dihydro-2H-imidazole-2-one or a salt thereof.

2. A pharmaceutical comprising the compound or pharmaceutically acceptable salt according to Embodiment 1.

3. The pharmaceutical according to Embodiment 2, which is a GPR139 receptor antagonist.

4. The pharmaceutical according to Embodiment 2, which is a drug for preventing or treating depression, Alzheimer's disease, schizophrenia, drug addiction, sleep disorders, pain, or attention deficit hyperactivity disorder.

Non-Limiting Example Embodiments 2

Without limitation, some embodiments/clauses of the disclosure include:

1. A compound of Formula (I):

(I)

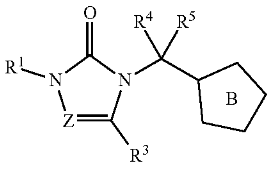, or a pharmaceutically acceptable salt thereof, wherein:

$R^1$ is a group represented by:

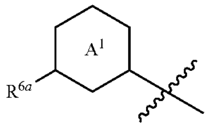

or

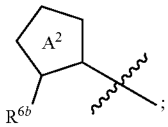;

ring $A^1$ is chosen from optionally further substituted 6-membered aromatic rings;

ring $A^2$ is chosen from optionally further substituted 5-membered monocyclic aromatic heterocyclic rings;

Z is C—$R^2$ or N;

$R^2$ and $R^3$ are each independently chosen from a hydrogen atom, halogen atoms, and optionally halogenated $C_{1-6}$ alkyl groups;

$R^4$ and $R^5$ are each independently chosen from a hydrogen atom and substituents;

$R^{6a}$ and $R^{6b}$ are each independently chosen from substituents; and ring B is chosen from optionally further substituted 5-membered monocyclic aromatic heterocyclic rings, provided that the compound or pharmaceutically acceptable salt is not 1-(3-chlorophenyl)-3-[(5-phenyl-1,3,4-oxadiazole-2-yl)methyl]1,3-dihydro-2H-imidazole-2-one or a salt thereof.

2. The compound or pharmaceutically acceptable salt according to Clause 1, wherein $R^1$ is a group represented by:

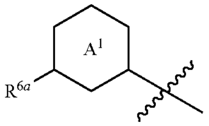, wherein:

ring $A^1$ is chosen from optionally further substituted 6-membered aromatic rings; and $R^{6b}$ is chosen from:

(1) optionally substituted $C_{3-10}$ cycloalkyl groups;

(2) optionally substituted $C_{6-14}$ aryl groups;

(3) optionally substituted 3- to 14-membered non-aromatic heterocyclic groups;

(4) optionally substituted 5- to 14-membered aromatic heterocyclic groups;

(5) optionally substituted mono- or di-$C_{1-6}$ alkylamino groups;

(6) optionally substituted N—$C_{1-6}$ alkyl-N-3- to 14-membered non-aromatic heterocyclic amino groups;

(7) optionally substituted $C_{1-6}$ alkoxy groups;

(8) optionally substituted $C_{6-14}$ aryloxy groups; and (9) optionally substituted 3- to 14-membered non-aromatic heterocyclic oxy groups.

3. The compound or pharmaceutically acceptable salt according to Clause 1 or 2, wherein $R^1$ is a group represented by:

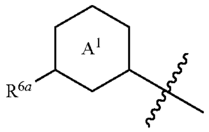
, wherein:

ring $A^1$ is chosen from 6-membered aromatic rings optionally further substituted with 1 to 3 substituents independently chosen from:

(a) halogen atoms;

(b) $C_{1-6}$ alkyl groups optionally substituted with 1 to 3 substituents independently chosen from (i) halogen atoms; and (ii) a hydroxy group;

(c) optionally halogenated $C_{1-6}$ alkoxy groups;

(d) $C_{3-10}$ cycloalkyl groups optionally substituted with 1 to 3 halogen atoms;

(e) $C_{2-6}$ alkenyl groups; and (f) 3- to 14-membered non-aromatic heterocyclic groups optionally substituted with 1 to 3 halogen atoms; and $R^{6a}$ is chosen from:

(1) $C_{3-10}$ cycloalkyl groups optionally substituted with 1 to 3 halogen atoms;

(2) $C_{6-14}$ aryl groups optionally substituted with 1 to 3 halogen atoms;

(3) 3- to 14-membered non-aromatic heterocyclic groups optionally substituted with 1 to 3 substituents independently chosen from:

(a) halogen atoms; and (b) optionally halogenated $C_{1-6}$ alkyl groups;

(4) 5- to 14-membered aromatic heterocyclic groups optionally substituted with 1 to 3 $C_{1-6}$ alkyl groups;

(5) mono- or di-$C_{1-6}$ alkylamino groups optionally substituted with 1 to 3 $C_{3-10}$ cycloalkyl groups optionally substituted with 1 to 3 halogen atoms;

(6) N—$C_{1-6}$ alkyl-N-3- to 14-membered non-aromatic heterocyclic amino groups;

(7) $C_{1-6}$ alkoxy groups optionally substituted with 1 to 3 substituents independently chosen from:

(a) $C_{1-6}$ alkoxy groups;

(b) $C_{3-10}$ cycloalkyl groups; and (c) 3- to 14-membered non-aromatic heterocyclic groups;

(8) $C_{6-14}$ aryloxy groups optionally substituted with 1 to 3 halogen atoms; and (9) 3- to 14-membered non-aromatic heterocyclic oxy groups.

4. The compound or pharmaceutically acceptable salt according to Clause 1 or 2, wherein $R^1$ is a group represented by:

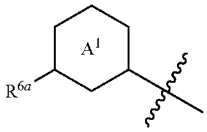
, wherein:

ring $A^1$ is chosen from:

(1) benzene rings optionally further substituted with 1 to 3 substituents independently chosen from:

(a) halogen atoms;

(b) $C_{1-6}$ alkyl groups optionally substituted with 1 to 3 substituents independently chosen from (i) halogen atoms; and (ii) a hydroxy group;

(c) optionally halogenated $C_{1-6}$ alkoxy groups;

(d) $C_{3-6}$ cycloalkyl groups optionally substituted with 1 to 3 halogen atoms;

(e) $C_{2-6}$ alkenyl groups; and (f) piperidyl groups optionally substituted with 1 to 3 halogen atoms;

(2) pyridine rings optionally further substituted with 1 to 3 substituents independently chosen from:

(a) halogen atoms;

(b) optionally halogenated $C_{1-6}$ alkyl groups;

(c) optionally halogenated $C_{1-6}$ alkoxy groups; and (d) $C_{3-6}$ cycloalkyl groups; and (3) pyrimidine rings optionally further substituted with 1 or 2 optionally halogenated $C_{1-6}$ alkyl groups; and $R^{6a}$ is chosen from:

(1) $C_{3-6}$ cycloalkyl groups optionally substituted with 1 to 3 halogen atoms;

(2) phenyl groups optionally substituted with 1 to 3 halogen atoms;

(3) morpholinyl groups optionally substituted with 1 to 3 substituents independently chosen from:

(a) halogen atoms; and (b) optionally halogenated $C_{1-6}$ alkyl groups;

(4) piperidyl groups optionally substituted with 1 to 3 halogen atoms;

(5) pyrrolidinyl groups optionally substituted with 1 to 3 halogen atoms;

(6) a 4-oxa-7-azaspiro[2.5]octyl group;

(7) imidazolyl groups optionally substituted with 1 to 3 $C_{1-6}$ alkyl groups;

(8) mono- or di-$C_{1-6}$ alkylamino groups optionally substituted with 1 to 3 $C_{3-6}$ cycloalkyl groups optionally substituted with 1 to 3 halogen atoms;

(9) N—$C_{1-6}$ alkyl-N-tetrahydropyranylamino groups;

(10) $C_{1-6}$ alkoxy groups optionally substituted with 1 to 3 substituents independently chosen from:

(a) $C_{1-6}$ alkoxy groups;

(b) $C_{3-6}$ cycloalkyl groups optionally substituted with 1 to 3 halogen atoms;

(c) an oxetanyl group; and (d) a tetrahydrofuryl group;

(11) phenoxy groups optionally substituted with 1 to 3 halogen; and

(12) a tetrahydropyranyloxy group.

5. The compound or pharmaceutically acceptable salt according to Clause 1 or 2, wherein the group represented by:

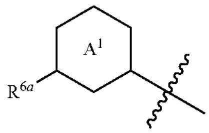

is a group represented by:

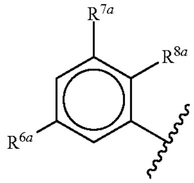
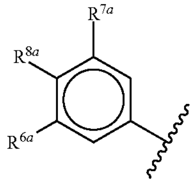
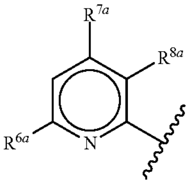
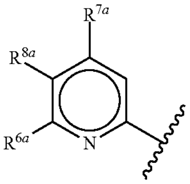
or
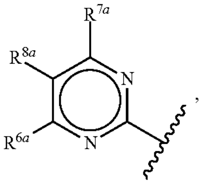
, wherein:

$R^{6a}$ is as defined in Clause 2;

$R^{7a}$ is chosen from:

(a) a hydrogen atom;

(b) halogen atoms;

(c) $C_{1-6}$ alkyl groups optionally substituted with 1 to 3 substituents independently chosen from (i) halogen atoms; and (ii) a hydroxy group;

(d) optionally halogenated $C_{1-6}$ alkoxy groups;

(e) $C_{3-10}$ cycloalkyl groups optionally substituted with 1 to 3 halogen atoms;

(f) $C_{2-4}$ alkenyl groups; and (g) 3- to 14-membered non-aromatic heterocyclic groups optionally substituted with 1 to 3 halogen atoms; and $R^{8a}$ is chosen from:

(a) a hydrogen atom;

(b) halogen atoms; and (c) $C_{1-6}$ alkyl groups.

6. The compound or pharmaceutically acceptable salt according to Clause 1 or 2, wherein the group represented by:

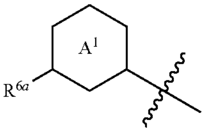

is a group represented by:

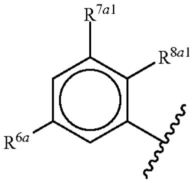
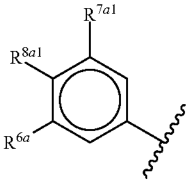
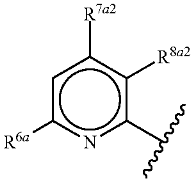
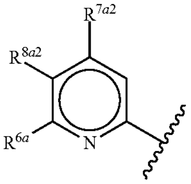
or
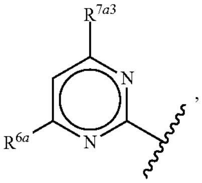
, wherein:

$R^{6a}$ is as defined in Clause 2;

$R^{7a1}$ is chosen from:

(a) halogen atoms;

(b) $C_{1-6}$ alkyl groups optionally substituted with 1 to 3 substituents independently chosen from halogen atoms and a hydroxy group;

(c) optionally halogenated $C_{1-6}$ alkoxy groups;

(d) $C_{3-6}$ cycloalkyl groups optionally substituted with 1 to 3 halogen atoms;

(e) $C_{2-6}$ alkenyl groups; and (f) piperidyl groups optionally substituted with 1 to 3 halogen atoms;

$R^{7a2}$ is chosen from:

(a) a hydrogen atom;

(b) optionally halogenated $C_{1-6}$ alkyl groups;

(c) optionally halogenated $C_{1-6}$ alkoxy groups; and (d) $C_{3-6}$ cycloalkyl groups;

$R^{7a3}$ is chosen from optionally halogenated $C_{1-6}$ alkyl groups;

$R^{8a1}$ is chosen from:

(a) a hydrogen atom;

(b) halogen atoms; and (c) $C_{1-6}$ alkyl groups; and $R^{8a2}$ is chosen from:

(a) a hydrogen atom;

(b) halogen atoms; and (c) $C_{1-6}$ alkyl groups.

7. The compound or pharmaceutically acceptable salt according to Clause 1 or 2, wherein the group represented by:

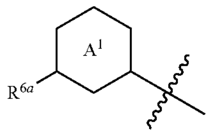

is a group represented by:

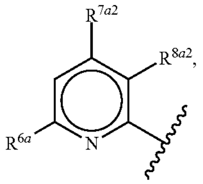

wherein:

$R^{6a}$ is as defined in Clause 2;

$R^{7a}$ is chosen from halogenated $C_{1-6}$ alkyl groups; and $R^{8a2}$ is chosen from a hydrogen atom and halogen atoms.

8. The compound or pharmaceutically acceptable salt according to Clause 1 or 2, wherein the group represented by:

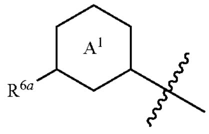

is a group represented by:

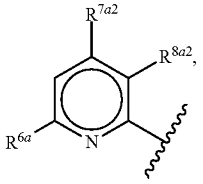

wherein:

$R^{6a}$ is as defined in Clause 2;

$R^{7a2}$ is chosen from halogenated $C_{1-6}$ alkyl groups; and $R^{8a2}$ is a hydrogen atom.

9. The compound or pharmaceutically acceptable salt according to Clause 1, wherein $R^1$ is a group represented by:

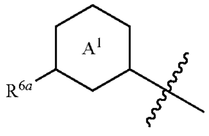

, wherein:

ring $A^1$ is chosen from pyridine rings optionally further substituted with 1 or 2 substituents independently chosen from:

(a) halogen atoms; and (b) halogenated $C_{1-6}$ alkyl groups; and $R^{6a}$ is chosen from morpholinyl groups optionally substituted with 1 to 3 $C_{1-6}$ alkyl groups.

10. The compound or pharmaceutically acceptable salt according to Clause 1, wherein $R^1$ is a group represented by:

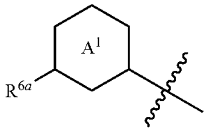

, wherein:

ring $A^1$ is chosen from pyridine rings further substituted with one halogenated $C_{1-6}$ alkyl group; and $R^{6a}$ is chosen from morpholinyl groups substituted with one $C_{1-6}$ alkyl group.

11. The compound or pharmaceutically acceptable salt according to Clause 1, wherein $R^1$ is a group represented by:

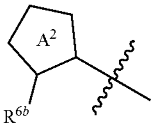

, wherein:

ring $A^1$ is chosen from optionally further substituted 5-membered monocyclic aromatic heterocyclic rings; and $R^{6a}$ is chosen from optionally substituted $C_{1-6}$ alkyl groups.

12. The compound or pharmaceutically acceptable salt according to Clause 1 or 11, wherein:

ring $A^2$ is chosen from 5-membered monocyclic aromatic heterocyclic rings optionally further substituted with 1 to 3 optionally halogenated $C_{1-6}$ alkyl groups; and $R^{6b}$ is chosen from $C_{1-6}$ alkyl groups optionally substituted with 1 to 3 $C_{3-10}$ cycloalkyl groups.

13. The compound or pharmaceutically acceptable salt according to Clause 1 or 11, wherein:

ring $A^2$ is chosen from pyrazole rings optionally further substituted with 1 to 3 optionally halogenated $C_{1-6}$ alkyl groups; and $R^{6b}$ is chosen from $C_{1-6}$ alkyl groups optionally substituted with 1 to 3 $C_{3-6}$ cycloalkyl groups.

14. The compound or pharmaceutically acceptable salt according to Clause 1 or 11, wherein the group represented by:

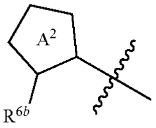

is a group represented by:

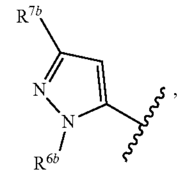

wherein:

$R^{6b}$ is chosen from $C_{1-6}$ alkyl groups optionally substituted with 1 to 3 $C_{3-10}$ cycloalkyl groups; and $R^{7b}$ is chosen from optionally halogenated $C_{1-6}$ alkyl groups.

15. The compound or pharmaceutically acceptable salt according to any one of Clauses 1-14, wherein ring B is chosen from 5-membered monocyclic aromatic heterocyclic rings optionally further substituted with 1 to 3 $C_{1-6}$ alkyl groups.

16. The compound or pharmaceutically acceptable salt according to any one of Clauses 1-15, wherein ring B is chosen from pyrazole rings optionally further substituted with 1 to 3 $C_{1-6}$ alkyl groups.

17. The compound or pharmaceutically acceptable salt according to any one of Clauses 1-15, wherein ring B is chosen from pyrazole rings further substituted with one $C_{1-6}$ alkyl group.

18. The compound or pharmaceutically acceptable salt according to any one of Clauses 1-16, wherein ring B is:

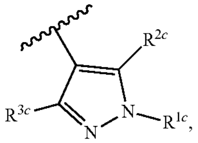

wherein:

$R^{1c}$ is chosen from a hydrogen atom and $C_{1-6}$ alkyl groups; and $R^{2c}$ and $R^{3c}$ are each independently chosen from a hydrogen atom and $C_{1-6}$ alkyl groups.

19. The compound or pharmaceutically acceptable salt according to any one of Clauses 1-16, wherein ring B is:

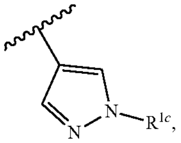

wherein $R^{1c}$ is chosen from $C_{1-6}$ alkyl groups.

20. The compound or pharmaceutically acceptable salt according to any one of Clauses 1-19, wherein:

Z is C—$R^2$; and $R^2$ is chosen from a hydrogen atom and optionally halogenated $C_{1-6}$ alkyl groups.

21. The compound or pharmaceutically acceptable salt according to any one of Clauses 1-20, wherein:

Z is C—$R^2$; and $R^2$ is chosen from a hydrogen atom and $C_{1-3}$ alkyl groups.

22. The compound or pharmaceutically acceptable salt according to any one of Clauses 1-21, wherein:

Z is C—$R^2$ and $R^2$ is chosen from $C_{1-3}$ alkyl groups.

23. The compound or pharmaceutically acceptable salt according to any one of Clauses 1-19, wherein Z is N.

24. The compound or pharmaceutically acceptable salt according to any one of Clauses 1-23, wherein $R^3$ is chosen from a hydrogen atom and $C_{1-3}$ alkyl groups.

25. The compound or pharmaceutically acceptable salt according to any one of Clauses 1-24, wherein $R^3$ is chosen from $C_{1-3}$ alkyl groups.

26. The compound or pharmaceutically acceptable salt according to any one of Clauses 1-25, wherein $R^4$ and $R^5$ are each independently chosen from a hydrogen atom and $C_{1-6}$ alkyl groups.

27. The compound or pharmaceutically acceptable salt according to any one of Clauses 1-26, wherein $R^4$ and $R^5$ are each independently chosen from a hydrogen atom and optionally substituted $C_{1-6}$ alkyl groups.

28. The compound or pharmaceutically acceptable salt according to any one of Clauses 1-27, wherein:

$R^4$ is chosen from a hydrogen atom and $C_{1-6}$ alkyl groups; and $R^5$ is a hydrogen atom.

29. The compound or pharmaceutically acceptable salt according to any one of Clauses 1-28, wherein $R^4$ and $R^5$ are both hydrogen atoms.

30. A compound chosen from Examples 1-167, or a pharmaceutically acceptable salt thereof.

31. A pharmaceutical composition comprising:

at least one compound or pharmaceutically acceptable salt according to any one of Clauses 1-30; and at least one pharmaceutically acceptable carrier.

32. A method of treating or preventing a disease in a mammal in need thereof, the method comprising administering to the mammal at least one compound according to any one of Clauses 1-30.

33. The method according to Clause 32, wherein the disease is chosen from depression, Alzheimer's disease, schizophrenia, drug addiction, sleep disorders, pain, and attention deficit hyperactivity disorder.

34. The method according to Clause 32 or 33, wherein the mammal is a human.

35. The method according to any one of Clauses 32-34, further comprising administering to the mammal at least one combination drug.

The definitions of each of the substituents used in the present specification will be described in detail hereinafter. Unless specified otherwise, each substituent is defined as follows.

Non-limiting examples of "halogen atoms" in the present specification include fluorine, chlorine, bromine, and iodine.

Non-limiting examples of "$C_{1-6}$ alkyl groups" in the present specification include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, and 2-ethylbutyl.

Non-limiting examples of "optionally halogenated $C_{1-6}$ alkyl groups" in the present specification include $C_{1-6}$ alkyl groups which may have from 1 to 7, for example, from 1 to 5, halogen atoms. Additional non-limiting examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4- trifluorobutyl, isobutyl, sec-butyl, tert-butyl, pentyl, isopentyl, neopentyl, 5,5,5-trifluoropentyl, hexyl, and 6,6,6-trifluorohexyl.

Non-limiting examples of "$C_{2-6}$ alkenyl groups" in the present specification include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, and 5-hexenyl.

Non-limiting examples of "$C_{2-6}$ alkynyl groups" in the present specification include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and 4-methyl-2-pentynyl.

Non-limiting examples of "$C_{3-10}$ cycloalkyl groups" in the present specification include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, and adamantyl.

Non-limiting examples of "optionally halogenated $C_{3-10}$ cycloalkyl groups" in the present specification include $C_{3-10}$ cycloalkyl groups which may have from 1 to 7, for example, from 1 to 5, halogen atoms. Additional non-limiting examples thereof include cyclopropyl, 2,2-difluorocyclopropyl, 2,3-difluorocyclopropyl, cyclobutyl, difluorocyclobutyl, cyclopentyl, cyclohexyl, cycloheptyl, and cyclooctyl.

Non-limiting examples of "$C_{3-10}$ cycloalkenyl groups" in the present specification include cyclopropenyl, cyclobutenyl, cyclopentenyl, cyclohexenyl, cycloheptenyl, and cyclooctenyl.

Non-limiting examples of "$C_{6-14}$ aryl groups" in the present specification include phenyl, 1-naphthyl, 1-anthryl, 2-anthryl, and 9-anthryl.

Non-limiting examples of "$C_{7-16}$ aralkyl groups" in the present specification include benzyl, phenethyl, naphthylmethyl, and phenylpropyl.

Non-limiting examples of "$C_{1-6}$ alkoxy groups" in the present specification include methoxy, ethoxy, propoxy, isopropoxy, butoxy, isobutoxy, sec-butoxy, tert-butoxy, pentyloxy, and hexyloxy.

Non-limiting examples of "optionally halogenated $C_{1-6}$ alkoxy groups" in the present specification include $C_{1-6}$ alkoxy groups which may have from 1 to 7, for example, from 1 to 5, halogen atoms. Additional non-limiting examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, and hexyloxy.

Non-limiting examples of "$C_{3-10}$ cycloalkyloxy groups" in the present specification include cyclopropyloxy, cyclobutyloxy, cyclopentyloxy, cyclohexyloxy, cycloheptyloxy, and cyclooctyloxy.

Non-limiting examples of "$C_{1-6}$ alkylthio groups" in the present specification include methylthio, ethylthio, propylthio, isopropylthio, butylthio, sec-butylthio, tert-butylthio, pentylthio, and hexylthio.

Non-limiting examples of "optionally halogenated $C_{1-6}$ alkylthio groups" in the present specification include $C_{1-6}$ alkylthio groups which may have from 1 to 7, for example, from 1 to 5, halogen atoms. Additional non-limiting examples thereof include methylthio, difluoromethylthio, trifluoromethylthio, ethylthio, propylthio, isopropylthio, butylthio, 4,4,4-trifluorobutylthio, pentylthio, and hexylthio.

Non-limiting examples of "$C_{1-6}$ alkyl-carbonyl groups" in the present specification include acetyl, propanoyl, butanoyl, 2-methylpropanoyl, pentanoyl, 3-methylbutanoyl, 2-methylbutanoyl, 2,2-dimethylpropanoyl, hexanoyl, and heptanoyl.

Non-limiting examples of "optionally halogenated $C_{1-6}$ alkyl-carbonyl groups" in the present specification include $C_{1-6}$ alkyl-carbonyl groups which may have from 1 to 7, for example, from 1 to 5, halogen atoms. Additional non-limiting examples thereof include, acetyl, chloroacetyl, trifluoroacetyl, trichloroacetyl, propanoyl, butanoyl, pentanoyl, and hexanoyl.

Non-limiting examples of "$C_{1-6}$ alkoxy-carbonyl groups" in the present specification include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, and hexyloxycarbonyl.

Non-limiting examples of "$C_{6-14}$ aryl-carbonyl groups" in the present specification include benzoyl, 1-naphthoyl, and 2-naphthoyl.

Non-limiting examples of "$C_{7-16}$ aralkyl-carbonyl groups" in the present specification include phenylacetyl and phenylpropionyl.

Non-limiting examples of "5- to 14-membered aromatic heterocyclic carbonyl groups" in the present specification include nicotinoyl, isonicotinoyl, thenoyl, and furoyl.

Non-limiting examples of "3- to 14-membered non-aromatic heterocyclic carbonyl groups" in the present specification include morpholinylcarbonyl, piperidinylcarbonyl, and pyrrolidinylcarbonyl.

Non-limiting examples of "mono- or di-$C_{1-6}$ alkyl-carbamoyl groups" in the present specification include methylcarbamoyl, ethylcarbamoyl, dimethylcarbamoyl, diethylcarbamoyl, and N-ethyl-N-methylcarbamoyl.

Non-limiting examples of "mono- or di-$C_{7-16}$ aralkyl-carbamoyl groups" in the present specification include benzylcarbamoyl and phenethylcarbamoyl.

Non-limiting examples of "$C_{1-6}$ aralkylsulfonyl groups" in the present specification include methylsulfonyl, ethylsulfonyl, propylsulfonyl, isopropylsulfonyl, butylsulfonyl, sec-butylsulfonyl, and tert-butylsulfonyl.

Non-limiting examples of "optionally halogenated $C_{1-6}$ alkylsulfonyl groups" in the present specification include $C_{1-6}$ alkylsulfonyl groups which may have from 1 to 7, for example, from 1 to 5, halogen atoms. Additional non-limiting examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl, and hexylsulfonyl.

Non-limiting examples of "$C_{6-14}$ arylsulfonyl groups" in the present specification include phenylsulfonyl, 1-naphthylsulfonyl, and 2-naphthylsulfonyl.

Non-limiting examples of "substituents" in the present specification include halogen atoms, cyano groups, nitro groups, optionally substituted hydrocarbon groups, optionally substituted heterocyclic groups, acyl groups, optionally substituted amino groups, optionally substituted carbamoyl groups, optionally substituted thiocarbamoyl groups, optionally substituted sulfamoyl groups, optionally substituted hydroxy groups, optionally substituted sulfanyl (SH) groups, and optionally substituted silyl groups.

Non-limiting examples of "hydrocarbon groups" (including "hydrocarbon groups" in "optionally substituted hydrocarbon groups") in the present specification include $C_{1-6}$ alkyl groups, $C_{2-6}$ alkenyl groups, $C_{2-6}$ alkynyl groups, $C_{3-10}$ cycloalkyl groups, $C_{3-10}$ cycloalkenyl groups, $C_{6-14}$ aryl groups, and $C_{7-16}$ aralkyl groups.

Non-limiting examples of "optionally substituted hydrocarbon groups" in the present specification include hydrocarbon groups which may have substituents independently chosen from substituent group A.

Substituent Group A:

(1) halogen atoms;
(2) nitro groups;
(3) cyano groups;
(4) oxo groups;
(5) hydroxy groups;
(6) optionally halogenated $C_{1-6}$ alkoxy groups;
(7) $C_{6-14}$ aryloxy groups (for example, phenoxy or naphthoxy);
(8) $C_{7-16}$ aralkyloxy groups (for example, benzyloxy);
(9) 5- to 14-membered aromatic heterocyclic oxy groups (for example, pyridyloxy);
(10) 3- to 14-membered non-aromatic heterocyclic oxy groups (for example, morpholinyloxy or piperidinyloxy);
(11) $C_{1-6}$ alkyl-carbonyloxy groups (for example, acetoxy or propanoyloxy);
(12) $C_{6-14}$ aryl-carbonyloxy groups (for example, benzoyloxy, 1-naphthoyloxy, or 2-naphthoyloxy);
(13) $C_{1-6}$ alkoxy-carbonyloxy groups (for example, methoxycarbonyloxy, ethoxycarbonyloxy, propoxycarbonyloxy, or butoxycarbonyloxy);
(14) mono- or di-$C_{1-6}$ alkyl-carbamoyloxy groups (for example, methylcarbamoyloxy, ethylcarbamoyloxy, dimethylcarbamoyloxy, or diethylcarbamoyloxy);
(15) $C_{6-14}$ aryl-carbamoyloxy groups (for example, phenylcarbamoyloxy or naphthylcarbamoyloxy);
(16) 5- to 14-membered aromatic heterocyclic carbonyloxy groups (for example, nicotinoyloxy);
(17) 3- to 14-membered non-aromatic heterocyclic carbonyloxy groups (for example, morpholinylcarbonyloxy, or piperidinylcarbonyloxy);
(18) optionally halogenated $C_{1-6}$ alkylsulfonyloxy groups (for example, methylsulfonyloxy or trifluoromethylsulfonyloxy);
(19) $C_{6-14}$ arylsulfonyloxy groups optionally substituted with $C_{1-6}$ alkyl groups (for example, phenylsulfonyloxy or toluenesulfonyloxy);
(20) optionally halogenated $C_{1-6}$ alkylthio groups;
(21) 5- to 14-membered aromatic heterocyclic groups;
(22) 3- to 14-membered non-aromatic heterocyclic groups;
(23) formyl groups;
(24) carboxy groups;
(25) optionally halogenated $C_{1-6}$ alkyl-carbonyl groups;
(26) $C_{6-14}$ aryl-carbonyl groups;
(27) 5- to 14-membered aromatic heterocyclic carbonyl groups;
(28) 3- to 14-membered non-aromatic heterocyclic carbonyl groups;
(29) $C_{1-6}$ alkoxy-carbonyl groups;
(30) $C_{6-14}$ aryloxy-carbonyl groups (for example, phenyloxycarbonyl, 1-naphthyloxycarbonyl, or 2-naphthyloxycarbonyl);
(31) $C_{7-16}$ aralkyloxy-carbonyl groups (for example, benzyloxycarbonyl or phenethyloxycarbonyl);
(32) carbamoyl groups;
(33) thiocarbamoyl groups;
(34) mono- or di-$C_{1-6}$ alkyl-carbamoyl groups;
(35) $C_{6-14}$ aryl-carbamoyl groups (for example, phenylcarbamoyl);
(36) 5- to 14-membered aromatic heterocyclic carbamoyl groups (for example, pyridylcarbamoyl or thienylcarbamoyl);
(37) 3- to 14-membered non-aromatic heterocyclic carbamoyl groups (for example, morpholinylcarbamoyl or piperidinylcarbamoyl);
(38) optionally halogenated $C_{1-6}$ alkylsulfonyl groups;
(39) $C_{6-14}$ arylsulfonyl groups;
(40) 5- to 14-membered aromatic heterocyclic sulfonyl groups (for example, pyridylsulfonyl or thienylsulfonyl);
(41) optionally halogenated $C_{1-6}$ alkylsulfinyl groups;
(42) $C_{6-14}$ arylsulfinyl groups (for example, phenylsulfinyl, 1-naphthylsulfinyl, or 2-naphthylsulfinyl);
(43) 5- to 14-membered aromatic heterocyclic sulfinyl groups (for example, pyridylsulfinyl or thienylsulfinyl);
(44) amino groups;
(45) mono- or di-$C_{1-6}$ alkylamino groups (for example, methylamino, ethylamino, propylamino, isopropylamino, butylamino, dimethylamino, diethylamino, dipropylamino, dibutylamino, or N-ethyl-N-methylamino);
(46) mono- or di-$C_{6-14}$ arylamino groups (for example, phenylamino);
(47) 5- to 14-membered aromatic heterocyclic amino groups (for example, pyridylamino);
(48) $C_{7-16}$ aralkylamino groups (for example, benzylamino);
(49) formylamino groups;
(50) $C_{1-6}$ alkyl-carbonylamino groups (for example, acetylamino, propanoylamino, or butanoylamino);
(51) ($C_{1-6}$ alkyl)($C_{1-6}$ alkyl-carbonyl)amino groups (for example, N-acetyl-N-methylamino);
(52) $C_{6-14}$ aryl-carbonylamino groups (for example, phenylcarbonylamino or naphthylcarbonylamino);
(53) $C_{1-6}$ alkoxy-carbonylamino groups (for example, methoxycarbonylamino, ethoxycarbonylamino, propoxycarbonylamino, butoxycarbonylamino, or tert-butoxycarbonylamino);
(54) $C_{7-16}$ aralkyloxy-carbonylamino groups (for example, benzyloxycarbonylamino);
(55) $C_{1-6}$ alkylsulfonylamino groups (for example, methylsulfonylamino or ethylsulfonylamino);
(56) $C_{6-14}$ arylsulfonylamino groups optionally substituted with $C_{1-6}$ alkyl groups (for example, phenylsulfoylamino or toluenesulfonylamino);
(57) optionally halogenated $C_{1-6}$ alkyl groups;
(58) $C_{2-6}$ alkenyl groups;
(59) $C_{2-6}$ alkynyl groups;
(60) $C_{3-10}$ cycloalkyl groups;
(61) $C_{3-10}$ cycloalkenyl groups; and
(62) $C_{6-14}$ aryl groups.

In some embodiments, the number of the aforementioned substituents in the "optionally substituted hydrocarbon group" is, for example, from 1 to 5, for example, from 1 to 3. When the number of substituents is 2 or greater, the respective substituents may be the same or different from one another.

Non-limiting examples of "heterocyclic groups" (including "heterocyclic groups" in "optionally substituted heterocyclic groups") in the present specification include (i) aromatic heterocyclic groups, (ii) non-aromatic heterocyclic groups, and (iii) 7- to 10-membered heterocyclic bridged ring groups, each containing from 1 to 4 heteroatoms chosen from nitrogen atoms, sulfur atoms, and oxygen atoms in addition to carbon atoms as annular atoms.

Non-limiting examples of "aromatic heterocyclic groups" (including "5- to 14-membered aromatic heterocyclic groups") in the present specification include 5- to 14-membered (for example, 5- to 10-membered) aromatic heterocyclic groups containing from 1 to 4 heteroatoms chosen from nitrogen atoms, sulfur atoms, and oxygen atoms in addition to carbon atoms as annular atoms.

Non-limiting examples of these "aromatic heterocyclic groups" include 5- or 6-membered monocyclic aromatic heterocyclic groups such as thienyl, furyl, pyrrolyl, imidazolyl, pyrazolyl, thiazolyl, isothiazolyl, oxazolyl, isooxazolyl, pyridyl, pyradinyl, pyrimidinyl, pyridadinyl, 1,2,4-oxadiazolyl, 1,3,4-oxadiazolyl, 1,2,4-thiadiazolyl, 1,3,4-thiadiazolyl, triazolyl, tetrazolyl, and triadinyl; and 8- to 14-membered condensed polycyclic (for example, 2- or 3-cyclic) aromatic heterocyclic groups such as benzothiophenyl, benzofuranyl, benzoimidazolyl, benzooxazolyl, benzoisooxazolyl, benzothiazolyl, benzoisothiazolyl, benzotriazolyl, imidazopyridinyl, thienopyridinyl, fluoropyridinyl, pyrrolopyridinyl, pyrazolopyridinyl, oxazolopyridinyl, thiazolopyridinyl, imidazopyradinyl, imidazopyrimidinyl, thienopyrimidinyl, fluoropyrimidinyl, pyrrolopyrimidinyl, pyrazolopyrimidinyl, oxazolopyrimidinyl, thiazolopyrimidinyl, pyrazolotriadinyl, naphtho[2,3-b]thienyl, phenoxathiinyl, indolyl, isoindolyl, 1H-indazolyl, purinyl, isoquinolyl, quinolyl, phthaladinyl, naphthylidinyl, quinoxalinyl, quinazolinyl, cinnolinyl, carbazolyl, β-carbolinyl, phenanthridinyl, acridinyl, phenadinyl, phenothiadinyl, and phenoxadinyl.

Non-limiting examples of "non-aromatic heterocyclic groups" (including "3- to 14-membered non-aromatic heterocyclic groups") in the present specification include 3- to 14-membered (for example, 4- to 10-membered) non-aromatic heterocyclic groups containing from 1 to 4 heteroatoms chosen from nitrogen atoms, sulfur atoms, and oxygen atoms in addition to carbon atoms as annular atoms.

Additional non-limiting examples of these "non-aromatic heterocyclic groups" include 3- to 8-membered monocyclic non-aromatic heterocyclic groups such as aziridinyl, oxylanyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperadinyl, tetrahydropyridinyl, dihydropyridinyl, dihydrothiopyranyl, tetrahydropyrimidinyl, tetrahydropyridazonyl, dihydropyranyl, tetrahydropyranyl, tetrahydrothiopyranyl, morpholinyl, thiomorpholinyl, azepanyl, diazepanyl, azepinyl, oxepanyl, azocanyl, and azocanyl; and 9- to 14-membered condensed polycyclic (for example, 2- or 3-cyclic) non-aromatic heterocyclic groups such as dihydrobenzofuranyl, dihydrobenzoimidazolyl, dihydrobenzothiazolyl, dihydrobenzoisothiazolyl, dihydronaphtho[2,3-b]thienyl, tetrahydroisoquinolyl, tetrahydroquinolyl, 4H-quinolidinyl, indolinyl, isoindolinyl, tetrahydrothieno[2,3-c]pyridinyl, tetrahydrobenzoazepinyl, tetrahydroquinoxalinyl, tetrahydrophenanthridinyl, hexahydrophenothiadinyl, hexahydrophenoxadinyl, tetrahydrophthaladinyl, tetrahydronaphthylidinyl, tetrahydroquinazolinyl, tetrahydrocinnolinyl, tetrahydrocarbazolyl, tetrahydro-β-carbolinyl, tetrahydroacrydinyl, tetrahydrophenadinyl, tetrahydrothioxanthenyl, and octahydroisoquinolyl.

Non-limiting examples of "7- to 10-membered heterocyclic bridged ring groups" in the present specification include quinuclidinyl and 7-azabicyclo[2.2.1]heptanyl.

Non-limiting examples of "nitrogen-containing heterocyclic groups" in the present specification include "heterocyclic groups" containing at least one nitrogen atom as an annular atom.

Non-limiting examples of "optionally substituted heterocyclic groups" in the present specification include heterocyclic groups which may have substituents independently chosen from substituent group A.

The number of substituents in the "optionally substituted heterocyclic groups" is, for example, from 1 to 3. When the number of substituents is 2 or greater, the respective substituents may be the same or different from one another.

Non-limiting examples of "acyl groups" in the present specification include formyl groups, carboxy groups, thiocarbamoyl groups, sulfino groups, sulfo groups, sulfamoyl groups, and phosphono groups which may each have 1 or 2 substituents independently chosen from $C_{1-6}$ alkyl groups, $C_{2-6}$ alkenyl groups, $C_{3-10}$ cycloalkyl groups, $C_{3-10}$ cycloalkenyl groups, $C_{6-14}$ aryl groups, $C_{7-16}$ aralkyl groups, 5- to 14-membered aromatic heterocyclic groups, and 3- to 14-membered non-aromatic heterocyclic groups which may each have from 1 to 3 substituents independently chosen from halogen atoms, optionally halogenated $C_{1-6}$ alkoxy groups, a hydroxy group, a nitro group, a cyano group, an amino groups, and a carbamoyl group.

Additional non-limiting examples of acyl groups include hydrocarbon-sulfonyl groups, heterocycle-sulfonyl groups, hydrocarbon sulfinyl groups, and heterocycle-sulfinyl groups.

Here, a hydrocarbon-sulfonyl group refers to a sulfonyl group to which a hydrocarbon group is bonded; a heterocycle-sulfonyl group refers to a sulfonyl group to which a heterocyclic group is bonded; a hydrocarbon-sulfinyl group refers to a sulfinyl group to which a hydrocarbon group is bonded; and a heterocycle-sulfinyl group refers to a sulfinyl group to which a heterocyclic group is bonded.

Further non-limiting examples of "acyl groups" include formyl groups, carboxy groups, $C_{1-6}$alkyl-carbonyl groups, $C_{2-6}$ alkenyl-carbonyl groups (for example, crotonoyl), $C_{3-10}$ cycloalkyl-carbonyl groups (for example, cyclobutanecarbonyl, cyclopentanecarbonyl, cyclohexanecarbonyl, or cycloheptanecarbonyl), $C_{3-10}$ cycloalkenyl-carbonyl groups (for example, 2-cyclohexenecarbonyl), $C_{6-14}$ aryl-carbonyl groups, $C_{7-16}$ aralkyl-carbonyl groups, 5- to 14-membered aromatic heterocyclic carbonyl groups, 3- to 14-membered non-aromatic heterocyclic carbonyl groups, $C_{1-6}$ alkoxy-carbonyl groups, $C_{6-14}$ aryloxy-carbonyl groups (for example, phenyloxycarbonyl or naphthyloxycarbonyl), $C_{7-16}$ aralkyloxy-carbonyl groups (for example, benzyloxycarbonyl or phenethyloxycarbonyl), carbamoyl groups, mono- or di-$C_{1-6}$ alkyl-carbamoyl groups, mono- or di-$C_{2-6}$ alkenyl-carbamoyl groups (for example, diallylcarbamoyl), mono- or di-$C_{3-10}$ cycloalkyl-carbamoyl groups (for example, cyclopropylcarbamoyl), mono- or di-$C_{6-14}$ aryl-carbamoyl groups (for example, phenylcarbamoyl), mono- or di-$C_{7-16}$ aralkyl-carbamoyl groups, 5- to 14-membered aromatic heterocyclic carbamoyl groups (for example, pyridylcarbamoyl), thiocarbamoyl groups, mono- or di-$C_{1-6}$ alkyl-thiocarbamoyl groups (for example, methylthiocarbamoyl or N-ethyl-N-methylthiocarbamoyl), mono- or di-$C_{2-6}$ alkenyl-thiocarbamoyl groups (for example, diallylthiocarbamoyl), mono- or di-$C_{3-10}$ cycloalkyl-thiocarbamoyl groups (for example, cyclopropylthiocarbamoyl or cyclohexylthiocarbamoyl), mono- or di-$C_{6-14}$ aryl-thiocarbamoyl groups (for example, phenylthiocarbamoyl), mono- or di-$C_{7-16}$ aralkyl-thiocarbamoyl groups (for example, benzylthiocarbamoyl or phenethylthiocarbamoyl), 5- to 14-membered aromatic heterocyclic thiocarbamoyl groups (for example, pyridylthiocarbamoyl), sulfino groups, $C_{1-6}$ alkylsulfinyl groups (for example, methylsulfinyl or ethylsulfinyl), sulfo groups, $C_{1-6}$ alkylsulfonyl groups, $C_{6-14}$ arylsulfonyl groups, phosphono groups, and mono- or di-$C_{1-6}$ alkylphosphono groups (for example, dimethylphosphono, diethylphosphono, diisopropylphosphono, or dibutylphosphono).

Non-limiting examples of "optionally substituted amino groups" in the present specification include amino groups which may have 1 or 2 substituents independently chosen from $C_{1-6}$ alkyl groups, $C_{2-6}$ alkenyl groups, $C_{3-10}$ cycloalkyl groups, $C_{6-14}$ aryl groups, $C_{7-16}$ aralkyl groups, $C_{1-6}$ alkyl-carbonyl groups, $C_{6-14}$ aryl-carbonyl groups, $C_{7-16}$ aralkyl-carbonyl groups, 5- to 14-membered aromatic heterocyclic carbonyl groups, 3- to 14-membered non-aromatic heterocyclic carbonyl groups, $C_{1-6}$ alkoxy-carbonyl groups, 5- to 14-membered aromatic heterocyclic groups, carbamoyl groups, mono- or di-$C_{1-6}$ alkyl-carbamoyl groups, mono- or di-$C_{7-16}$ aralkyl-carbamoyl groups, CJ-6 alkylsulfonyl groups, and $C_{6-14}$ arylsulfonyl groups which may each have from 1 to 3 substituents independently chosen from substituent group A.

Non-limiting examples of optionally substituted amino groups include amino groups, mono- or di-(optionally halogenated $C_{1-6}$ alkyl)amino groups (for example, methylamino, trifluoromethylamino, dimethylamino, ethylamino, diethylamino, propylamino, or dibutylamino), mono- or di-$C_{2-6}$ alkenylamino groups (for example, diallylamino), mono- or di-$C_{3-10}$ cycloalkylamino groups (for example, cyclopropylamino, cyclohexylamino), mono- or di-$C_{6-14}$ arylamino groups (for example, phenylamino), mono- or di-$C_{7-16}$ aralkylamino groups (for example, benzylamino, or dibenzylamino), mono- or di-(optionally halogenated $C_{1-6}$ alkyl)-carbonylamino groups (for example, acetylamino or propionylamino), mono- or di-$C_{6-14}$ aryl-carbonyl groups (for example, benzoylamino), mono- or di-$C_{7-16}$ aralkyl-carbonylamino groups (for example, benzylcarbonylamino), mono- or di-5- to 14-membered aromatic heterocyclic carbonylamino groups (for example, nicotinoylamino or isonicotinoylamino), mono- or di-3- to 14-membered non-aromatic heterocyclic carbonylamino groups (for example, piperidinylcarbonylamino), mono- or di-$C_{1-6}$ alkoxy-carbonylamino groups (for example, tert-butoxycarbonylamino), 5- to 14-membered aromatic heterocyclic amino groups (for example, pyridylamino), carbamoylamino groups, (mono- or di-$C_{1-6}$ alkyl-carbamoyl)amino groups (for example, methylcarbamoylamino), (mono- or di-$C_{7-16}$ aralkyl-carbamoyl)amino groups (for example, benzylcarbamoylamino), $C_{1-6}$ alkylsulfonylamino groups (for example, methylsulfonylamino or ethylsulfonylamino), $C_{6-14}$ arylsulfonylamino groups (for example, phenylsulfonylamino), ($C_{1-6}$ alkyl)($C_{1-6}$ alkyl-carbonyl)amino groups (for example, N-acetyl-N-methylamino), and ($C_{1-6}$ alkyl)($C_{6-14}$ aryl-carbonyl)amino groups (for example, N-benzoyl-N-methylamino) groups.

Non-limiting examples of "optionally substituted carbamoyl groups" in the present specification include carbamoyl groups which may have 1 or 2 substituents independently chosen from $C_{1-6}$ alkyl groups, $C_{2-6}$ alkenyl groups, $C_{3-10}$ cycloalkyl groups, $C_{6-14}$ aryl groups, $C_{7-16}$ aralkyl groups, $C_{1-6}$ alkyl-carbonyl groups, $C_{6-14}$ aryl-carbonyl groups, $C_{7-16}$ aralkyl-carbonyl groups, 5- to 14-membered aromatic heterocyclic carbonyl groups, 3- to 14-membered non-aromatic heterocyclic carbonyl groups, $C_{1-6}$ alkoxy-carbonyl groups, 5- to 14-membered aromatic heterocyclic groups, carbamoyl groups, mono- or di-$C_{1-6}$ alkyl-carbamoyl groups, and mono- or di-$C_{7-16}$ aralkyl-carbamoyl groups which may each have from 1 to 3 substituents independently chosen from substituent group A.

Additional non-limiting examples of optionally substituted carbamoyl groups include carbamoyl groups, mono- or di-$C_{1-6}$ alkyl-carbamoyl groups, mono- or di-$C_{2-6}$ alkenyl-carbamoyl groups (for example, diallylcarbamoyl), mono- or di-$C_{3-10}$ cycloalkyl-carbamoyl groups (for example, cyclopropylcarbamoyl or cyclohexylcarbamoyl), mono- or di-$C_{6-14}$ aryl-carbamoyl groups (for example, phenylcarbamoyl), mono- or di-$C_{7-16}$ aralkyl-carbamoyl groups, mono- or di-$C_{1-6}$ alkyl-carbonyl-carbamoyl groups (for example, acetylcarbamoyl or propionylcarbamoyl), mono- or di-$C_{6-14}$ aryl-carbonyl-carbamoyl groups (for example, benzoylcarbamoyl), and 5- to 14-membered aromatic heterocyclic carbamoyl groups (for example, pyridylcarbamoyl).

Non-limiting examples of "optionally substituted thiocarbamoyl groups" in the present specification include thiocarbamoyl groups which may have 1 or 2 substituents independently chosen from $C_{1-6}$ alkyl groups, $C_{2-6}$ alkenyl groups, $C_{3-10}$ cycloalkyl groups, $C_{6-14}$ aryl groups, $C_{7-16}$ aralkyl groups, $C_{1-6}$ alkyl-carbonyl groups, $C_{6-14}$ aryl-carbonyl groups, $C_{7-16}$ aralkyl-carbonyl groups, 5- to 14-membered aromatic heterocyclic carbonyl groups, 3- to 14-membered non-aromatic heterocyclic carbonyl groups, $C_{1-6}$ alkoxy-carbonyl groups, 5- to 14-membered aromatic heterocyclic groups, carbamoyl groups, mono- or di-$C_{1-6}$ alkyl-carbamoyl groups, and mono- or di-$C_{7-16}$ aralkyl-carbamoyl groups which may each have from 1 to 3 substituents independently chosen from substituent group A.

Additional non-limiting examples of optionally substituted thiocarbamoyl groups include thiocarbamoyl groups, mono- or di-$C_{1-6}$ alkyl-thiocarbamoyl groups (for example, methylthiocarbamoyl, ethylthiocarbamoyl, dimethylthiocarbamoyl, diethylthiocarbamoyl, or N-ethyl-N-methylthiocarbamoyl), mono- or di-$C_{2-6}$ alkenyl-thiocarbamoyl groups (for example, diallylthiocarbamoyl), mono- or di-$C_{3-10}$ cycloalkyl-thiocarbamoyl groups (for example, cyclopropylthiocarbamoyl or cyclohexylthiocarbamoyl), mono- or di-$C_{6-14}$ aryl-thiocarbamoyl groups (for example, phenylthiocarbamoyl), mono- or di-$C_{7-16}$ aralkyl-thiocarbamoyl groups (for example, benzylthiocarbamoyl or phenethylthiocarbamoyl), mono- or di-$C_{1-6}$ alkyl-carbonyl-thiocarbamoyl groups (for example, acetylthiocarbamoyl or propionylthiocarbamoyl), mono- or di-$C_{6-14}$ aryl-carbonyl-thiocarbamoyl groups (for example, benzoylthiocarbamoyl), and 5- to 14-membered aromatic heterocyclic thiocarbamoyl groups (for example, pyridylthiocarbamoyl).

Non-limiting examples of "optionally substituted sulfamoyl groups" in the present specification include sulfamoyl groups which may have 1 or 2 substituents independently chosen from $C_{1-6}$ alkyl groups, $C_{2-6}$ alkenyl groups, $C_{3-10}$ cycloalkyl groups, $C_{6-14}$ aryl groups, $C_{7-16}$ aralkyl groups, $C_{1-6}$ alkyl-carbonyl groups, $C_{6-14}$ aryl-carbonyl groups, $C_{7-16}$ aralkyl-carbonyl groups, 5- to 14-membered aromatic heterocyclic carbonyl groups, 3- to 14-membered non-aromatic heterocyclic carbonyl groups, $C_{1-6}$ alkoxy-carbonyl groups, 5- to 14-membered aromatic heterocyclic groups, carbamoyl groups, mono- or di-$C_{1-6}$ alkyl-carbamoyl groups, and mono- or di-$C_{7-16}$ aralkyl-carbamoyl groups which may each have from 1 to 3 substituents independently chosen from substituent group A.

Additional non-limiting examples of optionally substituted sulfamoyl groups include sulfamoyl groups, mono- or di-$C_{1-6}$ alkyl-sulfamoyl groups (for example, methylsulfamoyl, ethylsulfamoyl, dimethylsulfamoyl, diethylsulfamoyl, or N-ethyl-N-methylsulfamoyl), mono- or di-$C_{2-6}$ alkenyl-sulfamoyl groups (for example, diallylsulfamoyl), mono- or di-$C_{3-10}$ cycloalkyl-sulfamoyl groups (for example, cyclopropylsulfamoyl, cyclohexylsulfamoyl), mono- or di-$C_{6-14}$ aryl-sulfamoyl groups (for example, phenylsulfamoyl), mono- or di-$C_{7-16}$ aralkyl-sulfamoyl groups (for example, benzylsulfamoyl, or phenethylsulfamoyl), mono- or di-$C_{1-6}$ alkyl-carbonyl-sulfamoyl groups (for example, acetylsulfamoyl or propionylsulfamoyl), mono- or di-$C_{6-14}$ aryl-carbonyl-sulfamoyl groups (for example, benzoylsulfamoyl), and 5- to 14-membered aromatic heterocyclic sulfamoyl groups (for example, pyridylsulfamoyl).

Non-limiting examples of "optionally substituted hydroxy groups" in the present specification include hydroxy groups which may have substituents independently chosen from $C_{1-6}$ alkyl groups, $C_{2-6}$ alkenyl groups, $C_{3-10}$ cycloalkyl groups, $C_{6-14}$ aryl groups, $C_{7-16}$ aralkyl groups, $C_{1-6}$ alkyl-carbonyl groups, $C_{6-14}$ aryl-carbonyl groups, $C_{7-16}$ aralkyl-carbonyl groups, 5- to 14-membered aromatic heterocyclic carbonyl groups, 3- to 14-membered non-aromatic heterocyclic carbonyl groups, $C_{1-6}$ alkoxy-carbonyl groups, 5- to 14-membered aromatic heterocyclic groups, carbamoyl groups, mono- or di-$C_{1-6}$ alkyl-carbamoyl groups, mono- or di-$C_{7-16}$ aralkyl-carbamoyl groups, $C_{1-6}$ alkylsulfonyl groups, and $C_{6-14}$ arylsulfonyl groups which may each have from 1 to 3 substituents independently chosen from substituent group A.

Non-limiting examples of optionally substituted hydroxy groups include hydroxy groups, $C_{1-6}$ alkoxy groups, $C_{2-6}$ alkenyloxy groups (for example, allyloxy, 2-butenyloxy, 2-pentenyloxy, or 3-hexenyloxy), $C_{3-10}$ cycloalkyloxy groups (for example, cyclohexyloxy), $C_{6-14}$ aryloxy groups (for example, phenoxy or naphthyloxy), $C_{7-16}$ aralkyloxy groups (for example, benzyloxy or phenethyloxy), $C_{1-6}$ alkyl-carbonyloxy groups (for example, acetyloxy, propionyloxy, butyryloxy, isobutyryloxy, or pivaloyloxy), $C_{6-14}$ aryl-carbonyloxy groups (for example, benzoyloxy), $C_{7-16}$ aralkyl-carbonyloxy groups (for example, benzylcarbonyloxy), 5- to 14-membered aromatic heterocyclic carbonyloxy groups (for example, nicotinoyloxy), 3- to 14-membered non-aromatic heterocyclic carbonyloxy groups (for example, piperidinylcarbonyloxy), $C_{1-6}$ alkoxy-carbonyloxy groups (for example, tert-butoxycarbonyloxy), 5- to 14-membered aromatic heterocyclic oxy groups (for example, pyridyloxy), carbamoyloxy groups, $C_{1-6}$ alkyl-carbamoyloxy groups (for example, methylcarbamoyloxy), $C_{7-16}$ aralkyl-carbamoyloxy groups (for example, benzylcarbamoyloxy), $C_{1-6}$ alkylsulfonyloxy groups (for example, methylsulfonyloxy or ethylsulfonyloxy), and $C_{6-14}$ arylsulfonyloxy groups (for example, phenylsulfonyloxy).

Non-limiting examples of "optionally substituted sulfanyl groups" in the present specification include sulfanyl groups and halogenated sulfanyl groups which may have substituents independently chosen from $C_{1-6}$ alkyl groups, $C_{2-6}$ alkenyl groups, $C_{3-10}$ cycloalkyl groups, $C_{6-14}$ aryl groups, $C_{7-16}$ aralkyl groups, $C_{1-6}$ alkyl-carbonyl groups, $C_{6-14}$ aryl-carbonyl groups, and 5- to 14-membered aromatic heterocyclic groups which may each have from 1 to 3 substituents independently chosen from substituent group A."

Additional non-limiting examples of optionally substituted sulfanyl groups include sulfanyl (—SH) groups, $C_{1-6}$ alkylthio groups, $C_{2-6}$ alkenylthio groups (for example, allylthio, 2-butenylthio, 2-pentenylthio, or 3-hexenylthio), $C_{3-10}$ cycloalkylthio groups (for example, cyclohexylthio), $C_{6-14}$ arylthio groups (for example, phenylthio or naphthylthio), $C_{7-16}$ aralkylthio groups (for example, benzylthio or phenethylthio), $C_{1-6}$ alkyl-carbonylthio groups (for example, acetylthio, propionylthio, butylthio, isobutylthio, or pivaloylthio), $C_{6-14}$ aryl-carbonylthio groups (for example, benzoylthio), 5- to 14-membered aromatic heterocyclic thio groups (for example, pyridylthio), and halogenated thio groups (for example, pentafluorothio).

Non-limiting examples of "optionally substituted silyl groups" in the present specification include silyl groups which may have from 1 to 3 substituents independently chosen from $C_{1-6}$ alkyl groups, $C_{2-6}$ alkenyl groups, $C_{3-10}$ cycloalkyl groups, $C_{6-14}$ aryl groups, and $C_{7-16}$ aralkyl groups which may each have from 1 to 3 substituents independently chosen from substituent group A.

Non-limiting examples of optionally substituted silyl groups include tri-$C_{1-6}$ alkylsilyl groups (for example, trimethylsilyl or tert-butyl(dimethyl)silyl).

Non-limiting examples of "hydrocarbon rings" in the present specification include $C_{6-14}$ aromatic hydrocarbon rings, $C_{3-10}$ cycloalkanes, and $C_{3-10}$ cycloalkenes.

Non-limiting examples of "$C_{6-14}$ aromatic hydrocarbon groups" in the present specification include benzene and naphthalene.

Non-limiting examples of "$C_{3-10}$ cycloalkanes" in the present specification include cyclopropane, cyclobutane, cyclopentane, cyclohexane, cycloheptane, and cyclooctane.

Non-limiting examples of "$C_{3-10}$ cycloalkenes" in the present specification include cyclopropene, cyclobutene, cyclopentene, cyclohexene, cycloheptene, and cyclooctene.

Non-limiting examples of "heterocyclic rings" in the present specification include aromatic heterocyclic rings and non-aromatic heterocyclic rings which respectively contain from 1 to 4 heteroatoms chosen from nitrogen atoms, sulfur atoms, and oxygen atoms in addition to carbon atoms as annular atoms.

Non-limiting examples of "aromatic heterocyclic rings" in the present specification include 5- to 14-membered (for example, 5- to 10-membered) aromatic heterocyclic rings containing from 1 to 4 heteroatoms chosen from nitrogen atoms, sulfur atoms, and oxygen atoms in addition to carbon atoms as annular atoms. Additional non-limiting examples of these "aromatic heterocyclic rings" include 5- or 6-membered monocyclic aromatic heterocyclic rings such as thiophene, furan, pyrrole, imidazole, pyrazole, thiazole, isothiazole, oxazole, isooxazole, pyridine, pyrazine, pyrimidine, pyridazine, 1,2,4-oxadiazole, 1,3,4-oxadiazolyl, 1,2,4-thiadiazole, 1,3,4-thiadiazole, triazole, tetrazole, and triazine; and 8- to 14-membered condensed polycyclic (for example, 2- or 3-cyclic) aromatic heterocyclic rings such as benzothiophene, benzofuran, benzoimidazole, benzooxazole, benzoisooxazole, benzothiazole, benzoisothiazole, benzotriazole, imidazopyridine, thienopyridine, fluoropyridine, pyrrolopyridine, pyrazolopyridine, oxazolopyridine, thiazolopyridine, imidazopyradine, imidazopyrimidine, thienopyrimidine, fluoropyrimidine, pyrrolopyrimidine, pyrazolopyrimidine, oxazolopyrimidine, thiazolopyrimidine, pyrazolotriazine, naphtho[2,3-b]thiophene, phenoxathiine, indole, isoindole, 1H-indazole, purine, isoquinoline, quinoline, phthalazine, naphthylidine, quinoxaline, quinazoline, cinnoline, carbazole, β-carboline, phenanthridine, acridine, phenazine, phenothiazine, and phenoxazine.

Non-limiting examples of "non-aromatic heterocyclic rings" in the present specification include 3- to 14-membered (for example, 4- to 10-membered) non-aromatic heterocyclic rings containing from 1 to 4 heteroatoms chosen from nitrogen atoms, sulfur atoms, and oxygen atoms in addition to carbon atoms as annular atoms. Additional non-limiting examples of these "non-aromatic heterocyclic rings" include 3- to 8-membered monocyclic non-aromatic heterocyclic rings such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisooxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, and oxepane; and 9- to 14-membered condensed polycyclic (for example, 2- or 3-cyclic) non-aromatic heterocyclic groups such as dihydrobenzofuran, dihydrobenzoimidazole, dihydrobenzothiazole, dihydrobenzoisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzoazepine, tetrahydroquinoxaline, tetrahydrophenanthridine, hexahydrophenothiazine, hexahydrophenoxazine, tetrahydrophthalazine, tetrahydronaphthylidine, tetrahydroquinazoline, tetrahydrocinnoline, tetrahydrocarbazole, tetrahydro-R-carboline, tetrahydroacridine, tetrahydrophenadine, tetrahydrothioxanthene, and octahydroisoquinole.

Non-limiting examples of "nitrogen-containing heterocyclic rings" in the present specification include "heterocyclic rings" containing at least one nitrogen atom as an annular atom.

Non-limiting examples of "6-membered aromatic rings" in the present specification include benzene, pyridine, pyridazine, pyrimidine, pyrazine, and triazine.

Non-limiting examples of "5-membered monocyclic aromatic heterocyclic rings" in the present specification include thiophene, furan, pyrrole, imidazole, pyrazole, thiazole, isothiazole, oxazole, isooxazole, 1,2,4-oxadiazole, 1,3,4-oxadiazolyl, 1,2,4-thiadiazole, 1,3,4-thiadiazole, triazole, and tetrazole.

The definitions of each of the symbols in Formula (I) will be described in detail hereinafter.

In some embodiments, $R^1$ is a group represented by:

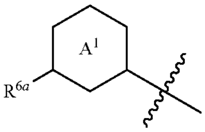

or

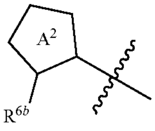

, wherein:

- ring $A^1$ is chosen from optionally further substituted 6-membered aromatic rings;
- ring $A^2$ is chosen from optionally further substituted 5-membered monocyclic aromatic heterocyclic rings; and
- $R^{6a}$ and $R^{6b}$ are each independently chosen from substituents.

In some embodiments, $R^1$ is a group represented by:

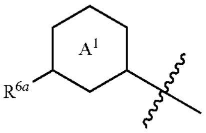

.

In some embodiments, the "6-membered aromatic ring" of the "optionally further substituted 6-membered aromatic ring" represented by ring $A^1$ is benzene, pyridine, or pyrimidine. In some embodiments, the "6-membered aromatic ring" of the "optionally further substituted 6-membered aromatic ring" represented by ring $A^1$ is pyridine.

Non-limiting examples of optional substituents in the "optionally further substituted 6-membered aromatic ring" represented by ring $A^1$ are substituents independently chosen from substituent group A. In some embodiments, the number of these optional substituents is an integer from 1 to 3. When the number of optional substituents is 2 or greater, the respective substituents may be the same or different from one another.

In some embodiments, ring $A^1$ is chosen from 6-membered aromatic ring (for example, benzene, pyridine, or pyrimidine) optionally further substituted with 1 to 3 substituents independently chosen from.

- (a) halogen atoms (for example, fluorine atoms, chlorine atoms, or bromine atoms);
- (b) $C_{1-6}$ alkyl groups (for example, methyl, ethyl, or isopropyl) optionally substituted with 1 to 3 substituents independently chosen from: (i) halogen atoms (for example, fluorine atoms); and (ii) a hydroxy group;
- (c) optionally halogenated $C_{1-6}$ alkoxy groups (for example, trifluoromethoxy, 2,2-difluoroethoxy, or 2,2,2-trifluoroethoxy);
- (d) $C_{3-10}$ cycloalkyl groups (for example, cyclopropyl) optionally substituted with 1 to 3 halogen atoms (for example, fluorine atoms);
- (e) $C_{2-6}$ alkenyl groups (for example, vinyl); and
- (f) 3- to 14-membered non-aromatic heterocyclic groups (for example, 3- to 8-membered monocyclic non-aromatic heterocyclic groups (for example, piperidyl)) optionally substituted with 1 to 3 halogen atoms (for example, fluorine atoms).

In some embodiments, ring $A^1$ is chosen from:

- (1) benzene rings optionally further substituted with 1 to 3 substituents independently chosen from:
  - (a) halogen atoms (for example, fluorine atoms, chlorine atoms, or bromine atoms);
  - (b) $C_{1-6}$ alkyl groups (for example, methyl, ethyl, or isopropyl) optionally substituted with 1 to 3 substituents independently chosen from (i) halogen atoms (for example, fluorine atoms); and (ii) a hydroxy group;
  - (c) optionally halogenated $C_{1-6}$ alkoxy groups (for example, trifluoromethoxy, 2,2-difluoroethoxy, or 2,2,2-trifluoroethoxy);
  - (d) $C_{3-10}$ cycloalkyl groups (for example, cyclopropyl) optionally substituted with 1 to 3 halogen atoms (for example, fluorine atoms);
  - (e) $C_{2-6}$ alkenyl groups (for example, vinyl); and
  - (f) 3- to 14-membered non-aromatic heterocyclic groups (for example, 3- to 8-membered monocyclic non-aromatic heterocyclic groups (for example, piperidyl)) optionally substituted with 1 to 3 halogen atoms (for example, fluorine atoms);
- (2) pyridine rings optionally further substituted with 1 to 3 substituents independently chosen from:
  - (a) halogen atoms (for example, fluorine atoms or chlorine atoms);
  - (b) optionally halogenated $C_{1-6}$ alkyl groups (for example, methyl, difluoromethyl, or trifluoromethyl);
  - (c) optionally halogenated $C_{1-6}$ alkoxy groups (for example, 2,2,2-trifluoroethoxy); and
  - (d) $C_{3-10}$ cycloalkyl groups (for example, cyclopropyl); and (3) pyrimidine rings optionally further substituted with 1 or 2 optionally halogenated $C_{1-6}$ alkyl groups (for example, trifluoromethyl).

In some embodiments, ring $A^1$ is chosen from:

(1) benzene rings optionally further substituted with 1 to 3 substituents independently chosen from:
   (a) halogen atoms (for example, fluorine atoms, chlorine atoms, or bromine atoms);
   (b) $C_{1-6}$ alkyl groups (for example, methyl, ethyl, or isopropyl) optionally substituted with 1 to 3 substituents independently chosen from: (i) halogen atoms (for example, fluorine atoms); and (ii) a hydroxy group;
   (c) optionally halogenated $C_{1-6}$ alkoxy groups (for example, trifluoromethoxy, 2,2-difluoroethoxy, or 2,2,2-trifluoroethoxy);
   (d) $C_{3-6}$ cycloalkyl groups (for example, cyclopropyl) optionally substituted with 1 to 3 halogen atoms (for example, fluorine atoms);
   (e) $C_{2-6}$ alkenyl groups (for example, vinyl); and
   (f) piperidyl groups optionally substituted with 1 to 3 halogen atoms (for example, fluorine atoms);

(2) pyridine rings optionally further substituted with 1 to 3 substituents independently chosen from:
   (a) halogen atoms (for example, fluorine atoms or chlorine atoms);
   (b) optionally halogenated $C_{1-6}$ alkyl groups (for example, methyl, difluoromethyl, or trifluoromethyl);
   (c) optionally halogenated $C_{1-6}$ alkoxy groups (for example, 2,2,2-trifluoroethoxy); and
   (d) $C_{3-6}$ cycloalkyl groups (for example, cyclopropyl); or (3) pyrimidine rings optionally further substituted with 1 or 2 optionally halogenated $C_{1-6}$ alkyl groups (for example, trifluoromethyl).

In some embodiments, ring $A^1$ is chosen from pyridine rings further substituted with 1 or 2 substituents independently chosen from:
   (a) halogen atoms (for example, fluorine atoms); and
   (b) halogenated $C_{1-6}$ alkyl groups (for example, trifluoromethyl).

In some embodiments, ring $A^1$ is chosen from pyridine rings further substituted with one halogenated $C_{1-6}$ alkyl group (for example, trifluoromethyl).

In some embodiments, ring $A^1$ is chosen from pyridine rings further substituted with one trifluoromethyl group.

In some embodiments, ring $A^1$ is chosen from optionally further substituted benzene rings, optionally further substituted pyridine rings, and optionally further substituted pyrimidine rings.

In some embodiments, ring $A^1$ is chosen from optionally further substituted pyridine rings.

In some embodiments, ring $A^1$ is chosen from further substituted pyridine rings.

In some embodiments, $R^{6a}$ is chosen from:

(1) optionally substituted $C_{3-10}$ cycloalkyl groups (for example, cyclohexyl);

(2) optionally substituted $C_{6-14}$ aryl groups (for example, phenyl);

(3) optionally substituted 3- to 14-membered non-aromatic heterocyclic groups (for example, 3- to 8-membered monocyclic non-aromatic heterocyclic groups (for example, morpholinyl, piperidyl, or pyrrolidinyl) or 6- to 9-membered non-aromatic spiro heterocyclic groups (for example, 4-oxa-7-azaspiro[2.5]octyl));

(4) optionally substituted 5- to 14-membered aromatic heterocyclic groups (for example, 5- or 6-membered monocyclic aromatic heterocyclic groups (for example, imidazolyl));

(5) —$NR^9R^{10}$, wherein:
   $R^9$ is chosen from:
      (A) optionally substituted $C_{1-6}$ alkyl groups (for example, methyl); and
      (B) optionally substituted 3- to 14-membered non-aromatic heterocyclic groups (for example, 3- to 8-membered monocyclic non-aromatic heterocyclic groups (for example, tetrahydropyranyl); and
   $R^{10}$ is chosen from:
      (A) a hydrogen atom; and
      (B) optionally substituted $C_{1-6}$ alkyl groups (for example, methyl)); and (6) —$OR^{11}$, wherein $R^{11}$ is chosen from:
   (A) optionally substituted $C_{1-6}$ alkyl groups (for example, methyl);
   (B) optionally substituted $C_{6-14}$ aryl groups (for example, phenyl); and
   (C) optionally substituted 3- to 14-membered non-aromatic heterocyclic groups (for example, 3- to 8-membered monocyclic non-aromatic heterocyclic groups (for example, tetrahydropyranyl)).

In some embodiments, the optional substituents in the "optionally substituted $C_{1-6}$ alkyl groups", the "optionally substituted $C_{3-10}$ cycloalkyl groups", the "optionally substituted $C_{6-14}$ aryl groups", the "optionally substituted 3- to 14-membered non-aromatic heterocyclic groups", and the "5- to 14-membered aromatic cyclic groups" described above are substituents independently chosen from substituent group A. In some embodiments, the number of these optional substituents is an integer from 1 to 3. When the number of optional substituents is 2 or greater, the respective optional substituents may be the same or different from one another.

In some embodiments, the "3- to 14-membered non-aromatic heterocyclic groups" of the "optionally substituted 3- to 14-membered non-aromatic heterocyclic groups" described above is chosen from 6- to 9-membered non-aromatic spiro heterocyclic groups.

In some embodiments, $R^{6b}$ is chosen from:

(1) optionally substituted $C_{3-10}$ cycloalkyl groups (for example, cyclohexyl);

(2) optionally substituted $C_{6-14}$ aryl groups (for example, phenyl);

(3) optionally substituted 3- to 14-membered non-aromatic heterocyclic groups (for example, 3- to 8-membered monocyclic non-aromatic heterocyclic groups (for example, morpholinyl, piperidyl, or pyrrolidinyl) or 6- to 9-membered non-aromatic spiro heterocyclic groups (for example, 4-oxa-7-azaspiro[2.5]octyl));

(4) optionally substituted 5- to 14-membered aromatic heterocyclic groups (for example, 5- or 6-membered monocyclic aromatic heterocyclic groups (for example, imidazolyl));

(5) optionally substituted mono- or di-$C_{1-6}$ alkylamino groups (for example, methylamino);

(6) optionally substituted N—$C_{1-6}$ alkyl-N-3- to 14-membered non-aromatic heterocyclic amino groups (for example, N—$C_{1-6}$ alkyl-N-3- to 8-membered monocyclic aromatic heterocyclic amino groups (for example, N-methyl-N-tetrahydropyranylamino));

(7) optionally substituted $C_{1-6}$ alkoxy groups (for example, methoxy);

(8) optionally substituted $C_{6-14}$ aryloxy groups (for example, phenoxy); and (9) optionally substituted 3- to 14-membered non-aromatic heterocyclic oxy groups (for example, 3- to 8-membered monocyclic non-aromatic heterocyclic oxy groups (for example, tetrahydropyranyloxy)).

In some embodiments, $R^{6a}$ is chosen from:

(1) $C_{3-10}$ cycloalkyl groups (for example, cyclohexyl) optionally substituted with 1 to 3 halogen atoms (for example, fluorine atoms);

(2) $C_{6-14}$ aryl groups (for example, phenyl) optionally substituted with 1 to 3 halogen atoms (for example, fluorine atoms);

(3) 3- to 14-membered non-aromatic heterocyclic groups (for example, 3- to 8-membered monocyclic non-aromatic heterocyclic groups (for example, morpholinyl, piperidyl, or pyrrolidinyl) or 6- to 9-membered non-aromatic spiro heterocyclic groups (for example, 4-oxa-7-azaspiro[2.5]octyl)) optionally substituted with 1 to 3 substituents independently chosen from:

(a) halogen atoms (for example, fluorine atoms); and (b) optionally halogenated $C_{1-6}$ alkyl groups (for example, methyl or difluoromethyl);

(4) optionally substituted 5- to 14-membered aromatic heterocyclic groups (for example, a 5- or 6-membered monocyclic aromatic heterocyclic group (for example, imidazolyl)) optionally substituted with 1 to 3 $C_{1-6}$ alkyl groups (for example, methyl);

(5) mono- or di-$C_{1-6}$ alkylamino groups (for example, methylamino) optionally substituted with 1 to 3 $C_{3-10}$ cycloalkyl groups (for example, cyclobutyl) optionally substituted with 1 to 3 halogen atoms (for example, fluorine atoms);

(6) N—$C_{1-6}$ alkyl-N-3- to 14-membered non-aromatic heterocyclic amino group (for example, N—$C_{1-6}$ alkyl-N-3- to 8-membered monocyclic aromatic heterocyclic amino groups (for example, N-methyl-N-tetrahydropyranylamino));

(7) $C_{1-6}$ alkoxy groups (for example, methoxy) optionally substituted with 1 to 3 substituents independently chosen from:

(a) $C_{1-6}$ alkoxy groups (for example, methoxy);

(b) $C_{3-10}$ cycloalkyl groups (for example, cyclopropyl or cyclobutyl) optionally substituted with 1 to 3 halogen atoms (for example, fluorine atoms); and (c) 3- to 14-membered non-aromatic heterocyclic groups (for example, 3- to 8-membered monocyclic non-aromatic heterocyclic groups (for example, oxetanyl or tetrahydrofuryl));

(8) $C_{6-14}$ aryloxy groups (for example, phenoxy) optionally substituted with 1 to 3 halogen atoms (for example, fluorine atoms); and (9) 3- to 14-membered non-aromatic heterocyclic oxy groups (for example, 3- to 8-membered monocyclic non-aromatic heterocyclic oxy groups (for example, tetrahydropyranyloxy)).

In some embodiments, $R^{6a}$ is chosen from:

(1) $C_{3-6}$ cycloalkyl groups (for example, cyclohexyl) optionally substituted with 1 to 3 halogen atoms (for example, fluorine atoms);

(2) phenyl groups optionally substituted with 1 to 3 halogen atoms (for example, fluorine atoms);

(3) morpholinyl groups optionally substituted with 1 to 3 substituents independently chosen from:

(a) halogen atoms (for example, fluorine atoms); and (b) optionally halogenated $C_{1-6}$ alkyl groups (for example, methyl or difluoromethyl);

(4) piperidyl groups optionally substituted with 1 to 3 halogen atoms (for example, fluorine atoms);

(5) pyrrolidinyl groups optionally substituted with 1 to 3 halogen atoms (for example, fluorine atoms);

(6) a 4-oxa-7-azaspiro[2.5]octyl group;

(7) imidazolyl groups optionally substituted with 1 to 3 $C_{1-6}$ alkyl groups (for example, methyl);

(8) mono- or di-$C_{1-6}$ alkylamino groups (for example, methylamino) optionally substituted with 1 to 3 $C_3$ cycloalkyl groups (for example, cyclobutyl) optionally substituted with 1 to 3 halogen atoms (for example, fluorine atoms);

(9) N—$C_{1-6}$ alkyl-N-tetrahydropyranylamino groups (for example, N-methyl-N-tetrahydropyranylamino);

(10) $C_{1-6}$ alkoxy groups (for example, methoxy) optionally substituted with 1 to 3 substituents independently chosen from:

(a) $C_{1-6}$ alkoxy groups (for example, methoxy);

(b) $C_{3-6}$ cycloalkyl groups (for example, cyclopropyl or cyclobutyl) optionally substituted with 1 to 3 halogen atoms (for example, fluorine atoms);

(c) an oxetanyl group; and (d) a tetrahydrofuryl group;

(11) phenoxy groups optionally substituted with 1 to 3 halogen atoms (for example, fluorine atoms); and

(12) a tetrahydropyranyloxy group.

In some embodiments, $R^{6a}$ is a morpholinyl group optionally substituted with 1 to 3 $C_{1-6}$ alkyl groups (for example, methyl).

In some embodiments, $R^{6a}$ is a morpholinyl group substituted with one $C_{1-6}$ alkyl group (for example, methyl).

In some embodiments, the group represented by:

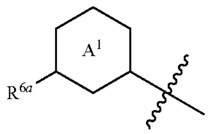

is a group represented by:

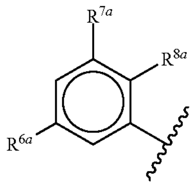

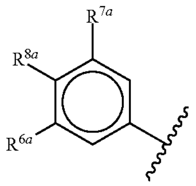

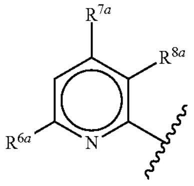

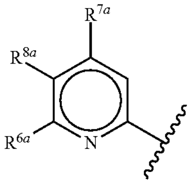

or

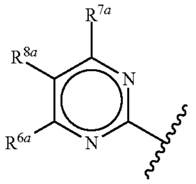

, wherein $R^{7a}$ and $R^{8a}$ are each independently chosen from a hydrogen atom and substituents, and other symbols are as defined above.

In some embodiments, $R^{7a}$ is chosen from:

(a) a hydrogen atom;

(b) halogen atoms (for example, a chlorine atom or a bromine atom);

(c) optionally substituted $C_{1-6}$ alkyl groups (for example, methyl, ethyl, or isopropyl);

(d) optionally substituted $C_{1-6}$ alkoxy groups (for example, methoxy or ethoxy);

(e) optionally substituted $C_{3-10}$ cycloalkyl groups (for example, cyclopropyl);

(f) optionally substituted $C_{2-6}$ alkenyl groups (for example, vinyl); and (g) optionally substituted 3- to 14-membered non-aromatic heterocyclic groups (for example, 3- to 8-membered monocyclic non-aromatic heterocyclic groups (for example, piperidyl)).

In some embodiments, $R^{7a}$ is:

(a) a hydrogen atom;

(b) halogen atoms (for example, a chlorine atom or a bromine atom);

(c) $C_{1-6}$ alkyl groups (for example, methyl, ethyl, isopropyl) optionally substituted with 1 to 3 substituents independently chosen from (i) halogen atoms (for example, fluorine atoms); and (ii) a hydroxy group;

(d) optionally halogenated $C_{1-6}$ alkoxy groups (for example, trifluoromethoxy, 2,2-difluoroethoxy, 2,2,2-trifluoroethoxy);

(e) $C_{3-10}$ cycloalkyl groups (for example, cyclopropyl) optionally substituted with 1 to 3 halogen atoms (for example, fluorine atoms);

(f) $C_{2-6}$ alkenyl groups (for example, vinyl); or (g) 3- to 14-membered non-aromatic heterocyclic groups (for example, 3- to 8-membered monocyclic non-aromatic heterocyclic groups (for example, piperidyl)) optionally substituted with 1 to 3 halogen atoms (for example, fluorine atoms).

In some embodiments, $R^{7a}$ is chosen from:

(a) a hydrogen atom;

(b) halogen atoms (for example, a chlorine atom or a bromine atom);

(c) $C_{1-6}$ alkyl groups (for example, methyl, ethyl, or isopropyl) optionally substituted with 1 to 3 substituents independently chosen from (i) halogen atoms (for example, fluorine atoms); and (ii) a hydroxy group;

(d) optionally halogenated $C_{1-6}$ alkoxy groups (for example, trifluoromethoxy, 2,2-difluoroethoxy, or 2,2,2-trifluoroethoxy);

(e) $C_{3-6}$ cycloalkyl groups (for example, cyclopropyl) optionally substituted with 1 to 3 halogen atoms (for example, fluorine atoms);

(f) $C_{2-6}$ alkenyl groups (for example, vinyl); and (g) piperidyl groups optionally substituted with 1 to 3 halogen atoms (for example, fluorine atoms).

In some embodiments, $R^{7a}$ is chosen from halogenated $C_{1-6}$ alkyl groups (for example, trifluoromethyl).

In some embodiments, $R^{7a}$ is a trifluoromethyl group.

In some embodiments, $R^{7a}$ is chosen from:

(a) a hydrogen atom;

(b) halogen atoms (for example, a fluorine atom or a chlorine atom); and (c) optionally substituted $C_{1-6}$ alkyl groups (for example, methyl).

In some embodiments, $R^{8a}$ is chosen from:

(a) a hydrogen atom;

(b) halogen atoms (for example, a fluorine atom or a chlorine atom); and (c) $C_{1-6}$ alkyl groups (for example, methyl).

In some embodiments, $R^{8a}$ is chosen from a hydrogen atom and halogen atoms (for example, a fluorine atom).

In some embodiments, $R^{7a}$ is a hydrogen atom or a fluorine atom.

In some embodiments, $R^{8a}$ is a hydrogen atom.

In some embodiments, the group represented by:

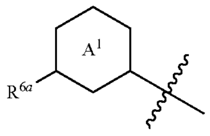

is a group represented by:

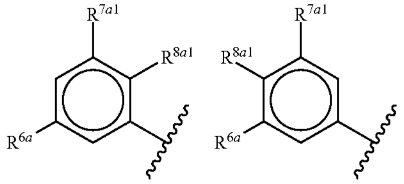

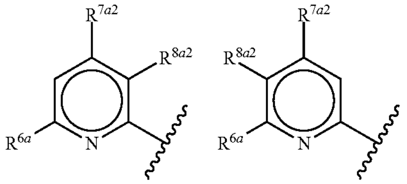

or

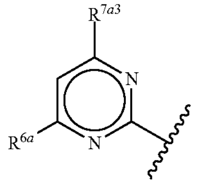

, wherein $R^{7a1}$, $R^{7a2}$, $R^{7a3}$, $R^{8a1}$, and $R^{8a2}$ are each independently chosen from a hydrogen atom and substituents, and other symbols are as defined above.

In some embodiments, $R^{7a1}$ is chosen from:

(a) halogen atoms (for example, a chlorine atom or a bromine atom);

(b) $C_{1-6}$ alkyl groups (for example, methyl, ethyl, or isopropyl) optionally substituted with 1 to 3 substituents independently chosen from (i) halogen atoms (for example, fluorine atoms); and (ii) a hydroxy group;

(c) optionally halogenated $C_{1-6}$ alkoxy groups (for example, trifluoromethoxy, 2,2-difluoroethoxy, or 2,2,2-trifluoroethoxy);

(d) $C_{3-10}$ cycloalkyl groups (for example, cyclopropyl) optionally substituted with 1 to 3 halogen atoms (for example, fluorine atoms);

(e) $C_{2-6}$ alkenyl groups (for example, vinyl); and (f) 3- to 14-membered non-aromatic heterocyclic groups (for example, 3- to 8-membered monocyclic non-aromatic heterocyclic groups (for example, piperidyl)) optionally substituted with 1 to 3 halogen atoms (for example, fluorine atoms).

In some embodiments, $R^{7a1}$ is chosen from:

(a) halogen atoms (for example, a chlorine atom or a bromine atom);

(b) $C_{1-6}$ alkyl groups (for example, methyl, ethyl, or isopropyl) optionally substituted with 1 to 3 substituents independently chosen from (i) halogen atoms (for example, fluorine atoms); and (ii) a hydroxy group;

(c) optionally halogenated $C_{1-6}$ alkoxy groups (for example, trifluoromethoxy, 2,2-difluoroethoxy, or 2,2,2-trifluoroethoxy);

(d) $C_3$ cycloalkyl groups (for example, cyclopropyl) optionally substituted with 1 to 3 halogen atoms (for example, fluorine atoms);

(e) $C_{2-6}$ alkenyl groups (for example, vinyl); and (f) piperidyl groups optionally substituted with 1 to 3 halogen atoms (for example, fluorine atoms).

In some embodiments, $R^{7a2}$ is chosen from:

(a) a hydrogen atom;

(b) optionally halogenated $C_{1-6}$ alkyl groups (for example, trifluoromethyl);

(c) optionally halogenated $C_{1-6}$ alkoxy groups (for example, 2,2,2-trifluoroethoxy); and (d) $C_{3-10}$ cycloalkyl groups (for example, cyclopropyl).

In some embodiments, $R^{7a2}$ is chosen from:

(a) a hydrogen atom;

(b) optionally halogenated $C_{1-6}$ alkyl groups (for example, trifluoromethyl);

(c) optionally halogenated $C_{1-6}$ alkoxy groups (for example, 2,2,2-trifluoroethoxy); and (d) $C_{3-6}$ cycloalkyl groups (for example, cyclopropyl).

In some embodiments, $R^{7a2}$ is a halogenated $C_{1-6}$ alkyl group (for example, trifluoromethyl).

In some embodiments, $R^{7a2}$ is a trifluoromethyl group.

In some embodiments, $R^{7a3}$ is an optionally halogenated $C_{1-6}$ alkyl group (for example, trifluoromethyl).

In some embodiments, $R^{8a1}$ is chosen from:

(a) a hydrogen atom;

(b) halogen atoms (for example, a fluorine atom or a chlorine atom); and (c) $C_{1-6}$ alkyl groups (for example, methyl).

In some embodiments, $R^{8a2}$ is chosen from:

(a) a hydrogen atom;

(b) halogen atoms (for example, a fluorine atom or a chlorine atom); and (c) $C_{1-6}$ alkyl groups (for example, methyl).

In some embodiments, $R^{8a2}$ is chosen from a hydrogen atom and halogen atoms (for example, a fluorine atom).

In some embodiments, $R^{8a2}$ is a hydrogen atom or a fluorine atom.

In some embodiments, $R^{8a2}$ is a hydrogen atom.

In some embodiments, the group represented by:

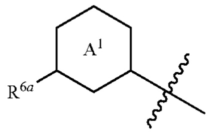

is a group represented by:

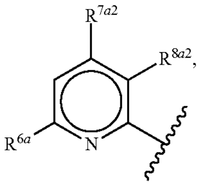

wherein the symbols in the formula are each as defined above.

In some embodiments, $R^{7a2}$ is chosen from halogenated $C_{1-6}$ alkyl groups (for example, trifluoromethyl).

In some embodiments, $R^{7a2}$ is a trifluoromethyl group.

In some embodiments, $R^{8a2}$ is chosen from a hydrogen atom and halogen atoms (for example, a fluorine atom).

In some embodiments, $R^{8a2}$ is a hydrogen atom or a fluorine atom.

In some embodiments, $R^{8a2}$ is a hydrogen atom.

In some embodiments, the "5-membered monocyclic aromatic heterocyclic group" of the "optionally further substituted 5-membered monocyclic aromatic heterocyclic group" represented by ring $A^2$ is pyrazole.

Non-limiting examples of optional substituents in the "optionally further substituted 5-membered monocyclic aromatic heterocyclic ring" represented by ring $A^2$ are substituents independently chosen from substituent group A. In some embodiments, the number of these optional substituents is an integer from 1 to 3. When the number of optional substituents is 2 or greater, the respective substituents may be the same or different from one another.

In some embodiments, ring $A^2$ is chosen from 5-membered monocyclic aromatic heterocyclic rings (for example, pyrazole) optionally further substituted with 1 to 3 optionally halogenated $C_{1-6}$ alkyl groups (for example, trifluoromethyl).

In some embodiments, ring $A^2$ is a pyrazole ring optionally further substituted with 1 to 3 optionally halogenated $C_{1-6}$ alkyl groups (for example, trifluoromethyl).

In some embodiments, ring $A^2$ is a pyrazole ring further substituted with one halogenated $C_{1-6}$ alkyl group (for example, trifluoromethyl).

In some embodiments, ring $A^2$ is a pyrazole ring further substituted with one trifluoromethyl group.

In some embodiments, ring $A^2$ is an optionally further substituted pyrazole group. In some embodiments, ring $A^2$ is a further substituted pyrazole ring.

In some embodiments, $R^{6b}$ is an optionally substituted $C_{1-6}$ alkyl group (for example, ethyl).

Non-limiting examples of optional substituents in the "optionally substituted $C_{1-6}$ alkyl group" described above are substituents independently chosen from substituent group A. In some embodiments, the number of these optional substituents is an integer from 1 to 3. When the number of optional substituents is 2 or greater, the respective substituents may be the same or different from one another.

In some embodiments, $R^{6b}$ is a $C_{1-6}$ alkyl group (for example, ethyl) optionally substituted with 1 to 3 $C_{3-10}$ cycloalkyl groups (for example, cyclobutyl).

In some embodiments, $R^{6b}$ is a $C_{1-6}$ alkyl group (for example, ethyl) optionally substituted with 1 to 3 $C_{3-6}$ cycloalkyl groups (for example, cyclobutyl).

In some embodiments, the group represented by:

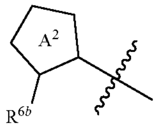

is a group represented by:

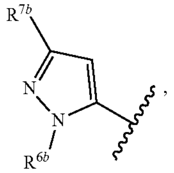

wherein $R^{7b}$ is chosen from a hydrogen atom and substituents, and all other symbols are as defined above.

In some embodiments, $R^{7b}$ is an optionally substituted $C_{1-6}$ alkyl group (for example, methyl).

In some embodiments, $R^{7b}$ is an optionally halogenated $C_{1-6}$ alkyl group (for example, trifluoromethyl).

In some embodiments, $R^{7b}$ is a halogenated $C_{1-6}$ alkyl group (for example, trifluoromethyl).

In some embodiments, $R^{7b}$ is a trifluoromethyl group.

In some embodiments, Z is C—$R^2$ or N. In some embodiments, $R^2$ is chosen from a hydrogen atom, halogen atoms, and optionally halogenated $C_{1-6}$ alkyl groups.

In some embodiments, Z is C—$R^2$. In some embodiments, $R^2$ is chosen from a hydrogen atom and optionally halogenated $C_{1-6}$ alkyl groups (for example, methyl or ethyl).

In some embodiments, $R^2$ is chosen from a hydrogen atom and $C_{1-6}$ alkyl groups (for example, methyl or ethyl).

In some embodiments, $R^2$ is chosen from a hydrogen atom and $C_{1-3}$ alkyl groups (for example, methyl).

In some embodiments, $R^2$ is chosen from $C_{1-3}$ alkyl groups (for example, methyl).

In some embodiments, Z is N or C—$R^2$, wherein $R^2$ is chosen from a hydrogen atom and optionally halogenated $C_{1-6}$ alkyl groups (for example, methyl or ethyl).

In some embodiments, Z is N or C—$R^2$, wherein $R^2$ is chosen from a hydrogen atom and $C_{1-6}$ alkyl groups (for example, methyl or ethyl).

In some embodiments, Z is C—$R^2$, wherein $R^2$ is chosen from a hydrogen atom and $C_{1-3}$ alkyl groups (for example, methyl).

In some embodiments, Z is C—$R^2$, wherein $R^2$ is chosen from $C_{1-3}$ alkyl groups (for example, methyl).

In some embodiments, $R^3$ is chosen from a hydrogen atom, halogen atoms (for example, a chlorine atom), and optionally halogenated $C_{1-6}$ alkyl groups (for example, methyl, ethyl, or trifluoromethyl).

In some embodiments, $R^3$ is chosen from a hydrogen atom and $C_{1-6}$ alkyl groups (for example, methyl).

In some embodiments, $R^3$ is chosen from a hydrogen atom and $C_{1-3}$ alkyl groups (for example, methyl).

In some embodiments, $R^3$ is a $C_{1-3}$ alkyl group (for example, methyl).

In some embodiments, $R^4$ and Rare each independently chosen from a hydrogen atom and substituents.

In some embodiments, $R^4$ and Rare each independently chosen from a hydrogen atom and optionally substituted $C_{1-6}$ alkyl groups (for example, methyl).

Non-limiting examples of optional substituents in the "optionally substituted $C_{1-6}$ alkyl group" described above are substituents independently chosen from substituent group A. In some embodiments, the number of these optional substituents is an integer from 1 to 3. When the number of optional substituents is 2 or greater, the respective substituents may be the same or different from one another.

In some embodiments, $R^4$ and Rare each independently chosen from a hydrogen atom and $C_{1-6}$ alkyl groups (for example, methyl).

In some embodiments, $R^4$ is chosen from a hydrogen atom and $C_{1-6}$ alkyl groups (for example, methyl).

In some embodiments, $R^5$ is a hydrogen atom.

In some embodiments, $R^4$ and $R^5$ are both hydrogen atoms.

In some embodiments, ring B is an optionally further substituted 5-membered monocyclic aromatic heterocyclic ring.

In some embodiments, the "5-membered monocyclic aromatic heterocyclic group" of the "optionally further substituted 5-membered monocyclic aromatic heterocyclic group" represented by ring B is a pyrazole ring (for example, 1H-pyrazole-4-yl).

Non-limiting examples of optional substituents in the "optionally further substituted 5-membered monocyclic aromatic heterocyclic ring" represented by ring B are substituents independently chosen from substituent group A. In some embodiments, the number of these optional substituents is an integer from 1 to 3. When the number of optional substituents is 2 or greater, the respective substituents may be the same or different from one another.

In some embodiments, ring B is a 5-membered monocyclic aromatic heterocyclic ring (for example, pyrazole) optionally further substituted with 1 to 3 $C_{1-6}$ alkyl groups (for example, methyl, ethyl, or isopropyl).

In some embodiments, ring B is a pyrazole ring (for example, 1H-pyrazole-4-yl) optionally further substituted with 1 to 3 $C_{1-6}$ alkyl groups (for example, methyl, ethyl, or isopropyl).

In some embodiments, ring B is a pyrazole ring (for example, 1H-pyrazole-4-yl) further substituted with one $C_{1-6}$ alkyl group (for example, ethyl).

In some embodiments, ring B is an optionally further substituted pyrazole group.

In some embodiments, ring B is a further substituted pyrazole ring.

In some embodiments, ring B is a cyclic group represented by:

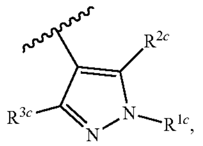

wherein:

$R^{1c}$ is chosen from a hydrogen atom and $C_{1-6}$ alkyl groups (for example, ethyl or isopropyl); and $R^{2c}$ and $R^{3c}$ are each independently chosen from a hydrogen atom and $C_{1-6}$ alkyl groups (for example, methyl).

In some embodiments, $R^{1c}$ is a $C_{1-6}$ alkyl group (for example, ethyl or isopropyl, for example, ethyl).

In some embodiments, $R^{2c}$ is chosen from a hydrogen atom and $C_{1-6}$ alkyl groups (for example, methyl), and $R^{3c}$ is a hydrogen atom. In some embodiments, $R^{2c}$ and $R^{3c}$ are both hydrogen atoms.

In some embodiments, ring B is a cyclic group represented by:

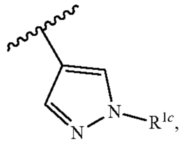

wherein $R^{1c}$ is chosen from $C_{1-6}$ alkyl groups (for example, ethyl)).

The compound represented by Formula (I) does not include 1-(3-chlorophenyl)-3-[(5-phenyl-1,3,4-oxadiazole-2-yl)methyl]1,3-dihydro-2H-imidazole-2-one.

Non-limiting examples of Compound (I) include the following subformulae.

Also disclosed herein is a compound (also referred to herein as Compound A) chosen from compounds of Formula (I) and pharmaceutically acceptable salts thereof, wherein:

$R^1$ is a group represented by:

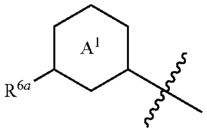

or

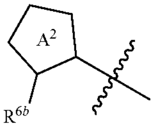

;

ring $A^1$ is chosen from optionally further substituted 6-membered aromatic rings (for example, benzene, pyridine, or pyrimidine);

$R^{6a}$ is chosen from:

(1) optionally substituted $C_{3-10}$ cycloalkyl groups (for example, cyclohexyl);

(2) optionally substituted $C_{6-14}$ aryl groups (for example, phenyl);

(3) optionally substituted 3- to 14-membered non-aromatic heterocyclic groups (for example, 3- to 8-membered monocyclic non-aromatic heterocyclic groups (for example, morpholinyl, piperidyl, or pyrrolidinyl) or 6- to 9-membered non-aromatic spiro heterocyclic groups (for example, 4-oxa-7-azaspiro[2.5]octyl));

(4) optionally substituted 5- to 14-membered aromatic heterocyclic groups (for example, 5- or 6-membered monocyclic aromatic heterocyclic groups (for example, imidazolyl));

(5) optionally substituted mono- or di-$C_{1-6}$ alkylamino groups (for example, methylamino);

(6) optionally substituted N—$C_{1-6}$ alkyl-N-3- to 14-membered non-aromatic heterocyclic amino groups (for example, N—$C_{1-6}$ alkyl-N-3- to 8-membered monocyclic aromatic heterocyclic amino groups (for example, N-methyl-N-tetrahydropyranylamino));

(7) optionally substituted $C_{1-6}$ alkoxy groups (for example, methoxy);

(8) optionally substituted $C_{6-14}$ aryloxy groups (for example, phenoxy); and (9) optionally substituted 3- to 14-membered non-aromatic heterocyclic oxy groups (for example, 3- to 8-membered monocyclic non-aromatic heterocyclic oxy groups (for example, tetrahydropyranyloxy));

ring $A^2$ is chosen from optionally further substituted 5-membered monocyclic aromatic heterocyclic rings (for example, pyrazole);

$R^{6b}$ is chosen from optionally substituted $C_{1-6}$ alkyl groups (for example, ethyl);

Z is C—$R^2$ or N;

$R^2$ is chosen from a hydrogen atom and optionally halogenated $C_{1-6}$ alkyl groups (for example, methyl or ethyl);

$R^3$ is chosen from a hydrogen atom, halogen atoms (for example, a chlorine atom), and optionally halogenated $C_{1-6}$ alkyl groups (for example, methyl, ethyl, or trifluoromethyl);

$R^4$ and $R^5$ are each independently chosen from a hydrogen atom and optionally substituted $C_{1-6}$ alkyl groups (for example, methyl); and ring B is chosen from optionally further substituted 5-membered monocyclic aromatic heterocyclic rings (for example, pyrazole).

Also disclosed herein is a compound (also referred to herein as Compound B) chosen from compounds of Formula (I) and pharmaceutically acceptable salts thereof, wherein:

$R^1$ is a group represented by:

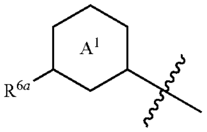

or

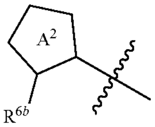

;

ring $A^1$ is chosen from 6-membered aromatic rings (for example, benzene, pyridine, or pyrimidine) optionally further substituted with 1 to 3 substituents independently chosen from:

(a) halogen atoms (for example, fluorine atoms, chlorine atoms, or bromine atoms);

(b) $C_{1-6}$ alkyl groups (for example, methyl, ethyl, or isopropyl) optionally substituted with 1 to 3 substituents independently chosen from (i) halogen atoms (for example, fluorine atoms); and (ii) a hydroxy group;

(c) optionally halogenated $C_{1-6}$ alkoxy groups (for example, trifluoromethoxy, 2,2-difluoroethoxy, or 2,2,2-trifluoroethoxy);

(d) $C_{3-10}$ cycloalkyl groups (for example, cyclopropyl) optionally substituted with 1 to 3 halogen atoms (for example, fluorine atoms);

(e) $C_{2-6}$ alkenyl groups (for example, vinyl); and (f) 3- to 14-membered non-aromatic heterocyclic groups (for example, 3- to 8-membered monocyclic non-aromatic heterocyclic groups (for example, piperidyl)) optionally substituted with 1 to 3 halogen atoms (for example, fluorine atoms);

$R^{6a}$ is chosen from:

(1) $C_{3-10}$ cycloalkyl groups (for example, cyclohexyl) optionally substituted with 1 to 3 halogen atoms (for example, fluorine atoms);

(2) CF-14 aryl groups (for example, phenyl) optionally substituted with 1 to 3 halogen atoms (for example, fluorine atoms);

(3) 3- to 14-membered non-aromatic heterocyclic groups (for example, 3- to 8-membered monocyclic non-aromatic heterocyclic groups (for example, morpholinyl, piperidyl, or pyrrolidinyl) or 6- to 9-membered non-aromatic spiro heterocyclic groups (for example, 4-oxa-7-azaspiro[2.5]octyl)) optionally substituted with 1 to 3 substituents independently chosen from:

(a) halogen atoms (for example, fluorine atoms); and (b) optionally halogenated $C_{1-6}$ alkyl groups (for example, methyl or difluoromethyl);

(4) 5- to 14-membered aromatic heterocyclic groups (for example, 5- or 6-membered monocyclic aromatic heterocyclic groups (for example, imidazolyl)) optionally substituted with 1 to 3 $C_{1-6}$ alkyl groups (for example, methyl);

(5) mono- or di-$C_{1-6}$ alkylamino groups (for example, methylamino) optionally substituted with 1 to 3 $C_{3-10}$ cycloalkyl groups (for example, cyclobutyl) optionally substituted with 1 to 3 halogen atoms (for example, fluorine atoms);

(6) N—$C_{1-6}$ alkyl-N-3- to 14-membered non-aromatic heterocyclic amino groups (for example, N—$C_{1-6}$ alkyl-N-3- to 8-membered monocyclic aromatic heterocyclic amino groups (for example, N-methyl-N-tetrahydropyranylamino));

(7) $C_{1-6}$ alkoxy groups (for example, methoxy) optionally substituted with 1 to 3 substituents independently chosen from:

(a) $C_{1-6}$ alkoxy groups (for example, methoxy);

(b) $C_{3-10}$ cycloalkyl groups (for example, cyclopropyl or cyclobutyl); and (c) 3- to 14-membered non-aromatic heterocyclic groups (for example, 3- to 8-membered monocyclic non-aromatic heterocyclic groups (for example, oxetanyl or tetrahydrofuryl));

(8) $C_{6-14}$ aryloxy groups (for example, phenoxy) optionally substituted with 1 to 3 halogen atoms (for example, fluorine atoms); and (9) 3- to 14-membered non-aromatic heterocyclic oxy groups (for example, a 3- to 8-membered monocyclic non-aromatic heterocyclic oxy groups (for example, tetrahydropyranyloxy)).

In some embodiments, the group represented by:

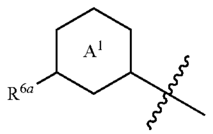

is a group represented by:

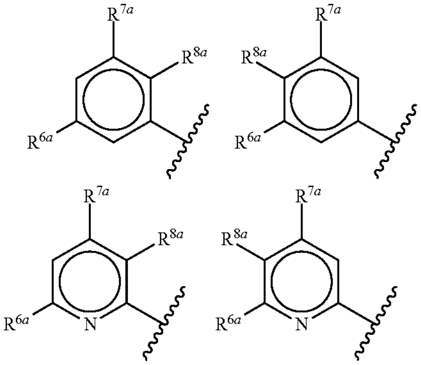

or

-continued

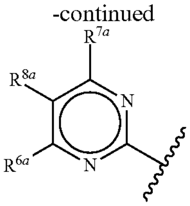

, wherein:

$R^{6a}$ is as defined above;

$R^{7a}$ is chosen from:

(a) a hydrogen atom;

(b) halogen atoms (for example, a chlorine atom or a bromine atom);

(c) $C_{1-6}$ alkyl groups (for example, methyl, ethyl, or isopropyl) optionally substituted with 1 to 3 substituents independently chosen from (i) halogen atoms (for example, fluorine atoms); and (ii) a hydroxy group;

(d) optionally halogenated $C_{1-6}$ alkoxy groups (for example, trifluoromethoxy, 2,2-difluoroethoxy, or 2,2,2-trifluoroethoxy);

(e) $C_{3-10}$ cycloalkyl groups (for example, cyclopropyl) optionally substituted with 1 to 3 halogen atoms (for example, fluorine atoms);

(f) $C_{2-6}$ alkenyl groups (for example, vinyl); and (g) 3- to 14-membered non-aromatic heterocyclic groups (for example, 3- to 8-membered monocyclic non-aromatic heterocyclic groups (for example, piperidyl)) optionally substituted with 1 to 3 halogen atoms (for example, fluorine atoms); and $R^{8a}$ is chosen from:

(a) a hydrogen atom;

(b) halogen atoms (for example, a fluorine atom or a chlorine atom); and (c) $C_{1-6}$ alkyl groups (for example, methyl), ring $A^2$ is chosen from 5-membered monocyclic aromatic heterocyclic rings (for example, pyrazole) optionally further substituted with 1 to 3 optionally halogenated $C_{1-6}$ alkyl groups (for example, trifluoromethyl); and $R^{6b}$ is chosen from $C_{1-6}$ alkyl groups (for example, ethyl) optionally substituted with 1 to 3 $C_{3-10}$ cycloalkyl groups (for example, cyclobutyl).

In some embodiments, the group represented by:

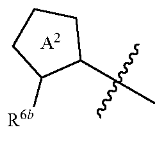

is a group represented by:

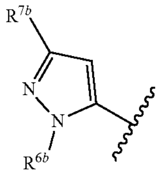

, wherein:

$R^{6b}$ is as defined above; and $R^{7b}$ is chosen from optionally halogenated $C_{1-6}$ alkyl groups (for example, trifluoromethyl), Z is C—$R^2$ or N;

$R^2$ is chosen from a hydrogen atom and $C_{1-6}$ alkyl groups (for example, methyl or ethyl);

$R^3$ is chosen from a hydrogen atom, halogen atoms (for example, a chlorine atom), and optionally halogenated $C_{1-6}$ alkyl groups (for example, methyl, ethyl, or trifluoromethyl);

$R^4$ and $R^5$ are each independently chosen from a hydrogen atom and $C_{1-6}$ alkyl groups (for example, methyl); and ring B is chosen from 5-membered monocyclic aromatic heterocyclic rings (for example, pyrazole) optionally further substituted with 1 to 3 $C_{1-6}$ alkyl groups (for example, methyl, ethyl, or isopropyl).

Also disclosed herein is a compound (also referred to herein as Compound C) chosen from compounds of Formula (I) and pharmaceutically acceptable salts thereof, wherein:

$R^1$ is a group represented by:

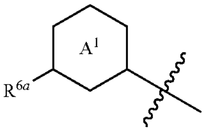
or
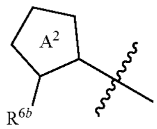
;

ring $A^1$ is chosen from:

(1) benzene rings optionally further substituted with 1 to 3 substituents independently chosen from:

(a) halogen atoms (for example, fluorine atoms, chlorine atoms, or bromine atoms);

(b) $C_{1-6}$ alkyl groups (for example, methyl, ethyl, or isopropyl) optionally substituted with 1 to 3 substituents independently chosen from (i) halogen atoms (for example, fluorine atoms); and (ii) a hydroxy group;

(c) optionally halogenated $C_{1-6}$ alkoxy groups (for example, trifluoromethoxy, 2,2-difluoroethoxy, or 2,2,2-trifluoroethoxy);

(d) $C_{3-10}$ cycloalkyl groups (for example, cyclopropyl) optionally substituted with 1 to 3 halogen atoms (for example, fluorine atoms);

(e) $C_{2-6}$ alkenyl groups (for example, vinyl); and (f) 3- to 14-membered non-aromatic heterocyclic groups (for example, 3- to 8-membered monocyclic non-aromatic heterocyclic groups (for example, piperidyl)) optionally substituted with 1 to 3 halogen atoms (for example, fluorine atoms);

(2) pyridine rings optionally further substituted with 1 to 3 substituents independently chosen from:

(a) halogen atoms (for example, fluorine atoms or chlorine atoms);

(b) optionally halogenated $C_{1-6}$ alkyl groups (for example, methyl, difluoromethyl, or trifluoromethyl);

(c) optionally halogenated $C_{1-6}$ alkoxy groups (for example, 2,2,2-trifluoroethoxy); and (d) $C_{3-10}$ cycloalkyl groups (for example, cyclopropyl); and (3) pyrimidine rings optionally further substituted with 1 or 2 optionally halogenated $C_{1-6}$ alkyl groups (for example, trifluoromethyl);

$R^{6a}$ is chosen from:

(1) $C_{3-10}$ cycloalkyl groups (for example, cyclohexyl) optionally substituted with 1 to 3 halogen atoms (for example, fluorine atoms);

(2) $C_{6-14}$ aryl groups (for example, phenyl) optionally substituted with 1 to 3 halogen atoms (for example, fluorine atoms);

(3) 3- to 14-membered non-aromatic heterocyclic groups (for example, 3- to 8-membered monocyclic non-aromatic heterocyclic groups (for example, morpholinyl, piperidyl, or pyrrolidinyl) or 6- to 9-membered non-aromatic spiro heterocyclic groups (for example, 4-oxa-7-azaspiro[2.5]octyl)) optionally substituted with 1 to 3 substituents independently chosen from:

(a) halogen atoms (for example, fluorine atoms); and (b) optionally halogenated $C_{1-6}$ alkyl groups (for example, methyl or difluoromethyl);

(4) 5- to 14-membered aromatic heterocyclic groups (for example, 5- or 6-membered monocyclic aromatic heterocyclic groups (for example, imidazolyl)) optionally substituted with 1 to 3 $C_{1-6}$ alkyl groups (for example, methyl);

(5) mono- or di-$C_{1-6}$ alkylamino groups (for example, methylamino) optionally substituted with 1 to 3 $C_{3-10}$ cycloalkyl groups (for example, cyclobutyl) optionally substituted with 1 to 3 halogen atoms (for example, fluorine atoms);

(6) N—$C_{1-6}$ alkyl-N-3- to 14-membered non-aromatic heterocyclic amino groups (for example, N—$C_{1-6}$ alkyl-N-3- to 8-membered monocyclic aromatic heterocyclic amino groups (for example, N-methyl-N-tetrahydropyranylamino));

(7) $C_{1-6}$ alkoxy groups (for example, methoxy) optionally substituted with 1 to 3 substituents independently chosen from:

(a) $C_{1-6}$ alkoxy groups (for example, methoxy); and (b) $C_{3-10}$ cycloalkyl groups (for example, cyclopropyl or cyclobutyl) optionally substituted with 1 to 3 halogen atoms (for example, fluorine atoms); and (c) 3- to 14-membered non-aromatic heterocyclic groups (for example, 3- to 8-membered monocyclic non-aromatic heterocyclic groups (for example, oxetanyl or tetrahydrofuryl));

(8) $C_{6-14}$ aryloxy groups (for example, phenoxy) optionally substituted with 1 to 3 halogen atoms (for example, fluorine atoms); and (9) 3- to 14-membered non-aromatic heterocyclic oxy groups (for example, 3- to 8-membered monocyclic non-aromatic heterocyclic oxy groups (for example, tetrahydropyranyloxy)).

In some embodiments, the group represented by:

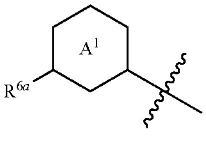

is a group represented by:

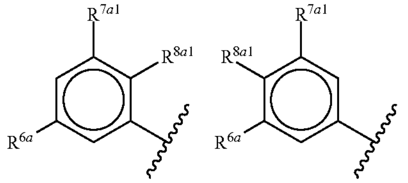

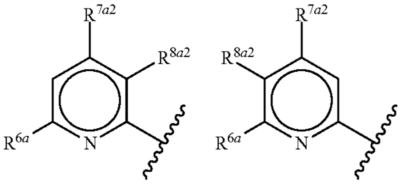

or

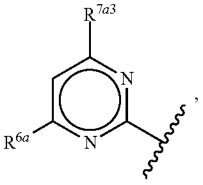

wherein:

$R^{6a}$ is as defined above;

$R^{7a1}$ is chosen from:

(a) halogen atoms (for example, a chlorine atom or a bromine atom);

(b) $C_{1-6}$ alkyl groups (for example, methyl, ethyl, or isopropyl) optionally substituted with 1 to 3 substituents independently chosen from (i) halogen atoms (for example, fluorine atoms); and (ii) a hydroxy group;

(c) optionally halogenated $C_{1-6}$ alkoxy groups (for example, trifluoromethoxy, 2,2-difluoroethoxy, or 2,2,2-trifluoroethoxy);

(d) $C_{3-10}$ cycloalkyl groups (for example, cyclopropyl) optionally substituted with 1 to 3 halogen atoms (for example, fluorine atoms);

(e) $C_{2-6}$ alkenyl groups (for example, vinyl); and (f) 3- to 14-membered non-aromatic heterocyclic groups (for example, 3- to 8-membered monocyclic non-aromatic heterocyclic groups (for example, piperidyl)) optionally substituted with 1 to 3 halogen atoms (for example, fluorine atoms);

$R^{7a2}$ is chosen from:

(a) a hydrogen atom;

(b) optionally halogenated $C_{1-6}$ alkyl groups (for example, trifluoromethyl);

(c) optionally halogenated $C_{1-6}$ alkoxy groups (for example, 2,2,2-trifluoroethoxy); and (d) $C_{3-10}$ cycloalkyl groups (for example, cyclopropyl);

$R^{7a3}$ is chosen from optionally halogenated $C_{1-6}$ alkyl groups (for example, trifluoromethyl);

$R^{8a1}$ is chosen from:

(a) a hydrogen atom;

(b) halogen atoms (for example, a fluorine atom or a chlorine atom); and (c) $C_{1-6}$ alkyl groups (for example, methyl); and $R^{8a2}$ is chosen from:

(a) a hydrogen atom;

(b) halogen atoms (for example, a fluorine atom or a chlorine atom); and (c) $C_{1-6}$ alkyl groups (for example, methyl);

ring $A^2$ is chosen from pyrazole rings optionally further substituted with 1 to 3 optionally halogenated $C_{1-6}$ alkyl groups (for example, trifluoromethyl); and $R^{6b}$ is chosen from $C_{1-6}$ alkyl groups (for example, ethyl) optionally substituted with 1 to 3 $C_{3-10}$ cycloalkyl groups (for example, cyclobutyl).

In some embodiments, the group represented by:

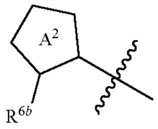

is a group represented by:

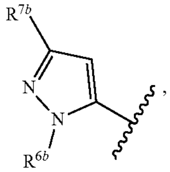

wherein the respective symbols are as in Compound B; and ring B is chosen from pyrazole rings (for example, 1H-pyrazole-4-yl) optionally further substituted with 1 to 3 $C_{1-6}$ alkyl groups (for example, methyl, ethyl, or isopropyl).

In some embodiments, ring B is:

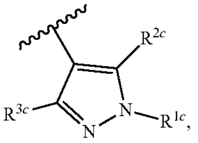

wherein:

$R^{1c}$ is chosen from a hydrogen atom and $C_{1-6}$ alkyl groups (for example, ethyl or isopropyl); and $R^{2c}$ and $R^{3c}$ are each independently chosen from a hydrogen atom and $C_{1-6}$ alkyl groups (for example, methyl).

Also disclosed herein is a compound (also referred to herein as Compound D) chosen from compounds of Formula (I) and pharmaceutically acceptable salts thereof, wherein:

$R^1$ is a group represented by:

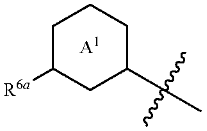

or

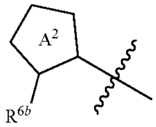

;

ring $A^1$ is chosen from:

(1) benzene rings optionally further substituted with 1 to 3 substituents independently chosen from:

(a) halogen atoms (for example, a fluorine atom, a chlorine atom, or a bromine atom);

(b) $C_{1-6}$ alkyl groups (for example, methyl, ethyl, or isopropyl) optionally substituted with 1 to 3 substituents independently chosen from (i) halogen atoms (for example, fluorine atoms); and (ii) a hydroxy group;

(c) optionally halogenated $C_{1-6}$ alkoxy groups (for example, trifluoromethoxy, 2,2-difluoroethoxy, or 2,2,2-trifluoroethoxy);

(d) $C_{3-6}$ cycloalkyl groups (for example, cyclopropyl) optionally substituted with 1 to 3 halogen atoms (for example, fluorine atoms);

(e) $C_{2-6}$ alkenyl groups (for example, vinyl); and (f) piperidyl groups optionally substituted with 1 to 3 halogen atoms (for example, fluorine atoms);

(2) pyridine rings optionally further substituted with 1 to 3 substituents independently chosen from:

(a) halogen atoms (for example, a fluorine atom or a chlorine atom);

(b) optionally halogenated $C_{1-6}$ alkyl groups (for example, methyl, difluoromethyl, or trifluoromethyl);

(c) optionally halogenated $C_{1-6}$ alkoxy groups (for example, 2,2,2-trifluoroethoxy); and (d) $C_6$ cycloalkyl groups (for example, cyclopropyl); and (3) pyrimidine rings optionally further substituted with 1 or 2 optionally halogenated $C_{1-6}$ alkyl groups (for example, trifluoromethyl);

$R^6$, is chosen from:

(1) $C_{3-6}$ cycloalkyl groups (for example, cyclohexyl) optionally substituted with 1 to 3 halogen atoms (for example, fluorine atoms);

(2) phenyl groups optionally substituted with 1 to 3 halogen atoms (for example, fluorine atoms);

(3) morpholinyl groups optionally substituted with 1 to 3 substituents independently chosen from:

(a) halogen atoms (for example, fluorine atoms); and (b) optionally halogenated $C_{1-6}$ alkyl groups (for example, methyl or difluoromethyl);

(4) piperidyl groups optionally substituted with 1 to 3 halogen atoms (for example, fluorine atoms);

(5) pyrrolidinyl groups optionally substituted with 1 to 3 halogen atoms (for example, fluorine atoms);

(6) a 4-oxa-7-azaspiro[2.5]octyl group;

(7) imidazolyl groups optionally substituted with 1 to 3 $C_{1-6}$ alkyl groups (for example, methyl);

(8) mono- or di-$C_{1-6}$ alkylamino groups (for example, methylamino) optionally substituted with 1 to 3 $C_{3-6}$ cycloalkyl groups (for example, cyclobutyl) optionally substituted with 1 to 3 halogen atoms (for example, fluorine atoms);

(9) N—$C_{1-6}$ alkyl-N-tetrahydropyranylamino groups (for example, N-methyl-N-tetrahydropyranylamino);

(10) $C_{1-6}$ alkoxy groups (for example, methoxy) optionally substituted with 1 to 3 substituents independently chosen from:

(a) $C_{1-6}$ alkoxy groups (for example, methoxy);

(b) $C_{3-6}$ cycloalkyl groups (for example, cyclopropyl or cyclobutyl) optionally substituted with 1 to 3 halogen atoms (for example, fluorine atoms);

(c) an oxetanyl group; and (d) a tetrahydrofuryl group;

(11) phenoxy groups optionally substituted with 1 to 3 halogen atoms (for example, fluorine atoms); and

(12) a tetrahydropyranyloxy group.

In some embodiments, the group represented by:

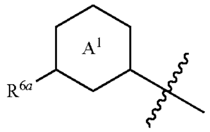

is a group represented by:

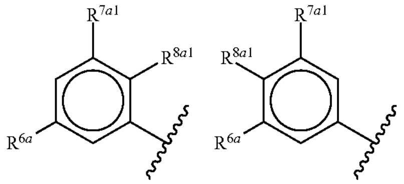

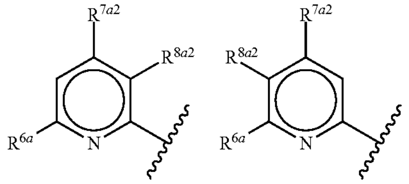

or

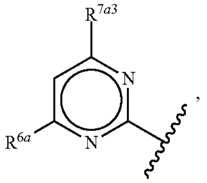

, wherein:

$R^{6a}$ is as defined above;

$R^{7a1}$ is chosen from:

(a) halogen atoms (for example, a chlorine atom or a bromine atom);

(b) $C_{1-6}$ alkyl groups (for example, methyl, ethyl, or isopropyl) optionally substituted with 1 to 3 substituents independently chosen from (i) halogen atoms (for example, fluorine atoms); and (ii) a hydroxy group;

(c) optionally halogenated $C_{1-6}$ alkoxy groups (for example, trifluoromethoxy, 2,2-difluoroethoxy, or 2,2,2-trifluoroethoxy);

(d) $C_{3-6}$ cycloalkyl groups (for example, cyclopropyl) optionally substituted with 1 to 3 halogen atoms (for example, fluorine atoms);

(e) $C_{2-6}$ alkenyl groups (for example, vinyl); and (f) piperidyl groups optionally substituted with 1 to 3 halogen atoms (for example, fluorine atoms);

$R^{7a2}$ is chosen from:

(a) a hydrogen atom;

(b) optionally halogenated $C_{1-6}$ alkyl groups (for example, trifluoromethyl);

(c) optionally halogenated $C_{1-6}$ alkoxy groups (for example, 2,2,2-trifluoroethoxy); and (d) $C_{3-6}$ cycloalkyl groups (for example, cyclopropyl);

$R^{7a3}$ is chosen from optionally halogenated $C_{1-6}$ alkyl groups (for example, trifluoromethyl);

$R^{8a1}$ is chosen from:

(a) a hydrogen atom;

(b) halogen atoms (for example, a fluorine atom or a chlorine atom); and (c) $C_{1-6}$ alkyl groups (for example, methyl); and $R^{8a2}$ is chosen from:

(a) a hydrogen atom;

(b) halogen atoms (for example, a fluorine atom or a chlorine atom); and (c) $C_{1-6}$ alkyl groups (for example, methyl).

In some embodiments, ring $A^1$ is chosen from pyrazole rings optionally further substituted with 1 to 3 optionally halogenated $C_{1-6}$ alkyl groups (for example, trifluoromethyl); and $R^{6b}$ is chosen from $C_{1-6}$ alkyl groups (for example, ethyl) optionally substituted with 1 to 3 $C_{3-6}$ cycloalkyl groups (for example, cyclobutyl).

In some embodiments, a group represented by:

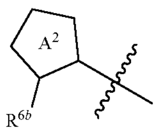

is a group represented by:

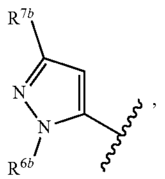

wherein:

$R^{6b}$ is as defined above; and other symbols are as in Compound B;

$R^4$ is chosen from a hydrogen atom and $C_{1-6}$ alkyl groups (for example, methyl);

$R^5$ is a hydrogen atom; and ring B is chosen from pyrazole rings (for example, 1H-pyrazole-4-yl) optionally further substituted with 1 to 3 $C_{1-6}$ alkyl groups (for example, methyl, ethyl, or isopropyl).

In some embodiments, ring B is a group represented by:

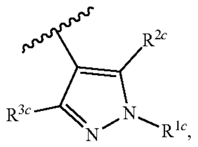

wherein the symbols are as in Compound B.

Also disclosed herein is a compound (also referred to herein as Compound E) chosen from compounds of Formula (I) and pharmaceutically acceptable salts thereof, wherein:

$R^1$ is a group represented by:

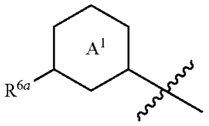
;

ring $A^1$ is chosen from pyridine rings optionally further substituted with 1 or 2 substituents independently chosen from:

(a) halogen atoms (for example, fluorine atoms); and (b) halogenated $C_{1-6}$ alkyl groups (for example, trifluoromethyl);

$R^{6a}$ is chosen from morpholinyl groups optionally substituted with 1 to 3 $C_{1-6}$ alkyl groups (for example, methyl).

In some embodiments, the group represented by:

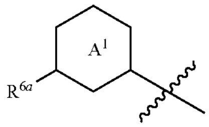

is a group represented by:

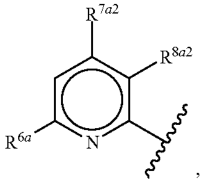
, wherein:

$R^{6a}$ is as defined above;

$R^{7a}$ is chosen from halogenated $C_{1-6}$ alkyl groups (for example, trifluoromethyl); and $R^{8a}$ is chosen from a hydrogen atom and halogen atoms (for example, a fluorine atom);

Z is C—$R^2$;

$R^2$ is chosen from a hydrogen atom and $C_{1-3}$ alkyl groups (for example, methyl);

$R^3$ is chosen from a hydrogen atom and $C_{1-3}$ alkyl groups (for example, methyl);

$R^4$ and $R^5$ are both hydrogen atoms; and ring B is chosen from pyrazole rings (for example, 1H-pyrazole-4-yl) further substituted with one $C_{1-6}$ alkyl group (for example, ethyl).

In some embodiments, ring B is a group represented by:

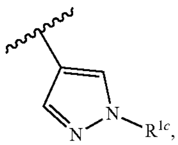

wherein $R^{1c}$ is chosen from $C_{1-6}$ alkyl groups (for example, ethyl).

Also disclosed herein is a compound (also referred to herein as Compound F) chosen from compounds of Formula (I) and pharmaceutically acceptable salts thereof, wherein:

$R^1$ is a group represented by:

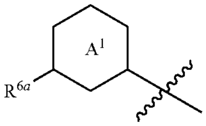
, wherein:

ring $A^1$ is chosen from pyridine rings further substituted with one halogenated $C_{1-6}$ alkyl group (for example, trifluoromethyl); and $R^{6a}$ is chosen from morpholinyl groups substituted with one $C_{1-6}$ alkyl group (for example, methyl).

In some embodiments, the group represented by:

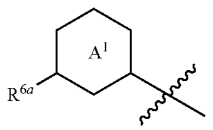

is a group represented by:

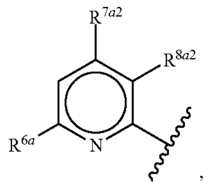

wherein:

$R^{6a}$ is as defined above;

$R^{7a2}$ is chosen from halogenated $C_{1-6}$ alkyl groups (for example, trifluoromethyl); and $R^{8a2}$ is a hydrogen atom;

Z is C—$R^2$;

$R^2$ is chosen from $C_{1-3}$ alkyl groups (for example, methyl);

$R^3$ is chosen from $C_{1-3}$ alkyl groups (for example, methyl);

$R^4$ and $R^5$ are both hydrogen atoms; and ring B is chosen from pyrazole rings (for example, 1H-pyrazole-4-yl) further substituted with one $C_{1-6}$ alkyl group (for example, ethyl).

In some embodiments, ring B is a group represented by:

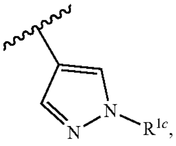

wherein $R^{1c}$ is chosen from $C_{1-6}$ alkyl groups (for example, ethyl).

Compounds of Formula (I) include, but are not limited to, the compounds of Examples 1 to 167 and pharmaceutically acceptable salts thereof (e.g., compounds of Examples 1 to 167).

When Compound (I) is a salt, such as a pharmaceutically acceptable salt, non-limiting examples of such a salt include metal salts, ammonium salts, salts with organic bases, salts with inorganic acids, salts with organic acids, and salts with basic or acidic amino acids. Non-limiting examples of metal salts include alkali metal salts such as sodium salts and potassium salts; alkali earth metal salts such as calcium salts, magnesium salts, and barium salts; and aluminum salts. Non-limiting examples of salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, and the like. Non-limiting examples of salts with inorganic acids include salts with hydrochloric acid, hydrobromic acid, nitric acid, phosphoric acid, and the like. Non-limiting examples of salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, and the like. Non-limiting examples of salts with basic amino acids include salts with arginine, lysine, ornithine, and the like, and non-limiting examples of salts with acidic amino acids include salts with aspartic acid, glutamic acid, and the like. For example, Compound (I) may be a pharmaceutically acceptable salt. Also for example, when the compound contains acidic functional groups, inorganic salts such as alkali metal salts (for example, sodium salts, potassium salts, or the like) or alkali earth metal salts (for example, calcium salts, magnesium salts, barium salts, or the like), ammonium salts, or the like may be used, and when the compound contains basic functional groups, salts with inorganic acids such as hydrochloric acid, hydrobromic acid, nitric acid, sulfuric acid, or phosphoric acid or salts with organic acids such as acetic acid, phthalic acid, fumaric acid, oxalic acid, tartaric acid, maleic acid, citric acid succinic acid, methanesulfonic acid or p-toluenesulfonic acid may be used.

When Compound (I) contains an isomer such as a tautomer, an enantiomer, a stereoisomer, a regioisomer, or a rotamer, any one of the isomers and mixtures thereof are also included in Compound (I). Further, when there is an enantiomer in Compound (I), an enantiomer split from a racemate is also included in Compound (I).

In some embodiments, Compound (I) may be a crystal; accordingly, a single crystal form and a mixed crystal form are included in Compound (I).

In some embodiments, Compound (I) may be a pharmaceutically acceptable cocrystal or cocrystal salt. As used herein, a cocrystal or cocrystal salt refers to a crystalline substance comprising two or more unique solids at room temperature, each of which has different physical characteristics (for example, structure, melting point, heat of fusion, hygroscopicity, solubility, stability, and the like). A cocrystal or cocrystal salt may be produced in accordance with a known co-crystallization method.

In some embodiments, Compound (I) may be a solvate (for example, a hydrate or the like) or a solvent-free substance, and both of these are included within the scope of Compound (I).

In some embodiments, compounds labeled or substituted with isotopes (for example, $^2H$, $^3H$, $^{11}C$, $^{14}C$, $^{18}F$, $^{35}S$, $^{125}I$, or the like) are also included in Compound (I). For example, in some embodiments, a compound labeled or substituted with an isotope can be used as a tracer (PET tracer) used in Positron Emission Tomography (PET). In some embodiments, a compound labeled or substituted with an isotope may be useful in fields such as medical diagnosis.

Non-limiting example methods for producing a compound of the present disclosure will be described hereinafter.

The starting materials or reagents used in each step of the following production method and the resulting compound may respectively form salts. Examples of such salts include the same salts as those of a compound of the present disclosure described above.

When the compound obtained in each step is a free compound, it may be converted to a target salt using a method known per se. Conversely, when the compound obtained in each step is a salt, it can be converted to a free form or another type of target salt with a method known per se.

The compound obtained in each step can be used in the next reaction directly as a reaction solution or after it is isolated as a crude product. Alternatively, the compound obtained in each step can be isolated and/or purified from the reaction mixture with a separation means such as concentration, crystallization, recrystallization, distillation, solvent extraction, fractional distillation, or chromatography in accordance with conventional techniques.

When the starting materials or reagents in each step are commercially available, commercially available products can be used directly.

In the reaction of each step, the reaction time may vary based on the reagents or solvents that are used. However, unless specified otherwise, the reaction time is ordinarily from 1 minute to 48 hours, for example, from 10 minutes to 8 hours.

In the reaction of each step, the reaction temperature may differ depending on the reagents or solvents that are used, but unless specified otherwise, the reaction temperature is ordinarily from −78° C. to 300° C., for example, from −78° C. to 150° C.

In the reaction of each step, the pressure may differ depending on the reagents or solvents that are used, but unless specified otherwise, the pressure is ordinarily from 1 atm to 20 atm, for example, from 1 atm to 3 atm.

In the reaction of each step, a microwave synthesizer such as an Initiator available from Biotage, for example, can be used. The reaction temperature may differ depending on the reagents or solvents that are used, but unless specified otherwise, the reaction temperature is ordinarily from room temperature to 300° C., for example, from 50° C. to 250° C. The reaction time may vary depending on the reagents or solvents that are used, but unless specified otherwise, the reaction time is ordinarily from 1 minute to 48 hours, for example, from 1 minute to 8 hours.

In the reaction of each step, unless specified otherwise, reagents are used in an amount of from 0.5 to 20 equivalents, for example, 0.8 to 5 equivalents, with respect to the substrate. When a reagent is used as a catalyst, the reagent is used in an amount of from 0.001 to 1 equivalent, for example, from 0.01 to 0.2 equivalents, with respect to the substrate. When a reagent also serves as a reaction solvent, the reagent is used in a solvent amount.

In the reaction of each step, unless specified otherwise, the reactions are performed without a solvent or after dissolution or suspension in an appropriate solvent. Non-limiting examples of solvents are the solvents described in the Examples or those described below.

Alcohols: methanol, ethanol, tert-butyl alcohol, 2-methoxyethanol, and the like;

Ethers: diethyl ether, diphenyl ether, tetrahydrofuran, 1,2-dimethoxyethane, and the like;

Aromatic hydrocarbons: chlorobenzene, toluene, xylene, and the like;

Saturated hydrocarbons: cyclohexane, hexane, and the like;

Amides: N,N-dimethylformamide, N-methylpyrrolidone, and the like;

Halogenated hydrocarbons: dichloromethane, carbon tetrachloride, and the like;

Nitriles: acetonitrile and the like;

Sulfoxides: dimethylsulfoxide and the like;

Aromatic organic bases: pyridine and the like;

Acid anhydrides: acetic anhydride and the like;

Organic acids: formic acid, acetic acid, trifluoroacetic acid, and the like;

Inorganic acids: hydrochloric acid, sulfuric acid, and the like;

Esters: ethyl acetate and the like;

Ketones: acetone, methyl ethyl ketone, and the like;

Water.

In some embodiments, two or more types of the above solvents may be mixed in appropriate ratios and used in the described methods.

In some embodiments, when a base is used in the reaction of each step, the bases listed below or the bases described in the Examples may be used.

Inorganic bases: sodium hydroxide, magnesium hydroxide, sodium carbonate, calcium carbonate, sodium bicarbonate, and the like;

Organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine, and the like;

Metal alkoxides: sodium ethoxide, potassium tert-butoxide, and the like;

Alkali metal hydrides: sodium hydride and the like;

Metal amides: sodium amide, lithium diisopropylamide, lithium hexamethyldisilazide, and the like;

Organic lithiums: n-butyllithium and the like.

In some embodiments, when an acid or an acidic catalyst is used in the reaction of each step, the acids or acidic catalysts listed below or the acids or acidic catalysts described in the Examples may be used.

Inorganic acids: hydrochloric acid, sulfuric acid, nitric acid, hydrobromic acid, phosphoric acid, and the like;

Organic acids: acetic acid, trifluoroacetic acid, citric acid, p-toluenesulfonic acid, 10-camphorsulfonic acids, and the like;

Lewis acids: boron trifluoride diethyl ether complex; zinc iodide, anhydrous aluminum chloride, anhydrous zinc chloride, anhydrous iron chloride, and the like.

Unless specified otherwise, the reactions of each step may be performed in accordance with methods known per se—for example, the methods described in Experimental Chemistry, 5th Edition, Vol. 13-19 (edited by the Chemical Society of Japan); New Experimental Chemistry, Vol. 14-15 (edited by the Chemical Society of Japan); Fine Organic Chemistry, Revised 2nd Edition (L. F. Tietze, Th. Eicher, Nankodo Co., Ltd.); Revised Organic Named Reactions: Reaction Mechanism and Essence (by Hideo Togo, Kodansha); ORGANIC SYNTHESES Collective Volume 1-VII (John Willey & Sons Inc.); Modern Organic Synthesis in the Laboratory, A Collection of Standard Experimental Procedures (by Jie Jack Li, published by OXFORD UNIVERSITY); Comprehensive Heterocyclic Chemistry III, Vol. 1 to Vol. 14 (Elsevier Japan KK)); Strategic Applications of Named Reactions in Organic Synthesis (translation supervised by Kiyoshi Tomioka, published by Kagaku-Dojin Publishing); Comprehensive Organic Transformations (VCH Publishers Inc.), 1989 Edition, or the like—or in accordance with a method described in the Examples.

In each step, protection or deprotection reactions of functional groups are performed in accordance with methods known per se—for example, Wiley-Interscience 2007 Edition "Protective Groups in Organic Synthesis, 4th Ed." (by Theodora W. Greene, Peter G. M. Wuts); Thieme 2004 Edition "Protecting Groups 3rd Ed." (by P. J. Kocienski) or the like—or in accordance with a method described in the Examples.

Examples of protecting groups of hydroxyl groups or phenolic hydroxyl groups such as alcohols include ether-type protecting groups such as methoxymethyl ethers, benzyl ethers, tert-butyldimethylsilyl ethers, and tetrahydropyranyl ethers; carboxylic acid ester-type protecting groups such as acetic acid esters; sulfonic acid ester-type protecting groups such as methanesulfonic acid esters; and carbonic acid ester-type protecting groups such as tert-butylcarbonate.

Non-limiting examples of protecting groups of carbonyl groups of aldehydes include acetal-type protecting groups such as dimethylacetal; and cyclic acetal-type protecting groups such as 1,3-dioxane.

Non-limiting examples of protecting groups of carbonyl groups of ketones include ketal-type protecting groups such as dimethyl ketal; cyclic ketal-type protecting groups such as 1,3-dioxane; oxime-type protecting groups such as O-methyloxime; and hydrazone-type protecting groups such as N,N-dimethylhydrazone.

Non-limiting examples of protecting groups of carboxyl groups include ester-type protecting groups such as methyl esters; and amide-type protecting groups such as N,N-dimethylamide.

Non-limiting examples of protecting groups of thiols include ether-type protecting groups such as benzylthioethers; and ester-type protecting groups such as thioacetic acid esters, thiocarbonates, and thiocarbamates.

Non-limiting examples of protecting groups of amino groups or aromatic heterocycles such as imidazole, pyrrole, and indole include carbamate-type protecting groups such as benzylcarbamate; amide-type protecting groups such as acetamide; alkylamine-type protecting groups such as N-triphenylmethylamine; and sulfonamide-type protecting groups such as methanesulfonamide and o-nitrobenzenesulfonamide.

Protecting groups can be removed using a method known per se such as, for example, a method using an acid, a base, a thiol, UV light, hydrazine, phenylhydrazine, sodium N-methyldithiocarbamate; tetrabutylammonium fluoride, palladium acetate, a trialkylsilyl hydride (for example, trimethylsilyl iodide or trimethylsilyl bromide), a reduction method, or the like.

When a reduction reaction is performed in a step, non-limiting examples of the reducing agent that may be used include metal hydrides such as lithium aluminum hydride, sodium triacetoxyborohydride, sodium cyanoborohydride, diisobutylaluminum hydride (DIBAL-H), sodium borohydride, and tetramethylammonium triacetoxyborohydride; boranes such as borane tetrahydrofuran complexes; Raney nickel; Raney cobalt; hydrogen; formic acid; and triethylsilane. When reducing a carbon-carbon double bond or triple bond, there is a method of using a catalyst such as palladium-carbon or a Lindlar catalyst.

When an oxidation reaction is performed in a step, non-limiting examples of the oxidizing agent that may be used include peracids such as m-chloroperbenzoic acid (mCPBA), hydrogen peroxide, and tert-butyl hydroperoxide; perchlorates such as tetrabutylammonium perchlorate; chlorites such as sodium chlorite; periodates such as sodium peridiodate, hypervalent iodine reagents such as iodosylbenzene; reagents containing manganese such as manganese dioxide and potassium permanganate; leads such as lead tetraacetate; reagents containing chromium such as pyridinium chlorochromate (PCC), pyridinium dichromate (PDC), and Jones reagent; halogen compounds such as N-bromosuccinimide (NBS); oxygen; ozone; sulfur trioxide/pyridine complex; osmium tetraoxide; selenium dioxide; and 2,3-dichloro-5,6-dicyano-1,4-benzoquinone (DDQ).

When a radical cyclization reaction is performed in a step, non-limiting examples of the radical initiator that may be used include azo compounds such as azobisisobutyronitrile (AIBN); water-soluble radical initiators such as 4-4'-azobis-4-cyanopentanoic acid (ACPA); triethyl boron in the presence of air or oxygen; and benzoyl peroxide. In addition, non-limiting examples of the radical reaction reagent that may be used include tributylstannane, tris-trimethylsilylsilane, 1,1,2,2-tetraphenyldisilane, diphenylsilane, and samarium diiodide.

When a Wittig reaction is performed in a step, non-limiting examples of the Wittig reagent that may be used include alkylidene phosphoranes. For example, alkylidene phosphoranes can be prepared by a method known per se, such as by reacting a phosphonium salt and a strong base.

When a Horner-Emmons reaction is performed in a step, non-limiting examples of the reagent that may be used include phosphonoacetic acid esters such as methyl dimethylphosphonoacetate and ethyl diethylphosphonoacetate; and bases such as alkali metal hydrides and organic lithiums.

When a Friedal-Crafts reaction is performed in a step, non-limiting examples of the reagent that may be used include combinations of Lewis acids and acid chlorides or combinations of Lewis acids and alkylating agents (for example, alkyl halides, alcohols, olefins, and the like). Alternatively, an organic acid or an inorganic acid may also be used instead of a Lewis acid, and an acid anhydride such as acetic anhydride may also be used instead of an acid chloride.

When an aromatic nucleophilic substitution reaction is performed in a step, a nucleophilic agent (for example, amines, 2-pyridone, imidazole, or the like) and a base (for example, organic or inorganic bases or the like) are used as reagents.

When a carbanion-mediated nucleophilic addition reaction, a carbanion-mediated nucleophilic 1,4-addition reaction (Michael addition reaction), or a carbanion-mediated nucleophilic substitution reaction is performed in a step, non-limiting examples of a base that may be used to generate a carbanion include organic lithiums, metal alkoxides, organosilicon compounds, inorganic bases, and organic bases.

When a Grignard reaction is performed in a step, non-limiting examples of the Grignard reagent include arylmagnesium halides such as phenylmagnesium bromide; and alkylmagnesium halides such as methylmagnesium bromide. A Grignard reagent can be prepared with a method known per se, for example, by reacting an alkyl halide or an aryl halide with metallic magnesium using an ether or tetrahydrofuran as a solvent.

When a Knoevanegel reaction is performed in a step, an active methylene compound (for example, malonic acid, diethyl malonate, malononitrile, or the like) sandwiched between two electron-withdrawing groups and a base (for example, organic bases, metal oxides, or inorganic bases) may be used as reagents.

When a Vilsmeier-Haack reaction is performed in a step, phosphoryl chloride and an amide derivative (for example, N,N'-dimethylformamide or the like) may be used as reagents.

When an azidation reaction of carboxylic acids, alcohols, alkyl halides, and sulfonic acid esters is performed in a step, non-limiting examples of the azidation agent that may be used include diphenylphosphoryl azide (DPPA), trimethylsilyl azide, and sodium azide. For example, when azidating alcohol, a method using diphenylphosphoryl azide and 1,8-diazabicyclo[5.4.0]undeca-7-ene (DBU) or a method using trimethylsilyl azide and a Lewis acid may be employed.

When a Curtius rearrangement reaction is performed in a step, non-limiting examples of the solvent that may be used include toluene and dichloromethane.

When a reductive amination reaction is performed in a step, non-limiting examples of the reducing agent that may be used include sodium triacetoxyborohydride, sodium cyanoborohydride, sodium borohydride, hydrogen, and formic acid. When the substrate is an amine compound, non-limiting examples of the carbonyl compound that may be used include paraformaldehyde as well as aldehydes such as acetaldehyde and ketones such as cyclohexanone. When the substrate is a carbonyl compound, non-limiting examples of the amines that may be used include ammonia, primary amines such as methylamine; and secondary amines such as dimethylamine.

When a Mitsunobu reaction is performed in a step, azodicarboxylic acid esters (for example, diethyl azodicarboxylate (DEAD), diisopropyl azodicarboxylate (DIAD), and the like) and triphenylphosphine may be used as reagents. In addition, cyanomethylene tributylphosphorane (CMBP), cyanomethylene trimethylphosphorane (CMMP), or the like may also be used as a reagent.

When an esterification reaction or an amidation reaction is performed in a step, non-limiting examples of the reagent that may be used include acyl halides such as acid chlorides and acid bromides; and activated carboxylic acids such as acid anhydrides, active esters, and sulfuric acid esters. Non-limiting examples of activators of carboxylic acids include carbodiimide-based condensing agents such as 1-ethyl-3-(3-dimethylaminopropyl)carbodiimide hydrochloride (WSCD); triazine-based condensing agents such as 4-(4,6-dimethoxy-1,3,5-triazine-2-yl)-4-methylmorpholinium chloride-n-hydrate (DMT-MM); benzotriazole-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate; O-(7-azabenzotriazole-1-yl)-N,N,N',N'-tetramethyluronium hexafluorophosphate (HATU); sulfuric acid; or combinations thereof. When a carbodiimide-based condensing agent is used, additives such as 1-hydroxybenzotriazole (HOBt), N-hydroxysuccinimide (HOSu), and dimethylaminopyridine (DMAP) may be further added to the reaction.

When a urea formation reaction of an amine is performed in a step, non-limiting examples of the reagent that may be used include phosgene equivalents such as bis(trichloromethyl) carbonate, trichloromethyl chloroformate, and 1,1'-carbonyldiimidazole. When a urea formation reaction of a carboxylic acid is performed, non-limiting examples of the reagent that may be used include azidation reagents such as diphenylphosphoryl azide (DPPA). In addition, in some embodiments, this reaction is performed in the presence of a base. Non-limiting examples of bases include tertiary amines, aromatic amines, and basic salts.

When a dehydration condensation reaction is performed in a step, non-limiting examples of the solvent that may be used include alcohols such as ethanol or aromatic hydrocarbons such as toluene. Further, in some embodiments, the reaction can be accelerated by adding an acid such as p-toluenesulfonic acid or a dehydrating agent such as magnesium sulfate to the reaction.

When a coupling reaction is performed in a step, non-limiting examples of the metal catalyst that is used include palladium compounds such as palladium (II) acetate, tetrakis (triphenylphosphine) palladium (0), dichlorobis(triphenylphosphine) palladium (II), dichlorobis(triethylphosphine) palladium (II), tris(dibenzylideneacetone) dipalladium (0), and 1,1'-bis(diphenylphosphino) ferrocene palladium (II) chloride; nickel compounds such as tetrakis (triphenylphosphine) nickel (0); rhodium compounds such as tris(triphenylphosphine) rhodium (III) chloride; cobalt compounds; copper compounds such as copper oxide and copper (I) iodide; and platinum compounds. In some embodiments, a base may be further added to the reaction; non-limiting examples of such bases include inorganic bases. Further, in some embodiments, the reaction can be accelerated by adding heat, light, or a radical initiator such as benzoylperoxide or azobis isobutyronitrile to the reaction.

When a thiocarbonylation reaction is performed in a step, diphosphorus pentasulfide may be used as a thiocarbonylating agent; alternatively, diphosphous pentasulfide, reagents having a 1,3,2,4-dithiadiphosphetane-2,4-disulfide structure such as 2,4-bis(methoxyphenyl)-1,3,2,4-dithiadiphosphetane-2,4-disulfide (Lawesson reagent) may also be used.

When a Wohl-Ziegler reaction is used in a step, non-limiting examples of the halogenating reagent that may be used include N-iodosuccinimide, N-bromosuccinimide (NBS), N-chlorosuccinimide (NCS), bromine, and sulfuryl chloride. Further, in some embodiments, the reaction can be accelerated by adding heat, light, or a radical initiator such as benzoylperoxide or azobis isobutyronitrile to the reaction.

When a halogenation reaction of a hydroxy group is performed in a step, non-limiting examples of the halogenating agent that may be used include acid halides of hydrohalic acids and inorganic acids; specifically, in the case of chlorination, hydrochloric acid, thionyl chloride, phosphorus oxychloride, or the like may be used, and in the case of bromination, 48% hydrobromic acid or the like may be used. In addition, in some embodiments, a method of obtaining an alkyl halide from an alcohol by the action of triphenylphosphine and carbon tetrachloride or carbon tetrabromide may be used. Alternatively, in some embodiments, a method of synthesizing an alkyl halide via a two-step reaction in which an alcohol is converted to a sulfonic acid ester and then reacted with lithium bromide, lithium chloride, or sodium iodide may be employed.

When an Arbuzov reaction is performed in a step, non-limiting examples of the reagent that may be used include alkyl halides such as ethyl bromoacetate; and phosphites such as triethylphosphite or tri(isopropyl)phosphite.

When a sulfonic acid esterification reaction is performed in a step, non-limiting examples of the sulfonylating agent that may be used include methanesulfonyl chloride, p-toluenesulfonyl chloride, methanesulfonic anhydride, and p-toluenesulfonic acid anhydride.

When a hydrolysis reaction is performed in a step, an acid or a base may be used as a reagent. In addition, in some embodiments, when an acid hydrolysis reaction of a tert-butyl ester is performed, formic acid, triethylsilane, or the like may be added to reductively trap the tert-butyl cations produced as a by-product.

When a dehydration reaction is performed in a step, non-limiting examples of the dehydrating agent that may be used include sulfuric acid, diphosphorus pentasulfide, phosphorus oxychloride, N,N'-dicyclohexylcarbodiimide, alumina, and polyphosphoric acid.

Compound (I) can be produced in accordance with the reaction formulas illustrated below or methods conforming to these formulas. The starting materials of Compound (I) may be commercially available products or may be produced using methods known per se. Unless specified otherwise, the abbreviations in each general formula in the reaction formula are as defined above.

For example, Compound (Ia), in which Z in Compound (I) is C—H, can be produced from compound (1) or compound (4) using the following method. In the formula, $R^{101}$ and $R^{12}$ are substituents, and other symbols are each as defined above.

Non-limiting examples of the "substituents" indicated by $R^{101}$ and $R^{12}$ include methyl groups and ethyl groups.

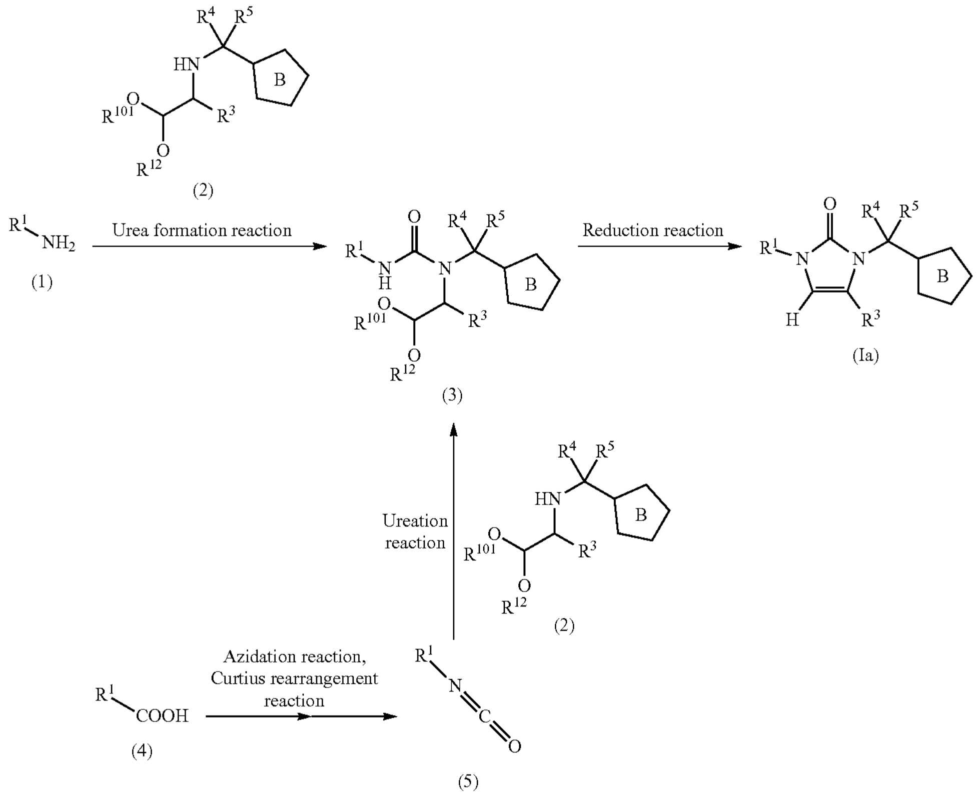

(1) (2) (3) (Ia) (4) (5)

Compound (3) can be produced by a urea formation reaction of compound (1) and compound (2).

Compound (5) can be produced by an azidation reaction of compound (4) followed by a Curtius rearrangement reaction.

Compound (3) can also be produced by a urea formation reaction of compound (5) and compound (2).

Compound (Ia) can be produced by a deprotection reaction of the acetal of compound (3), followed by an intramolecular cyclization reaction.

Compound (Ib), in which Z in Compound (I) is C—$CH_3$, can be produced from compound (1) with the following method. The symbols are each as defined above.

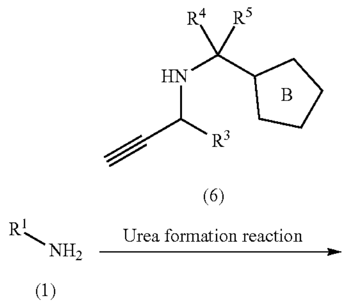

(6)

(1)

-continued

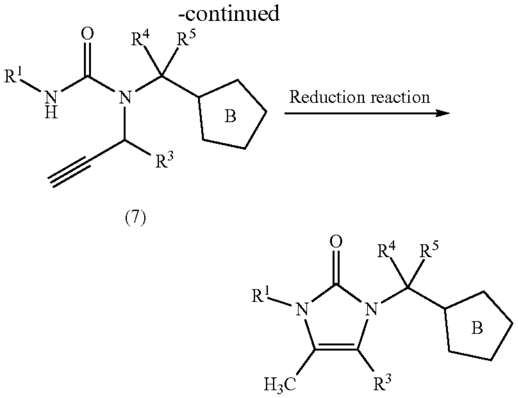

(7)

(Ib)

Compound (7) can be produced by a urea formation reaction of compound (1) and compound (6).

Compound (Ib) can be produced by a cyclization reaction by activation of the alkynes of compound (7), followed by an isomerization reaction by acid treatment. When a cyclization reaction is performed, non-limiting examples of the reagent that may be used include tetrabutylammonium fluoride (TBAF) and gold chloride (I). In addition, when an isomerization reaction is performed, non-limiting examples of the reagent that may be used include hydrochloric acid and trifluoroacetic acid.

Compound (Ic), in which Z in Compound (I) is C—$R^2$, can be produced from compound (1) using the following method. In the formula, L is a leaving group, $R^{13}$ and $R^{14}$ are substituents, and other symbols are each as defined above.

Non-limiting examples of the "leaving group" indicated by L include halogen atoms, $C_{1-6}$ alkylsulfonyloxy groups (for example, methanesulfonyloxy or ethanesulfonyloxy), and $C_{6-14}$ arylsulfonyloxy groups (for example, benzenesulfonyloxy or toluenesulfonyloxy) optionally substituted with $C_{1-6}$ alkyl groups.

Non-limiting examples of the "substituents" indicated by $R^3$ and $R^{14}$ include methyl groups and ethyl groups.

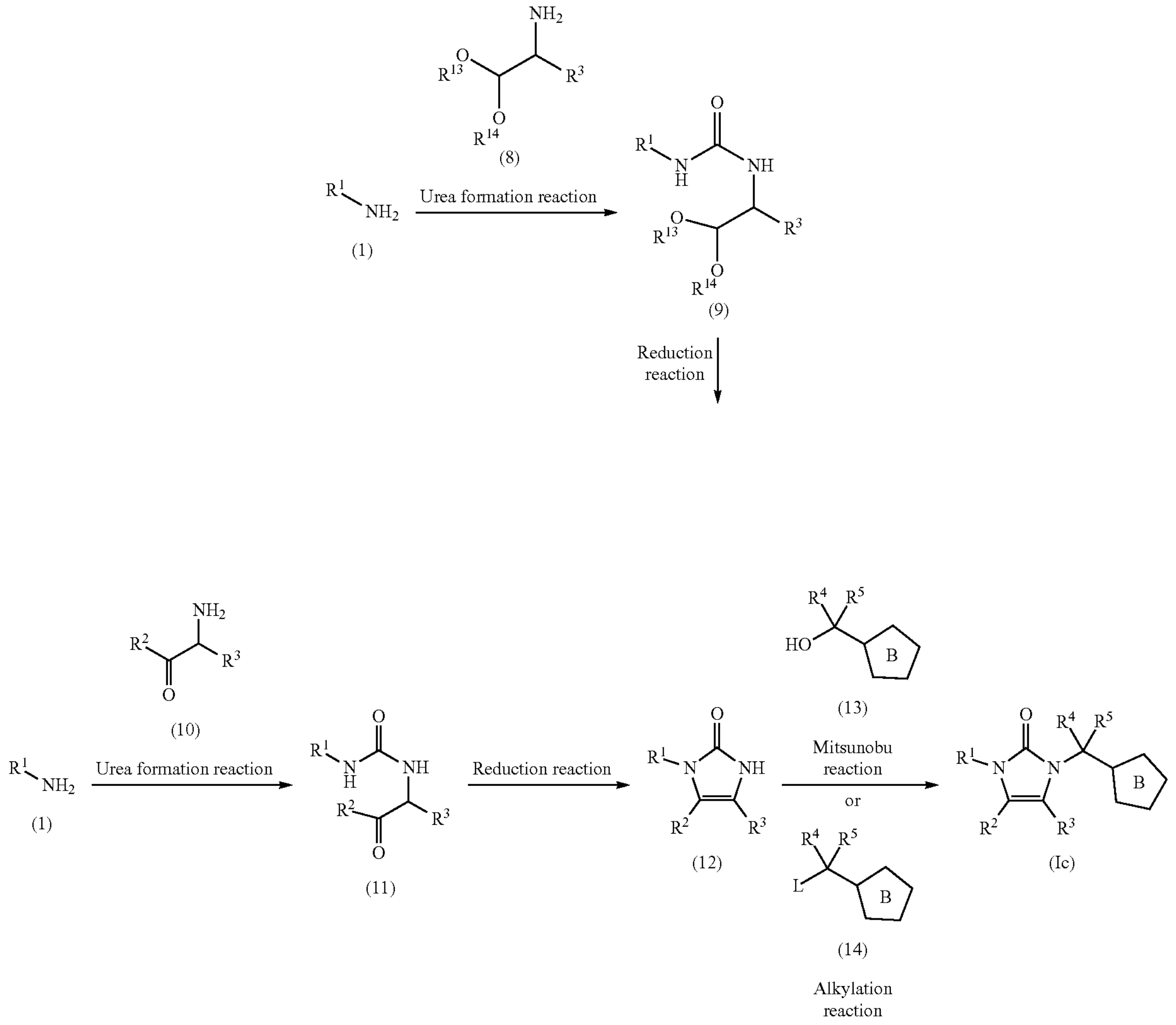

(8) (1) (9) (10) (1) (11) (12) (13) (14) (Ic)

Compound (9) can be produced by a urea formation reaction of compound (1) and compound (8).

Compound (12) can be produced by a deprotection reaction of the acetal of compound (9) followed by an intramolecular cyclization reaction.

Compound (11) can be produced by a urea formation reaction of compound (1) and compound (10).

Compound (12) can be produced by a urea formation reaction of compound (11). When an intromolecular cyclization reaction is performed, a non-limiting example of a reagent includes trifluoroacetic acid.

Compound (Ic) can be produced by a Mitsunobu reaction of compound (12) and compound (13).

Compound (Ic) can also be produced by an alkylation reaction of compound (12) and compound (14).

Compound (Id), in which Z in Compound (I) is N, can be produced from compound (15) using the following method. In the formula, $R^{15}$ is a substituent, and other symbols are each as defined above.

Non-limiting examples of the "substituents" indicated by $R^{15}$ include methyl groups and ethyl groups.

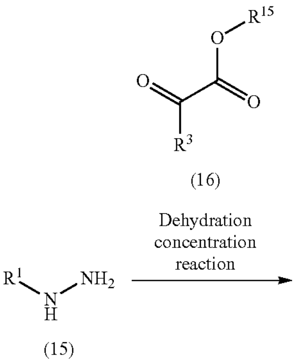

(16) (15)

-continued

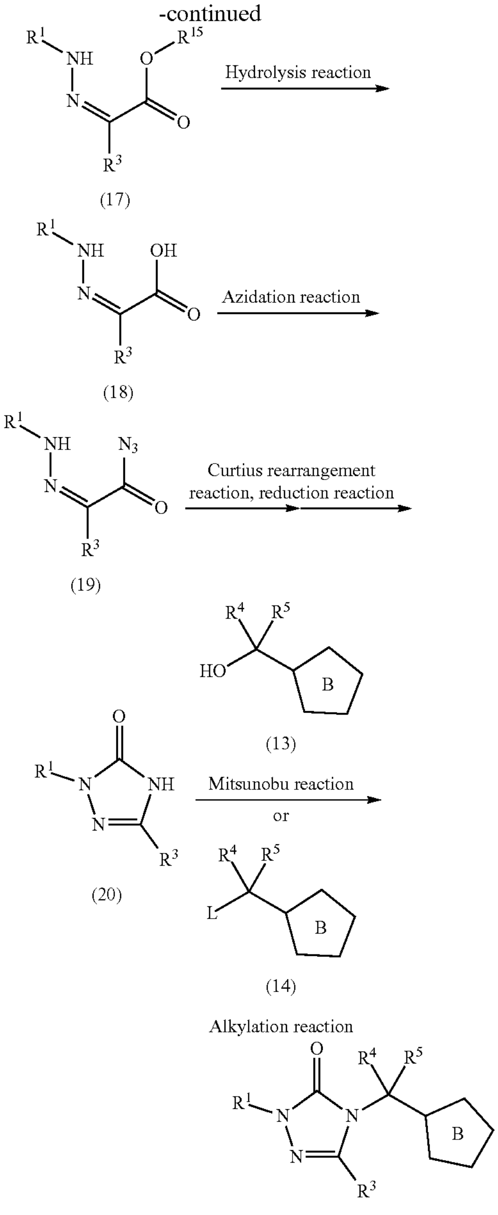

(17) (18) (19) (20) (13) (14) (Id)

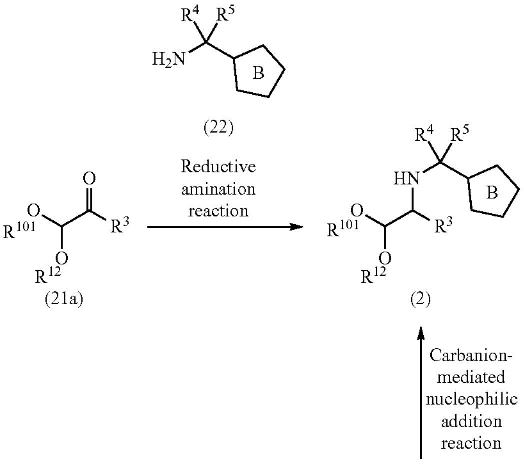

(22) (21a) (2)

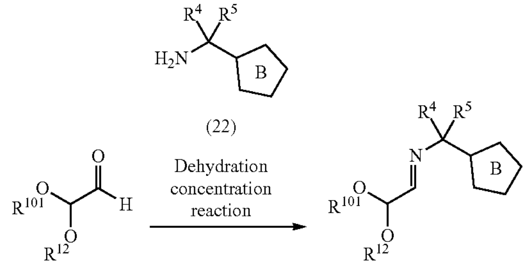

(22) (21b) (23)

Compound (17) can be produced by a dehydration condensation reaction of compound (15) and compound (16).

Compound (18) can be produced by a hydrolysis reaction of compound (17).

Compound (19) can be produced by an azidation of compound (18).

Compound (20) can be produced by a Curtius rearrangement reaction of compound (19) followed by a cyclization reaction.

Compound (Id) can be produced by a Mitsunobu reaction of compound (20) and compound (13).

Compound (Id) can also be produced by an alkylation reaction of compound (20) and compound (14).

Compound (2) can be produced from compound (21a) or (21b) with the following method. The symbols are each as defined above.

Compound (2) can be produced by a reductive amination reaction of compound (21a) and compound (22).

Compound (23) can be produced by a dehydration condensation reaction of compound (21b) and compound (22).

Compound (2) can also be produced by a carbanion-mediated nucleophilic addition reaction of compound (23). When a nucleophilic addition reaction is performed, non-limiting examples of the reagents that may be used include methylmagnesium bromide and trifluoromethyl trimethylsilane.

Compound (6) can be produced from compound (24) using the following method. In the formula, P is a protecting group of amino groups, and other symbols are each as defined above.

Non-limiting examples of the "protecting group" indicated by P include acetyl groups and o-nitrobenzenesulfonyl groups.

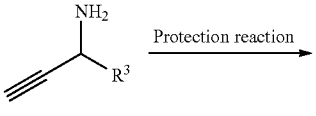

(24)

-continued

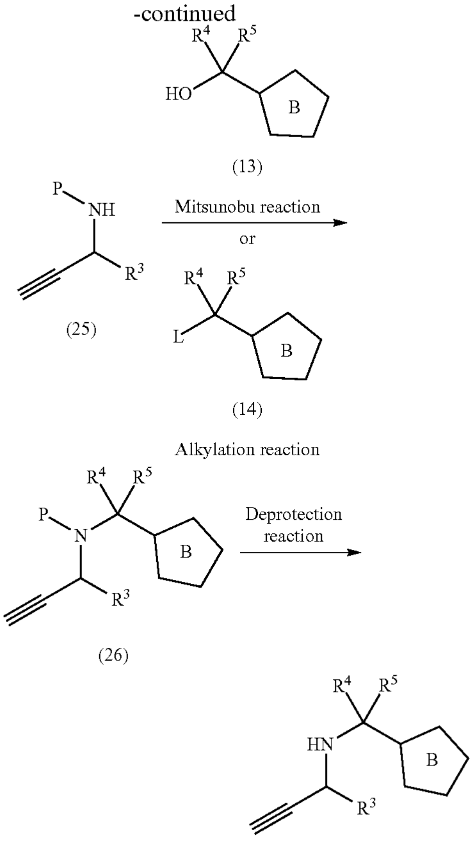

(13)
(25)
(14)
(26)
(6)

Compound (25) can be produced by a protection reaction of compound (24).

Compound (26) can be produced by a Mitsunobu reaction of compound (25) and compound (13).

Compound (26) can also be produced by an alkylation reaction of compound (25) and compound (14).

Compound (6) can be produced by a deprotection reaction of compound (26).

Compounds (1), (4), (8), (10), (13) to (16), (21a), (21b), (22), and (24) can be obtained as commercially available products or produced in accordance with methods known per se, similar methods, or methods described in the Examples.

In Compound (I) obtained in this way, a functional group in the molecule can be converted to a target functional group by combining known chemical reactions. Non-limiting examples of chemical reactions include oxidation reactions, reduction reactions, alkylation reactions, acylation reactions, urea formation reactions, hydrolysis reactions, amination reactions, esterification reactions, aryl coupling reactions, and deprotection reactions.

In a production method described above, when the starting material compound includes an amino group, a carboxyl group, a hydroxy group, a carbonyl group, or a mercapto group as a substituent, a protecting group that would be typically used in peptide chemistry or the like for these groups may be introduced, and the target compound can be obtained by removing the protecting group after the reaction as needed.

Configurational isomers (E- and Z-isomers) of Compound (I) can be isolated and purified by a separation means such as extraction, recrystallization, distillation, or chromatography at the point when isomerization occurs, and a pure compound can thus be produced. In addition, corresponding pure isomers can also be obtained by allowing the isomerization of double bonds to progress by heating, an acid catalyst, a transition metal complex, a metal catalyst, a radical species catalyst, photoirradiation, a strongly basic catalyst, or the like in accordance with the methods described on pages 251 to 253 of New Experimental Chemistry Vol. 14 (edited by the Chemical Society of Japan) and pages 273 to 274 of the 4th Edition of Experimental Chemistry Vol. 19 (edited by the Chemical Society of Japan) or methods conforming to these methods.

While a stereoisomer may be generated depending on which type of substituent is used in Compound (I), compounds in which this isomer is unaccompanied and mixtures thereof are also included within the scope of the present disclosure.

When the target product is to be obtained in a free state by the reaction described above, it may be converted to a salt in accordance with a conventional method, and when it is to be obtained as a salt, it may be converted to a free form or another salt in accordance with a conventional method. Illustratively, Compound (I) obtained in this way can be isolated and purified from the reaction solution by a known means such as, for example, dissolution, concentration, solvent extraction, fractional distillation, crystallization, recrystallization, or chromatography.

When Compound (I) exists as a configurational isomer, a diastereomer, a conformer, or the like, it can be respectively isolated by the aforementioned separation and purification means as desired. In addition, when Compound (1) is racemic, it can be separated into a d-form and an 1-form or an S-form and an R-form by an ordinary optical resolution means.

Compound (I) obtained in this way, as well as other reaction intermediates and the starting material compounds thereof, can be isolated and purified from the reaction mixture by methods known per se—for example, by using a means such as extraction, concentration, neutralization, filtration, distillation, recrystallization, column chromatography, thin film chromatography, preparative high performance liquid chromatography (preparative HPLC), or medium-pressure preparative liquid chromatography (medium-pressure preparative LC).

Compound (I), which is a salt, can be produced in accordance with a known means—for example, by adding an inorganic acid or an organic acid when Compound (I) is a basic compound or by adding an organic base or an inorganic base when Compound (I) is an acidic compound.

When enantiomers are present in Compound (I), these individual enantiomers and mixtures thereof are also included in the scope of the present disclosure. These isomers can also be optically resolved or produced individually as desired in accordance with known means.

In the present specification, a GPR139 receptor antagonist action includes a GPR139 receptor inverse agonist action. In some embodiments, a compound having a GPR139 receptor antagonist action is a compound having a GPR139 receptor inverse agonist.

As described in detail in the test examples below, the GPR139 receptor inverse agonist action can be confirmed, for example, by the reduced production or inhibited production of inositol monophosphate (also abbreviated as $IP_1$ in the present specification), a metabolite of inositol triphosphate, which is the second messenger in the downstream of signal transmission in GPR139 (also abbreviated as $IP_3$ in the present specification)).

Compound (I) can be used as a drug for preventing, treating, or diagnosing various diseases described below in mammals (for example, mice, rats, hamsters, rabbits, cats, dogs, cows, sheep, monkeys, humans, and the like). For example, Compound (I) is expected to be useful as a drug for preventing or treating diseases such as:

(1) Psychiatric disorders (for example, depression, major depression, depressive episodes, minor depressive disorder, bipolar depression, dysthymic disorder, persistent depressive disorder, emotional disturbance (for example, seasonal affective disorder or the like), recurrent depression, postpartum depression, stress disorder, major depression disorder accompanying mental illness (including delusional disorder and schizophrenia), manic illness or mixed mood episodes, hypomanic mood episodes, depressive episodes with atypical features, depressive episodes with depressive features, depressive episodes with catatonic features, post-stroke depressive episodes, depression with anhedonia, major depression with anhedonia, minor depressive disorder with anhedonia, bipolar depression with anhedonia, dysthymic disorder with anhedonia, persistent depressive disorder with anhedonia, emotional disturbance with anhedonia, recurrent depression with anhedonia, postpartum depression with anhedonia, stress disorder with anhedonia, bipolar disorder with anhedonia, schizophrenia with anhedonia, anxiety disorder with anhedonia, mood disorder with anhedonia, Alzheimer's disease with anhedonia, dementia with Lewy bodies, Parkinson's disease with anhedonia, Huntington's disease with anhedonia, refractory major depression with anhedonia, refractory bipolar disorder with anhedonia, depressive symptoms, manic illness, manic episodes, hypomanic episodes, maniform episodes, hypomaniform episodes, delirium, symptoms peripheral to dementia (psychiatric symptoms or behavioral disorders), anxiety, generalized anxiety disorder, anxiety syndrome, mood disorder, cyclothymic disorder, premenstrual dysphoric disorder, generalized anxiety disorder, anxiety syndrome, panic disorder, phobia, social phobia, social anxiety disorder, obsessive-compulsive disorder, post-traumatic stress syndrome, post-traumatic stress disorder, schizoaffective psychosis, paranoid-type or depression-type schizoaffective psychosis, paranoid-type personality disorder, Tourette syndrome, autism spectrum disorder, fragile X syndrome, Rett syndrome, maladjustment, bipolar disorder (including type I bipolar disorder and type II bipolar disorder), neurosis, drug addiction, schizophrenia (for example, positive symptom, negative symptom, cognitive impairment, paranoid schizophrenia, disorganized schizophrenia, catatonic schizophrenia, unspecialized schizophrenia, and residual schizophrenia), schizophrenia spectrum disorder, dyskinesia, mental retardation, paranoid tendency, schizophreniform disorder, catatonia, neurosis, fatigue, chronic fatigue syndrome, lack of energy, anxiety neurosis, obsessional neurosis, panic disorder, epilepsy, anxiety symptoms, unpleasant mental state, emotional abnormality, emotional circulation temperament, nervousness, fainting, addiction, sexual debility, attention deficit hyperactivity disorder (ADHD), psychotic major depression, intractable major depression, refractory depression, refractory major depression, cognitive impairment accompanying major depression, refractory bipolar disorder, temper tantrum, weight gain, weight loss, psychomotor agitation, psychomotor retardation, worthlessness, guilt feeling, impaired ability to think or concentrate, suicidal thoughts, suicide attempt, melancholia, psychotic disorder (for example, short-term psychotic disorder and shared psychotic disorder), obesity-induced mental illness, paranoia, Noonan's syndrome, Angelman syndrome, Prader-Willi syndrome, Beckwith-Wiedemann syndrome, Silver-Russell syndrome, tuberous sclerosis, Williams' syndrome, Kallmann syndrome, Rubinstein-Taybi syndrome, eating behavior disorder and food intake disorder groups, disorders, pica, merycism, avoidant/restrictive food intake disorder, anorexia, anorexia mentalis (anorexia nervosa and anorexia), psychogenic loss of appetite, atypical psychogenic loss of appetite, bulimia, neurogenic bulimia (bulimia nervosa), nervous increase in appetite, atypical neurogenic bulimia, binge eating disorder, psychogenic hyperphagia, psychogenic pregnancy vomiting, and psychogenic vomiting);

(2) Neurodegenerative disease (for example, Alzheimer's disease, senile dementia of the Alzheimer type, Parkinson's disease, Huntington's disease, dementia accompanying Huntington's disease, multi-infarct dementia, frontotemporal dementia, Parkinson type dementia, Parkinson type frontotemporal dementia, alcohol-related dementia or other drug-related dementia, dementia accompanying intracranial tumor or cerebral trauma, neurodegeneration accompanying cerebral trauma, neurodegeneration accompanying stroke, neurodegeneration accompanying cerebral infarction, neurodegeneration accompanying hypoglycemia, neurodegeneration accompanying epileptic seizure, neurodegeneration accompanying neurotoxin poisoning, multiple system atrophy, spinal cord injury, AIDS-related dementia, progressive supranuclear palsy, Pic's syndrome, Niemann-Pick syndrome, corticobasal degeneration, Down's syndrome, vascular dementia (VaD) (for example, multi-infarct dementia, strategic single infarct VaD, small vessel lesion dementia, hypoperfusion VaD, cerebral hemorrhage VaD, chronic subdural hematoma, and the like), postencephalitic Parkinsonism, Lewy body dementia, HIV dementia, amyotrophic lateral sclerosis (ALS), motor neuron disease (MND), Creutzfeldt-Jakob disease, prion disease, cerebral palsy, multiple sclerosis, and neuromyopathy);

(3) Amnestic disorders, mild cognitive impairment, learning disabilities (for example, dyslexia, dyscalculia, and dysgraphia], or cognitive/memory impairment with aging (for example, age-related memory impairment and senile dementia);

(4) Sleep disorders (for example, intrinsic sleep disorders (for example, psychophysiological insomnia and the like), extrinsic sleep disorders, Circadian rhythm disorders (for example, time zone change syndrome (jet lag), shift work sleep disorder, irregular sleep-wake pattern, delayed sleep phase syndrome, advanced sleep phase syndrome, non-24-hour sleep-wake syndrome, and the like), parasomnia (for example, arousal disorder from non-REM sleep (for example, sleepwalking type, sleep terror type, and the like), nightmare disorder, REM sleep disorder, and restless legs syndrome), sleep disorders accompanying internal medicine or psychiatric disorders (for example, chronic obstructive pulmonary disease, Alzheimer's disease, Parkinson's disease, cerebrovascular dementia, schizophrenia, depression, and anxiety), stress insomnia, insomnia, insomnia neuropathy, sleep apnea syndrome (for example, obstructive sleep apnea, central sleep apnea, and the like), sleep-related hypoventilation (for example, primary alveolar hypoventilation syndrome, congenital central hypoventilation syndrome, and the like), narcolepsy, cataplexy, and hypersomnia);

(5) Drug addiction (substance-related disorders and substance addiction) (for example, substance use disorders (for example, alcohol dependence, marijuana (including synthetic cannabinoids) dependence, hallucinogen (for example, ketamine, phencyclidine, and the like) dependence, inhalant dependence, opioid dependence, painkiller addiction, hypnotic addiction, anxiolytic dependence, psychostimulant (for example, amphetamine-type substances, cocaine, cathinone, synthetic cation, NMDA, NMDA-related drug (for example, MDA and the like), and the like) dependence, caffeine addiction, tobacco dependence, nicotine dependence, alcohol use disorder, *Cannabis* (including synthetic cannabinoids) use disorder, hallucinogen use disorder, inhalant use disorder, opioid use disorder, painkiller use disorder, hypnotic use disorder, anxiolytic use disorder, psychostimulant use disorder, caffeine use disorder, tobacco use disorder, nicotine use disorder, substance-induced disorders (for example, alcoholism, alcohol withdrawal, caffeinism, caffeine withdrawal, marijuana (including synthetic cannabinoids) addiction, marijuana (including synthetic cannabinoids) withdrawal, hallucinogen addiction, hallucinogen persistent perceptual disorder, inhalant addiction, opioid addiction, opioid withdrawal, painkiller addiction, hypnotic addiction, anxiolytic addiction, painkiller withdrawal, hypnotic withdrawal, anxiolytic withdrawal, psychostimulant addiction, psychostimulant withdrawal, caffeine withdrawal, tobacco withdrawal, nicotine withdrawal, substance (including alcohol, caffeine, marijuana, (including synthetic cannabinoids), hallucinogens, inhalants, opioids, painkillers, sleeping drugs, anti-anxiety drugs, psychostimulants, caffeine, tobacco, nicotine, and the like)-induced mental illness (for example, psychotic disorder, bipolar disorder and related disorders, depressive disorder, anxiety, obsessive-compulsive disorder and related disorders, sleeping disorders, sexual dysfunction, delirium, neurocognitive disorders, and the like), acute intoxication, harmful use (for example, antidepressant abuse, drug abuse, and the like), dependence syndrome (for example, drug dependence, non-narcotic painkiller addiction, and the like), withdrawal state (for example, drug withdrawal syndrome and the like), withdrawal state with delirium, psychotic disorders (for example, addictive psychosis, steroid psychosis, and the like), amnesia syndrome, residual and delayed psychotic disorders (for example, drug addiction depression and the like), psychiatric side effects, addictive mental disorders, drug-induced psychiatric disorders, drug preference, pharmacophobia, pharmacomania, and drug withdrawal);

(6) Respiratory depression induced by anesthetics, traumatic disease, neurodegenerative disease or the like;

(7) Pain (for example, psychogenic pain (somatoform disorder, pain disorder, somatization disorder, hypochondria, conversion disorder, chronic pain with depression, psychogenic glossodynia, psychogenic headache, psychogenic backache, psychogenic stomachache, neurologic ear pain, physical pain disorder, mental pain, and psychogenic dyspareunia), inflammatory pain, acute pain, cancer-related persistent pain, cancer-related breakthrough pain, cancer-related pain, persistent pain, somatic pain, breakthrough pain, chronic pain (for example, intractable pain, post thoracotomy pain syndrome, peripheral neuropathic pain, peripheral neuropathic pain, neuropathic pain, central nervous system disorder pain, central neuropathic pain, central post-stroke pain, and the like), tenderness, pantalgia, dull pain, skin pain, radiating pain, headache (for example, inflammatory headache, facial pain, occipital pain, dental facial pain, chronic daily headache, neuralgic headache, frontal headache, temporal headache, neck pain, heaviness of the head, pain in top of head, paroxysmal headache, cheek pain, traction headache, burning mouth syndrome, primary headache, headache due to mental illness, migraine, chronic cluster headache, cluster headache, trigeminal nerve/autonomic cephalalgia, recurrent cluster headache, paroxysmal hemicrania, recurrent paroxysmal hemicrania, chronic paroxysmal hemicrania, short-lasting unilateral neuralgiform headache with conjunctival injection and tearing, vascular headache, muscle contraction headache, tension-type headache, recurrent tension-type headache, chronic tension-type headache, cephalalgia traumatica, post-chronic trauma headache, medication overuse headache, Sluder neuralgia, Tolosa-Hunt syndrome, ocular headache, combined headache, hemicrania continua, primary cough headache, headache during primary exercise, primary headache associated with sexual activity, cold-stimulus headache, primary thunderclap headache, primary puncture-like headache, nummular headache, hypnic headache, new daily persistent headache, headache due to epileptic seizure, hypertensive headache, headache due to nasal/sinus disease, tension headache, and the like), trigeminal nerve disorders (for example, trigeminal neuralgia, atypical facial pain, trigeminal nerve hypersensitivity, trigeminal neuropathy, and the like), glossopharyngeal nerve disorders (for example, glossopharyngeal neuralgia and the like), vagus nerve disorders (for example, superior laryngeal neuralgia, vagal neuralgia, and the like), hypoglossal nerve disorder, multiple cranial neuropathy, postherpetic neuralgia, post-herpes zoster trigeminal neuralgia, multiple neuropathy after herpes zoster, neuralgic amyotrophy, phantom pain, stump neuralgia, deafferentation pain, lumbar sciatic neuralgia, upper limb mononeuropathy (for example, median nerve neuralgia, ulnar neuralgia, and the like), lower limb mononeuropathy (for example, meralgia paraesthetica and the like), rib neuropathy (for example, intercostal neuralgia and the like), neuropathic pain, diabetic neuropathic pain, diabetic neuralgia (for example, type 1 diabetic neuralgia, type 2 diabetic neuralgia, and the like), cardiac neuralgia, persistent somatic symptom disorder, epidemic pleural pain, autonomic reflex pain, myelalgia, lumbar puncture headache, ophthalmalgia, otalgia, thalamic pain, pharyngodynia, rhinalgia, toothache, jaw pain, glossodynia, rectalgia, arthralgia, Back pain, spondylalgia, myalgia, and neuralgia); and (8) Traumatic brain injury and associated disorders or complications, post-concussion syndrome, shaken baby syndrome, stroke, age-related macular degeneration (ARMD), ocular palatal tremor, convulsion, cerebral infarction, cerebral hemorrhage, hearing loss, radiation lethargy syndrome, anorexia nervosa, eating disorder, psychogenic loss of appetite, hyperphagia, other eating disorders, gambling addiction, video game addiction, obesity, diabetes, muscle spasm, Ménière disease, autonomic ataxia, alopecia, glaucoma, hypertension, heart disease, tachycardia, cardiac insufficiency, hyperpnea, bronchial asthma, apnea, sudden infant death syndrome, inflammatory disease, allergic disease, impotence, menopause disorder, infertility, cancer, immunodeficiency syndrome due to HIV infection, autoimmune encephalitis (for example, autoimmune limbic encephalitis), stress-induced immune deficiency syndrome, meninx, acromegaly, incontinence, metabolic syndrome, osteoporosis, peptic ulcer, irritable bowel syndrome, inflammatory bowel disease, ulcerative colitis, Crohn's disease, stress gastrointestinal disorders, vomiting, peptic ulcer, diarrhea, constipation, and postoperative ileus.

Compound (I) may also be used in the form of a prodrug.

A prodrug of Compound (I) refers to a compound that is converted to Compound (I) by a reaction induced by enzymes, gastric acids, or the like under physiological conditions in the body; that is, a compound that is transformed into Compound (I) by enzymatically inducing oxidation, reduction, hydrolysis, or the like, or a compound that is transformed into Compound (I) by inducing hydrolysis or the like with gastric acid or the like.

Non-limiting examples of prodrugs of Compound (I) include compounds in which an amino group of Compound (I) is acylated, alkylated, or phosphorylated (for example, compounds in which an amino group of Compound (I) is eicosanoylated, alanylated, pentylaminocarbonylated, (5-methyl-2-oxo-1,3-dioxol-4-yl)methoxycarbonylated, tetrahydrofuranylated, pyrrolidylmethylated, pivaloyloxymethylated or tert-butylated, and the like); compounds in which a hydroxy group of Compound (I) is acylated, alkylated, phosphorylated, or borated (for example, compounds in which a hydroxyl group of Compound (I) is acetylated, palmitoylated, propanoylated, pivaloylated, succinylated, fumarylated, alanylated, or dimethylaminomethylcarbonylated, and the like); and compounds in which a carboxy group of Compound (I) is esterified or amidated (for example, compounds in which a carboxyl group of Compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxol-4-yl) methyl esterified, cyclohexyloxycarbonylethyl esterified, or methylamidated, and the like). These compounds can be produced from Compound (I) in accordance with a method known per se. A prodrug of Compound (I) may be a compound that transforms into Compound (I) under physiological conditions such as those as described in "Development of Pharmaceutical Products" vol. 7, Molecule Design, p. 163-198, Hirokawa Shoten (1990).

Compound (I) may exhibit favorable pharmacokinetics properties (for example, drug half-life in blood, intracerebral transferability, and metabolic stability) and low toxicity (for example, superior as a pharmaceutical from the perspectives of acute toxicity, chronic toxicity, genetic toxicity, reproduction toxicity, cardio-toxicity, drug interactions, carcinogenicity, and the like), allowing safe administration orally or non-orally to mammals (for example, humans, monkeys, cows, horses, pigs, mice, rats, hamsters, rabbits, cats, dogs, sheep, goats, and the like) either directly as a pharmaceutical or as a pharmaceutical composition mixed with at least one pharmaceutically acceptable carrier or the like.

As used herein, "non-oral administration" includes intravenous, intramuscular, subcutaneous, intraorgan, intranasal, intradermal, instillation, intracerebral, intrarectal, intravaginal, intraperitoneal, intratumoral, and proximal tumor administration, as well as direct administration into a lesion.

In some embodiments, the dose of Compound (I) differs depending on the administration route, symptoms, and the like. In some embodiments, when administered orally to a patient with depression (for example, an adult with a weight in the range of 40 kg to 80 kg; for example, 60 kg), the dose is, for example, 0.001 to 1000 mg/kg of body weight per day, for example, from 0.01 to 100 mg/kg of body weight per day, and for example, from 0.1 to 10 mg/kg of body weight per day. This amount can be spread out over, for example, 1 to 3 doses per day.

A pharmaceutical comprising Compound (I) can be used as Compound (I) alone or as a pharmaceutical composition prepared by mixing Compound (I) and at least one pharmaceutically acceptable carrier in accordance with a method known per se as a production method for pharmaceutical preparations (for example, a method described in the Japanese Pharmacopoeia. A pharmaceutical comprising Compound (I) may be safely administered orally or non-orally (intravenous, intramuscular, subcutaneous, intraorgan, intranasal, intradermal, instillation, intracerebral, intrarectal, intravaginal, intraperitoneal, or lesion administration or the like), for example, as a tablet (including sugar-coated tablets, film-coated tablets, sublingual tablets, orally disintegrating tablets, buccal tablets, and the like), a pill, a powdered drug, granules, a capsule (including soft capsules and microcapsules), a lozenge, a syrup, a liquid preparation, an emulsion, a suspension, a controlled-release formulation (for example, a rapid-release preparation, a sustained-release preparation, or a sustained-release microcapsule), an aerosol agent, a film agent (for example, an orally disintegrating film or an oral mucosal film), an injection (for example, a subcutaneous injection, an intravenous injection, an intramuscular injection, or an intraperitoneal injection), intravenous drip, a percutaneous absorption type preparation, an ointment, a lotion, a patch, a suppository (for example, a rectal suppository or a vaginal suppository), a pellet, a transnasal agent, a transpulmonary agent (inhalant), an ophthalmic solution, or the like.

Various organic or inorganic carriers commonly used as starting materials for preparations may be used as the "pharmaceutically acceptable carrier" described above. For example, in solid preparations, excipients, lubricants, binders, disintegrators, and the like may be used, and in liquid preparations, solvents, dissolution aids, suspending agents, isotonizing agents, buffers, analgesics, and the like may be used. In addition, additives for preparations such as preservatives, antioxidants, colorants, and sweeteners can also be used as necessary.

Examples of excipients include lactose, sucrose, D-mannitol, starch, corn starch, crystalline cellulose, and light silicic anhydride.

Non-limiting examples of lubricants include magnesium stearate, calcium stearate, talc, and colloidal silica.

Non-limiting examples of binders include crystalline cellulose, sucrose, D-mannitol, dextrin, hydroxypropylcellulose, hydroxypropylmethylcellulose, polyvinylpyrrolidone, starch, saccharose, gelatin, methylcellulose, and sodium carboxymethylcellulose.

Non-limiting examples of disintegrants include starch, carboxymethylcellulose, carboxymethylcellulose calcium, sodium carboxymethyl starch, and L-hydroxypropylcellulose.

Non-limiting examples of solvents include water for injection, alcohol, propylene glycol, macrogol, sesame oil, corn oil, and olive oil.

Non-limiting examples of dissolution aids include polyethylene glycol, propylene glycol, D-mannitol, benzyl benzoate, ethanol, trisaminomethane, cholesterol, triethanolamine, sodium carbonate, and sodium citrate.

Non-limiting examples of suspending agents include surfactants such as stearyltriethanolamine, sodium lauryl sulfate, lauryl aminopropionate, lecithin, benzalkonium chloride, benzethonium chloride, and glycerol monostearate; and hydrophilic polymers such as polyvinyl alcohol, polyvinylpyrrolidone, sodium carboxymethylcellulose, methylcellulose, hydroxymethylcellulose, hydroxyethylcellulose, and hydroxypropylcellulose.

Non-limiting examples of isotonizing agents include glucose, D-sorbitol, sodium chloride, glycerin, and D-mannitol.

Non-limiting examples of buffers include buffer solutions such as phosphate, acetate, carbonate, and citrate.

Non-limiting examples of analgesics include benzyl alcohol and the like.

Non-limiting examples of preservatives include paraoxybenzoate esters, chlorobutanol, benzyl alcohol, phenethyl alcohol, dehydroacetic acid, and sorbic acid.

Non-limiting examples of antioxidants include sulfite, ascorbic acid, and α-tocopherol.

Although differing depending on the dosage form, in some embodiments, the administration method, the carrier, and the like, the pharmaceutical composition may be produced in accordance with a conventional method by adding Compound (I) at a ratio of, for example, 0.01 to 100% (w/w), for example, 0.1 to 95% (w/w) with respect to the total amount of the pharmaceutical composition.

Compound (I) may also be used in combination with other active ingredients (referred to as combination drugs herein).

Non-limiting examples of combination drugs include acetylcholinesterase inhibitors (for example, donepezil, rivastigmine, galanthamine, and zanapezil), β-amyloid protein production, secretion, accumulation, aggregation and/or deposition inhibitors, β-secretase inhibitors (for example, 6-(4-biphenylyl)methoxy-2-[2-(N,N-dimethylamino)ethyl]tetralin, 6-(4-biphenylyl)methoxy-2-(N,N-dimethylamino)methyltetralin, 6-(4-biphenylyl)methoxy-2-(N,N-dipropylamino)methyltetralin, 2-(N,N-dimethylamino)methyl-6-(4'-methoxybiphenyl-4-yl)methoxytetralin, 6-(4-biphenylyl)methoxy-2-[2-(N,N-diethylamino)ethyl]tetralin, 2-[2-(N,N-dimethylamino)ethyl]-6-(4'-methylbiphenyl-4-yl)methoxytetralin, 2-[2-(N,N-dimethylamino)ethyl]-6-(4'-methoxybiphenyl-4-yl)methoxytetralin, 6-(2',4'-dimethoxybiphenyl-4-yl)methoxy-2-[2-(N,N-dimethylamino)ethyl]tetralin, 6-[4-(1,3-benzodioxole-5-yl)phenyl]methoxy-2-[2-(N,N-dimethylamino)ethyl]tetralin, and 6-(3',4'-dimethoxyphenyl-4-yl)methoxy-2-[2-(N,N-dimethylamino)ethyl]tetralin, optically active substances thereof, salts thereof, hydrates thereof, and OM99-2 (WO 01/00663)), γ-selectase inhibitors, β-amyloid protein aggregation inhibitors (for example, PTI-00703, Tramiprosate, PPI-368 (Japanese Translation of PCT Application No. H11-514333), PPI-558 (Japanese Translation of PCT Application No. 2001-500852), SKF-74652 (2-(4-Methoxyphenyl)-3-[4-[3-(diethylamino)propoxy]benzoyl]-5-chlorobenzofuran, Biochem. J. (1999), 340(1), 283-289)), β-amyloid vaccines, β-amyloid degrading enzymes and the like, brain function enhancers (for example, aniracetam and nicergoline), other Parkinson's disease medicines [(for example, dopamine receptor agonists (for example, L-dopers, bromocriptine, pergolide, talipexole, pramipexole, cabergoline, and amantadine), monoamine oxidase (MAO) inhibitors (for example, deprenyl, selegiline (selegiline), remacemide, and riluzole), anticholinergic agents (for example, trihexyphenidyl and biperiden), and COMT inhibitors (for example, entacapone)], amyotrophic lateral sclerosis therapeutics (for example, riluzole and neurotrophic factor), medicines for abnormal behavior, wandering, or the like accompanying the progression of dementia (for example, sedatives and anxiolytics), apoptosis inhibitors (for example, CPI-1189, Emricasan, CEP-1347), neuronal differentiation/regeneration promoters (for example, leteprinim, Xaliproden (SR-57746-A), SB-216763, Y-128, VX-853, prosaptide, 5,6-methoxy-2-[2,2,4,6,7-pentamethyl-3-(4-methylphenyl)-2,3-dihydro-1-benzofuran-5-yl]isoindoline, 5,6-dimethoxy-2-[3-(4-isopropylphenyl)-2,2,4,6,7-pentamethyl-2,3-dihydro-1-benzofuran-5-yl]isoindoline, 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole, and optically active substances, salts, and hydrates thereof), nonsteroidal anti-inflammatory drugs (meloxicam, tenoxicam, indomethacin, ibuprofen, celecoxib, rofecoxib, aspirin, indomethacin, and the like), steroids (dexamethasone, hexestrol, cortisone acetate, and the like), disease-modifying antirheumatic drugs (DMARDs), anti-cytokine drugs (for example, TNF inhibitors and MAP kinase inhibitors), pollakiuria and urinary incontinence medicines (for example, flavoxate hydrochloride, oxybutynn hydrochloride, and propiverine hydrochloride), phosphodiesterase inhibitors (for example, sildenafil (citrate)), dopaminergic drugs (for example, apomorphine), antiarrhythmic drugs (for example, mexiletine), sex hormones or derivatives thereof (for example, progesterone, estradiol, and estradiol benzoate), osteoporosis medicines (for example, alfacalcidol, calcitriol, elcatonin, salmon calcitonin, estriol, iprivlavone, pamidronate disodium, alendronate sodium hydrate, and incadronate disodium), parathyroid hormone (PTH), calcium receptor antagonists, insomnia medicines (for example, benzodiazepine-based drugs, non-benzodiazepine-based drugs, melatonin agonists, and orexin receptor antagonists), schizophrenia medicines (for example, typical antipsychotics such as haloperidol; atypical antipsychotics such as clozapine, olanzapine, risperidone, and aripiprazole; drugs which affect metabotropic glutamate receptors or ion channel conjugate-type glutamate receptors; and phosphodiesterase inhibitors), benzodiazepin-based drugs (chlordiazepoxide, diazepam, potassium clorazepate, lorazepam, clonazepam, alprazolam, and the like), L-type calcium channel inhibitors (pregabalin and the like), tricyclic or tetracyclic antidepressants (imipramine hydrochloride, amitriptyline hydrochloride, desipramine hydrochloride, clomipramine hydrochloride, and the like), selective serotonin reuptake inhibitors (fluvoxamine maleate, fluoxetine hydrochloride, citalopram hydrobromide, sertraline hydrochloride, paraxetine hydrochloride, escitalopram oxalate, and the like), serotonin and norepinephrine reuptake inhibitors (venlafaxine hydrochloride, duloxetine hydrochloride, desvenlafacine hydrochloride, and the like), noradrenaline reuptake inhibitors (reboxetine mesylate and the like), mirtazapine, trazodone hydrochloride, nefazodone hydrochloride, bupropion hydrochloride, setiptiline maleate, 5-HT2A antagonists (for example, pimavanserin tartrate), 5-HT2A inverse agonists, 5-HT3 antagonists (cyamemazine and the like), non-heart-selective p inhibitors (propranolol hydrochloride, oxiprenolol hydrochloride, and the like), histamine H1 antagonists (hydroxyzine hydrochloride and the like), schizophrenia medicines (chlorpromazine, haloperidol, sulpiride, clozapine, trifluoperazine hydrochloride, fluphenazine hydrochloride, olanzapine, quetiapine fumarate, risperidone, aripiprazole, and the like), CRF antagonists, other antianxiety drugs (meprobamate and the like), tachykinin antagonists (aprepitant, saredutant, and the like), drugs which affect metabotropic glutamate receptors, drugs which affect GABA receptors, drugs which affect acetylcholine receptors, CCK antagonists, β3-adrenaline antagonists (amibegron and the like), GAT-1 inhibitors (tiagabine hydrochloride and the like), N-type calcium channel inhibitors, type-2 carbonate dehydrase inhibitors, NMDA glycine site agonists, NMDA antagonists (ketamine, S-ketamine, R-ketamine, ketamine metabolites (for example, (2S,6S;2R,6R)-hydroxynorketamine, (2R,6R)-hydroxynorketamine, and the like), memantine, and the like), peripheral benzodiazepine receptor agonists, vasopressin antagonists, vasopressin V1b antagonists, vasopressin V1a antagonists, phosphodiesterase inhibitors, opioid inhibitors, opioid agonists, uridine, nicotinic acid agonists, thyroid hormones (T3 and T4), TSH, TRH, MAO inhibitors (phenylzine sulfate, tranylcypromine sulfate, moclobemide, and the like), bipolar disorder medicines (lithium carbonate, sodium valproate, lamotrigine, riluzole, felbamate, and the like), cannabinoid CB1 antagonists (rimonabant and the like), FAAH inhibitors, sodium channel inhibitors, anti-ADHD drugs (methylphenidate hydrochloride, methamphetamine hydrochloride, and the like), alcohol dependence medicines, autism medicines, chronic fatigue syndrome medicines, seizure medicines, fibromyalgia medicines, headache medicines, medicines for quitting smoking, myasthenia gravis medicines, cerebral infarction medicines, mania medicines, hypersomnia medicines, pain medicines, dysthymia medicines, autonomic ataxia medicines, male and female sexual dysfunction medicines, migraine medicines, pathological gambling medicines, restless legs syndrome medicines, substance dependence medicines, alcohol-related disease medicines, irritable bowel syndrome medicines, dyslipidemia medicines such as hypocholesterolemic drugs (statin series (pravastatin sodium, atorvastatin, simvastatin, rosuvastatin, and the like), fibrates (clofibrate and the like), and squalene synthesis inhibitors), abnormal behavior medicines or drugs for suppressing dementia-induced wandering (sedatives, antianxiety drugs, and the like), anti-obesity drugs, antidiabetic drugs, diabetic complication medicines, antihypertensive drugs, antihypotensive drugs, diuretics, chemotherapeutic agents, immune modifiers, antithrombotic agents, anticancer agents, and the like.

Two or more types of the combination drugs described above may also be used in combinations at appropriate ratios.

Further, when using a compound of the present disclosure to treat or prevent one or more of the diseases described above, the compound or pharmaceutically acceptable salt can also be used in combination with biologics (for example, antibody drugs, nucleic acids (for example, antisense oligonucleotide, siRNA, decoys, and the like) or nucleic acid derivatives, aptamer drugs, peptide drugs, and vaccine preparations). Additionally, the compound or pharmaceutically acceptable salt may also be used in combination with gene therapy or the like or used in combination with treatments employed in psychiatric cases in which drugs are not used.

Non-limiting examples of antibody drugs and vaccine preparations include vaccine preparations for angiotensin IL, vaccine preparations for CETP, CETP antibodies, TNFα antibodies and antibodies against other cytokines, amyloid β vaccine preparations, type I diabetes vaccines (for example, DIAPEP-277 available from Peptor), anti-HIV antibodies or HIV vaccine preparations, antibodies or vaccine preparations for cytokines, renin/angiotensin enzymes or products thereof, antibodies or vaccine preparations for enzymes or proteins involved in lipid metabolism in blood, antibodies or vaccines related to enzymes or proteins involved in the blood congealing fibrinogenolysis system, and antibodies or vaccine preparations for proteins involved in carbohydrate metabolism or insulin resistance. In addition, Compound (I) may also be used in combination with biologics related to growth factors such as GH or IGF.

Non-limiting examples of gene therapies include therapies using genes related to cytokines, renin/angiotensin enzymes and products thereof, G-proteins, and G-protein coupled receptors and phosphoric acid enzymes thereof, therapies using DNA decoys such as NFκB decoys, therapies using antisense, therapies using genes related to enzymes or proteins involved in lipid metabolism in blood (for example, genes related to the metabolism, excretion, and absorption of cholesterol, triglyceride, HDL cholesterol, or phospholipids in blood), therapies using genes related to enzymes or proteins involved in angiogenic therapy for peripheral vascular disease or the like (for example, growth factors such as HGF and VEGF), therapies using genes related to proteins involved in carbohydrate metabolism or insulin resistance, and gene therapies using antisense for cytokines such as TNF, virus vectors (for example, adenovirus, lentivirus, adeno-associated virus, retrovirus, vaccinia virus, herpes virus, human papillomavirus, Sendai virus, and the like), or non-virus vectors (for example, plasmids, lipid particles, and the like).

Non-limiting examples of treatments employed in psychiatric cases that do not use drugs include psychotherapies including modified electroconvulsive therapy, deep brain stimulation, repetitive transcranial magnetic stimulation, and cognitive behavior therapy.

In addition, a compound of the present disclosure can be used in combination with various organ regeneration methods such as heart regeneration, kidney regeneration, pancreas regeneration, and blood vessel regeneration, cell transplantation therapy utilizing bone marrow cells (marrow monocytes and marrow stem cells), or artificial organs utilizing tissue engineering (for example, artificial blood vessels and myocardial cell sheets), each of which uses internal or external cells (including genetic modification).

In some embodiments, combining compound (I) with a combination drug may enable one or more of the following outcomes:

(1) the dose can be reduced in comparison to cases in which Compound (I) or the combination drug is administered alone;

(2) a drug to be used in combination with Compound (I) can be chosen in accordance with the symptoms (mild symptoms, severe symptoms, or the like) of the patient;

(3) a long treatment period can be established by selecting a combination drug with a different mechanism of action than that of Compound (I);

(4) therapeutic effects can be maintained by selecting a combination drug with a different mechanism of action than that of Compound (I); and (5) a synergistic effect can be achieved by using Compound (I) in combination with the combination drug.

The use of Compound (I) and a combination drug in combination will be referred to as the "combination agent of the present disclosure".

When using the combination agent of the present disclosure, the administration periods of Compound (I) and the combination drug are not limited, and Compound (I) or a pharmaceutical composition thereof and the combination drug or a pharmaceutical composition thereof may be administered to the subject simultaneously or at different times. The dose of the combination drug need only conform to a dose that is used clinically and may be chosen appropriately based on the subject, the administration route, the disease, the combination, or the like.

The administration form of the combination agent of the present disclosure is not limited as long as Compound (I) and the combination drug are combined at the time of administration. Non-limiting examples of such administration forms include: (1) administration of a single preparation obtained by formulating Compound (I) and the combination drug simultaneously; (2) simultaneous administration of two types of preparations obtained by separately formulating Compound (I) and the combination drug for the same administration route; (3) administration of two types of preparations obtained by separately formulating Compound (I) and the combination drug for the same administration route at different times; (4) simultaneous administration of two types of preparations obtained by separately formulating Compound (I) and the combination drug for different administration routes; and (5) administration of two types of preparations obtained by separately formulating Compound (I) and the combination drug for different administration routes at different times (for example, administration in the order of Compound (I) followed by the combination drug, or administration in the reverse order).

In some embodiments, the combination agent of the present disclosure has low toxicity, and Compound (I) and/or the combination drug described above can be mixed with at least one pharmaceutically acceptable carrier in accordance with a known method and safely administered orally or non-orally (for example, via topical, rectal, or intravenous administration) as a pharmaceutical composition, for example, a tablet (for example, sugar-coated tablets and film-coated tablets), a powdered drug, granules, a capsule (for example, soft capsules), a liquid preparation, an injection, a suppository, a sustained-release preparation, or the like. An injection can be administered by intravenous, intramuscular, subcutaneous or intraorgan administration or administered directly into the lesion.

Non-limiting examples of pharmaceutically acceptable carriers that may be used in the production of the combination agent of the present disclosure include those described above.

The blending ratio of Compound (I) and the combination drug in the combination agent of the present disclosure can be chosen appropriately based on the subject, the administration route, the disease, and the like.

For example, although the content of Compound (I) in the combination agent of the present disclosure differs depending on the form of the preparation, in some embodiments, the content is around 0.01 to 100 wt. %, for example, around 0.1 to 50 wt. %, for example, around 0.5 to 20 wt. % with respect to the entire preparation.

Although the content of the combination drug in the combination agent of the present disclosure varies based on the form of the preparation, the content is ordinarily around 0.01 to 100 wt. %, for example, around 0.1 to 50 wt. %, for example, around 0.5 to 20 wt. % with respect to the entire preparation.

EXAMPLES

The present disclosure will be described in further detail hereinafter using examples, test examples, and formulation examples. However, these examples, test examples, and formulation examples do not limit the present disclosure and may be modified without departing from the scope of the present disclosure.

"Room temperature" in the examples below ordinarily refers to a temperature between about 10° C. and about 35° C. Unless specified otherwise, the ratio indicated in a mixed solvent refers to the volume ratio. Additionally, unless specified otherwise, % refers to wt. %.

Unless specified otherwise, elution in column chromatography in the examples was performed under observation by Thin Layer Chromatography (TLC). In TLC observations, 60 $F_{254}$ available from Merck was used as a TLC plate, and the solvent used as an eluting solvent in column chromatography was used as a developing solvent. In addition, a UV detector was used for detection. In silica gel column chromatography, an aminopropylsilane-bonded silica gel was used when indicated as NH, and a 3-(2,3-dihydroxypropoxy)propylsilane-bonded silica gel was used when indicated as Diol. In preparative high-performance liquid chromatography (HPLC), an octadecyl-bonded silica gel was used when indicated as C18. Unless specified otherwise, the ratio indicated in an eluting solvent refers to the volume ratio.

ADC/SpecManager software or the like was used for $^1$H NMR analysis. Subtle proton peaks of hydroxyl groups, amino groups, or the like may not be noted.

MS was measured by LC/MS. An ESI method or an APCI method was used as an ionization method. Data indicates actual measurements (found). Molecular ion peaks are ordinarily observed, but data may also be observed as fragment ions. In the case of a salt, a molecular ion peak or fragment ion peak of the free form is observed.

The unit of sample concentration (c) in the optical rotation ($[\alpha]_D$) is g/100 mL.

Elemental analysis values (Anal.) are indicated as calculated values (Calcd) and actual measurements (Found).

Peaks according to powder X-ray diffraction in the examples refer to peaks measured at room temperature with ULtima IV (Rigaku Corporation, Japan) using CuKα rays as a radiation source. The measurement conditions were as follows.

Electric pressure/Electric current: 40 kV/50 mA

Scan speed: 6 degree/min

Scan range of 2 Theta: 2-35 degrees

The degree of crystallization according to powder X-ray diffraction in the examples was calculated by Hermans method.

The following abbreviations are used in the examples below.

mp: melting point
MS: mass spectrum
M: molar concentration
N: normality
$CDCl_3$: heavy chloroform
DMSO-$d_6$: heavy dimethylsulfoxide
$^1$H NMR: proton nuclear magnetic resonance
LC/MS: liquid chromatography-mass spectrometry
ESI: electrospray ionization
APCI: atmospheric pressure chemical ionization
$CH_3CN$: acetonitrile
DIPEA: diisopropylethylamine
NBS: N-bromosuccinimide
BINAP: 2,2'-bis(diphenylphosphino)-1,1'-binaphthyl
TFA: trifluoroacetic acid
THF: tetrahydrofuran
DMSO: dimethylsulfoxide
DME: 1,2-dimethoxyethane DMF: N,N-dimethylformamide
$Pd_2(dba)_3$: tris(dibenzylideneacetone)dipalladium (0)
$Pd(dba)_2$: bis(dibenzylideneacetone)palladium (0)
$PdCl_2(dppf)$: dichloro(1,1'-bis(diphenylphosphino)ferrocene)palladium
TEA: triethylamine
DPPA: diphenylphosphoryl azide
DEAD: diethyl azodicarboxylate
MeOH: methanol
$PPh_3$: triphenylphosphine
EtOH: ethanol
$NaBH_4$: sodium borohydride
TBAF: tetrabutylammonium fluoride
NFSI: N-fluorobenzenesulfonimide

Example 1

1-[(1-Ethyl-1H-pyrazole-4-yl)methyl]-3-[4'-fluoro-5-(trifluoromethyl)[1,1'-biphenyl]-3-yl]-1,3-dihydro-2H-imidazole-2-one

A) 4'-Fluoro-5-(trifluoromethyl)-[1,1'-biphenyl]-3-amine

Potassium carbonate (1.73 g) and $PdCl_2$ (dppf) (0.457 g) were added to a mixture of (4-fluorophenyl)boronic acid (1.84 g) and 3-bromo-5-trifluoromethyl)aniline (3.00 g) at room temperature and stirred overnight at 80° C. in a nitrogen atmosphere. The mixture was diluted with ethyl acetate and added to water at room temperature. After the organic layer was separated and washed with water and a saturated saline solution, it was dried with anhydrous sodium sulfate and concentrated under reduced pressure. The residue was purified by silica gel column chromatography (NH, ethyl acetate/hexane). After the resulting solid was washed with diisopropyl ether, it was dried under reduced pressure to obtain the title compound (3.45 g).

$^1$H NMR (300 MHz, $CDCl_3$) S 3.93 (2H, brs), 6.88 (1H, s), 6.97 (1H, s), 7.06-7.18 3H, m), 7.46-7.56 (2H, m).

B) 1-[4'-Fluoro-5-(trifluoromethyl)[1,1'-biphenyl]-3-yl]-1,3-dihydro-2H-imidazole-2-one Bis(trichloromethyl) carbonate (370 mg) and TEA (378 mg) were added to a toluene solution (10 mL) of 4'-fluoro-5-(trifluoromethyl)-[1,1'-biphenyl]-3-amine (636 mg) at room temperature. The mixture was stirred overnight. Next, 2,2-dimethoxyethylamine (0.266 mL) was added to the mixture at room temperature. After the mixture was stirred for one hour at room temperature, it was concentrated at reduced pressure. The residue was diluted with $CH_3CN$ (5.0 mL), and water (1.0 mL) and trifluoroacetic acid (1.0 mL) were added at room temperature. The mixture was stirred for five hours at 60° C. The mixture was diluted with ethyl acetate and added to water at room temperature. After the organic layer was separated and washed with a saturated sodium bicarbonate aqueous solution and a saturated saline solution, it was dried with anhydrous sodium sulfate and concentrated under reduced pressure. The residue was purified by silica gel column chromatography (ethyl acetate/hexane). After the resulting solid was washed with diisopropyl ether, it was dried under reduced pressure to obtain the target compound (245 mg).

MS: $[M+H]^+$ 309.2.

C) 1-[(1-Ethyl-1H-pyrazole-4-yl)methyl]-3-[4'-fluoro-5-(trifluoromethyl)[1,1'-biphenyl]-3-yl]-1,3-dihydro-2H-imidazole-2-one First, 1-[4'-fluoro-5-(trifluoromethyl)[1,1'-biphenyl]-3-yl]-1,3-dihydro-2H-imidazole-2-one (40 mg) was added to a DMF (0.5 mL) suspension of sodium hydride (60% content, 12.4 mg) at room temperature. The mixture was stirred for ten minutes at room temperature. A DMF (0.30 mL) solution of 4-(chloromethyl)-1-ethyl-1H-pyrazole (26.9 mg) was dropped into the mixture at room temperature. The mixture was stirred overnight at room temperature. The mixture was diluted with ethyl acetate and added to water at room temperature. After the organic layer was separated and washed with water and a saturated saline solution, it was dried with anhydrous sodium sulfate and concentrated under reduced pressure. The residue was purified by silica gel column chromatography (ethyl acetate/hexane) to obtain the title compound (13 mg).

$^1$H NMR (300 MHz, $CDCl_3$) δ 1.48 (3H, t, J=7.3 Hz), 4.09-4.21 (2H, m), 4.74 (2H, s), 6.38 (1H, d, J=3.0 Hz), 6.64 (1H, d, J=3.0 Hz), 7.16 (2H, t, J=8.7 Hz), 7.49 (2H, d, J=10.5 Hz), 7.54-7.68 (3H, m), 7.78 (1H, s), 8.07-8.20 (1H, m).

Example 2

1-[(1-Ethyl-1H-pyrazole-4-yl)methyl]-3-{2-fluoro-5-[(2R)-2-methylmorpholine-4-yl]-3-(trifluoromethyl)phenyl}-1,3-dihydro-2H-imidazole-2-one

A) (2R)-4-[4-Fluoro-3-nitro-5-(trifluoromethyl)phenyl]-2-methylmorpholine

A mixture of 5-bromo-2-fluoro-1-nitro-3-(trifluoromethyl)benzene (5.00 g), (2R)-2-methylmorpholine hydrochloride (2.39 g), BINAP (1.08 g), palladium (II) acetate (0.390 g), cesium carbonate (17.0 g), and toluene (40 mL) was stirred for 16 hours at 100° C. in a nitrogen atmosphere. The insoluble matter was filtered out with Celite®, and the filtrate was distilled out under reduced pressure. The residue was purified by silica gel column chromatography (NH, ethyl acetate/hexane) to obtain the title compound (1.85 g).

MS: $[M+H]^+$ 309.2.

B) 2-Fluoro-5-[(2R)-2-methylmorpholine-4-yl]-3-(trifluoromethyl)aniline

A mixture of (2R)-4-[4-fluoro-3-nitro-5-(trifluoromethyl)phenyl]-2-methylmorpholine (1.85 g), 10% palladium-carbon (0.319 g), and EtOH (60 mL) was stirred for two hours at room temperature in a hydrogen atmosphere at normal pressure. The catalyst was filtered out, and the filtrate was concentrated under reduced pressure. The residue was purified by silica gel column chromatography (NH, ethyl acetate/hexane) to obtain the title compound (1.67 g).

MS: $[M+H]^+$ 279.2.

C) N-(2,2-Dimethoxyethyl)-N'-{2-fluoro-5-[(2R)-2-methylmorpholine-4-yl]-3-(trifluoromethyl)phenyl}urea Bis(trichloromethyl) carbonate (0.571 g) was added to a mixture of 2-fluoro-5-[(2R)-2-methylmorpholine-4-yl]-3-(trifluoromethyl)aniline (1.07 g) and THF (30 mL) at 0° C., and the mixture was stirred for four hours at room temperature. Next, 2,2-dimethoxyethaneamine (0.404 g) and TEA (0.389 g) were added to the mixture and stirred overnight at room temperature. Water was added to the mixture, which was then extracted with ethyl acetate. After the organic layer was separated and washed with water and a saturated saline solution, it was dried with anhydrous sodium sulfate and concentrated under reduced pressure. The residue was purified by silica gel column chromatography (NH, ethyl acetate/hexane) to obtain the title compound (1.25 g).

MS: $[M+H]^+$ 410.1.

D) 1-{2-Fluoro-5-[(2R)-2-methylmorpholine-4-yl]-3-(trifluoromethyl)phenyl}-1,3-dihydro-2H-imidazole-2-one TFA (15.4 g) was added to a mixture of N-(2,2-dimethoxyethyl)-N'-{2-fluoro-5-[(2R)-2-methylmorpholine-4-yl]-3-(trifluoromethyl)phenyl}urea (1.25 g), $CH_3CN$ (20 mL), and water (mL). After the mixture was stirred for three hours at 60° C., the reaction mixture was concentrated. The residue was purified by silica gel column chromatography (ethyl acetate/hexane) to obtain the title compound (722 mg).

MS: $[M+H]^+$ 346.2.

E) Ethyl 1-ethyl-1H-pyrazole-4-carboxylate

A mixture of potassium carbonate (197 g), ethyl 1H-pyrazole-4-carboxylate (100 g), ethyl iodide (122 g), and DMF (250 mL) was stirred overnight at room temperature. The mixture was added to water at room temperature and extracted with ethyl acetate. After the organic layer was separated and washed with water and a saturated saline solution, it was dried with anhydrous magnesium sulfate and concentrated under reduced pressure to obtain the title compound (121 g).

$^1$H NMR (300 MHz, DMSO-$d_6$) δ 1.26 (3H, t, J=7.2 Hz), 1.37 (3H, t, J=7.2 Hz), 4.19 (4H, m), 7.84 (1H, s), 8.33 (1H, s).

F) (1-Ethyl-1H-pyrazole-4-yl)methanol

A mixture of ethyl 1-ethyl-1H-pyrazole-4-carboxylate (48.0 g) and THF (100 mL) was added to a mixture of lithium aluminum hydride (16.3 g) and THF (400 mL) at 0-10° C., and the mixture was stirred for one hour at room temperature. After the mixture was diluted with THF (150 mL) and cooled to 0° C., sodium sulfate decahydrate (110 g) was added at 0-10° C. and stirred for one hour at room temperature. Impurities were filtered out, and the filtrate was distilled out under reduced pressure to obtain the title compound (29.9 g).

$^1$H NMR (300 MHz, DMSO-$d_6$) δ 1.33 (3H, t, J=7.3 Hz), 4.07 (2H, q, J=7.2 Hz), 4.32 (2H, d, J=5.3 Hz), 4.77 (1H, t, J=5.5 Hz), 7.32 (1H, s), 7.59 (1H, s)

G) 4-(Chloromethyl)-1-ethyl-1H-pyrazole hydrochloride

Thionyl chloride (4.39 g) was added to a mixture of (1-ethyl-1H-pyrazole-4-yl)methanol (2.33 g) and $CH_3$ (20 mL) at room temperature, and the mixture was stirred overnight at the same temperature. The mixture was concentrated to obtain the title compound (3.23 g).

$^1$H NMR (300 MHz, DMSO-$d_6$) δ 1.34 (3H, t, J=7.2 Hz), 4.10 (2H, q, J=7.4 Hz), 4.69 (2H, s), 7.50 (OH, s), 7.85 (OH, s), 12.32 (1H, bs).

H) 1-[(1-Ethyl-1H-pyrazole-4-yl)methyl]-3-{2-fluoro-5-[(2R)-2-methylmorpholine-4-yl]-3-(trifluoromethyl)phenyl}-1,3-dihydro-2H-imidazole-2-one First, 1-{2-fluoro-5-[(2R)-2-methylmorpholine-4-yl]-3-(trifluoromethyl)phenyl}-1,3-dihydro-2H-imidazole-2-one (100 mg) was added to a mixture of sodium hydride (60% content, 29.0 mg) and DMF (3 mL) at room temperature. After the mixture was stirred for 30 minutes at room temperature, a mixture of 4-(chloromethyl)-1-ethyl-1H-pyrazole hydrochloride (79 mg) and DMF (2 mL) and sodium iodide (43.4 mg) were added and stirred overnight at room temperature. Water was added to the mixture, which was then extracted with ethyl acetate. After the organic layer was separated and washed with water and a saturated saline solution, it was dried with anhydrous sodium sulfate and concentrated under reduced pressure. The residue was purified by silica gel column chromatography (NH, ethyl acetate/hexane) to obtain the title compound (70.0 mg).

$^1$H NMR (300 MHz, DMSO-$d_6$) δ 1.14 (3H, d, J=6.0 Hz), 1.34 (3H, t, J=7.2 Hz), 2.27-2.47 (OH, m), 2.63-2.74 (OH, m), 3.52-3.73 (4H, m), 3.86-3.95 (OH, m), 4.09 (2H, q, J=7.3 Hz), 4.61 (2H, s), 6.74-6.79 (2H, m), 7.19 (1H, dd, J=4.9, 3.4 Hz), 7.34 (1H, dd, J=6.0, 3.0 Hz), 7.43 (1H, s), 7.73 (1H, s).

Example 18

1-[(1-Ethyl-1H-pyrazole-4-yl)methyl]-4-methyl-3-{6-[(2R)-2-methylmorpholine-4-yl]-4-(trifluoromethyl)pyridine-2-yl}-1,3-dihydro-2H-imidazole-2-one A) N-[(1-Ethyl-1H-pyrazole-4-yl)methyl]prop-2-yne-1-amine Prop-2-yne-1-amine (0.928 mL) was added to a mixture of 1-ethyl-1H-pyrazole-4-carbaldehyde (1.20 g) and toluene (10 mL), and the mixture was heat-refluxed for two hours. After the mixture was cooled, the mixture was added to a mixture of $NaBH_4$ (0.366 g) and MeOH (10 mL) at 0° C. and stirred for one hour at the same temperature. The mixture was concentrated under reduced pressure, and the residue was purified by silica gel column chromatography (NH, ethyl acetate/hexane) to obtain the title compound (1.21 g).

$^1$H NMR (300 MHz, DMSO-$d_6$) δ 1.33 (3H, t, J=7.3 Hz), 2.09-2.22 (1H, m), 3.06 (1H, t, J=2.4 Hz), 3.26 (2H, d, J=2.6 Hz), 3.57 (2H, s), 4.06 (2H, q, J=7.2 Hz), 7.30 (1H, s), 7.57 (1H, s).

B) (2R)-4-[6-Chloro-4-(trifluoromethyl)pyridine-2-yl]-2-methylmorpholine

A mixture of 2,6-dichloro-4-(trifluoromethyl)pyridine (140 g), potassium carbonate (224 g), (2R)-2-methylmorpholine hydrochloride (94.0 g), and DMSO (1400 mL) was stirred for five hours at 100° C. After the mixture was cooled to room temperature, the mixture was diluted with water and stirred for 30 minutes at room temperature. After the solid that was generated was filtered out, it was dried under reduced pressure to obtain the title compound (180 g).

MS: $[M+H]^+$ 281.0.

C) 6-[(2R)-Methylmorpholine-4-yl]-4-(trifluoromethyl)pyridine-2-amine

A mixture of (2R)-4-[6-chloro-4-(trifluoromethyl)pyridine-2-yl]-2-methylmorpholine (800 mg), diphenylmethanimine (0.622 mL), Pd $(dba)_2$ (246 mg), BINAP (355 mg), sodium tert-butoxide (411 mg), and toluene (13 mL) was heated for one hour at 140° C. under microwave irradiation, and methanol (10 mL) and 1 N hydrochloric acid (10 mL) were added. The mixture was stirred for 30 minutes at room temperature, and water was added and extracted with ethyl acetate. The organic layer was dried with magnesium sulfate and concentrated under reduced pressure. The residue was purified by silica gel column chromatography (NH, ethyl acetate/hexane) and then by silica gel column chromatography (ethyl acetate/hexane) to obtain the title compound (612 mg).

$^1$H NMR (300 MHz, DMSO-$d_6$) δ 1.13 (3H, d, J=6.0 Hz), 2.42 (1H, dd, J=12.8, 10.2 Hz), 2.74 (1H, td, J=12.3, 3.6 Hz), 3.41-3.61 (2H, in), 3.82-3.92 (1H, m), 3.96-4.17 (2H, m), 5.98 (1H, s), 6.08 (1H, s), 6.13 (2H, s).

D) N-[(1-Ethyl-1H-pyrazole-4-yl)methyl]-N'-{6-[(2R)-2-methylmorpholine-4-yl]-4-(trifluoromethyl)pyridine-2-yl}-N-prop-2-yne-1-ylurea TEA (0.107 mL) and bis(trichloromethyl) carbonate (114 mg) were added to a mixture of 6-[(2R)-Methylmorpholine-4-yl]-4-(trifluoromethyl)pyridine-2-amine (200 mg) and THF (3 mL) at 0° C. and stirred for two hours at room temperature. A mixture of N-[(1-ethyl-1H-pyrazole-4-yl)methyl]prop-2-yne-1-amine (214 mg) and THF (2 mL) and TEA (0.107 mL) were added to the mixture and stirred overnight at room temperature. Water was added to the mixture, which was then extracted with ethyl acetate. After the organic layer was separated and washed with water and a saturated saline solution, it was dried with anhydrous sodium sulfate and concentrated under reduced pressure. The residue was purified by silica gel column chromatography (ethyl acetate/hexane) to obtain the title compound (248 mg).

MS: $[M+H]^+$ 451.3.

H) 1-[(1-Ethyl-1H-pyrazole-4-yl)methyl]-4-methyl-3-{6-[(2R)-2-methylmorpholine-4-yl]-4-(trifluoromethyl)pyridine-2-yl}-1,3-dihydro-2H-imidazole-2-one A 1 M TBAF/THF solution (0.244 mL) was added to a mixture of N-[(1-ethyl-1H-pyrazole-4-yl)methyl]-N'-(6-[(2R)-2-methylmorpholine-4-yl]-4-(trifluoromethyl)pyridine-2-yl)-N-prop-2-yne-1-ylurea (100 mg) and THF (1 mL) at room temperature, and the mixture was stirred for 30 minutes at 80° C. in a sealed tube. After the mixture was cooled to room temperature, it was poured into a 2N hydrogen chloride/ethanol solution (1 mL), and the mixture was stirred for five minutes at room temperature. After the mixture was concentrated under reduced pressure, the residue was purified by silica gel column chromatography (NH, ethyl acetate/hexane) to obtain the title compound (74.6 g).

$^1$H NMR (300 MHz, DMSO-$d_6$) δ 1.13-1.17 (3H, m), 1.33 (3H, t, J=7.3 Hz), 2.16 (3H, d, J=1.1 Hz), 2.54-2.63 (1H, m), 2.90 (11H, td, J=12.4, 3.4 Hz), 3.47-3.60 (2H, m), 3.90 (1H, dd, J=11.5, 2.4 Hz), 4.06-4.21 (4H, m), 4.56 (2H, s), 6.44 (1H, d, J=1.1 Hz), 7.02 (1H, s), 7.29 (1H, s), 7.42 (1H, s), 7.72 (1H, s).

Example 30

3-[(1-Ethyl-1H-pyrazole-4-yl)methyl]-1-{3-fluoro-6-[(2R)-2-methylmorpholine-4-yl]-4-(trifluoromethyl)pyridine-2-yl}-1,3-dihydro-2H-imidazole-2-one A) N-[(1-Ethyl-1H-pyrazole-4-yl)methyl]-1,1-dimethoxypropane-2-amine First, 1,1-dimethoxypropane-2-amine (331 mg) was added to a mixture of 1-ethyl-1H-pyrazole-4-carbaldehyde (300 mg) and toluene (4 mL), and the mixture was heat-refluxed at 130° C. for two hours. After the mixture was cooled to room temperature, the mixture was added to a suspension of NaBH. (183 mg) and MeOH (4 mL) at 0° C. and stirred for 30 minutes at the same temperature. The mixture was purified by silica gel column chromatography (NH, ethyl acetate/hexane) to obtain the title compound (510 mg).

MS: $[M+H]^+$ 228.2.

B) (2R)-4-[6-Chloro-4-(trifluoromethyl)pyridine-2-yl]-2-methylmorpholine

A mixture of 2,6-dichloro-4-(trifluoromethyl)pyridine (140 g), potassium carbonate (224 g), (2R)-2-methylmorpholine hydrochloride (94.0 g), and DMSO (1400 mL) was stirred for five hours at 100° C. After the mixture was cooled to room temperature, the mixture was diluted with water and stirred for 30 minutes at room temperature. After the solid that was generated was filtered out, it was dried under reduced pressure to obtain the title compound (180 g).

C) (2R)-4-[6-Chloro-5-iodo-4-(trifluoromethyl)pyridine-2-yl]-2-methylmorpholine

A 2 M lithium diisopropylazanide solution (240 mL) was added to a mixture of (2R)-4-[6-chloro-4-(trifluoromethyl)pyridine-2-yl]-2-methylmorpholine (90.0 g) and THF (720 mL) at −60° C. in an argon atmosphere and stirred for 30 minutes at the same temperature. A mixture of iodine (122 g) and THF (180 mL) was added to the mixture at −60° C. and stirred for 30 minutes at the same temperature. The mixture was neutralized with 2 N hydrochloric acid and extracted with ethyl acetate. After the organic layer was separated and washed with water, a 20% sodium thiosulfate aqueous solution, and a saturated saline solution, it was dried with anhydrous magnesium sulfate and concentrated under reduced pressure. The resulting residue was washed with diisopropyl ether to obtain the title compound (101 g).

MS: $[M+H]^+$ 406.9.

D) 3-Fluoro-6-[(2R)-methylmorpholine-4-yl]-4-(trifluoromethyl)pyridine-2-amine

A 1.0 M isopropyl magnesium chloride-lithium chloride/THF solution (9.40 mL) was dropped into a mixture of (2R)-4-[6-chloro-5-iodo-4-(trifluoromethyl)pyridine-2-yl]-2-methylmorpholine (3.00 g) and THF (15 mL) at 0° C. in a nitrogen atmosphere and stirred for 40 minutes at the same temperature. The mixture was dropped into a mixture of NFSI (3.72 g), THF (12 ML), and heptane (6 mL) at 0° C. in a nitrogen atmosphere and stirred for 30 minutes at the same temperature. The mixture was neutralized with 2 N hydrochloric acid and extracted with ethyl acetate. After the organic layer was separated and washed with a saturated saline solution, it was dried with anhydrous magnesium sulfate and concentrated under reduced pressure. The residue was purified by silica gel column chromatography (NH, ethyl acetate/hexane). A mixture of the resulting oily substance, $Pd_2$ $(dba)_3$ (353 mg), BINAP (480 mg), diphenylmethanimine (0.84 mL), sodium tert-butoxide (555 mg), and toluene (13 mL) were irradiated with microwaves for one hour at 140° C. Next, MeOH (20 mL) and 2 N hydrochloric acid (20 mL) were added to the mixture at room temperature. After the mixture was stirred for 30 minutes at room temperature, water was added and extracted with ethyl acetate. The organic layer was separated, dried with anhydrous magnesium sulfate, and concentrated under reduced pressure. The residue was purified by silica gel column chromatography (NH, ethyl acetate/hexane) to obtain the title compound (370 mg).

MS: $[M+H]^+$ 280.1

E) N-(1,1-Dimethoxypropane-2-yl)-N-[(1-ethyl-1H-pyrazole-4-yl)methyl]-N'-{3-fluoro-6-[(2R)-2-methylmorpholine-4-yl]-4-(trifluoromethyl)pyridine-2-yl}urea Bis(trichloromethyl) carbonate (96.0 mg) was added to a mixture of 3-fluoro-6-[(2R)-methylmorpholine-4-yl]-4-(trifluoromethyl)pyridine-2-amine (167 mg), TEA (0.208 mL), and THF (3 mL) at 0° C. and stirred for 30 minutes at the same temperature. A mixture of N-[(1-ethyl-1H-pyrazole-4-yl)methyl]-1,1-dimethoxypropane-2-amine (163 mg), TEA (0.125 mL), and THF (2 mL) was added to the mixture at 0° C., heated to room temperature, and stirred for one hour at the same temperature. The mixture was purified by silica gel column chromatography (ethyl acetate/hexane) to obtain the title compound (170 mg).

MS: $[M+H]^+$ 533.2.

H) 1-[(1-Ethyl-1H-pyrazole-4-yl)methyl]-3-{2-fluoro-5-[(2R)-2-methylmorpholine-4-yl]-4-(trifluoromethyl)pyridine-2-yl}4-methyl-1,3-dihydro-2H-imidazole-2-one TFA (1.5 mL) was added to a mixture of N-(1,1-dimethoxypropane-2-yl)-N-[(1-ethyl-1H-pyrazole-4-yl)methyl]-N'-{3-fluoro-6-[(2R)-2-methylmorpholine-4-yl]-4-(trifluoromethyl)pyridine-2-yl}urea (171 mg), $CH_3CN$ (5 mL), and water (1 mL), and the mixture was stirred for 1.5 hours at 60° C. After the mixture was cooled to room temperature and concentrated at reduced pressure, the residue was purified by silica gel column chromatography (NH, ethyl acetate/hexane) followed by silica gel column chromatography (from ethyl acetate/hexane to ethyl acetate/methanol), and the resulting purified product was crystallized with ethyl acetate/heptane to obtain the title compound (92.3 mg).

$^1H$ NMR (300 MHz, DMSO-$d_6$) δ 1.15 (3H, d, J=6.4 Hz), 1.32 (3H, t, J=7.2 Hz), 2.09 (3H, d, J=1.1 Hz), 2.52-2.59 (OH, m), 2.78-2.93 (1H, m), 3.46-3.64 (2H, m), 3.84-3.94 (1H, m), 3.97-4.18 (4H, m), 4.61 (2H, s), 6.59 (1H, d, J=1.1 Hz), 7.11 (1H, d, J=3.0 Hz), 7.37 (1H, s), 7.70 (1H, s).

Example 60

1-[(1-Ethyl-1H-pyrazole-4-yl)methyl]-4,5-dimethyl-3-{6-[(2R)-2-methylmorpholine-4-yl]-4-(trifluoromethyl)pyridine-2-yl}-1,3-dihydro-2H-imidazole-2-one A) (2R)-4-[6-Chloro-4-(trifluoromethyl)pyridine-2-yl]-2-methylmorpholine A mixture of 2,6-dichloro-4-(trifluoromethyl)pyridine (3.10 g), (2R)-methylmorpholine hydrochloride (1.98 g), DIPEA (7.52 mL), and DMSO (6 mL) was heated for 30 minutes at 160° C. under microwave irradiation. The mixture was diluted with ethyl acetate and water and extracted with ethyl acetate. After the organic layer was washed with water and a saturated saline solution, it was dried with anhydrous sodium sulfate and concentrated under reduced pressure. The residue was purified by silica gel column chromatography (ethyl acetate/hexane) to obtain the title compound (3.63 g).

MS: $[M+H]^+$ 281.0.

B) 6-[(2R)-Methylmorpholine-4-yl]-4-(trifluoromethyl)pyridine-2-amine

A mixture of (2R)-4-[6-chloro-4-(trifluoromethyl)pyridine-2-yl]-2-methylmorpholine (800 mg), diphenylmethanimine (0.622 mL), Pd $(dba)_2$ (246 mg), BINAP (355 mg), sodium tert-butoxide (411 mg), and toluene (13 mL) was heated for one hour at 140° C. under microwave irradiation, and methanol (10 mL) and 1 N hydrochloric acid (10 mL) were added. The mixture was stirred for 30 minutes at room temperature, water was added, and then the mixture was extracted with ethyl acetate. The organic layer was dried with magnesium sulfate and concentrated under reduced pressure. The residue was purified by silica gel column chromatography (NH, ethyl acetate/hexane) and then by silica gel column chromatography (ethyl acetate/hexane) to obtain the title compound (612 mg).

$^1H$ NMR (300 MHz, DMSO-$d_6$) δ 1.13 (3H, d, J=6.0 Hz), 2.42 (1H, dd, J=12.8, 10.2 Hz), 2.74 (1H, td, J=12.3, 3.6 Hz), 3.41-3.61 (2H, m), 3.82-3.92 (1H, m), 3.96-4.17 (2H, m), 5.98 (1H, s), 6.08 (1H, s), 6.13 (2H, s).

C) 2-(But-3-yne-2-yl)-1H-isoindole-1,3(2H)-dione

A DEAD/toluene solution (40% content, 41.0 g) was added to a mixture of but-3-yne-2-ol (6.00 g), phthalimide (15.1 g), $PPh_3$ (26.9 g), and THF (171 mL) at 0° C., and the mixture was heated to room temperature and stirred for 72 hours at the same temperature. The mixture was concentrated under reduced pressure, and the resulting residue was diluted with ethyl acetate/hexane (200 mL). The insoluble matter was filtered out, and the insoluble matter was washed with ethyl acetate/hexane (200 mL). The filtrate and the washing solution were concentrated under reduced pressure, and the residue was purified by silica gel column chromatography (ethyl acetate/hexane) (twice) to obtain the title compound (7.08 g).

MS: $[M+H]^+$ 200.1.

D) But-3-yne-2-amine hydrochloride

Hydrazine monohydrate (3.52 g) was added to a mixture of 2-(but-3-yne-2-yl)-1H-isoindole-1,3(2H)-dione (7.00 g) and EtOH (150 mL), and the mixture was stirred for 45 minutes at 70° C. After the mixture was cooled to room temperature, the insoluble matter was filtered out, and the insoluble matter was washed with ethanol (150 mL). The filtrate and the washing solution were distilled out at 30° C. and 45 mmHg to obtain a but-3-yne-2-amine/ethanol solution. A 2 N hydrogen chloride/ethanol solution (35.1 mL) was added to the mixture, and after the mixture was stirred for 30 minutes at room temperature, it was concentrated at reduced pressure to obtain the title compound (3.09 g).

$^1H$ NMR (300 MHz, DMSO-$d_6$) δ 1.43 (3H, d, J=6.8 Hz), 3.67 (1H, d, J=2.3 Hz), 4.03-4.24 (OH, m), 8.68 (3H, br s).

E) N-(But-3-yne-2-yl)-2-nitrobenzene-1-sulfonamide

2-Nitrobenzenesulfonylchloride (5.77 g) and TEA (9.90 mL) were added to a mixture of but-3-yne-2-amine hydrochloride (2.50 g) and pyridine (50 mL) at room temperature, and the mixture was stirred for 12 hours at the same temperature. The mixture was concentrated, and the residue was purified by silica gel column chromatography (NH, ethyl acetate/hexane) and silica gel column chromatography (ethyl acetate/hexane) to obtain the title compound (2.41 g).

$^1$H NMR (300 MHz, DMSO-$d_6$) δ 1.32 (3H, d, J=6.8 Hz), 3.09 (1H, d, J=2.3 Hz), 3.33 (OH, s), 4.05-4.25 (OH, m), 7.82-7.90 (1H, m), 7.95-7.98 (1H, m), 8.02-8.10 (1H, m), 8.69 (1H, d, J=8.3 Hz).

F) Ethyl 1-ethyl-1H-pyrazole-4-carboxylate

A mixture of potassium carbonate (197 g), ethyl 1H-pyrazole-4-carboxylate (100 g), ethyl iodide (122 g), and DMF (250 mL) was stirred overnight at room temperature. The mixture was added to water at room temperature and extracted with ethyl acetate. After the organic layer was separated and washed with water and a saturated saline solution, it was dried with anhydrous magnesium sulfate and concentrated under reduced pressure to obtain the title compound (121 g).

$^1$H NMR (300 MHz, DMSO-$d_6$) δ 1.26 (3H, t, J=7.2 Hz), 1.37 (3H, t, J=7.2 Hz), 4.12-4.27 (4H, m), 7.84 (1H, s), 8.33 (1H, s).

G) (1-Ethyl-1H-pyrazole-4-yl)methanol

A mixture of ethyl 1-ethyl-1H-pyrazole-4-carboxylate (48.0 g) and THF (100 mL) was added dropwise to a mixture of lithium aluminum hydride (16.3 g) and THF (400 mL) at 0-10° C., and the mixture was stirred for one hour at room temperature. After the mixture was diluted with THF (150 mL) and cooled to 0° C., sodium sulfate decahydrate (110 g) was added at 0-10° C. and stirred for one hour at room temperature. The insoluble matter was filtered out, and the filtrate was distilled out under reduced pressure to obtain the title compound (29.9 g).

$^1$H NMR (300 MHz, DMSO-$d_6$) δ 1.33 (3H, t, J=7.3 Hz), 4.07 (2H, q, J=7.2 Hz), 4.32 (2H, d, J=5.3 Hz), 4.77 (1H, t, J=5.5 Hz), 7.32 (1H, s), 7.59 (1H, s).

H) N-(But-3-yne-2-yl)-N-[(1-ethyl-1H-pyrazole-4-yl)methyl]-2-nitrobenzene-1-sulfonamide A mixture of N-(but-3-yne-2-yl)-2-nitrobenzene-1-sulfonamide (3.09 g), (1-ethyl-1H-pyrazole-4-yl)methanol (1.79 g), cyanomethylene tributylphosphorane (3.43 g), and THF (15 mL) was heated for 12 hours at 100° C. under microwave irradiation. After the mixture was cooled to room temperature, it was purified by silica gel column chromatography (ethyl acetate/hexane) to obtain the title compound (2.56 g).

MS: $[M+H]^+$ 363.1.

I) N-[(1-Ethyl-1H-pyrazole-4-yl)methyl]but-3-yne-2-amine

Mercaptoacetic acid (3.25 g) was added to a mixture of N-(but-3-yne-2-yl)-N-[(1-ethyl-1H-pyrazole-4-yl)methyl]-2-nitrobenzene-1-sulfonamide (2.56 g), lithium hydroxide monohydrate (2.96 g), and DMF (30 mL) at 0° C., and the mixture was stirred for one hour at room temperature. The mixture was diluted with ethyl acetate (100 mL) and toluene (100 mL), and the insoluble matter was filtered out and washed with ethyl acetate (50 mL). The filtrate and the washing solution were concentrated under reduced pressure, and the residue was purified by silica gel column chromatography (NH, ethyl acetate/hexane) to obtain the title compound (1.12 g).

MS: [M+H]+ 178.2.

J) N-But-3-yne-2-yl-N-[(1-ethyl-1H-pyrazole-4-yl)methyl]-N'-{6-[(2R)-2-methylmorpholine-4-yl]-4-(trifluoromethyl)pyridine-2-yl}urea Bis(trichloromethyl) carbonate (43.4 mg) was added to a mixture of 6-[(2R)-methylmorpholine-4-yl]-4-(trifluoromethyl)pyridine-2-amine (85.0 mg), TEA (0.095 mL), and THF (3 mL) at 0° C. and the mixture was stirred for 30 minutes at the same temperature. A mixture of N-[(1-ethyl-1H-pyrazole-4-yl)methyl]but-3-yne-2-amine (69.2 mg), TEA (0.054 mL), and THF (2 mL) was added to the mixture at 0° C. and the mixture was stirred for one hour at room temperature. The mixture was purified by silica gel column chromatography (ethyl acetate/hexane) to obtain the title compound (120 mg).

MS: $[M+H]^+$ 465.2.

K) 1-[(1-Ethyl-1H-pyrazole-4-yl)methyl]-4,5-dimethyl-3-{6-[(2R)-2-methylmorpholine-4-yl]-4-(trifluoromethyl)pyridine-2-yl}-1,3-dihydro-2H-imidazole-2-one A 1 M TBAF/THF solution (1.0 mL) was added to a mixture of N-but-3-yne-2-yl-N-[(1-ethyl-1H-pyrazole-4-yl)methyl]-N'-{6-[(2R)-2-methylmorpholine-4-yl]-4-(trifluoromethyl)pyridine-2-yl}urea (360 mg) and THF (5 mL), and the mixture was stirred for two hours at 60° C. After the mixture was cooled to room temperature, a 2 N hydrogen chloride/ethanol solution (5.0 mL) was added, and the mixture was stirred for 30 minutes at room temperature and then concentrated under reduced pressure. The residue was purified by silica gel column chromatography (NH, ethyl acetate/hexane), and the resulting purified product was crystallized with ethyl acetate/hexane to obtain the title compound (252 mg).

$^1$H NMR (300 MHz, DMSO-$d_6$) δ 1.15 (3H, d, J=6.0 Hz), 1.32 (3H, t, J=7.3 Hz), 2.04 (3H, d, J=1.1 Hz), 2.11 (3H, s), 2.54-2.65 (1H, m), 2.79-3.01 (1H, m), 3.43-3.64 (2H, m), 3.84-3.97 (1H, m), 4.02-4.22 (4H, m), 4.61 (2H, s), 7.00 (1H, s), 7.25 (1H, s), 7.37 (1H, d, J=0.8 Hz), 7.69 (1H, s).

Example 91

2-{2-fluoro-5-[(2R)-2-methylmorpholine-4-yl]-3-(trifluoromethyl)phenyl}-5-methyl-4-{[1-(propane-2-yl)-1H-pyrazole-4-yl]methyl}-2,4-dihydro-3H-1,2,4-triazole-3-one A) 5-Bromo-2-fluoro-3-(trifluoromethyl)phenyl) hydrazine A di-μ-methoxybis(1,5-cyclooctadiene)diiridium (I) (0.236 g) and then 4,4'-di-tert-butyl-2,2'-bipyridine (0.191 g) were added to a THF (50 mL) solution of degassed 4,4,4',4',5,5,5',5'-octamethyl-2,2'-bi-1,3,2-dioxaborolane (2.71 g). After the mixture was stirred for ten minutes, 4-bromo-1-fluoro-2-(trifluoromethyl)benzene (5.03 g) was added. The mixture was stirred overnight at 40° C. in a nitrogen atmosphere. The mixture was concentrated under reduced pressure. The residue was dissolved in methanol (50 mL), and di-tert-butyl azodicarboxylate (4.08 g) and copper (II) acetate (3.21 g) were added. The mixture was stirred for 2.5 hours at 45° C. in a nitrogen atmosphere. The mixture was filtered, and the filtrate was concentrated under reduced pressure. The residue was diluted with ethyl acetate, and a saturated ammonium chloride aqueous solution was added at room temperature. After the organic layer was separated and washed with a saturated sodium bicarbonate aqueous solution and a saturated saline solution, it was dried with anhydrous sodium sulfate and concentrated under reduced pressure. The residue was purified by silica gel column chromatography (ethyl acetate/hexane). After the resulting solid was washed with diisopropyl ether, it was dried under reduced pressure. The resulting solid was suspended in methanol (25 mL), and a 4 M hydrogen chloride/ethyl acetate solution (25 mL) was added at room temperature. The mixture was stirred overnight at room temperature. The mixture was concentrated under reduced pressure, and the residue was diluted with ethyl acetate and added to a saturated sodium bicarbonate aqueous solution at room temperature. After the organic layer was separated and washed with water and a saturated saline solution, it was dried with anhydrous sodium sulfate and concentrated under reduced pressure to obtain the title compound (1.42 g).

$^1$H NMR (300 MHz, $CDCl_3$) δ 3.64 (2H, br s), 5.62 (1H, br s), 7.04 (1H, dd, J=5.7, 2.6 Hz), 7.54 (1H, dd, J=7.0, 2.4 Hz).

B) Ethyl 2-(2-(5-bromo-2-fluoro-3-(trifluoromethyl) phenyl)hydrazinylidene)propanoate Ethyl pyruvate (0.635 mL) was added to a methanol (20 mL) solution of 5-bromo-2-fluoro-3-(trifluoromethyl)phenyl)hydrazine (1.42 g) at 0° C. The mixture was stirred for two hours at room temperature. The solvent was distilled out under reduced pressure, and the residue was suspended in diisopropyl ether. The precipitate was filtered out and dried under reduced pressure to obtain the title compound (1.45 g).

MS: [M+H]+ 371.0.

C) 2-(2-(5-Bromo-2-fluoro-3-(trifluoromethyl)phenyl)hydrazinylidene)propanoic acid A 2 M sodium hydroxide aqueous solution (5.0 mL) was added to a methanol (20 mL) solution of ethyl 2-(2-(5-bromo-2-fluoro-3-(trifluoromethyl)phenyl)hydrazinylidene) propanoate (1.93 g) at room temperature. The mixture was stirred for two hours at 40° C. The mixture was concentrated under reduced pressure, and after the residue was diluted with water (15 mL), 1 M hydrochloric acid (10 mL) was dropped into the mixture. After the precipitate was filtered out and washed with water, it was dried under reduced pressure to obtain the title compound (1.48 g).

$^1$H NMR (300 MHz, DMSO-$d_6$) δ1.55 (3H, s), 6.86 (1H, dd, J=5.7, 2.6 Hz), 7.62 (1H, dd, J=7.2, 2.3 Hz), 9.04 (1H, br s), 11.87 (1H, br d, J=2.6 Hz).

D) 2-{2-[5-Bromo-2-fluoro-3-(trifluoromethyl)phenyl]hydrazinylidene}propanoyl azide Diphenylphosphoyl azide (1.21 mL) and TEA (0.783 mL) were added to a THF (15 mL) solution of 2-(2-(5-bromo-2-fluoro-3-(trifluoromethyl)phenyl)hydrazinylidene)propanoic acid (1.48 g) at room temperature. The mixture was stirred overnight at room temperature. The mixture was diluted with ethyl acetate and added to water. After the organic layer was separated and washed with water and a saturated saline solution, it was dried with anhydrous sodium sulfate and concentrated under reduced pressure. The residue was suspended in diisopropyl ether. After the precipitate was filtered out and washed with diisopropyl ether, it was dried under reduced pressure to obtain the title compound (1.03 g).

$^1$H NMR (300 MHz, $CDCl_3$) δ 2.16 (3H, s), 7.32 (1H, dd, J=5.7, 2.3 Hz), 7.92 (1H, br d, J=2.6 Hz), 7.97 (1H, dd, J=6.6, 2.4 Hz).

E) 2-[5-Bromo-2-fluoro-3-(trifluoromethyl)phenyl]-5-methyl-2,4-dihydro-3H-1,2,4-triazole-3-one A mixture of 2-{2-[5-bromo-2-fluoro-3-(trifluoromethyl) phenyl]hydrazinylidene}propanoyl azide (1.59 g) and toluene (15 mL) was stirred for two hours at 110° C. The mixture was purified by silica gel column chromatography (ethyl acetate/hexane) to obtain the title compound (1.09 g).

$^1$H NMR (300 MHz, $CDCl_3$) δ2.32 (3H, s), 7.73 (1H, dd, J=5.5, 2.4 Hz), 7.92 (1H, dd, J=6.0, 2.6 Hz), 9.73-10.14 (1H, m).

F) 2-[5-Bromo-2-fluoro-3-(trifluoromethyl)phenyl]-5-methyl-4-{[1-(propane-2-yl)-1H-pyrazole-4-yl] methyl}-2,4-dihydro-3H-1,2,4-triazole-3-one Cyanomethylene tributyl phosphorane (703 mg) was added to a mixture of 2-[5-bromo-2-fluoro-3-(trifluoromethyl)phenyl]-5-methyl-2,4-dihydro-3H-1,2,4-triazole-3-one (495 mg), [1-(propane-2-yl)-1H-pyrazole-4-yl]methanol (408 mg), and THF (10 mL), and the mixture was stirred for four hours at 80° C. The mixture was purified by silica gel column chromatography (NH, ethyl acetate/hexane) to obtain the title compound (463 mg).

MS: $[M+H]^+$ 462.1.

G) 2-{2-Fluoro-5-[(2R)-2-methylmorpholine-4-yl]-3-(trifluoromethyl)phenyl}-5-methyl-4-{[1-(propane-2-yl)-1H-pyrazole-4-yl]methyl}-2,4-dihydro-3H-1,2,4-triazole-3-one A mixture of 2-[5-bromo-2-fluoro-3-(trifluoromethyl) phenyl]-5-methyl-4-{[1-(propane-2-yl)-1H-pyrazole-4-yl] methyl}-2,4-dihydro-3H-1,2,4-triazole-3-one (47.4 mg), (2R)-2-methylmorpholine hydrochloride (21.2 mg), $Pd_2$ $(dba)_3$ (9.91 mg), sodium tert-butoxide (52.0 mg), dicyclohexyl(2',4',6'-triisopropylbiphenyl-2-yl)phosphine (10.3 mg), and toluene (2.0 mL) was stirred overnight at 80° C. in a nitrogen atmosphere. The mixture was purified by silica gel column chromatography (NH, ethyl acetate/hexane) and HPLC (C18, mobile phase: water/$CH_3CN$ (10 mM ammonium bicarbonate system)) and concentrated under reduced pressure to obtain the title compound (12.6 mg).

$^1$H NMR (300 MHz, DMSO-$d_6$) δ 1.14 (3H, d, J=6.0 Hz), 1.38 (6H, d, J=6.4 Hz), 2.29 (3H, s), 2.37 (1H, dd, J=11.3, 10.2 Hz), 2.63-2.77 (1H, m), 3.49-3.75 (4H, m), 3.84-3.97 (1H, m), 4.47 (OH, q, J=6.7 Hz), 4.71 (2H, s), 7.20-7.27 (1H, m), 7.32 (1H, dd, J=6.0, 3.0 Hz), 7.44 (1H, s), 7.80 (1H, s).

Example 99

1-[1-(2-Cyclobutylethyl)-3-(trifluoromethyl)-1H-pyrazole-5-yl]-3-[(I-ethyl-1H-pyrazole-4-yl)methyl]-4-methyl-1,3<dihydro-2H-imidazole-2-one A) N-[(1-Ethyl-1H-pyrazole-4-yl)methyl]-1,1-dimethoxypropane-2-amine First, 1,1-dimethoxypropane-2-amine (331 mg) was added to a mixture of 1-ethyl-1H-pyrazole-4-carbaldehyde (300 mg) and toluene (4 mL), and the mixture was refluxed for two hours. After the mixture was cooled, the mixture was added to a mixture of $NaBH_4$ (183 mg) and MeOH (4 mL) at 0° C. and stirred for 30 minutes at the same temperature. The mixture was purified by silica gel column chromatography (NH, ethyl acetate/hexane) to obtain the title compound (510 mg).

MS: $[M+H]^+$ 228.1.

B) Ethyl 1-(2-cyclobutylethyl)-3-(trifluoromethyl)-1H-pyrazole-5-carboxylate

Methanesulfonyl chloride (1.54 g) and TEA (1.36 g) were added to a mixture of 2-cyclobutylethane-1-ol (900 mg) and THF (20 mL) and stirred for 30 minutes at room temperature. The mixture was neutralized at 0° C. with a saturated sodium bicarbonate aqueous solution and extracted with ethyl acetate. After the organic layer was separated and washed with water and a saturated saline solution, it was dried with anhydrous magnesium sulfate and concentrated under reduced pressure to obtain a crude product of 2-cyclobutyl methanesulfonate (1.6 g). The crude product of 2-cyclobutyl methanesulfonate (1.6 g) and potassium carbonate (1.55 g) were added to a mixture of ethyl 3-(trifluoromethyl)-1H-pyrazole-5-carboxylate (1.56 g) and DMF (15 mL) and stirred overnight at room temperature. Water was added to the mixture, which was then extracted with ethyl acetate. After the organic layer was separated and washed with water and a saturated saline solution, it was dried with anhydrous sodium sulfate and concentrated under reduced pressure. The residue was purified by silica gel column chromatography (ethyl acetate/hexane) to obtain the title compound (1.99 g).

MS: $[M+H]^+$ 291.1.

C) N'-[1-(2-Cyclobutylethyl)-3-(trifluoromethyl)-1H-pyrazole-5-yl]-N-(1,1-dimethoxypropane-2-yl)-N-[(1-ethyl-1H-pyrazole-4-yl)methyl]urea A 4 M lithium hydroxide aqueous solution (5.14 mL) was added to a mixture of ethyl 1-(2-cyclobutylethyl)-3-(trifluoromethyl)-1H-pyrazole-5-carboxylate (1.99 g), THF (15 mL), and MeOH (5 mL), and the mixture was stirred for two hours at room temperature. The mixture was neutralized with 6 N hydrochloric acid at 0° C. and extracted with ethyl acetate. After the organic layer was separated and washed with water and a saturated saline solution, it was dried with anhydrous magnesium sulfate and concentrated under reduced pressure to obtain a crude product of 1-(2-cyclobutylethyl)-3-(trifluoromethyl)-1H-pyrazole-5-carboxylic acid. TEA (46.3 mg) and DPPA (126 mg) were added to the crude product of 1-(2-cyclobutylethyl)-3-(trifluoromethyl)-1H-pyrazole-5-carboxylic acid (100 mg) and toluene (1 mL) at room temperature. After the mixture was stirred for 30 minutes at room temperature, N-[(1-ethyl-1H-pyrazole-4-yl)methyl]-1,1-dimethoxypropane-2-amine (87 mg) was added. The mixture was stirred for two hours at 100° C. in an argon atmosphere. The residue was purified by HPLC (C18, mobile phase: water/$CH_3CN$ (10 mM ammonium bicarbonate system)) to obtain the title compound (185 mg).

MS: $[M+H]^+$ 487.3.

D) 1-[1-(2-Cyclobutylethyl)-3-(trifluoromethyl)-1H-pyrazole-5-yl]-3-[(1-ethyl-1H-pyrazole-4-yl)methyl]-4-methyl-1,3-dihydro-2H-imidazole-2-one TFA (1 mL) was added to a mixture of N'-[1-(2-cyclobutylethyl)-3-(trifluoromethyl)-1H-pyrazole-5-yl]-N-(1,1-dimethoxypropane-2-yl)-N-[(1-ethyl-1H-pyrazole-4-yl)methyl]urea (185 mg), $CH_3CN$ (2 mL), and water (0.4 mL) at room temperature, and the mixture was stirred for one hour at 60° C. The mixture was concentrated under reduced pressure, and the residue was purified by silica gel column chromatography (NH, ethyl acetate/hexane) to obtain the title compound (104 g).

$^1H$ NMR (300 MHz, $CDCl_3$) δ 1.46 (3H, td, J=7.3, 1.3 Hz), 1.50-1.64 (2H, m), 1.70-2.02 (4H, m), 2.11-2.15 (3H, m), 2.15-2.25 (1H, m), 4.01 (2H, t, J=7.4 Hz), 4.13 (2H, qd, J=7.4, 1.0 Hz), 4.71 (2H, s), 6.01 (1H, d, J=1.4 Hz), 6.42 (1H, s), 7.46 (2H, d, J=5.1 Hz).

Example 103

4-Methy-3-{6-[(2R)-2-methylmorpholine-4-yl]-4-(trifluoromethyl)pyridine-2-yl}-1-{[1-(propane-2-yl)-1H-pyrazole-4-yl]methyl}-1,3-dihydro-2H-imidazole-2-one A) N-[(1-Propane-2-yl)-1H-pyrazole-4-yl]methyl}prop-2-yne-1-amine Prop-2-yne-1-amine (1.07 g) was added to a mixture of 1-isopropyl-1H-pyrazole-4-carbaldehyde (2.07 g) and toluene (30 mL), and the mixture was stirred for three hours at 80° C. After the mixture as cooled, the mixture was concentrated, and MeOH (30 mL) was added to the resulting residue. $NBH_4$ (0.851 g) was added at 0° C. and stirred for one hour at the same temperature. The mixture was concentrated, and the residue was purified by silica gel column chromatography (NH, ethyl acetate/hexane) to obtain the title compound (2.00 g).

MS: [M+H]~178.2.

B) N'-{6-[(2R)-2-methylmorpholine-4-yl]-4-(trifluoromethyl)pyridine-2-yl}-N-{[1-(propane-2-yl)-1H-pyrazole-4-yl]methyl}-N-prop-2-yne-1-ylurea Bis(trichloromethyl) carbonate (115 mg) and TEA (117 mg) were added to a mixture of 6-[(2R)-methylmorpholine-4-yl]-4-(trifluoromethyl)pyridine-2-amine (202.0 mg) and THF (15 mL) at 0° C. and stirred for 30 minutes at room temperature. After the mixture was concentrated, the residue was suspended in THF (15 mL). A mixture of N-[{1-propane-2-yl)-1H-pyrazole-4-yl]methyl}prop-2-yne-1-amine (144 mg), THF (4 mL), and TEA (218 mg) was added, and the mixture was stirred overnight at room temperature. The mixture was added to a saturated sodium bicarbonate aqueous solution and extracted with ethyl acetate. The organic layer was separated, dried with anhydrous sodium sulfate, and concentrated under reduced pressure. The residue was purified by silica gel column chromatography (ethyl acetate/hexane) to obtain the title compound (58.0 mg).

MS: $[M+H]^+$ 465.3.

C) 4-Methyl-3-{6-[(2R)-2-methylmorpholine-4-yl]-4-(trifluoromethyl)pyridine-2-yl}-1-{[1-(propane-2-yl)-1H-pyrazole-4-yl]methyl}-1,3-dihydro-2H-imidazole-2-one A 1 M TBAF/THF solution (0.118 mL) was added to a mixture of N'-{6-[(2R)-2-methylmorpholine-4-yl]-4-(trifluoromethyl)pyridine-2-yl}-N-{[1-(propane-2-yl)-1H-pyrazole-4-yl]methyl}-N-prop-2-yne-1-ylurea (50 mg) and THF (2 mL), and the mixture was stirred for two hours at 80° C. in a sealed tube. After the mixture was cooled, a 4 N hydrogen chloride/ethyl acetate solution (1 mL) was added to the mixture, and after the mixture was stirred for five minutes at room temperature, the reaction solution was concentrated. The resulting residue was purified by silica gel column chromatography (NH, ethyl acetate/hexane) to obtain the title compound (20 mg).

$^1$H NMR (300 MHz, $CDCl_3$) δ 1.26 (3H, d, J=6.0 Hz), 1.49 (6H, d, J=6.8 Hz), 2.20 (3H, d, J=1.1 Hz), 2.67 (1H, dd, J=12.8, 10.2 Hz), 2.93-3.10 (1H, m), 3.56-3.76 (2H, m), 3.93-4.10 (3H, m), 4.46 (1H, spt, J=6.7 Hz), 4.66 (2H, s), 6.01 (1H, d, J=1.5 Hz), 6.65 (1H, s), 7.42 (OH, s), 7.47 (OH, s), 7.49 (OH, s).

Example 110

1-[(1-Ethyl-1-pyrazole-4-yl)methyl]-3-[6={[(1-fluorocyclobutyl)methyl]amino}-4-(trifluoromethyl)pyridine-2-yl]-4-methyl-1,3-dihydro-2H-imidazole-2-one A) 6-Chloro-4-(trifluoromethyl)pyridine-2-amine A mixture of 2,6-dichloro-4-(trifluoromethyl)pyridine (1 g), diphenylmethanimine (1.1 g), $Pd_2$ $(dba)_3$ (0.21 g), BINAP (0.29 g), sodium tert-butoxide (0.67 g), and toluene (17 mL) was irradiated with microwaves for one hour at 140° C. A 2 N hydrogen chloride/ethanol solution (10 mL) was added to the mixture at room temperature. After the mixture was stirred for one hour at room temperature, a saturated sodium bicarbonate aqueous solution was added and extracted with ethyl acetate. The organic layer was separated, dried with anhydrous magnesium sulfate, and concentrated under reduced pressure. The residue was purified by silica gel column chromatography (ethyl acetate/hexane) to obtain the title compound (277 mg).

$^1$H NMR (300 MHz, $CDCl_3$) δ 6.66 (1H, s), 6.77-6.83 (1H, m), 7.00 (2H, s).

B) N'-[6-Chloro-4-(trifluoromethyl)pyridine-2-yl]-N-[(1-ethyl-1H-pyrazole-4-yl)methyl]-N-prop-2-yne-1-ylurea TEA (0.13 g) and bis(trichloromethyl) carbonate (0.18 g) were added to a mixture of 6-chloro-4-(trifluoromethyl) pyridine-2-amine (0.24 g) and THF (8 mL) at 0° C. After the reaction mixture was stirred for one hour at room temperature, a THF (1 mL) solution of N-[(1-ethyl-1H-pyrazole-4-yl)methyl]prop-2-yne-1-amine (0.20 mg) and TEA (0.5 mL) were added. The mixture was stirred for 12 hours at room temperature. Water was added to the mixture, which was then extracted with ethyl acetate. The organic layer was separated, dried with anhydrous magnesium sulfate, and concentrated under reduced pressure. The residue was purified by silica gel column chromatography (ethyl acetate/hexane) to obtain the title compound (0.32 g).

MS: $[M+H]^+$ 386.1.

C) 3-[6-Chloro-4-(trifluoromethyl)pyridine-2-yl]-1-[(1-ethyl-1H-pyrazole-4-yl)methyl]-4-methyl-1,3-dihydro-2H-imidazole-2-one A 1 M TBAF/THF solution (0.91 mL) was added to a mixture of N'-[6-chloro-4-(trifluoromethyl)pyridine-2-yl]-N-[(1-ethyl-1H-pyrazole-4-yl)methyl]-N-prop-2-yne-1-ylurea (320 mg) and THF (3 mL), and the mixture was stirred for one hour at 80° C. A 2 N hydrogen chloride/ethanol solution (1 mL) was added to the reaction mixture and stirred for 10 minutes at room temperature. A saturated sodium bicarbonate aqueous solution was added to the mixture and extracted with ethyl acetate. The organic layer was separated, dried with anhydrous magnesium sulfate, and concentrated under reduced pressure. The residue was purified by silica gel column chromatography (ethyl acetate/hexane) to obtain the title compound (0.11 g).

MS: $[M+H]^+$ 386.2.

D) 1-[(1-Ethyl-1H-pyrazole-4-yl)methyl]-3-[6-{[(1-fluorocyclobutyl)methyl]amino}-4-(trifluoromethyl) pyridine-2-yl]-4-methyl-1,3-dihydro-2H-imidazole-2-one A mixture of 1-(1-fluorocyclobutyl)methanamine hydrochloride (21.7 mg), sodium tert-butoxide (49.8 mg), and DME (1 mL) was stirred for ten minutes at room temperature. A THF (0.5 mL) solution of 3-[6-chloro-4-(trifluoromethyl)pyridine-2-yl]-1-[(1-ethyl-1H-pyrazole-4-yl)methyl]-4-methyl-1,3-dihydro-2H-imidazole-2-one (50 mg), a chloro-(2-dicyclohexylphosphino-2',6'-diisopropoxy-1,1'-biphenyl)[2-(2-aminoethyl)phenyl]palladium (II)-methyl-tert-butyl ether adduct (4.7 mg), and dicyclohexyl(2',6'-diisopropoxybiphenyl-2-yl)phosphine (6.1 mg) were added to the mixture at room temperature. After the mixture was irradiated with microwaves for one hour at 110° C. and purified by silica gel column chromatography (ethyl acetate/hexane), it was further purified by HPLC (C18, mobile phase: water/$CH_3CN$ (10 mM TFA system)). The resulting fraction was concentrated under reduced pressure to obtain the title compound (26 mg).

$^1$H NMR (300 MHz, $CDCl_3$) S 0.85-0.94 (1H, m), 1.47 (3H, t, J=7.3 Hz), 1.79-1.94 (1H, m), 2.08-2.19 (1H, m), 2.08-2.09 (1H, m), 2.21 (3H, d, J=1.3 Hz), 2.24-2.46 (2H, m), 3.62-3.75 (11H, m), 3.66-3.67 (1H, m), 4.09 (1H, s), 4.10-4.18 (2H, m), 4.63-4.70 (1H, m), 4.66 (1H, s), 4.92 (1H, br t, J=5.6 Hz), 5.99-6.02 (1H, m), 6.51 (1H, s), 7.32-7.36 (1H, m), 7.34 (1H, s), 7.47 (2H, d, J=8.7 Hz).

Example 127

3-[(1-Ethyl-1H-pyrazole-4-yl)methyl]-1-{3 fluoro-6-[(2R)-2-methylmorpholine-4-yl]-4-(trifluoromethyl) pyridine-2-yl}-4-(trifluoromethyl)-1,3-dihydro-2H-imidazole-2-one A) (1E)-N-[(1-Ethyl-1H-pyrazole-4-yl)methyl]-2,2-dimethoxyethane-1-imine Dimethoxyacetaldehyde (1.27 g) was added to a mixture of 1-(1-ethyl-1H-pyrazole-4-yl)methanamine (731 mg) and toluene (10 mL), and the mixture was stirred for two hours at 100° C. After the mixture was cooled, it was concentrated at reduced pressure to obtain the title compound (1.23 mg).

$^1$H NMR (300 MHz, DMSO-$d_6$) δ 1.33 (3H, t, J=7.2 Hz), 3.30 (6H, s), 4.08 (2H, q, J=7.3 Hz), 4.44 (2H, d, J=0.8 Hz), 4.62 (1H, d, J=4.9 Hz), 7.29 (1H, s), 7.51-7.57 (1H, m), 7.58 (1H, s).

B) N-[(1-Ethyl-1H-pyrazole-4-yl)methyl]-1,1,1-trifluoro-3,3-dimethoxypropane-2-amine TFA (228 mg) was added to a mixture of (1E)-N-[(1-ethyl-1H-pyrazole-4-yl)methyl]-2,2-dimethoxyethane-1-imine (423 mg), potassium hydrogen fluoride (117 mg), DMF (439 mg), and $CH_3CN$ (4 mL) at 0° C. and stirred for five minutes at the same temperature. Trimethyl(trifluoromethylmethyl)silane (355 mg) was added to the mixture at 0° C., and the mixture was stirred for 15 minutes at room temperature. The residue was purified by HPLC (C18, mobile phase: water/$CH_3CN$ (10 mM ammonium bicarbonate system)). The resulting fraction was concentrated under reduced pressure to obtain the title compound (75 mg).

MS: [M+H]$^+$ 282.2.

C) N-[(1-ethyl-1H-pyrazole-4-yl)methyl]-N'-{3-fluoro-6-[(2R)-2-methylmorpholine-4-yl]-4-(trifluoromethyl)pyridine-2-yl}-1,1,1-trifluoro-3,3-dimethoxypropane-2-yl)urea Bis(trichloromethyl) carbonate (26.4 mg) was added to a mixture of 3-fluoro-6-[(2R)-2-methylmorpholine-4-yl]4-(trifluoromethyl)pyridine-2-amine (62 mg), TEA (53.9 mg), and THF (2 mL), and the mixture was stirred for 30 minutes at the same temperature. A THF (1 mL) solution of N-[(1-ethyl-1H-pyrazole-4-yl)methyl]-1,1,1-trifluoro-3,3-dimethoxypropane-2-amine (73 mg) and TEA (33.7 mg) was added to the mixture at 0° C. and stirred for 30 minutes at room temperature. The mixture was purified by silica gel column chromatography (ethyl acetate/hexane) to obtain the title compound (116 mg).

MS: [M+H]~587.3.

D) 3-[(1-Ethyl-1H-pyrazole-4-yl)methyl]-1-{3-fluoro-6-[(2R)-2-4-yl]-4-(trifluoromethyl)pyridine-2-yl}-4-(trifluoromethyl)-1,3-dihydro-2H-imidazole-2-one A mixture of N-[(1-ethyl-1H-pyrazole-4-yl)methyl]-N'-{3-fluoro-6-[(2R)-2-methylmorpholine-4-yl]-4-(trifluoromethyl)pyridine-2-yl}-1,1,1-trifluoro-3,3-dimethoxypropane-2-yl)urea (116 mg), TFA (666 mg), $CH_3CN$ (3 mL), and water (0.3 mL) was irradiated with microwaves for three hours at 130° C. After the mixture was cooled, it was concentrated under reduced pressure, and the resulting residue was purified by silica gel column chromatography (NH, ethyl acetate/hexane) to obtain the title compound (64 mg).

$^1$H NMR (300 MHz, DMSO-$d_6$) δ 1.15 (3H, d, J=6.0 Hz), 1.31 (3H, t, J=7.3 Hz), 2.54-2.62 (1H, m), 2.81-2.95 (1H, m), 3.45-3.63 (2H, m), 3.83-3.96 (1H, m), 4.04-4.19 (4H, m), 4.72 (2H, s), 7.26 (1H, d, J=3.0 Hz), 7.36 (1H, s), 7.70 (1H, s), 7.76-7.81 (1H, in).

Example 134

3-[4-(2,2-Dimethylmorpholine-4-yl)-6-(trifluoromethyl)pyrimidine-2-yl]-1-[(1-ethyl-H-pyrazole-4-yl)methyl]-4-methyl-1,3-dihydro-2H-imidazole-2-one A) 4-(2,2-Dimethylmorpholine-4-yl)-6-(trifluoromethyl)pyrimidine-2-amine A mixture of 2,2-dimethylmorpholine (61.2 mg), 4-chloro-6-(trifluoromethyl)pyrimidine-2-amine (70.0 mg), DIPEA (0.186 mL), and n-butyl alcohol (1 mL) was stirred overnight at 120° C. The mixture was purified by silica gel column chromatography (NH, ethyl acetate/hexane) to obtain the title compound (90.0 mg).

MS: [M+H]+ 277.2.

B) N'-[4-(2,2-Dimethylmorpholine-4-yl)-6-(trifluoromethyl)pyrimidine-2-yl]-N-[(1-ethyl-1H-pyrazole-4-yl)methyl]-N-prop-2-yne-1-ylurea Bis(trichloromethyl) carbonate (19.3 mg) was added to a mixture of 4-(2,2-dimethylmorpholine-4-yl)-6-(trifluoromethyl)pyrimidine-2-amine and THF (2 mL) at 0° C., and the mixture was stirred for four hours at room temperature. Next, N-[(1-ethyl-1H-pyrazole-4-yl)methyl]prop-2-yne-1-amine (31.9 mg) and TEA (24.7 mg) were added to the mixture and stirred overnight at room temperature. Water was added to the mixture, which was then extracted with ethyl acetate. After the organic layer was separated and washed with water and a saturated saline solution, it was dried with anhydrous sodium sulfate and concentrated under reduced pressure. The residue was purified by silica gel column chromatography (ethyl acetate/hexane) to obtain the title compound (73.1 mg).

MS: [M+H]$^+$ 466.3.

C) 3-[4-(2,2-Dimethylmorpholine-4-yl)-6-(trifluoromethyl)pyrimidine-2-yl]-1-[(1-ethyl-1H-pyrazole-4-yl)methyl]-4-methyl-1,3-dihydro-2H-imidazole-2-one A 1 M TBAF/THF solution (0.2 mL) was added to a mixture of N'-[4-(2,2-dimethylmorpholine-4-yl)-6-(trifluoromethyl)pyrimidine-2-yl]-N-[(1-ethyl-1H-pyrazole-4-yl)methyl]-N-prop-2-yne-1-ylurea (73.1 mg) and THF (2 mL), and the mixture was stirred for two hours at 60° C. After the mixture was cooled to room temperature, a 2 M hydrogen chloride/ethanol solution (0.12 mL) was added. After the mixture was stirred for 30 minutes at room temperature, it was concentrated under reduced pressure. The residue was purified by silica gel column chromatography (NH, ethyl acetate/hexane). The resulting product was purified by HPLC (C18, mobile phase: water/$CH_3CN$ (10 mM ammonium bicarbonate system)). The resulting fraction was concentrated under reduced pressure to obtain the title compound (34.1 mg).

$^1$H NMR (300 MHz, DMSO-$d_6$) δ 1.16 (6H, s), 1.34 (3H, t, J=7.3 Hz), 2.00-2.06 (3H, m), 3.55-3.79 (6H, m), 4.08 (2H, q, J=7.3 Hz), 4.53 (2H, s), 6.38 (1H, d, J=1.5 Hz), 7.26 (1H, s), 7.40-7.42 (1H, m), 7.72 (1H, s).

The compounds of the examples are shown in the following tables. In the tables, MS represents actual measurements. The compounds of the following tables were produced in accordance with the methods described in the examples above or similar methods.

TABLE 1

| Example No. | IUPAC Name | Structure | Salt | MS |
|---|---|---|---|---|
| 1 | 1-[(1-ethyl-1H-pyrazol-4-yl)methyl]-3-[4'-fluoro-5-(trifluoromethyl)[1,1'-biphenyl]-3-yl]-1,3-dihydro-2H-imidazol-2-one | 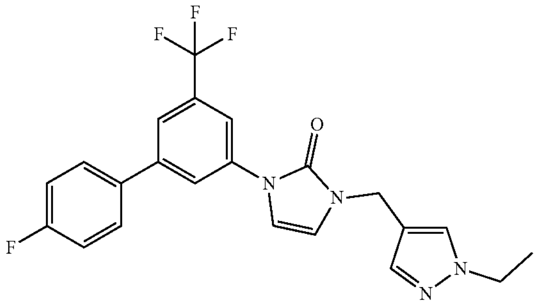 [SMILES: CCn1cc(Cn2ccn(-c3cc(-c4ccc(F)cc4)cc(C(F)(F)F)c3)c2=O)cn1] | | 431.2 |
| 2 | 1-[(1-ethyl-1H-pyrazol-4-yl)methyl]-3-{2-fluoro-5-[(2R)-2-methylmorpholin-4-yl]-3-(trifluoromethyl)phenyl}-1,3-dihydro-2H-imidazol-2-one | 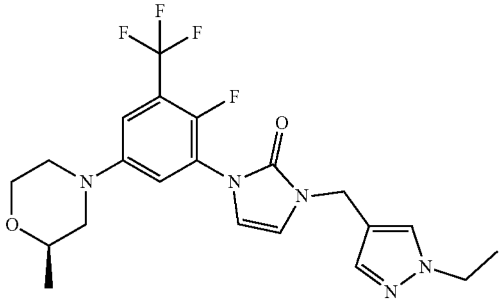 | | 454.2 |
| 3 | 1-[(1-ethyl-1H-pyrazol-4-yl)methyl]-3-[4'-fluoro-5-(trifluoromethyl)[1,1'-biphenyl]-3-yl]-4-methyl-1,3-dihydro-2H-imidazol-2-one | 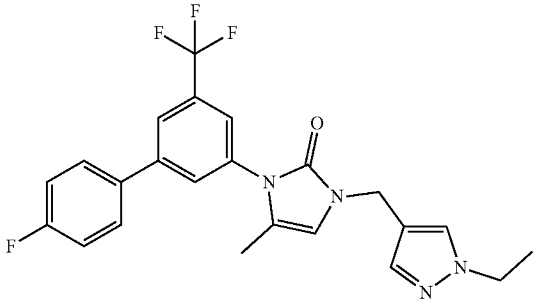 [SMILES: CCn1cc(Cn2cc(C)n(-c3cc(-c4ccc(F)cc4)cc(C(F)(F)F)c3)c2=O)cn1] | | 445.2 |
| 4 | 1-[(1-ethyl-1H-pyrazol-4-yl)methyl]-3-{2-fluoro-5-[(2R)-2-methylmorpholin-4-yl]-3-(trifluoromethyl)phenyl}-4-methyl-1,3-dihydro-2H-imidazol-2-one | 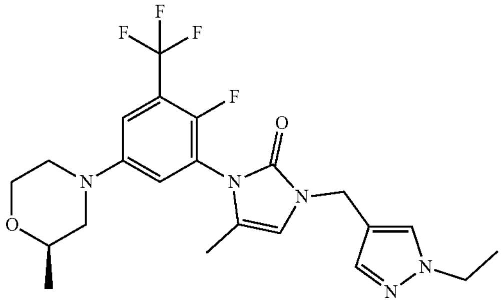 [SMILES: CCn1cc(Cn2cc(C)n(-c3cc(N4CCO[C@H](C)C4)cc(C(F)(F)F)c3F)c2=O)cn1] | | 468.3 |
| 5 | 1-[(1-ethyl-1H-pyrazol-4-yl)methyl]-3-[3-(4-fluorophenoxy)-5-(trifluoromethyl)phenyl]-4-methyl-1,3-dihydro-2H-imidazol-2-one | 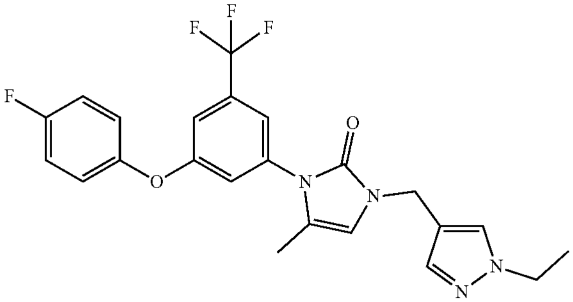 [SMILES: CCn1cc(Cn2cc(C)n(-c3cc(Oc4ccc(F)cc4)cc(C(F)(F)F)c3)c2=O)cn1] | | 461.2 |

TABLE 1-continued

| Example No. | IUPAC Name | Structure | Salt | MS |
|---|---|---|---|---|
| 6 | 1-[(1-ethyl-1H-pyrazol-4-yl)methyl]-4-methyl-3-{3-[(oxan-4-yl)oxy]-5-(trifluoromethyl)phenyl}-1,3-dihydro-2H-imidazol-2-one | 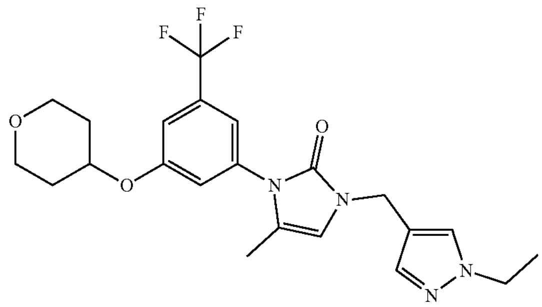 [SMILES: CCn1cc(Cn2cc(C)n(-c3cc(OC4CCOCC4)cc(C(F)(F)F)c3)c2=O)cn1] | | 451.2 |
| 7 | 3-{3-[(3,3-difluorocyclobutyl)methoxy]-5-(trifluoromethyl)phenyl}-1-[(1-ethyl-1H-pyrazol-4-yl)methyl]-4-methyl-1,3-dihydro-2H-imidazol-2-one | 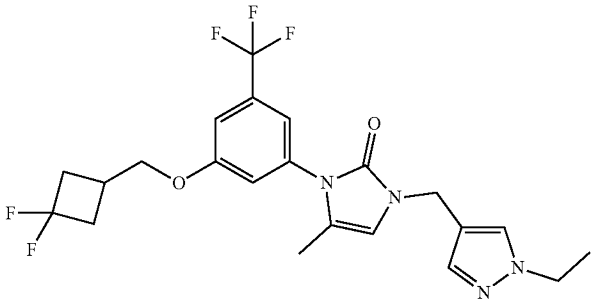 [SMILES: CCn1cc(Cn2cc(C)n(-c3cc(OCC4CC(F)(F)C4)cc(C(F)(F)F)c3)c2=O)cn1] | | 471.2 |
| 8 | 1-[(1-ethyl-1H-pyrazol-4-yl)methyl]-3-{2-methyl-5-[(2R)-2-methylmorpholin-4-yl]-3-(trifluoromethyl)phenyl}-1,3-dihydro-2H-imidazol-2-one | 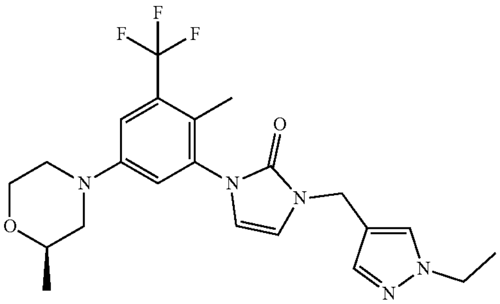 [SMILES: CCn1cc(Cn2ccn(-c3cc(N4CCO[C@H](C)C4)cc(C(F)(F)F)c3C)c2=O)cn1] | | 450.2 |
| 9 | 1-[1-(1-ethyl-1H-pyrazol-4-yl)ethyl]-3-{2-fluoro-5-[(2R)-2-methylmorpholin-4-yl]-3-(trifluoromethyl)phenyl}-1,3-dihydro-2H-imidazol-2-one | 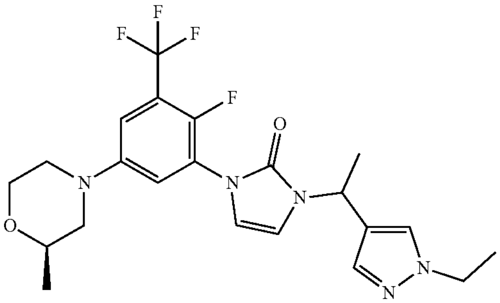 [SMILES: CCn1cc(C(C)n2ccn(-c3cc(N4CCO[C@H](C)C4)cc(C(F)(F)F)c3F)c2=O)cn1] | | 468.3 |
| 10 | 1-[(1-ethyl-1H-pyrazol-4-yl)methyl]-3-{2-fluoro-5-[methyl(oxan-4-yl)amino]-3-(trifluoromethyl)phenyl}-1,3-dihydro-2H-imidazol-2-one | 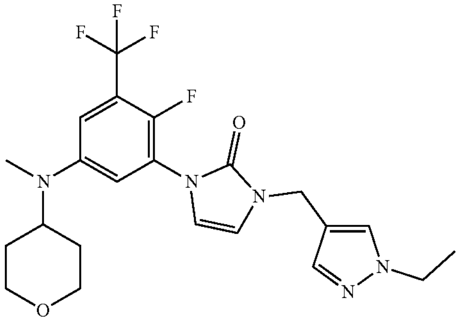 [SMILES: CCn1cc(Cn2ccn(-c3cc(N(C)C4CCOCC4)cc(C(F)(F)F)c3F)c2=O)cn1] | | 468.2 |

TABLE 1-continued

| Example No. | IUPAC Name | Structure | Salt | MS |
| --- | --- | --- | --- | --- |
| 11 | 1-[(1-ethyl-1H-pyrazol-4-yl)methyl]-3-{2-fluoro-5-[(2S)-2-methylmorpholin-4-yl]-3-(trifluoromethyl)phenyl}-1,3-dihydro-2H-imidazol-2-one | 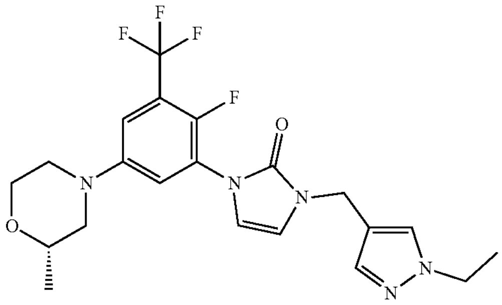 [SMILES: CCn1cc(Cn2ccn(-c3cc(N4CCO[C@@H](C)C4)cc(C(F)(F)F)c3F)c2=O)cn1] | | 454.2 |
| 12 | 1-[5-(2,2-dimethylmorpholin-4-yl)-2-fluoro-3-(trifluoromethyl)phenyl]-3-[(1-ethyl-1H-pyrazol-4-yl)methyl]-1,3-dihydro-2H-imidazol-2-one | 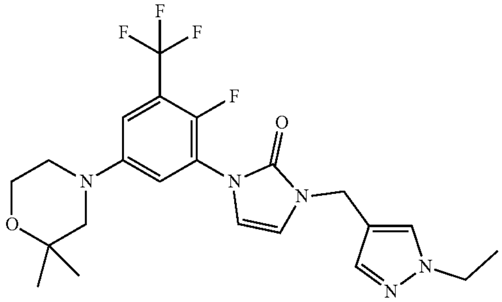 [SMILES: CCn1cc(Cn2ccn(-c3cc(N4CCOC(C)(C)C4)cc(C(F)(F)F)c3F)c2=O)cn1] | | 468.3 |
| 13 | 1-[(1-ethyl-5-methyl-1H-pyrazol-4-yl)methyl]-3-{2-fluoro-5-[(2R)-2-methylmorpholin-4-yl]-3-(trifluoromethyl)phenyl}-1,3-dihydro-2H-imidazol-2-one | 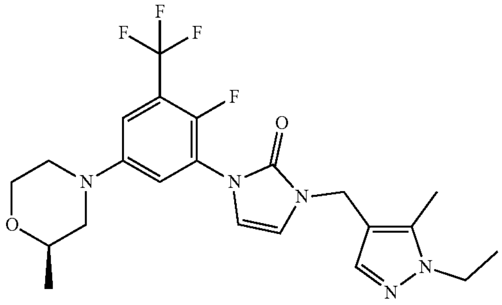 [SMILES: CCn1ncc(Cn2ccn(-c3cc(N4CCO[C@H](C)C4)cc(C(F)(F)F)c3F)c2=O)c1C] | | 468.2 |
| 14 | 1-[(1-ethyl-1H-pyrazol-4-yl)methyl]-4-methyl-3-{3-[(2R)-2-methylmorpholin-4-yl]-5-(trifluoromethyl)phenyl}-1,3-dihydro-2H-imidazol-2-one | 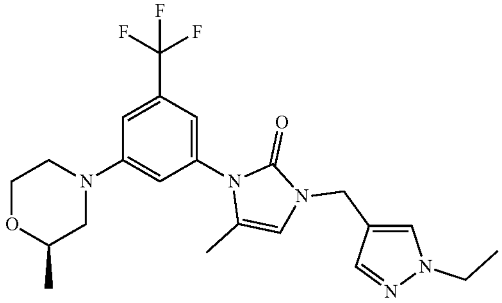 [SMILES: CCn1cc(Cn2cc(C)n(-c3cc(N4CCO[C@H](C)C4)cc(C(F)(F)F)c3)c2=O)cn1] | | 450.3 |
| 15 | 1-{2-chloro-5-[(2R)-2-methylmorpholin-4-yl]-3-(trifluoromethyl)phenyl}-3-[(1-ethyl-1H-pyrazol-4-yl)methyl]-1,3-dihydro-2H-imidazol-2-one | 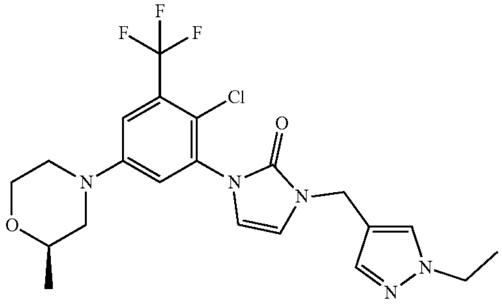 | | 470.2 |

TABLE 1-continued

| Example No. | IUPAC Name | Structure | Salt | MS |
|---|---|---|---|---|
| 16 | 1-[(1-ethyl-1H-pyrazol-4-yl)methyl]-4,5-dimethyl-3-(3-[(2R)-2-methylmorpholin-4-yl]-5-(trifluoromethyl)phenyl}-1,3-dihydro-2H-imidazol-2-one | 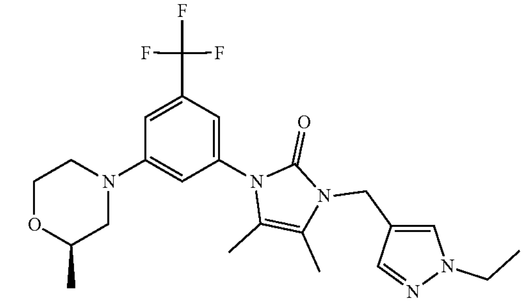 [SMILES: CCn1cc(Cn2c(C)c(C)n(-c3cc(N4CCO[C@H](C)C4)cc(C(F)(F)F)c3)c2=O)cn1] | | 464.3 |
| 17 | 3-[3-(cyclopropylmethoxy)-5-(trifluoromethyl)phenyl]-1-[(1-ethyl-1H-pyrazol-4-yl)methyl]-4-methyl-1,3-dihydro-2H-imidazol-2-one | 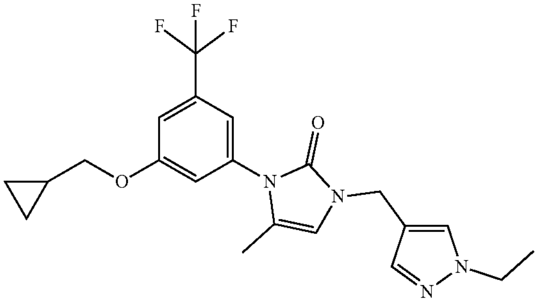 [SMILES: CCn1cc(Cn2cc(C)n(-c3cc(OCC4CC4)cc(C(F)(F)F)c3)c2=O)cn1] | | 421.3 |
| 18 | 1-[(1-ethyl-1H-pyrazol-4-yl)methyl]-4-methyl-3-{6-[(2R)-2-methylmorpholin-4-yl]-4-(trifluoromethyl)pyridin-2-yl}-1,3-dihydro-2H-imidazol-2-one | 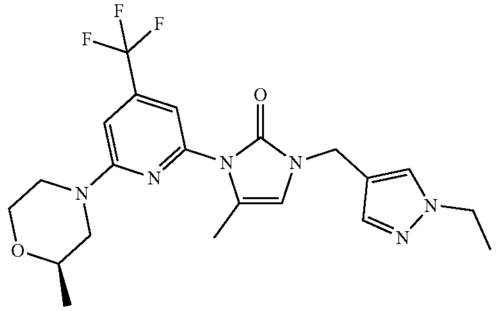 [SMILES: CCn1cc(Cn2cc(C)n(-c3cc(C(F)(F)F)cc(N4CCO[C@H](C)C4)n3)c2=O)cn1] | | 451.3 |
| 19 | 3-[3-(4,4-difluoropiperidin-1-yl)-5-(trifluoromethyl)phenyl]-1-[(1-ethyl-1H-pyrazol-4-yl)methyl]-4-methyl-1,3-dihydro-2H-imidazol-2-one | 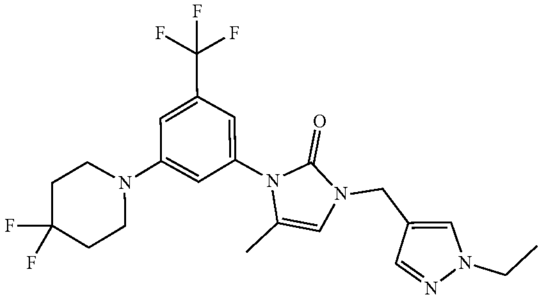 [SMILES: CCn1cc(Cn2cc(C)n(-c3cc(N4CCC(F)(F)CC4)cc(C(F)(F)F)c3)c2=O)cn1] | | 470.3 |
| 20 | 3-{3-[2-(difluoromethyl)morpholin-4-yl]-5-(trifluoromethyl)phenyl}-1-[(1-ethyl-1H-pyrazol-4-yl)methyl]-4-methyl-1,3-dihydro-2H-imidazol-2-one | 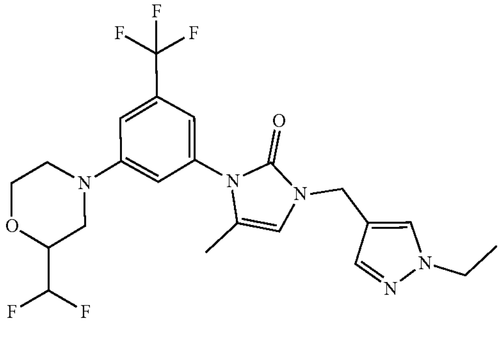 [SMILES: CCn1cc(Cn2cc(C)n(-c3cc(N4CCOC(C(F)F)C4)cc(C(F)(F)F)c3)c2=O)cn1] | | 486.2 |

TABLE 1-continued

| Example No. | IUPAC Name | Structure | Salt | MS |
|---|---|---|---|---|
| 21 | 1-[(1-ethyl-1H-pyrazol-4-yl)methyl]-4-methyl-3-[3-(4-methyl-1H-imidazol-1-yl)-5-(trifluoromethyl)phenyl]-1,3-dihydro-2H-imidazol-2-one | 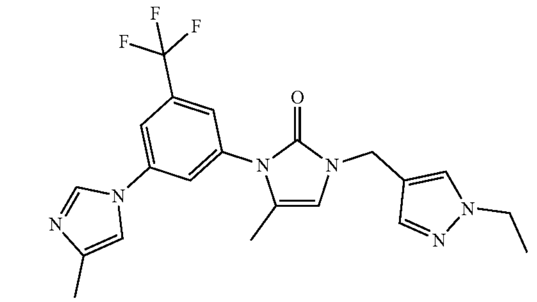 [SMILES: CCn1cc(Cn2cc(C)n(-c3cc(-n4cnc(C)c4)cc(C(F)(F)F)c3)c2=O)cn1] | | 431.2 |
| 22 | 3-{3-[(2,2-difluorocyclopropyl)methoxy]-5-(trifluoromethyl)phenyl}-1-[(1-ethyl-1H-pyrazol-4-yl)methyl]-4-methyl-1,3-dihydro-2H-imidazol-2-one | 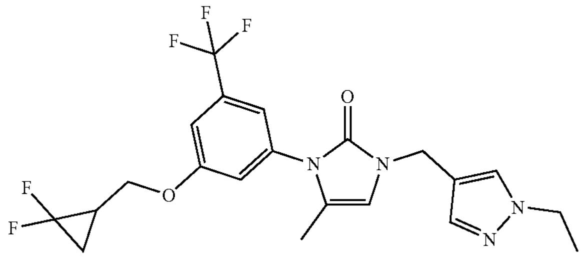 [SMILES: CCn1cc(Cn2cc(C)n(-c3cc(OCC4CC4(F)F)cc(C(F)(F)F)c3)c2=O)cn1] | | 457.2 |
| 23 | 3-{3-[(2R,6S)-2,6-dimethylmorpholin-4-yl]-5-(trifluoromethyl)phenyl}-1-[(1-ethyl-1H-pyrazol-4-yl)methyl]-4-methyl-1,3-dihydro-2H-imidazol-2-one | 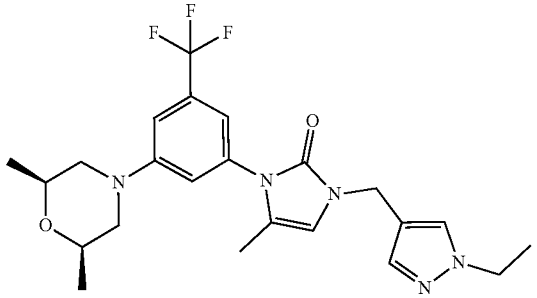 [SMILES: CCn1cc(Cn2cc(C)n(-c3cc(N4C[C@@H](C)O[C@@H](C)C4)cc(C(F)(F)F)c3)c2=O)cn1] | | 464.3 |
| 24 | 3-[3-(3,3-difluoropyrrolidin-1-yl)-5-(trifluoromethyl)phenyl]-1-[(1-ethyl-1H-pyrazol-4-yl)methyl]-4-methyl-1,3-dihydro-2H-imidazol-2-one | 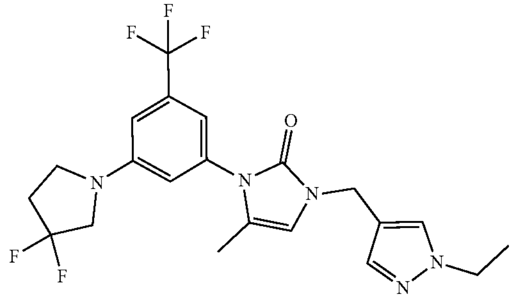 [SMILES: CCn1cc(Cn2cc(C)n(-c3cc(N4CCC(F)(F)C4)cc(C(F)(F)F)c3)c2=O)cn1] | | 456.2 |
| 25 | 3-[(1-ethyl-1H-pyrazol-4-yl)methyl]-1-{2-fluoro-5-[(2R)-2-methylmorpholin-4-yl]-3-(trifluoromethyl)phenyl}-4-methyl-1,3-dihydro-2H-imidazol-2-one | 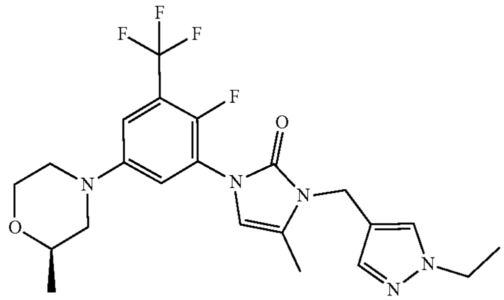 | | 468.3 |

TABLE 1-continued

| Example No. | IUPAC Name | Structure | Salt | MS |
|---|---|---|---|---|
| 26 | 1-[(1-ethyl-1H-pyrazol-4-yl)methyl]-3-{3-fluoro-6-[(2R)-2-methylmorpholin-4-yl]-4-(trifluoromethyl)pyridin-2-yl}-1,3-dihydro-2H-imidazol-2-one | 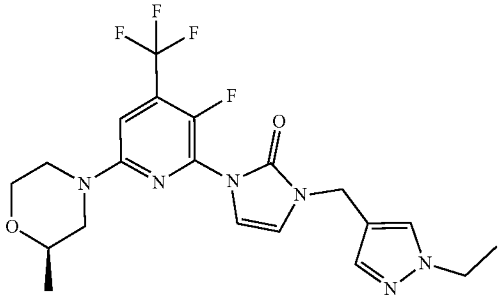 [SMILES: CCn1cc(Cn2ccn(-c3nc(N4CCO[C@H](C)C4)cc(C(F)(F)F)c3F)c2=O)cn1] | | 455.2 |
| 27 | 4-[(1-ethyl-1H-pyrazol-4-yl)methyl]-2-{2-fluoro-5-[(2R)-2-methylmorpholin-4-yl]-3-(trifluoromethyl)phenyl}-2,4-dihydro-3H-1,2,4-triazol-3-one | 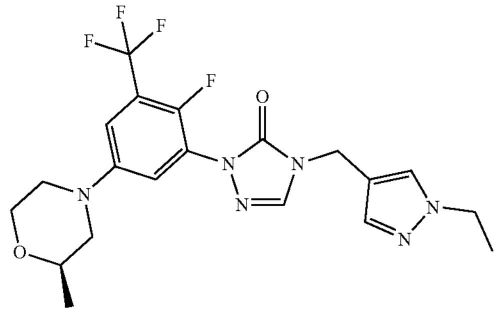 [SMILES: CCn1cc(Cn2cnn(-c3cc(N4CCO[C@H](C)C4)cc(C(F)(F)F)c3F)c2=O)cn1] | | 455.2 |
| 28 | 1-[(1-ethyl-1H-pyrazol-4-yl)methyl]-4-methyl-3-{3-[(2S)-2-methylmorpholin-4-yl]-5-(trifluoromethyl)phenyl}-1,3-dihydro-2H-imidazol-2-one | 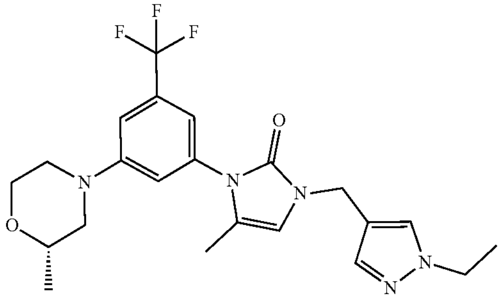 [SMILES: CCn1cc(Cn2cc(C)n(-c3cc(N4CCO[C@@H](C)C4)cc(C(F)(F)F)c3)c2=O)cn1] | | 450.2 |
| 29 | 3-[3-(2,2-dimethylmorpholin-4-yl)-5-(trifluoromethyl)phenyl]-1-[(1-ethyl-1H-pyrazol-4-yl)methyl]-4-methyl-1,3-dihydro-2H-imidazol-2-one | 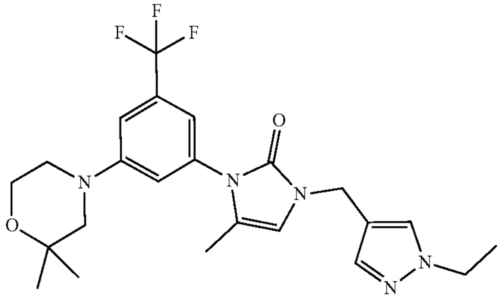 [SMILES: CCn1cc(Cn2cc(C)n(-c3cc(N4CCOC(C)(C)C4)cc(C(F)(F)F)c3)c2=O)cn1] | | 464.3 |
| 30 | 3-[(1-ethyl-1H-pyrazol-4-yl)methyl]-1-{3-fluoro-6-[(2R)-2-methylmorpholin-4-yl]-4-(trifluoromethyl)pyridin-2-yl}-4-methyl-1,3-dihydro-2H-imidazol-2-one | 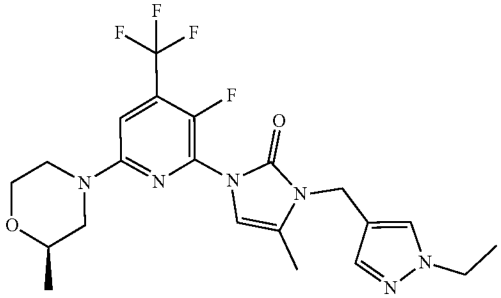 [SMILES: CCn1cc(Cn2c(C)cn(-c3nc(N4CCO[C@H](C)C4)cc(C(F)(F)F)c3F)c2=O)cn1] | | 469.2 |

TABLE 1-continued

| Example No. | IUPAC Name | Structure | Salt | MS |
|---|---|---|---|---|
| 31 | 1-{5-[(2R,6S)-2,6-dimethylmorpholin-4-yl]-2-fluoro-3-(trifluoromethyl)phenyl}-3-[(1-ethyl-1H-pyrazol-4-yl)methyl]-1,3-dihydro-2H-imidazol-2-one | 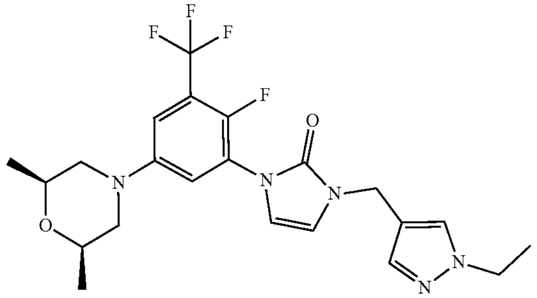 [SMILES: CCn1cc(Cn2ccn(-c3cc(N4C[C@@H](C)O[C@@H](C)C4)cc(C(F)(F)F)c3F)c2=O)cn1] | | 468.3 |
| 32 | 1-{3-chloro-2-fluoro-5-[(2R)-2-methylmorpholin-4-yl]phenyl}-3-[(1-ethyl-1H-pyrazol-4-yl)methyl]-1,3-dihydro-2H-imidazol-2-one | 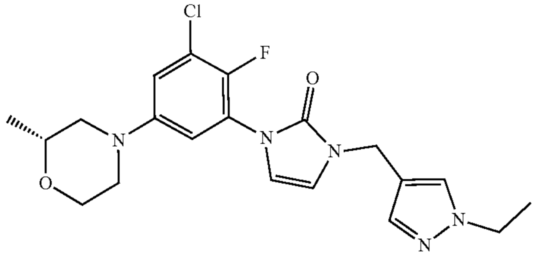 [SMILES: CCn1cc(Cn2ccn(-c3cc(N4CCO[C@H](C)C4)cc(Cl)c3F)c2=O)cn1] | | 420.2 |
| 33 | 3-[3-(4,4-difluorocyclohexyl)-5-(trifluoromethyl)phenyl]-1-[(1-ethyl-1H-pyrazol-4-yl)methyl]-4-methyl-1,3-dihydro-2H-imidazol-2-one | 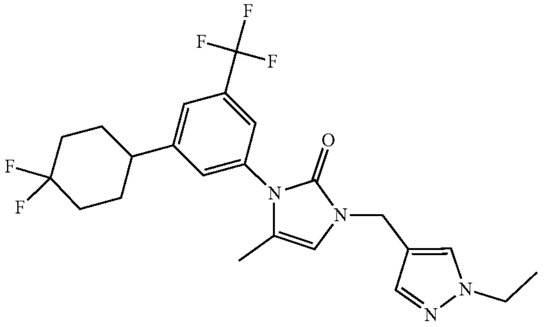 [SMILES: CCn1cc(Cn2cc(C)n(-c3cc(C4CCC(F)(F)CC4)cc(C(F)(F)F)c3)c2=O)cn1] | | 469.2 |
| 34 | 1-{5-[(2R,6R)-2,6-dimethylmorpholin-4-yl]-2-fluoro-3-(trifluoromethyl)phenyl}-3-[(1-ethyl-1H-pyrazol-4-yl)methyl]-1,3-dihydro-2H-imidazol-2-one | 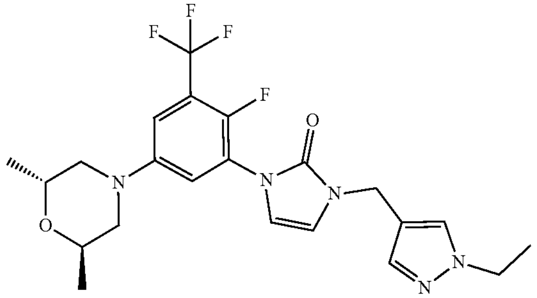 [SMILES: CCn1cc(Cn2ccn(-c3cc(N4C[C@@H](C)O[C@H](C)C4)cc(C(F)(F)F)c3F)c2=O)cn1] | | 468.2 |
| 35 | 1-{2-fluoro-5-[(2R)-2-methylmorpholin-4-yl]-3-(trifluoromethyl)phenyl}-3-{[1-(propan-2-yl)-1H-pyrazol-4-yl]methyl}-1,3-dihydro-2H-imidazol-2-one | 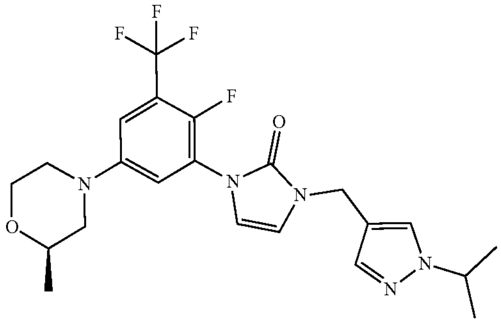 [SMILES: CC(C)n1cc(Cn2ccn(-c3cc(N4CCO[C@H](C)C4)cc(C(F)(F)F)c3F)c2=O)cn1] | | 468.3 |

TABLE 1-continued

| Example No. | IUPAC Name | Structure | Salt | MS |
|---|---|---|---|---|
| 36 | 1-[5-(4,4-difluoropiperidin-1-yl)-2-fluoro-3-(trifluoromethyl)phenyl]-3-[(1-ethyl-1H-pyrazol-4-yl)methyl]-1,3-dihydro-2H-imidazol-2-one | 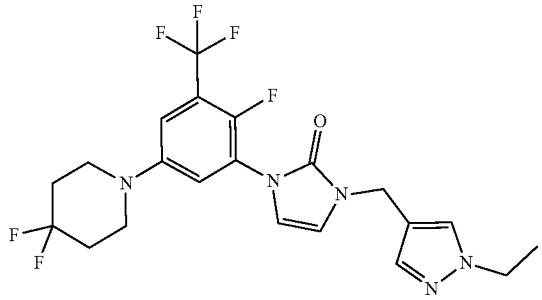 [SMILES: CCn1cc(Cn2ccn(-c3cc(N4CCC(F)(F)CC4)cc(C(F)(F)F)c3F)c2=O)cn1] | | 474.2 |
| 37 | 1-[5-(3,3-difluoropiperidin-1-yl)-2-fluoro-3-(trifluoromethyl)phenyl]-3-[(1-ethyl-1H-pyrazol-4-yl)methyl]-1,3-dihydro-2H-imidazol-2-one | 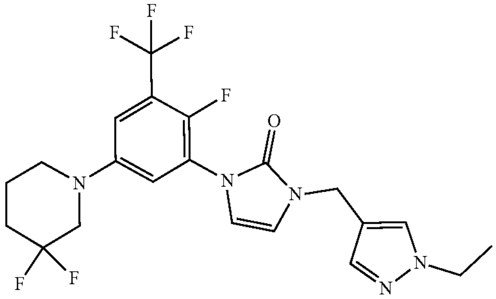 [SMILES: CCn1cc(Cn2ccn(-c3cc(N4CCCC(F)(F)C4)cc(C(F)(F)F)c3F)c2=O)cn1] | | 474.3 |
| 38 | 1-[(1-ethyl-1H-pyrazol-4-yl)methyl]-4-methyl-3-{3-[methyl(oxan-4-yl)amino]-5-(trifluoromethyl)phenyl}-1,3-dihydro-2H-imidazol-2-one | 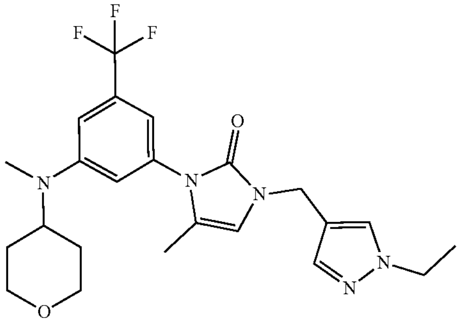 [SMILES: CCn1cc(Cn2cc(C)n(-c3cc(N(C)C4CCOCC4)cc(C(F)(F)F)c3)c2=O)cn1] | | 464.3 |
| 39 | 1-[5-(3,3-difluoropyrrolidin-1-yl)-2-fluoro-3-(trifluoromethyl)phenyl]-3-[(1-ethyl-1H-pyrazol-4-yl)methyl]-1,3-dihydro-2H-imidazol-2-one | 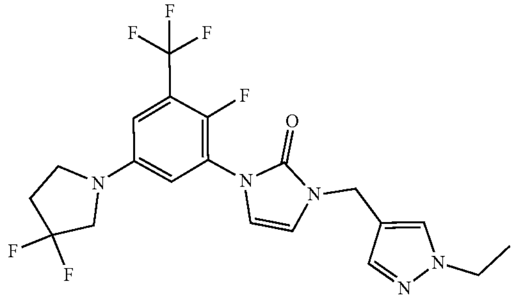 [SMILES: CCn1cc(Cn2ccn(-c3cc(N4CCC(F)(F)C4)cc(C(F)(F)F)c3F)c2=O)cn1] | | 460.2 |
| 40 | 1-[5-(2,2-difluoromorpholin-4-yl)-2-fluoro-3-(trifluoromethyl)phenyl]-3-[(1-ethyl-1H-pyrazol-4-yl)methyl]-1,3-dihydro-2H-imidazol-2-one | 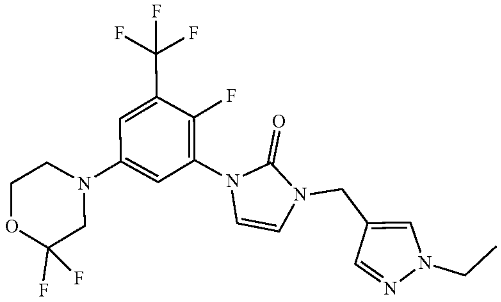 [SMILES: CCn1cc(Cn2ccn(-c3cc(N4CCOC(F)(F)C4)cc(C(F)(F)F)c3F)c2=O)cn1] | | 476.2 |

TABLE 1-continued

| Example No. | IUPAC Name | Structure | Salt | MS |
|---|---|---|---|---|
| 41 | 3-[3-(2,2-difluoromorpholin-4-yl)-5-(trifluoromethyl)phenyl]-1-[(1-ethyl-1H-pyrazol-4-yl)methyl]-4-methyl-1,3-dihydro-2H-imidazol-2-one | 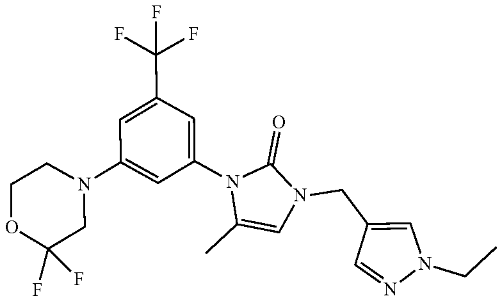 [SMILES: CCn1cc(Cn2cc(C)n(-c3cc(N4CCOC(F)(F)C4)cc(C(F)(F)F)c3)c2=O)cn1] | | 472.2 |
| 42 | 1-[(1-ethyl-1H-pyrazol-4-yl)methyl]-3-{3-methyl-6-[(2R)-2-methylmorpholin-4-yl]-4-(trifluoromethyl)pyridin-2-yl}-1,3-dihydro-2H-imidazol-2-one | 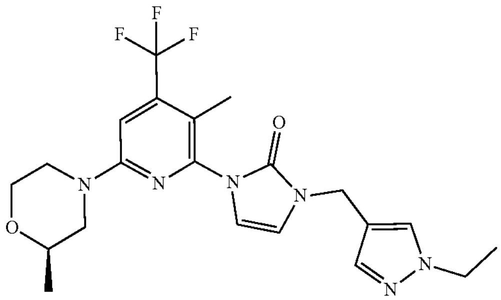 [SMILES: CCn1cc(Cn2ccn(-c3nc(N4CCO[C@H](C)C4)cc(C(F)(F)F)c3C)c2=O)cn1] | | 451.3 |
| 43 | 1-[(1-ethyl-1H-pyrazol-4-yl)methyl]-3-[2-fluoro-5-(4-oxa-7-azaspiro[2.5]octan-7-yl)-3-(trifluoromethyl)phenyl]-1,3-dihydro-2H-imidazol-2-one | 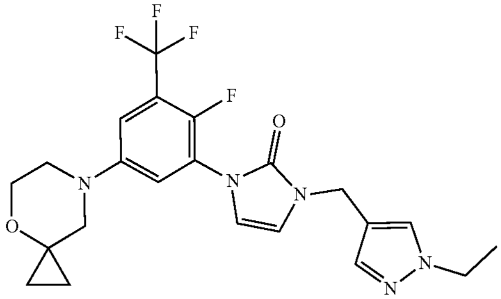 [SMILES: CCn1cc(Cn2ccn(-c3cc(N4CCOC5(CC5)C4)cc(C(F)(F)F)c3F)c2=O)cn1] | | 466.2 |
| 44 | 1-{3-cyclopropyl-2-fluoro-5-[(2R)-2-methylmorpholin-4-yl]phenyl}-3-[(1-ethyl-1H-pyrazol-4-yl)methyl]-1,3-dihydro-2H-imidazol-2-one | 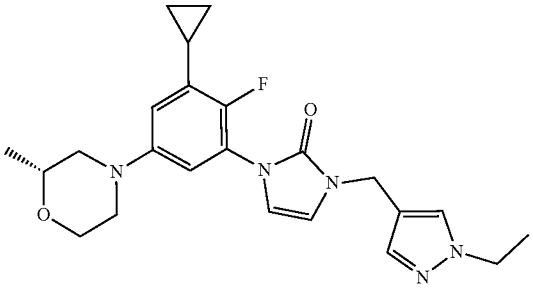 [SMILES: CCn1cc(Cn2ccn(-c3cc(N4CCO[C@H](C)C4)cc(C4CC4)c3F)c2=O)cn1] | | 426.3 |
| 45 | 3-[(1-ethyl-1H-pyrazol-4-yl)methyl]-4-methyl-1-{3-methyl-6-[(2R)-2-methylmorpholin-4-yl]-4-(trifluoromethyl)pyridin-2-yl}-1,3-dihydro-2H-imidazol-2-one | 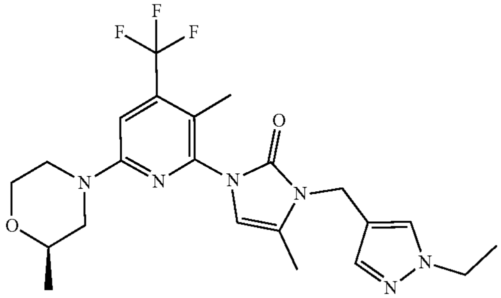 [SMILES: CCn1cc(Cn2c(C)cn(-c3nc(N4CCO[C@H](C)C4)cc(C(F)(F)F)c3C)c2=O)cn1] | | 465.3 |

TABLE 1-continued

| Example No. | IUPAC Name | Structure | Salt | MS |
|---|---|---|---|---|
| 46 | 1-{3-(2,2-difluoroethoxy)-5-[(2R)-2-methylmorpholin-4-yl]phenyl}-3-[(1-ethyl-1H-pyrazol-4-yl)methyl]-4,5-dimethyl-1,3-dihydro-2H-imidazol-2-one | 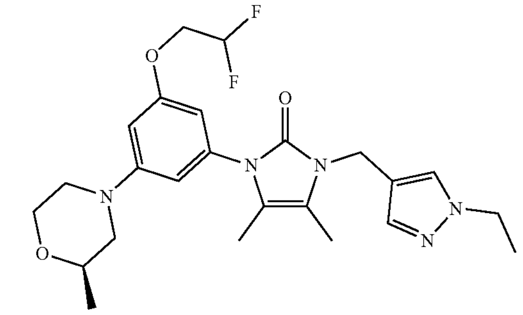 [SMILES: CCn1cc(Cn2c(C)c(C)n(-c3cc(OCC(F)F)cc(N4CCO[C@H](C)C4)c3)c2=O)cn1] | | 476.3 |
| 47 | 1-[(1-ethyl-1H-pyrazol-4-yl)methyl]-4,5-dimethyl-3-{3-[(2R)-2-methylmorpholin-4-yl]-5-(2,2,2-trifluoroethoxy)phenyl}-1,3-dihydro-2H-imidazol-2-one | 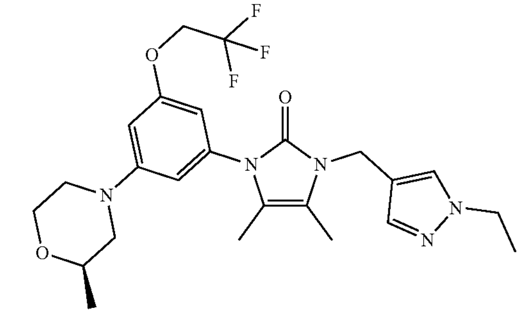 [SMILES: CCn1cc(Cn2c(C)c(C)n(-c3cc(OCC(F)(F)F)cc(N4CCO[C@H](C)C4)c3)c2=O)cn1] | | 494.3 |
| 48 | 1-[(1-ethyl-1H-pyrazol-4-yl)methyl]-3-[3-(methoxymethoxy)-5-(trifluoromethyl)phenyl]-4-methyl-1,3-dihydro-2H-imidazol-2-one | 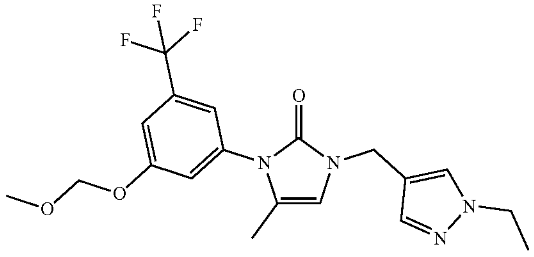 [SMILES: CCn1cc(Cn2cc(C)n(-c3cc(OCOC)cc(C(F)(F)F)c3)c2=O)cn1] | | 411.2 |
| 49 | 1-[(1-ethyl-1H-pyrazol-4-yl)methyl]-4-methyl-3-{3-[(oxetan-2-yl)methoxy]-5-(trifluoromethyl)phenyl}-1,3-dihydro-2H-imidazol-2-one | 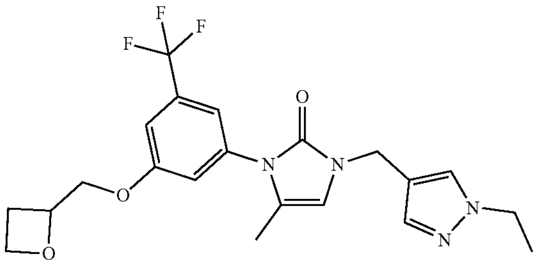 [SMILES: CCn1cc(Cn2cc(C)n(-c3cc(OCC4CCO4)cc(C(F)(F)F)c3)c2=O)cn1] | | 437.3 |
| 50 | 3-{3-[(2,2-difluorocyclopropyl)methoxy]-5-(trifluoromethyl)phenyl}-1-[(1-ethyl-1H-pyrazol-4-yl)methyl]-4-methyl-1,3-dihydro-2H-imidazol-2-one | 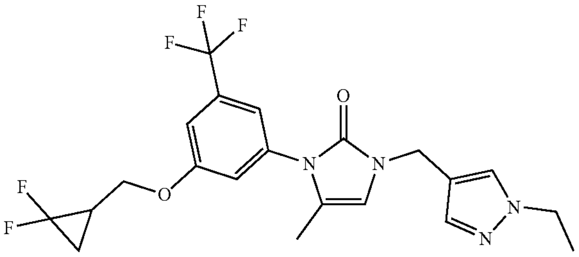 [SMILES: CCn1cc(Cn2cc(C)n(-c3cc(OCC4CC4(F)F)cc(C(F)(F)F)c3)c2=O)cn1] | | 457.2 |

TABLE 1-continued

| Example No. | IUPAC Name | Structure | Salt | MS |
|---|---|---|---|---|
| 51 | 3-{3-[(2,2-difluorocyclopropyl)methoxy]-5-(trifluoromethyl)phenyl}-1-[(1-ethyl-1H-pyrazol-4-yl)methyl]-4-methyl-1,3-dihydro-2H-imidazol-2-one | 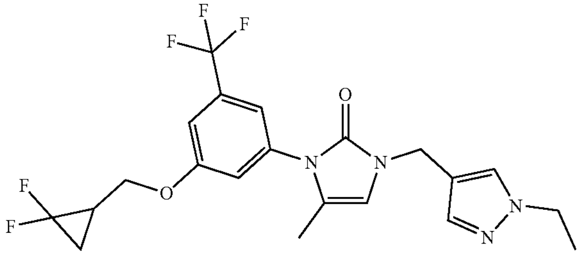 [SMILES: CCn1cc(Cn2cc(C)n(-c3cc(OCC4CC4(F)F)cc(C(F)(F)F)c3)c2=O)cn1] | | 457.2 |
| 52 | 1-[(1-ethyl-1H-pyrazol-4-yl)methyl]-3-{3-[(1-fluorocyclobutyl)methoxy]-5-(trifluoromethyl)phenyl}-4-methyl-1,3-dihydro-2H-imidazol-2-one | 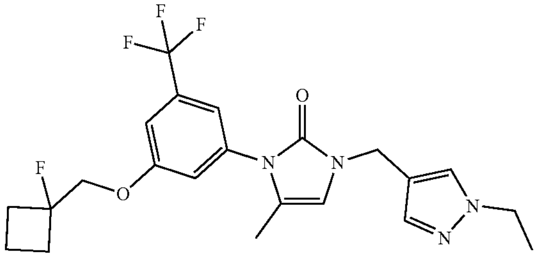 [SMILES: CCn1cc(Cn2cc(C)n(-c3cc(OCC4(F)CCC4)cc(C(F)(F)F)c3)c2=O)cn1] | | 453.3 |
| 53 | 3-[(1-ethyl-1H-pyrazol-4-yl)methyl]-1-{2-fluoro-5-[methyl(oxan-4-yl)amino]-3-(trifluoromethyl)phenyl}-4-methyl-1,3-dihydro-2H-imidazol-2-one | 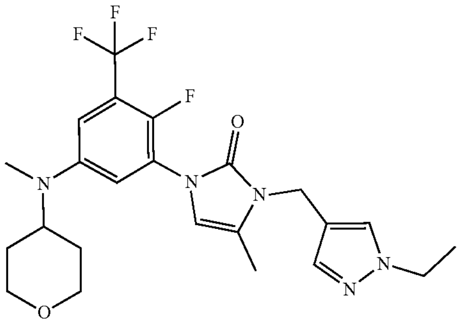 [SMILES: CCn1cc(Cn2c(C)cn(-c3cc(N(C)C4CCOCC4)cc(C(F)(F)F)c3F)c2=O)cn1] | | 482.3 |
| 54 | 1-[5-(2,2-difluoromorpholin-4-yl)-2-fluoro-3-(trifluoromethyl)phenyl]-3-[(1-ethyl-1H-pyrazol-4-yl)methyl]-4-methyl-1,3-dihydro-2H-imidazol-2-one | 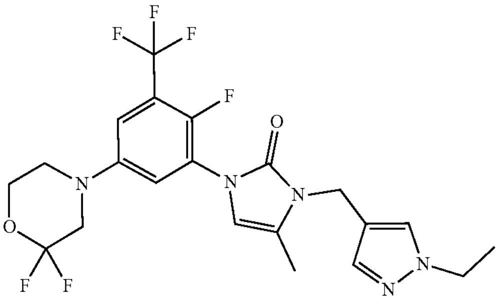 [SMILES: CCn1cc(Cn2c(C)cn(-c3cc(N4CCOC(F)(F)C4)cc(C(F)(F)F)c3F)c2=O)cn1] | | 490.1 |
| 55 | 3-[(1-ethyl-1H-pyrazol-4-yl)methyl]-1-{2-fluoro-5-[(2R)-2-methylmorpholin-4-yl]-3-(2,2,2-trifluoroethoxy)phenyl}-4-methyl-1,3-dihydro-2H-imidazol-2-one | 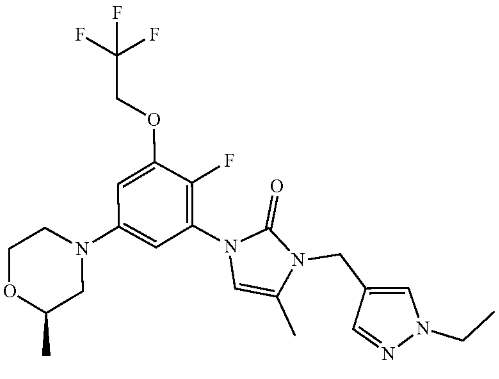 [SMILES: CCn1cc(Cn2c(C)cn(-c3cc(N4CCO[C@H](C)C4)cc(OCC(F)(F)F)c3F)c2=O)cn1] | | 498.3 |

TABLE 1-continued

| Example No. | IUPAC Name | Structure | Salt | MS |
|---|---|---|---|---|
| 56 | 1-[(1-ethyl-1H-pyrazol-4-yl)methyl]-3-{3-[(1-fluorocyclopropyl)methoxy]-5-(trifluoromethyl)phenyl}-4-methyl-1,3-dihydro-2H-imidazol-2-one | 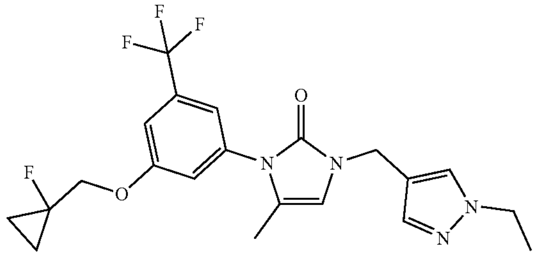 [SMILES: CCn1cc(Cn2cc(C)n(-c3cc(OCC4(F)CC4)cc(C(F)(F)F)c3)c2=O)cn1] | | 439.3 |
| 57 | 1-{2-chloro-5-[(2R)-2-methylmorpholin-4-yl]-3-(trifluoromethyl)phenyl}-3-[(1-ethyl-1H-pyrazol-4-yl)methyl]-4-methyl-1,3-dihydro-2H-imidazol-2-one | 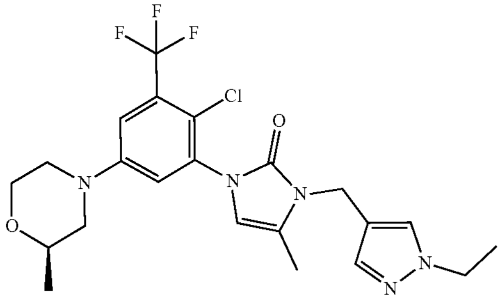 | | 484.2 |
| 58 | 1-{2-chloro-5-[methyl(oxan-4-yl)amino]-3-(trifluoromethyl)phenyl}-3-[(1-ethyl-1H-pyrazol-4-yl)methyl]-4-methyl-1,3-dihydro-2H-imidazol-2-one | 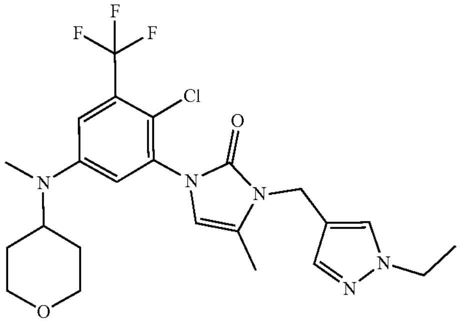 [SMILES: CCn1cc(Cn2c(C)cn(-c3cc(N(C)C4CCOCC4)cc(C(F)(F)F)c3Cl)c2=O)cn1] | | 498.3 |
| 59 | 1-[(1-ethyl-1H-pyrazol-4-yl)methyl]-3-{3-fluoro-6-[(2R)-2-methylmorpholin-4-yl]-4-(trifluoromethyl)pyridin-2-yl}-4,5-dimethyl-1,3-dihydro-2H-imidazol-2-one | 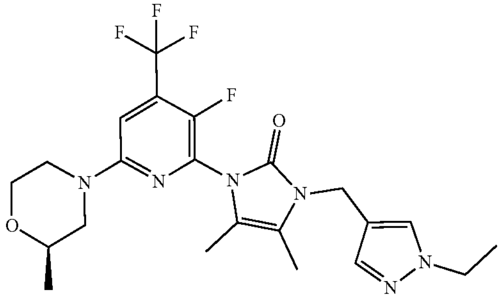 [SMILES: CCn1cc(Cn2c(C)c(C)n(-c3nc(N4CCO[C@H](C)C4)cc(C(F)(F)F)c3F)c2=O)cn1] | | 483.2 |
| 60 | 1-[(1-ethyl-1H-pyrazol-4-yl)methyl]-4,5-dimethyl-3-{6-[(2R)-2-methylmorpholin-4-yl]-4-(trifluoromethyl)pyridin-2-yl}-1,3-dihydro-2H-imidazol-2-one | 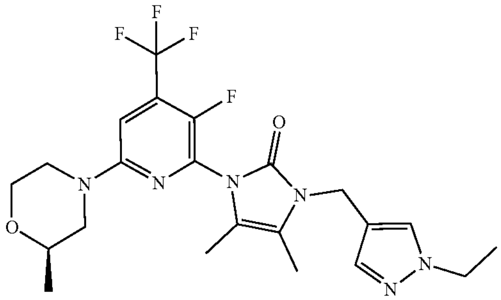 [SMILES: CCn1cc(Cn2c(C)c(C)n(-c3nc(N4CCO[C@H](C)C4)cc(C(F)(F)F)c3F)c2=O)cn1] | | 465.3 |

TABLE 1-continued

| Example No. | IUPAC Name | Structure | Salt | MS |
|---|---|---|---|---|
| 61 | 1-{2-fluoro-5-[methyl(oxan-4-yl)amino]-3-(trifluoromethyl)phenyl}-3-{[1-(propan-2-yl)-1H-pyrazol-4-yl]methyl}-1,3-dihydro-2H-imidazol-2-one | 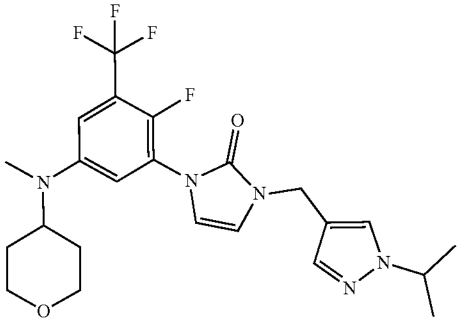 [SMILES: CC(C)n1cc(Cn2ccn(-c3cc(N(C)C4CCOCC4)cc(C(F)(F)F)c3F)c2=O)cn1] | | 482.3 |
| 62 | 3-[(1-ethyl-1H-pyrazol-4-yl)methyl]-4-methyl-1-{2-methyl-5-[(2R)-2-methylmorpholin-4-yl]-3-(trifluoromethyl)phenyl}-1,3-dihydro-2H-imidazol-2-one | 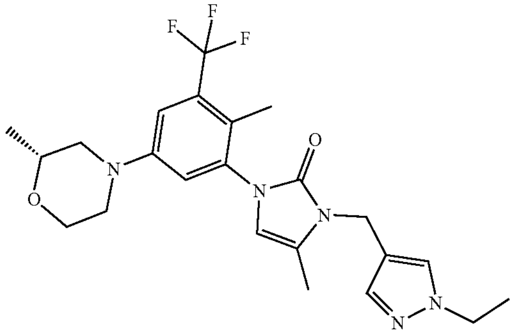 [SMILES: CCn1cc(Cn2c(C)cn(-c3cc(N4CCO[C@H](C)C4)cc(C(F)(F)F)c3C)c2=O)cn1] | | 464.3 |
| 63 | 1-[3-(2,2-difluoromorpholin-4-yl)-5-(trifluoromethyl)phenyl]-3-[(1-ethyl-1H-pyrazol-4-yl)methyl]-4,5-dimethyl-1,3-dihydro-2H-imidazol-2-one | 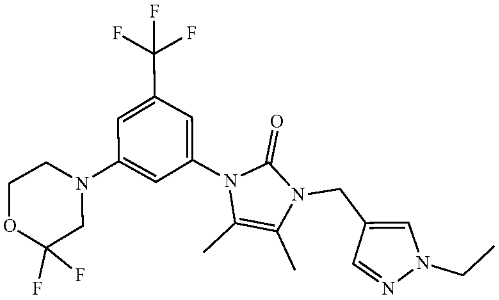 [SMILES: CCn1cc(Cn2c(C)c(C)n(-c3cc(N4CCOC(F)(F)C4)cc(C(F)(F)F)c3)c2=O)cn1] | | 486.2 |
| 64 | 1-{3-fluoro-6-[(2R)-2-methylmorpholin-4-yl]-4-(trifluoromethyl)pyridin-2-yl}-4-methyl-3-{[1-(propan-2-yl)-1H-pyrazol-4-yl]methyl}-1,3-dihydro-2H-imidazol-2-one | 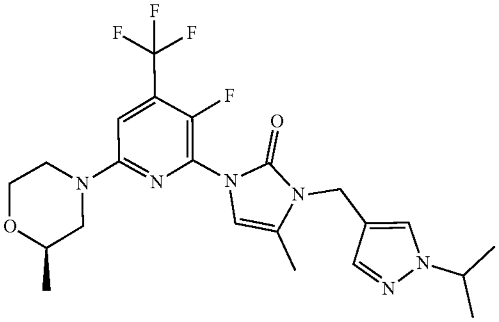 [SMILES: Cc1cn(-c2nc(N3CCO[C@H](C)C3)cc(C(F)(F)F)c2F)c(=O)n1Cc1cnn(C(C)C)c1] | | 483.3 |
| 65 | 3-{3-bromo-5-[(3,3-difluorocyclobutyl)methoxy]phenyl}-1-[(1-ethyl-1H-pyrazol-4-yl)methyl]-4-methyl-1,3-dihydro-2H-imidazol-2-one | 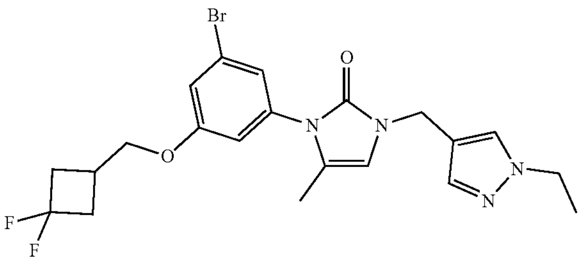 [SMILES: CCn1cc(Cn2cc(C)n(-c3cc(Br)cc(OCC4CC(F)(F)C4)c3)c2=O)cn1] | | 481.1 |

TABLE 1-continued

| Example No. | IUPAC Name | Structure | Salt | MS |
|---|---|---|---|---|
| 66 | 1-[(1-ethyl-1H-pyrazol-4-yl)methyl]-4-methyl-3-[3-{[(2S)-oxolan-2-yl]methoxy}-5-(trifluoromethyl)phenyl]-1,3-dihydro-2H-imidazol-2-one | 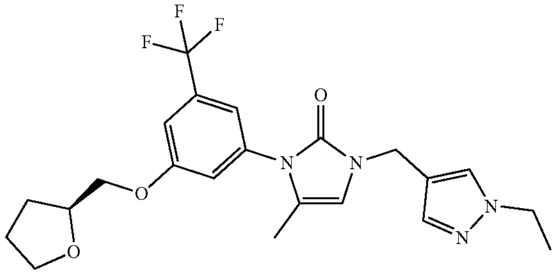 [SMILES: CCn1cc(Cn2cc(C)n(-c3cc(OC[C@@H]4CCCO4)cc(C(F)(F)F)c3)c2=O)cn1] | | 451.2 |
| 67 | 3-{3-cyclopropyl-5-[(3,3-difluorocyclobutyl)methoxy] phenyl}-1-[(1-ethyl-1H-pyrazol-4-yl)methyl]-4-methyl-1,3-dihydro-2H-imidazol-2-one | 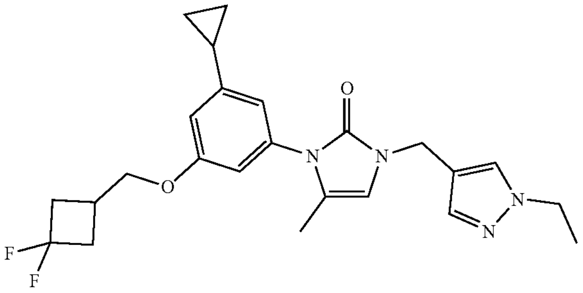 [SMILES: CCn1cc(Cn2cc(C)n(-c3cc(OCC4CC(F)(F)C4)cc(C4CC4)c3)c2=O)cn1] | | 443.3 |
| 68 | 3-{3-[(3,3-difluorocyclobutyl)methoxy]-5-(difluoromethyl)phenyl}-1-[(1-ethyl-1H-pyrazol-4-yl)methyl]-4-methyl-1,3-dihydro-2H-imidazol-2-one | 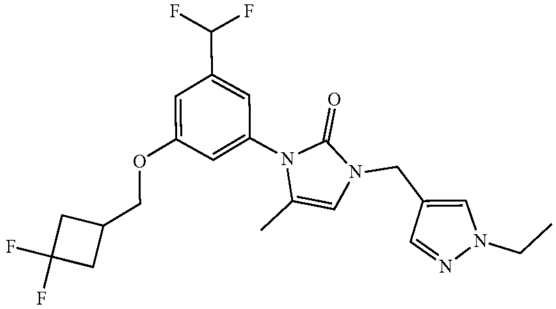 [SMILES: CCn1cc(Cn2cc(C)n(-c3cc(OCC4CC(F)(F)C4)cc(C(F)F)c3)c2=O)cn1] | | 453.3 |
| 69 | 1-{2-chloro-5-[(3,3-difluorocyclobutyl)methoxy]-3-(difluoromethyl)phenyl}-3-[(1-ethyl-1H-pyrazol-4-yl)methyl]-1,3-dihydro-2H-imidazol-2-one | 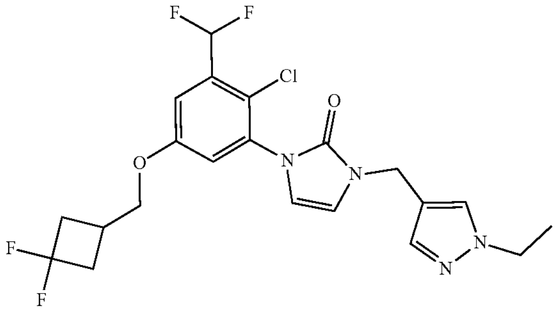 [SMILES: CCn1cc(Cn2ccn(-c3cc(OCC4CC(F)(F)C4)cc(C(F)F)c3Cl)c2=O)cn1] | | 473.2 |
| 70 | 1-[5-(2,2-difluoromorpholin-4-yl)-2-fluoro-3-(trifluoromethyl)phenyl]-3-[(1-ethyl-1H-pyrazol-4-yl)methyl]-4,5-dimethyl-1,3-dihydro-2H-imidazol-2-one | 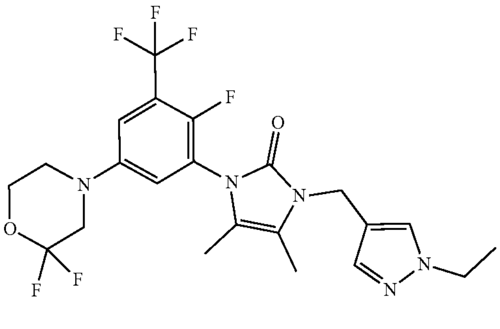 [SMILES: CCn1cc(Cn2c(C)c(C)n(-c3cc(N4CCOC(F)(F)C4)cc(C(F)(F)F)c3F)c2=O)cn1] | | 504.2 |

TABLE 1-continued

| Example No. | IUPAC Name | Structure | Salt | MS |
|---|---|---|---|---|
| 71 | 3-{3-(2,2-difluoroethoxy)-5-[(2R)-2-methylmorpholin-4-yl]phenyl}-1-[(1-ethyl-1H-pyrazol-4-yl)methyl]-4-methyl-1,3-dihydro-2H-imidazol-2-one | 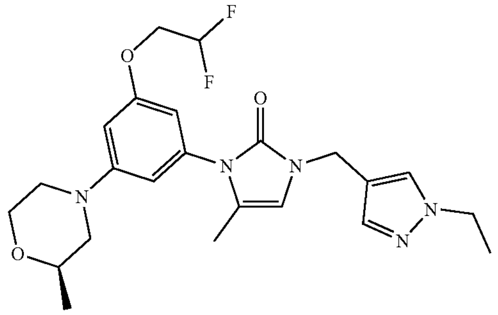 [SMILES: CCn1cc(Cn2cc(C)n(-c3cc(OCC(F)F)cc(N4CCO[C@H](C)C4)c3)c2=O)cn1] | | 462.3 |
| 72 | 1-[(1-ethyl-1H-pyrazol-4-yl)methyl]-4-methyl-3-{3-[(2R)-2-methylmorpholin-4-yl]-5-(2,2,2-trifluoroethoxy)phenyl}-1,3-dihydro-2H-imidazol-2-one | 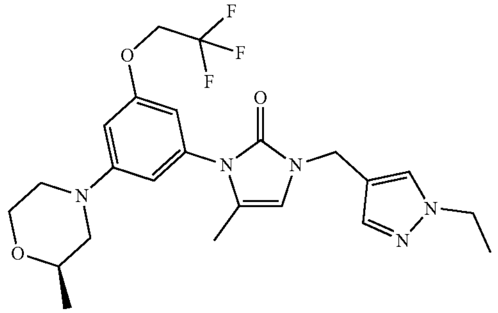 [SMILES: CCn1cc(Cn2cc(C)n(-c3cc(OCC(F)(F)F)cc(N4CCO[C@H](C)C4)c3)c2=O)cn1] | | 480.3 |
| 73 | 1-[(1-ethyl-1H-pyrazol-4-yl)methyl]-4,5-dimethyl-3-{3-[methyl(oxan-4-yl)amino]-5-(2,2,2-trifluoroethoxy)phenyl}-1,3-dihydro-2H-imidazol-2-one | 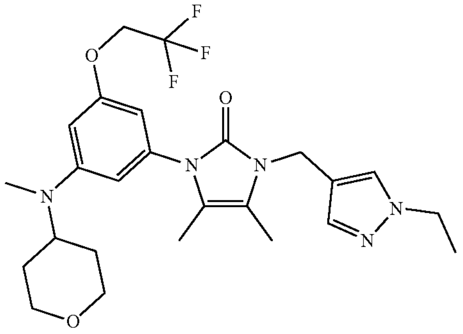 [SMILES: CCn1cc(Cn2c(C)c(C)n(-c3cc(OCC(F)(F)F)cc(N(C)C4CCOCC4)c3)c2=O)cn1] | | 508.3 |
| 74 | 1-{3-ethenyl-2-fluoro-5-[(2R)-2-methylmorpholin-4-yl]phenyl}-3-[(1-ethyl-1H-pyrazol-4-yl)methyl]-1,3-dihydro-2H-imidazol-2-one | 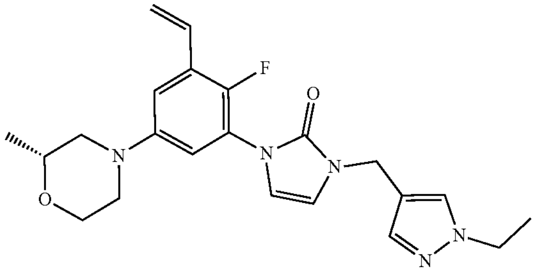 [SMILES: C=Cc1cc(N2CCO[C@H](C)C2)cc(-n2ccn(Cc3cnn(CC)c3)c2=O)c1F] | | 412.4 |
| 75 | 1-{3-fluoro-6-[(2R)-2-methylmorpholin-4-yl]-4-(trifluoromethyl)pyridin-2-yl}-3-{[1-(propan-2-yl)-1H-pyrazol-4-yl]methyl}-1,3-dihydro-2H-imidazol-2-one | 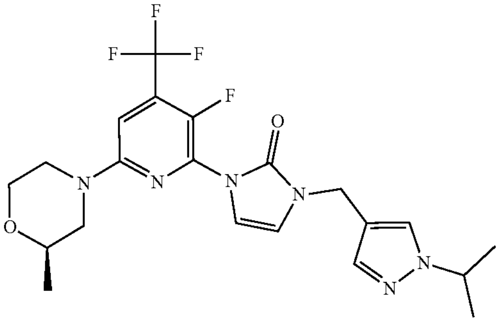 [SMILES: CC(C)n1cc(Cn2ccn(-c3nc(N4CCO[C@H](C)C4)cc(C(F)(F)F)c3F)c2=O)cn1] | | 469.3 |

TABLE 1-continued

| Example No. | IUPAC Name | Structure | Salt | MS |
|---|---|---|---|---|
| 76 | 1-{3-(difluoromethyl)-5-[methyl(oxan-4-yl)amino]phenyl}-4,5-dimethyl-3-{[1-(propan-2-yl)-1H-pyrazol-4-yl]methyl}-1,3-dihydro-2H-imidazol-2-one | 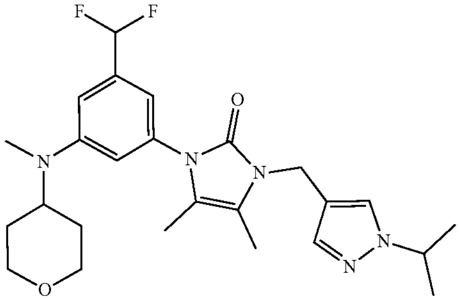 [SMILES: Cc1c(C)n(-c2cc(C(F)F)cc(N(C)C3CCOCC3)c2)c(=O)n1Cc1cnn(C(C)C)c1] | | 474.3 |
| 77 | 3-[1-(2-cyclobutylethyl)-3-(trifluoromethyl)-1H-pyrazol-5-yl]-1-[(1-ethyl-1H-pyrazol-4-yl)methyl]-4-methyl-1,3-dihydro-2H-imidazol-2-one | 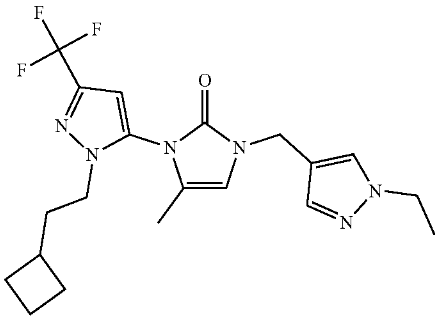 [SMILES: CCn1cc(Cn2cc(C)n(-c3cc(C(F)(F)F)nn3CCC3CCC3)c2=O)cn1] | | 423.3 |
| 78 | 1-{3-(2,2-difluorocyclopropyl)-2-fluoro-5-[(2R)-2-methylmorpholin-4-yl]phenyl}-3-[(1-ethyl-1H-pyrazol-4-yl)methyl]-1,3-dihydro-2H-imidazol-2-one | 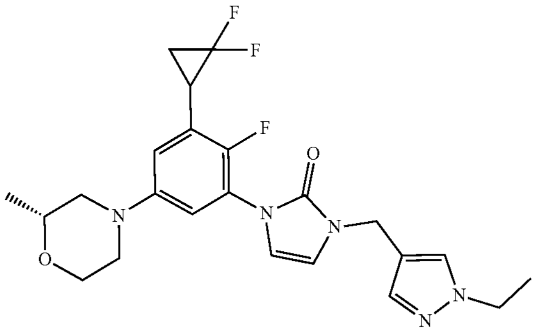 [SMILES: CCn1cc(Cn2ccn(-c3cc(N4CCO[C@H](C)C4)cc(C4CC4(F)F)c3F)c2=O)cn1] | | 462.2 |
| 79 | 1-[3-(difluoromethyl)-5-(2,2-dimethylmorpholin-4-yl)-2-fluorophenyl]-4-methyl-3-{[1-(propan-2-yl)-1H-pyrazol-4-yl]methyl}-1,3-dihydro-2H-imidazol-2-one | 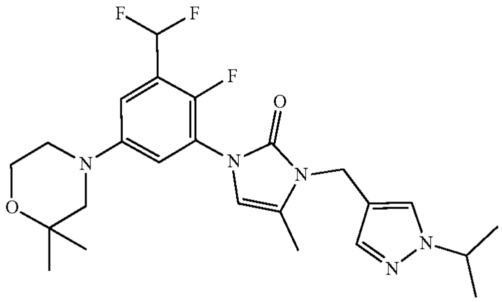 [SMILES: Cc1cn(-c2cc(N3CCOC(C)(C)C3)cc(C(F)F)c2F)c(=O)n1Cc1cnn(C(C)C)c1] | | 478.2 |
| 80 | 1-{3-ethyl-2-fluoro-5-[(2R)-2-methylmorpholin-4-yl]phenyl}-3-[(1-ethyl-1H-pyrazol-4-yl)methyl]-1,3-dihydro-2H-imidazol-2-one | 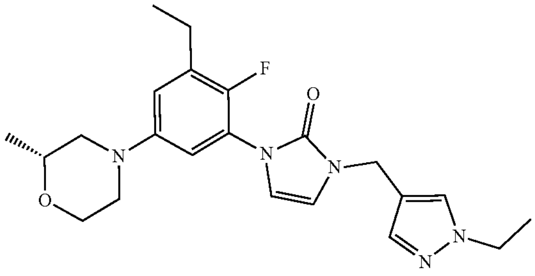 [SMILES: CCc1cc(N2CCO[C@H](C)C2)cc(-n2ccn(Cc3cnn(CC)c3)c2=O)c1F] | | 414.3 |

TABLE 1-continued

| Example No. | IUPAC Name | Structure | Salt | MS |
|---|---|---|---|---|
| 81 | 1-{3-ethyl-2-fluoro-5-[(2R)-2-methylmorpholin-4-yl]phenyl}-3-[(1-ethyl-1H-pyrazol-4-yl)methyl]-4-methyl-1,3-dihydro-2H-imidazol-2-one | 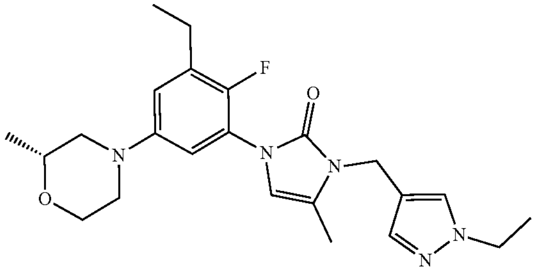 [SMILES: CCc1cc(N2CCO[C@H](C)C2)cc(-n2cc(C)n(Cc3cnn(CC)c3)c2=O)c1F] | | 428.3 |
| 82 | 3-{2-chloro-5-[(2R)-2-methylmorpholin-4-yl]-3-(trifluoromethyl)phenyl}-1-[(1-ethyl-1H-pyrazol-4-yl)methyl]-4-methyl-1,3-dihydro-2H-imidazol-2-one | 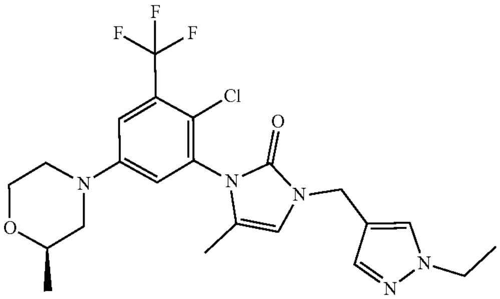 [SMILES: CCn1cc(Cn2cc(C)n(-c3cc(N4CCO[C@H](C)C4)cc(C(F)(F)F)c3Cl)c2=O)cn1] | | 484.1 |
| 83 | 1-{3-chloro-6-[methyl(oxan-4-yl)amino]-4-(trifluoromethyl)pyridin-2-yl}-3-[(1-ethyl-1H-pyrazol-4-yl)methyl]-4-methyl-1,3-dihydro-2H-imidazol-2-one | 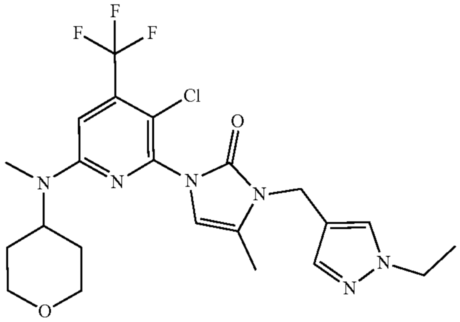 [SMILES: CCn1cc(Cn2c(C)cn(-c3nc(N(C)C4CCOCC4)cc(C(F)(F)F)c3Cl)c2=O)cn1] | | 499.2 |
| 84 | 1-{3-chloro-6-[(2R)-2-methylmorpholin-4-yl]-4-(trifluoromethyl)pyridin-2-yl}-3-[(1-ethyl-1H-pyrazol-4-yl)methyl]-4-methyl-1,3-dihydro-2H-imidazol-2-one | 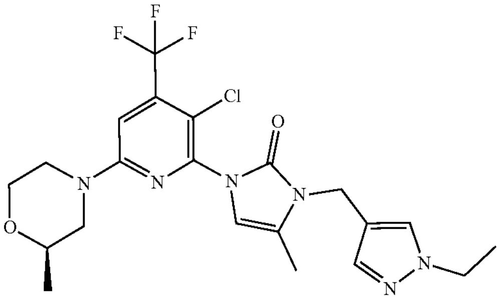 | | 485.1 |
| 85 | 1-{3-chloro-6-[(2R)-2-methylmorpholin-4-yl]-4-(trifluoromethyl)pyridin-2-yl}-4-methyl-3-{[1-(propan-2-yl)-1H-pyrazol-4-yl]methyl}-1,3-dihydro-2H-imidazol-2-one | 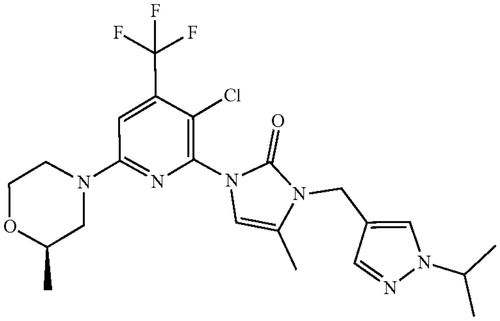 | | 499.2 |

TABLE 1-continued

| Example No. | IUPAC Name | Structure | Salt | MS |
|---|---|---|---|---|
| 86 | 1-[(1-ethyl-1H-pyrazol-4-yl)methyl]-4-methyl-3-{6-[methyl(oxan-4-yl)amino]-4-(trifluoromethyl)pyridin-2-yl}-1,3-dihydro-2H-imidazol-2-one | 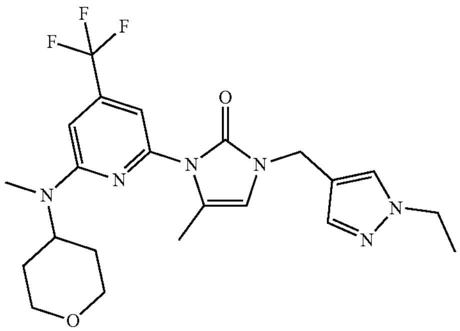 [SMILES: CCn1cc(Cn2cc(C)n(-c3cc(C(F)(F)F)cc(N(C)C4CCOCC4)n3)c2=O)cn1] | | 465.2 |
| 87 | 1-{2-fluoro-3-methyl-5-[(2R)-2-methylmorpholin-4-yl]phenyl}-4-methyl-3-{[1-(propan-2-yl)-1H-pyrazol-4-yl]methyl}-1,3-dihydro-2H-imidazol-2-one | 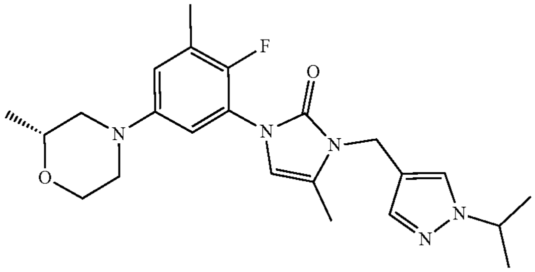 [SMILES: Cc1cc(N2CCO[C@H](C)C2)cc(-n2cc(C)n(Cc3cnn(C(C)C)c3)c2=O)c1F] | | 428.3 |
| 88 | 1-[(1-ethyl-1H-pyrazol-4-yl)methyl]-4-methyl-3-{3-[methyl(oxan-4-yl)amino]-5-(2,2,2-trifluoroethoxy)phenyl}-1,3-dihydro-2H-imidazol-2-one | 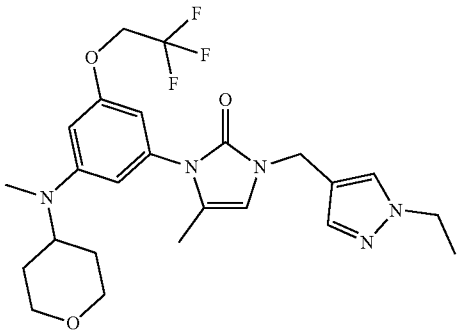 [SMILES: CCn1cc(Cn2cc(C)n(-c3cc(OCC(F)(F)F)cc(N(C)C4CCOCC4)c3)c2=O)cn1] | | 494.2 |
| 89 | 3-{3-bromo-5-[(2R)-2-methylmorpholin-4-yl]phenyl}-1-[(1-ethyl-1H-pyrazol-4-yl)methyl]-4-methyl-1,3-dihydro-2H-imidazol-2-one | 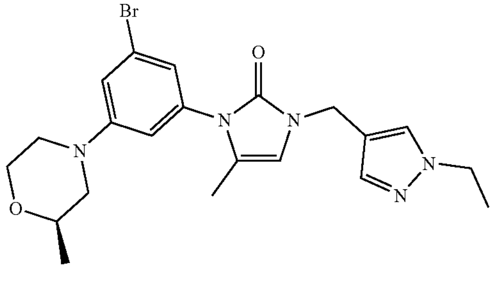 [SMILES: CCn1cc(Cn2cc(C)n(-c3cc(Br)cc(N4CCO[C@H](C)C4)c3)c2=O)cn1] | | 460.1 |
| 90 | 2-{2-fluoro-5-[(2S)-2-methylmorpholin-4-yl]-3-(trifluoromethyl)phenyl}-5-methyl-4-{[1-(propan-2-yl)-1H-pyrazol-4-yl]methyl}-2,4-dihydro-3H-1,2,4-triazol-3-one | 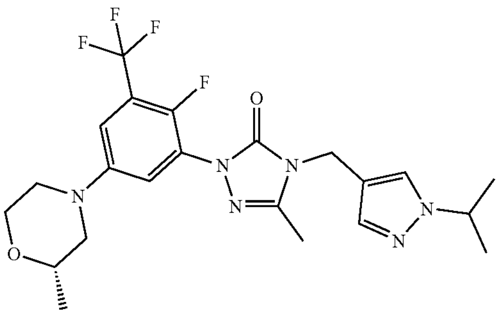 [SMILES: Cc1nn(-c2cc(N3CCO[C@@H](C)C3)cc(C(F)(F)F)c2F)c(=O)n1Cc1cnn(C(C)C)c1] | | 483.2 |

TABLE 1-continued

| Example No. | IUPAC Name | Structure | Salt | MS |
|---|---|---|---|---|
| 91 | 2-{2-fluoro-5-[(2R)-2-methylmorpholin-4-yl]-3-(trifluoromethyl)phenyl}-5-methyl-4-{[1-(propan-2-yl)-1H-pyrazol-4-yl]methyl}-2,4-dihydro-3H-1,2,4-triazol-3-one | 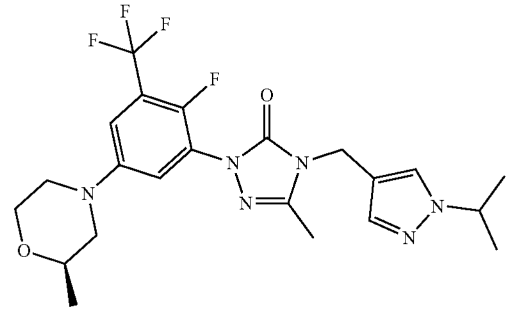 [SMILES: Cc1nn(-c2cc(N3CCO[C@H](C)C3)cc(C(F)(F)F)c2F)c(=O)n1Cc1cnn(C(C)C)c1] | | 483.3 |
| 92 | 2-{2-fluoro-5-[methyl(oxan-4-yl)amino]-3-(trifluoromethyl)phenyl}-5-methyl-4-{[1-(propan-2-yl)-1H-pyrazol-4-yl]methyl}-2,4-dihydro-3H-1,2,4-triazol-3-one | 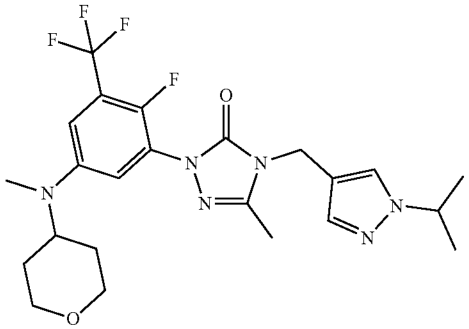 [SMILES: Cc1nn(-c2cc(N(C)C3CCOCC3)cc(C(F)(F)F)c2F)c(=O)n1Cc1cnn(C(C)C)c1] | | 497.2 |
| 93 | 2-[5-(2,2-dimethylmorpholin-4-yl)-2-fluoro-3-(trifluoromethyl)phenyl]-5-methyl-4-{[1-(propan-2-y])-1H-pyrazol-4-yl]methyl}-2,4-dihydro-3H-1,2,4-triazol-3-one | 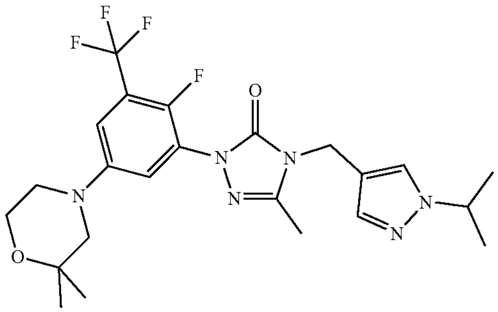 [SMILES: Cc1nn(-c2cc(N3CCOC(C)(C)C3)cc(C(F)(F)F)c2F)c(=O)n1Cc1cnn(C(C)C)c1] | | 497.2 |
| 94 | 2-[5-(3,3-difluoropyrrolidin-1-yl)-2-fluoro-3-(trifluoromethyl)phenyl]-5-methyl-4-{[1-(propan-2-yl)-1H-pyrazol-4-yl]methyl}-2,4-dihydro-3H-1,2,4-triazol-3-one | 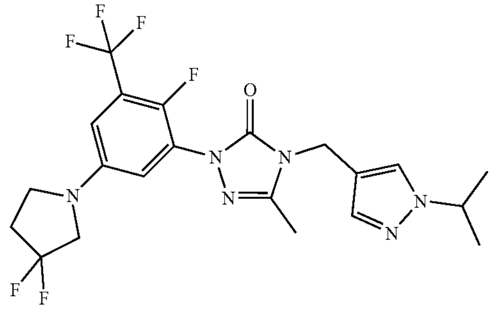 [SMILES: Cc1nn(-c2cc(N3CCC(F)(F)C3)cc(C(F)(F)F)c2F)c(=O)n1Cc1cnn(C(C)C)c1] | | 489.2 |

TABLE 1-continued

| Example No. | IUPAC Name | Structure | Salt | MS |
|---|---|---|---|---|
| 95 | 4-[(1-ethyl-1H-pyrazol-4-yl)methyl]-2-{2-fluoro-5-[methyl(oxan-4-yl)amino]-3-(trifluoromethyl)phenyl}-5-methyl-2,4-dihydro-3H-1,2,4-triazol-3-one | 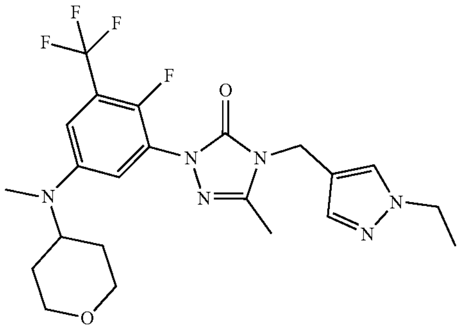 [SMILES: CCn1cc(Cn2c(C)nn(-c3cc(N(C)C4CCOCC4)cc(C(F)(F)F)c3F)c2=O)cn1] | | 483.2 |
| 96 | 2-[5-(2,2-dimethylmorpholin-4-yl)-2-fluoro-3-(trifluoromethyl)phenyl]-4-[(1-ethyl-1H-pyrazol-4-yl)methyl]-5-methyl-2,4-dihydro-3H-1,2,4-triazol-3-one | 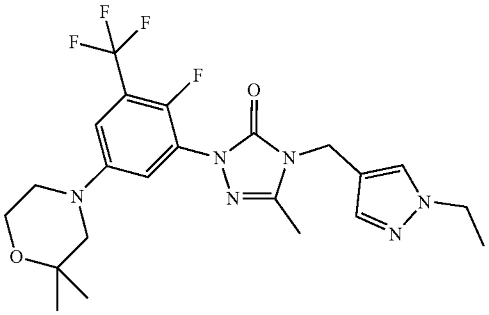 [SMILES: CCn1cc(Cn2c(C)nn(-c3cc(N4CCOC(C)(C)C4)cc(C(F)(F)F)c3F)c2=O)cn1] | | 483.2 |
| 97 | 2-[5-(4,4-difluoropiperidin-1-yl)-2-fluoro-3-(trifluoromethyl)phenyl]-4-[(1-ethyl-1H-pyrazol-4-yl)methyl]-5-methyl-2,4-dihydro-3H-1,2,4-triazol-3-one | 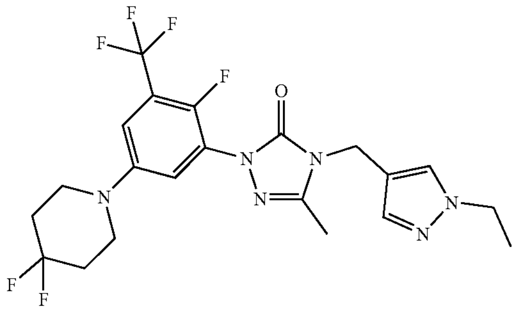 [SMILES: CCn1cc(Cn2c(C)nn(-c3cc(N4CCC(F)(F)CC4)cc(C(F)(F)F)c3F)c2=O)cn1] | | 489.2 |
| 98 | 1-{3-(difluoromethyl)-2-fluoro-5-[(2R)-2-methylmorpholin-4-yl]phenyl}-4-methyl-3-{[1-(propan-2-yl)-1H-pyrazol-4-yl]methyl}-1,3-dihydro-2H-imidazol-2-one | 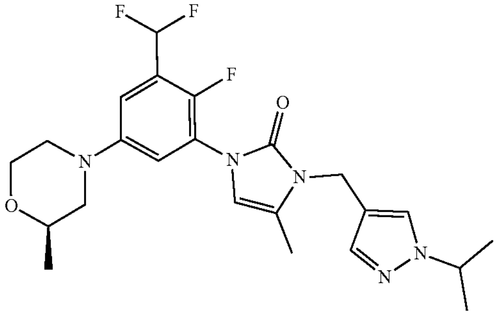 [SMILES: Cc1cn(-c2cc(N3CCO[C@H](C)C3)cc(C(F)F)c2F)c(=O)n1Cc1cnn(C(C)C)c1] | | 464.2 |

TABLE 1-continued

| Example No. | IUPAC Name | Structure | Salt | MS |
|---|---|---|---|---|
| 99 | 1-[1-(2-cyclobutylethyl)-3-(trifluoromethyl)-1H-pyrazol-5-yl]-3-[(1-ethyl-1H-pyrazol-4-yl)methyl]-4-methyl-1,3-dihydro-2H-imidazol-2-one | 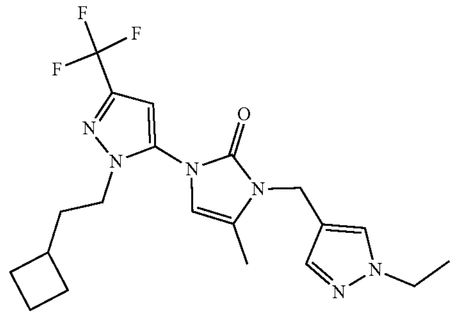 [SMILES: CCn1cc(Cn2c(C)cn(-c3cc(C(F)(F)F)nn3CCC3CCC3)c2=O)cn1] | | 423.3 |
| 100 | 1-[(1-ethyl-1H-pyrazol-4-yl)methyl]-4,5-dimethyl-3-[3-{[(2S)-oxolan-2-y]]methoxy}-5-(trifluoromethyl)phenyl]-1,3-dihydro-2H-imidazol-2-one | 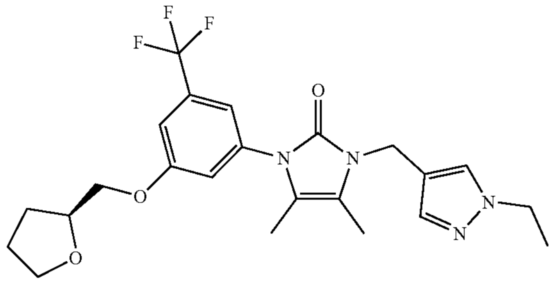 [SMILES: CCn1cc(Cn2c(C)c(C)n(-c3cc(OC[C@@H]4CCCO4)cc(C(F)(F)F)c3)c2=O)cn1] | | 465.2 |
| 101 | 4-methyl-3-[3-{[(2S)-oxolan-2-yl]methoxy}-5-(trifluoromethyl)phenyl]-1-{[1-(propan-2-yl)-1H-pyrazol-4-yl]methyl}-1,3-dihydro-2H-imidazol-2-one | 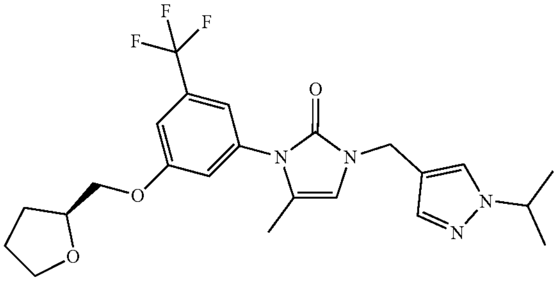 [SMILES: Cc1cn(Cc2cnn(C(C)C)c2)c(=O)n1-c1cc(OC[C@@H]2CCCO2)cc(C(F)(F)F)c1] | | 465.2 |
| 102 | 1-{6-[(2R)-2-methylmorpholin-4-yl]-4-(trifluoromethyl)pyridin-2-yl}-3-{[1-(propan-2-yl)-1H-pyrazol-4-yl]methyl}-1,3-dihydro-2H-imidazol-2-one | 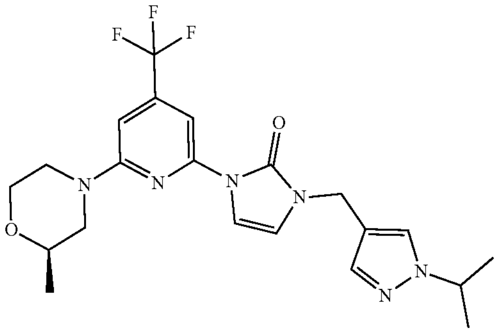 [SMILES: CC(C)n1cc(Cn2ccn(-c3cc(C(F)(F)F)cc(N4CCO[C@H](C)C4)n3)c2=O)cn1] | | 451.2 |
| 103 | 4-methyl-3-{6-[(2R)-2-methylmorpholin-4-yl]-4-(trifluoromethyl)pyridin-2-yl}-1-{[1-(propan-2-yl)-1H-pyrazol-4-yl]methyl}-1,3-dihydro-2H-imidazol-2-one | 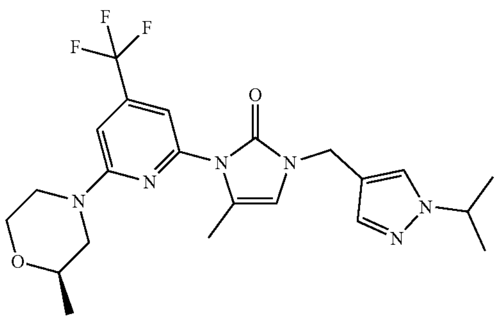 [SMILES: Cc1cn(Cc2cnn(C(C)C)c2)c(=O)n1-c1cc(C(F)(F)F)cc(N2CCO[C@H](C)C2)n1] | | 465.2 |

TABLE 1-continued

| Example No. | IUPAC Name | Structure | Salt | MS |
|---|---|---|---|---|
| 104 | 3-{3-cyclopropyl-5-[(2R)-2-methylmorpholin-4-yl]phenyl}-1-[(1-ethyl-1H-pyrazol-4-yl)methyl]-4-methyl-1,3-dihydro-2H-imidazol-2-one | 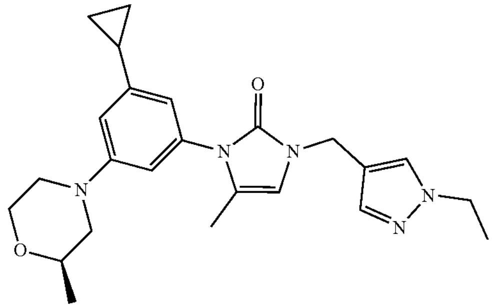 [SMILES: CCn1cc(Cn2cc(C)n(-c3cc(C4CC4)cc(N4CCO[C@H](C)C4)c3)c2=O)cn1] | | 422.3 |
| 105 | 1-[(1-ethyl-1H-pyrazol-4-yl)methyl]-4-methyl-3-{6-[(2R)-2-methylmorpholin-4-yl]-4-(2,2,2-trifluoroethoxy)pyridin-2-yl}-1,3-dihydro-2H-imidazol-2-one | 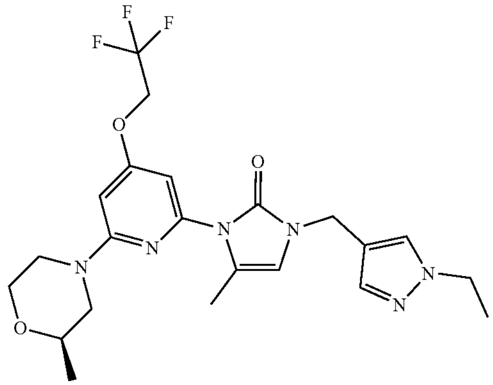 [SMILES: CCn1cc(Cn2cc(C)n(-c3cc(OCC(F)(F)F)cc(N4CCO[C@H](C)C4)n3)c2=O)cn1] | | 481.2 |
| 106 | 1-[(1-ethyl-1H-pyrazol-4-yl)methyl]-4-methyl-3-{6-[(oxolan-2-yl)methoxy]-4-(trifluoromethyl)pyridin-2-yl}-1,3-dihydro-2H-imidazol-2-one | 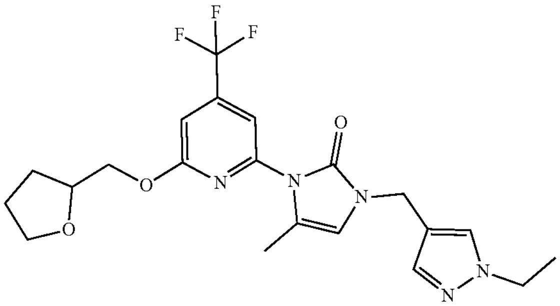 [SMILES: CCn1cc(Cn2cc(C)n(-c3cc(C(F)(F)F)cc(OCC4CCCO4)n3)c2=O)cn1] | | 452.2 |
| 107 | 1-[(1-ethyl-1H-pyrazol-4-yl)methyl]-3-[2-fluoro-5-{[(2S)-oxolan-2-yl]methoxy}-3-(trifluoromethyl)phenyl]-4-methyl-1,3-dihydro-2H-imidazol-2-one | 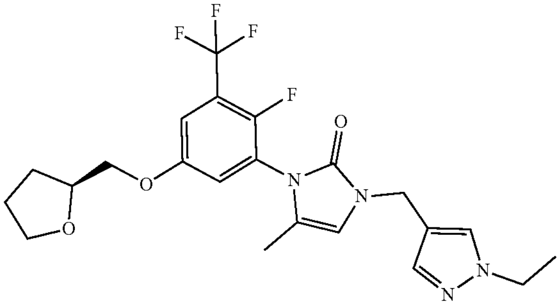 [SMILES: CCn1cc(Cn2cc(C)n(-c3cc(OC[C@@H]4CCCO4)cc(C(F)(F)F)c3F)c2=O)cn1] | | 469.1 |

TABLE 1-continued

| Example No. | IUPAC Name | Structure | Salt | MS |
|---|---|---|---|---|
| 108 | 1-[(1-ethyl-1H-pyrazol-4-yl)methyl]-4-methyl-3-{6-[(oxolan-2-yl)methoxy]-4-(trifluoromethyl)pyridin-2-yl}-1,3-dihydro-2H-imidazol-2-one | 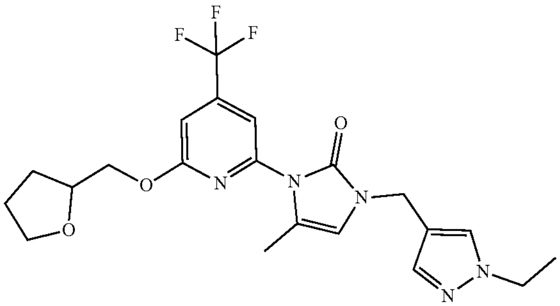 [SMILES: CCn1cc(Cn2cc(C)n(-c3cc(C(F)(F)F)cc(OCC4CCCO4)n3)c2=O)cn1] | | 452.2 |
| 109 | 1-[(1-ethyl-1H-pyrazol-4-yl)methyl]-4-methyl-3-{6-[(oxolan-2-yl)methoxy]-4-(trifluoromethyl)pyridin-2-yl}-1,3-dihydro-2H-imidazol-2-one | 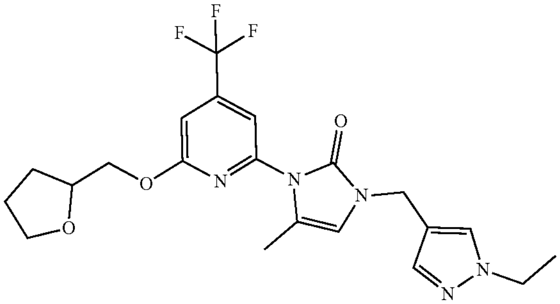 [SMILES: CCn1cc(Cn2cc(C)n(-c3cc(C(F)(F)F)cc(OCC4CCCO4)n3)c2=O)cn1] | | 452.2 |
| 110 | 1-[(1-ethyl-1H-pyrazol-4-yl)methyl]-3-[6-{[(1-fluorocyclobutyl)methyl]amino}-4-(trifluoromethyl)pyridin-2-yl]-4-methyl-1,3-dihydro-2H-imidazol-2-one | 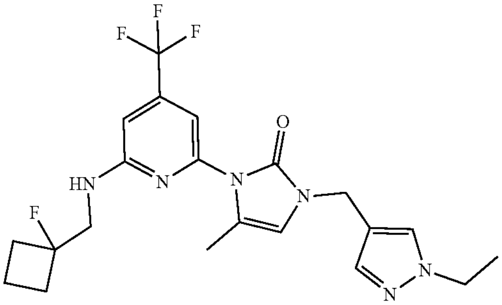 [SMILES: CCn1cc(Cn2cc(C)n(-c3cc(C(F)(F)F)cc(NCC4(F)CCC4)n3)c2=O)cn1] | | 453.2 |
| 111 | 3-[6-(2,2-difluoromorpholin-4-yl)-4-(trifluoromethyl)pyridin-2-yl]-1-[(1-ethyl-1H-pyrazol-4-yl)methyl]-4-methyl-1,3-dihydro-2H-imidazol-2-one | 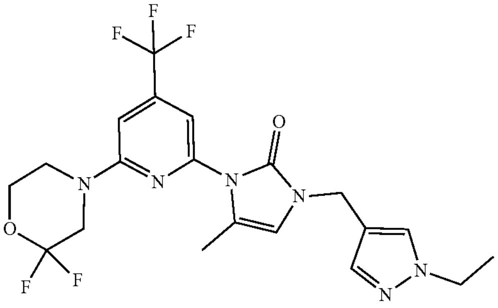 [SMILES: CCn1cc(Cn2cc(C)n(-c3cc(C(F)(F)F)cc(N4CCOC(F)(F)C4)n3)c2=O)cn1] | | 473.2 |
| 112 | 1-[6-(2,2-dimethylmorpholin-4-yl)-3-fluoro-4-(trifluoromethyl)pyridin-2-yl]-3-[(1-ethyl-1H-pyrazol-4-yl)methyl]-1,3-dihydro-2H-imidazol-2-one | 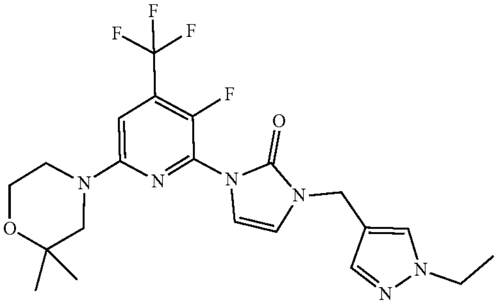 [SMILES: CCn1cc(Cn2ccn(-c3nc(N4CCOC(C)(C)C4)cc(C(F)(F)F)c3F)c2=O)cn1] | | 469.2 |

TABLE 1-continued

| Example No. | IUPAC Name | Structure | Salt | MS |
|---|---|---|---|---|
| 113 | 1-[(1-ethyl-1H-pyrazol-4-yl)methyl]-3-{2-fluoro-3-(2-hydroxypropan-2-yl)-5-[methyl(oxan-4-yl)amino]phenyl}-1,3-dihydro-2H-imidazol-2-one | 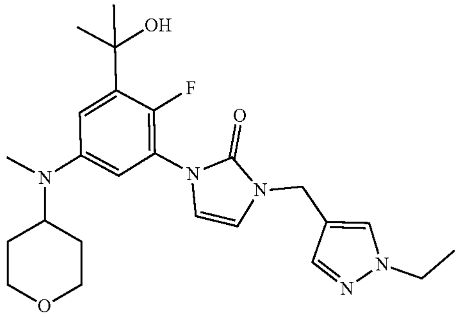 [SMILES: CCn1cc(Cn2ccn(-c3cc(N(C)C4CCOCC4)cc(C(C)(C)O)c3F)c2=O)cn1] | | 458.3 |
| 114 | 1-[(1-ethyl-1H-pyrazol-4-yl)methyl]-4,5-dimethyl-3-[6-{[(2R)-oxolan-2-yl]methoxy}-4-(trifluoromethyl)pyridin-2-yl]-1,3-dihydro-2H-imidazol-2-one | 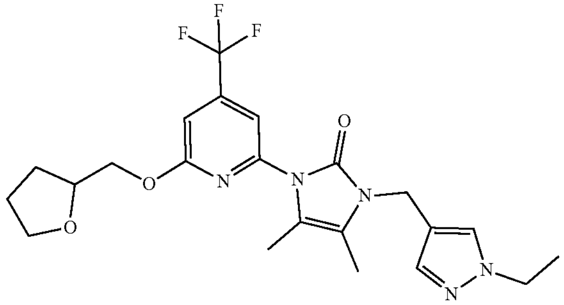 [SMILES: CCn1cc(Cn2c(C)c(C)n(-c3cc(C(F)(F)F)cc(OCC4CCCO4)n3)c2=O)cn1] | | 466.2 |
| 115 | 1-[(1-ethyl-1H-pyrazol-4-yl)methyl]-4,5-dimethyl-3-[6-{[(2S)-oxolan-2-yl]methoxy}-4-(trifluoromethyl)pyridin-2-yl]-1,3-dihydro-2H-imidazol-2-one | 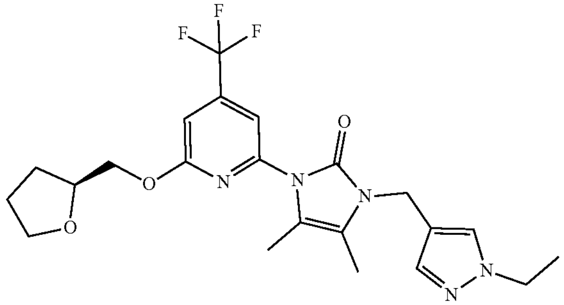 [SMILES: CCn1cc(Cn2c(C)c(C)n(-c3cc(C(F)(F)F)cc(OC[C@@H]4CCCO4)n3)c2=O)cn1] | | 466.3 |
| 116 | 1-[(1-ethyl-1H-pyrazol-4-yl)methyl]-3-{2-fluoro-5-[(oxan-4-yl)oxy]-3-(trifluoromethyl)phenyl}-1,3-dihydro-2H-imidazol-2-one | 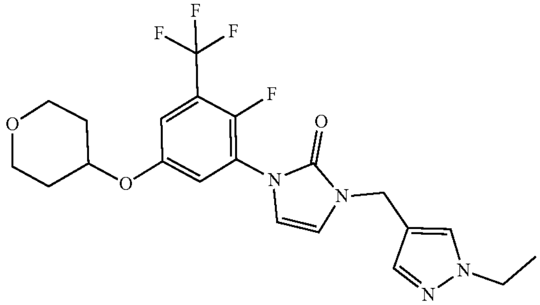 [SMILES: CCn1cc(Cn2ccn(-c3cc(OC4CCOCC4)cc(C(F)(F)F)c3F)c2=O)cn1] | | 455.2 |
| 117 | 3-[(1-ethyl-1H-pyrazol-4-yl)methyl]-1-{2-fluoro-5-[(oxan-4-yl)oxy]-3-(trifluoromethyl)phenyl}-4-methyl-1,3-dihydro-2H-imidazol-2-one | 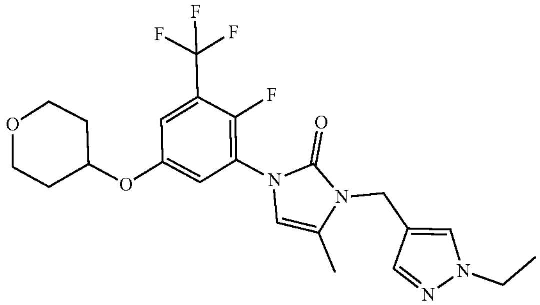 [SMILES: CCn1cc(Cn2c(C)cn(-c3cc(OC4CCOCC4)cc(C(F)(F)F)c3F)c2=O)cn1] | | 469.2 |

TABLE 1-continued

| Example No. | IUPAC Name | Structure | Salt | MS |
|---|---|---|---|---|
| 118 | 1-[(1-ethyl-1H-pyrazol-4-yl)methyl]-3-[2-fluoro-5-{[(2S)-oxolan-2-yl]methoxy}-3-(trifluoromethyl)phenyl]-1,3-dihydro-2H-imidazol-2-one | 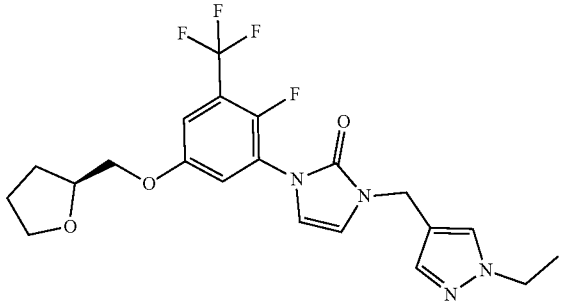 [SMILES: CCn1cc(Cn2ccn(-c3cc(OC[C@@H]4CCCO4)cc(C(F)(F)F)c3F)c2=O)cn1] | | 455.2 |
| 119 | 1-{2-fluoro-5-[(oxan-4-yl)oxy]-3-(trifluoromethyl)phenyl}-4-methyl-3-{[1-(propan-2-yl)-1H-pyrazol-4-yl]methyl}-1,3-dihydro-2H-imidazol-2-one | 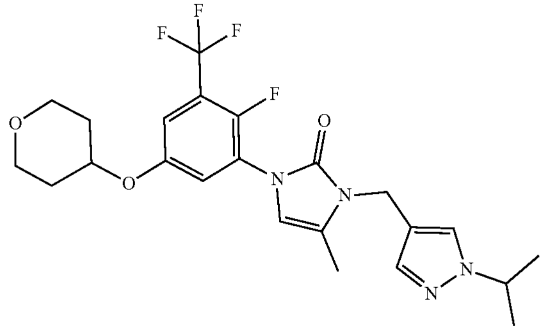 [SMILES: Cc1cn(-c2cc(OC3CCOCC3)cc(C(F)(F)F)c2F)c(=O)n1Cc1cnn(C(C)C)c1] | | 483.2 |
| 120 | 1-[6-(2,2-dimethylmorpholin-4-yl)-3-methyl-4-(trifluoromethyl)pyridin-2-yl]-3-[(1-ethyl-1H-pyrazol-4-yl)methyl]-4-methyl-1,3-dihydro-2H-imidazol-2-one | 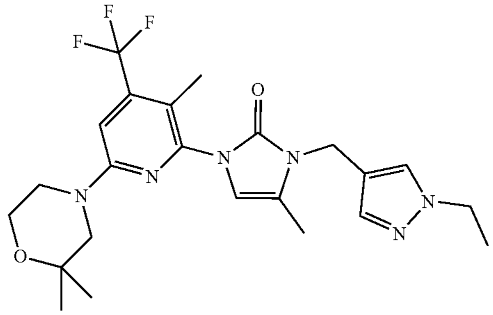 [SMILES: CCn1cc(Cn2c(C)cn(-c3nc(N4CCOC(C)(C)C4)cc(C(F)(F)F)c3C)c2=O)cn1] | | 479.2 |
| 121 | 1-[(1-ethyl-1H-pyrazol-4-yl)methyl]-3-[3-fluoro-6-{[(1-fluorocyclobutyl)methyl]amino}-4-(trifluoromethyl)pyridin-2-yl]-1,3-dihydro-2H-imidazol-2-one | 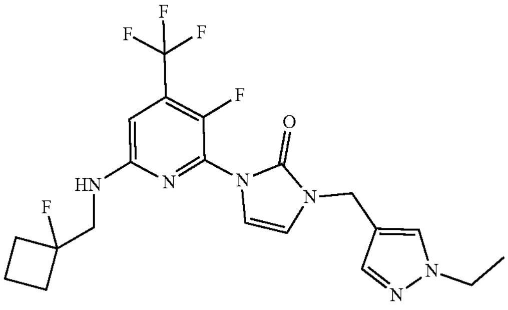 [SMILES: CCn1cc(Cn2ccn(-c3nc(NCC4(F)CCC4)cc(C(F)(F)F)c3F)c2=O)cn1] | | 457.2 |

TABLE 1-continued

| Example No. | IUPAC Name | Structure | Salt | MS |
|---|---|---|---|---|
| 122 | 1-[(1-ethyl-1H-pyrazol-4-yl)methyl]-3-{2-fluoro-3-(2-fluoropropan-2-yl)-5-[methyl(oxan-4-yl)amino]phenyl}-1,3-dihydro-2H-imidazol-2-one | 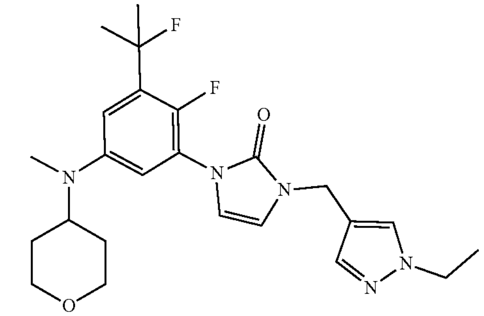 [SMILES: CCn1cc(Cn2ccn(-c3cc(N(C)C4CCOCC4)cc(C(C)(C)F)c3F)c2=O)cn1] | | 460.3 |
| 123 | 1-[6-(2,2-difluoromorpholin-4-yl)-3-fluoro-4-(trifluoromethyl)pyridin-2-yl]-3-[(1-ethyl-1H-pyrazol-4-yl)methyl]-1,3-dihydro-2H-imidazol-2-one | 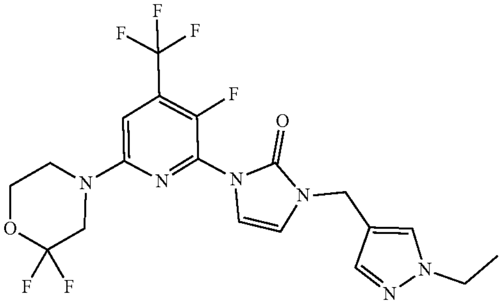 [SMILES: CCn1cc(Cn2ccn(-c3nc(N4CCOC(F)(F)C4)cc(C(F)(F)F)c3F)c2=O)cn1] | | 477.1 |
| 124 | 1-[(1-ethyl-1H-pyrazol-4-yl)methyl]-4-methyl-3-{4-[(2R)-2-methylmorpholin-4-yl]-6-(trifluoromethyl)pyrimidin-2-yl}-1,3-dihydro-2H-imidazol-2-one | 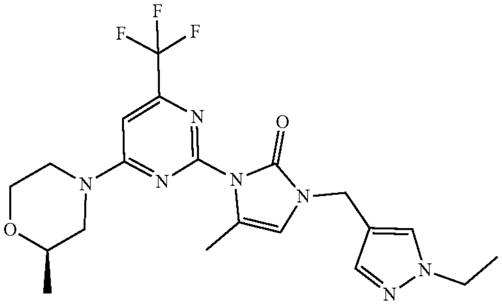 [SMILES: CCn1cc(Cn2cc(C)n(-c3nc(N4CCO[C@H](C)C4)cc(C(F)(F)F)n3)c2=O)cn1] | | 452.2 |
| 125 | 3-[6-(2,2-dimethylmorpholin-4-yl)-4-(trifluoromethyl)pyridin-2-yl]-1-[(1-ethyl-1H-pyrazol-4-yl)methyl]-4-methyl-1,3-dihydro-2H-imidazol-2-one | 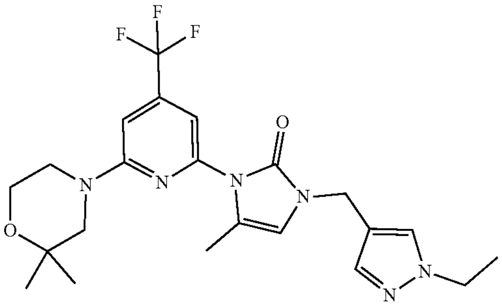 [SMILES: CCn1cc(Cn2cc(C)n(-c3cc(C(F)(F)F)cc(N4CCOC(C)(C)C4)n3)c2=O)cn1] | | 465.3 |
| 126 | 3-{4-cyclopropyl-6-[(2R)-2-methylmorpholin-4-yl]pyridin-2-yl}-4-methyl-1-{[1-(propan-2-yl)-1H-pyrazol-4-yl]methyl}-1,3-dihydro-2H-imidazol-2-one | 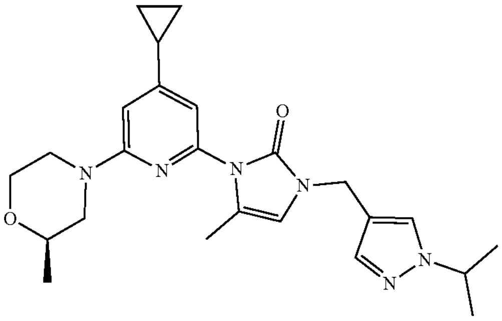 [SMILES: Cc1cn(Cc2cnn(C(C)C)c2)c(=O)n1-c1cc(C2CC2)cc(N2CCO[C@H](C)C2)n1] | | 437.3 |

TABLE 1-continued

| Example No. | IUPAC Name | Structure | Salt | MS |
|---|---|---|---|---|
| 127 | 3-[(1-ethyl-1H-pyrazol-4-yl)methyl]-1-{3-fluoro-6-[(2R)-2-methylmorpholin-4-yl]-4-(trifluoromethyl)pyridin-2-yl}-4-(trifluoromethyl)-1,3-dihydro-2H-imidazol-2-one | 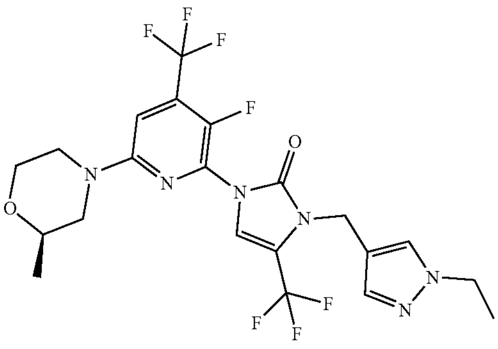 [SMILES: CCn1cc(Cn2c(C(F)(F)F)cn(-c3nc(N4CCO[C@H](C)C4)cc(C(F)(F)F)c3F)c2=O)cn1] | | 523.2 |
| 128 | 4-methyl-3-{6-[methyl(oxan-4-yl)amino]-4-(trifluoromethyl)pyridin-2-yl}-1-{[1-(propan-2-yl)-1H-pyrazol-4-yl]methyl}-1,3-dihydro-2H-imidazol-2-one | 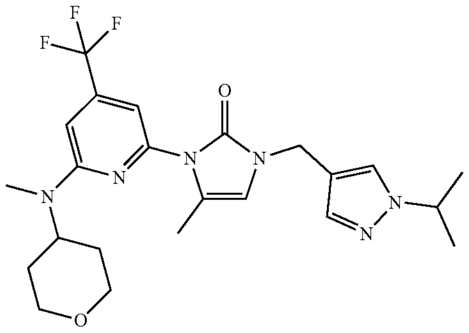 [SMILES: Cc1cn(Cc2cnn(C(C)C)c2)c(=O)n1-c1cc(C(F)(F)F)cc(N(C)C2CCOCC2)n1] | | 479.3 |
| 129 | 4-methyl-1-{6-[(2R)-2-methylmorpholin-4-yl]-4-(trifluoromethyl)pyridin-2-yl}-3-{[1-(propan-2-yl)-1H-pyrazol-4-yl]methyl}-1,3-dihydro-2H-imidazol-2-one | 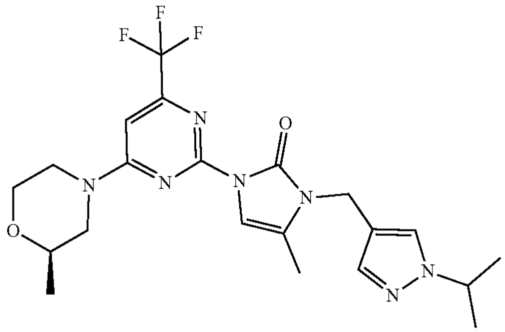 [SMILES: Cc1cn(-c2nc(N3CCO[C@H](C)C3)cc(C(F)(F)F)n2)c(=O)n1Cc1cnn(C(C)C)c1] | | 465.3 |
| 130 | 3-[4-cyclopropyl-6-(2,2-dimethylmorpholin-4-yl)pyridin-2-yl]-4-methyl-1-{[1-(propan-2-yl)-1H-pyrazol-4-yl]methyl}-1,3-dihydro-2H-imidazol-2-one | 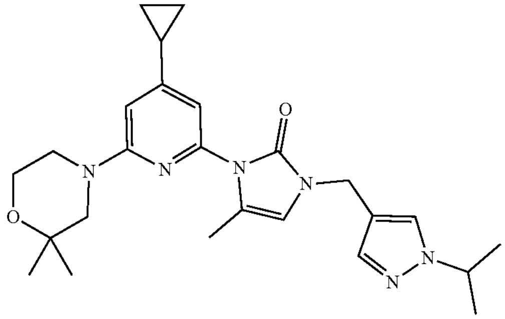 [SMILES: Cc1cn(Cc2cnn(C(C)C)c2)c(=O)n1-c1cc(C2CC2)cc(N2CCOC(C)(C)C2)n1] | | 451.3 |

TABLE 1-continued

| Example No. | IUPAC Name | Structure | Salt | MS |
|---|---|---|---|---|
| 131 | 1-[5-(2,2-difluorocyclopropyl)-4,4'-difluoro[1,1'-bipheny]]-3-yl]-3-[(1-ethyl-1H-pyrazol-4-yl)methyl]-1,3-dihydro-2H-imidazol-2-one | 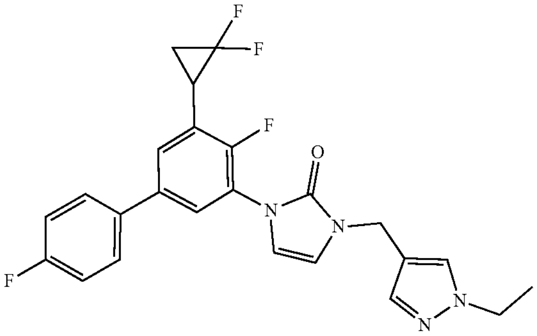 [SMILES: CCn1cc(Cn2ccn(-c3cc(-c4ccc(F)cc4)cc(C4CC4(F)F)c3F)c2=O)cn1] | | 457.3 |
| 132 | 1-[6-(2,2-dimethylmorpholin-4-yl)-3-fluoro-4-(trifluoromethyl)pyridin-2-yl]-3-{[1-(propan-2-yl)-1H-pyrazol-4-yl]methyl}-1,3-dihydro-2H-imidazol-2-one | 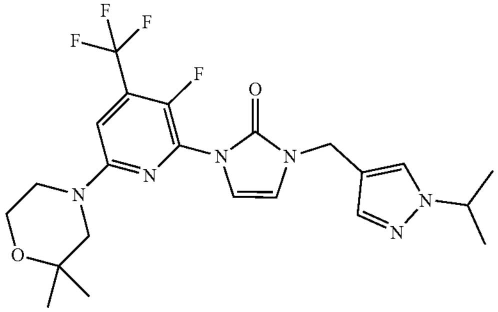 [SMILES: CC(C)n1cc(Cn2ccn(-c3nc(N4CCOC(C)(C)C4)cc(C(F)(F)F)c3F)c2=O)cn1] | | 483.2 |
| 133 | 1-[3-fluoro-6-{[(1-fluorocyclobutyl)methyl]amino}-4-(trifluoromethyl)pyridin-2-yl]-3-{[1-(propan-2-yl)-1H-pyrazol-4-yl]methyl}-1,3-dihydro-2H-imidazol-2-one | 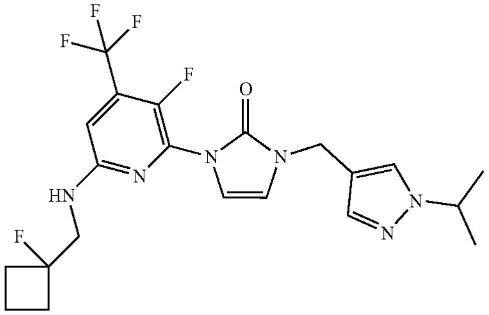 [SMILES: CC(C)n1cc(Cn2ccn(-c3nc(NCC4(F)CCC4)cc(C(F)(F)F)c3F)c2=O)cn1] | | 471.2 |
| 134 | 3-[4-(2,2-dimethylmorpholin-4-yl)-6-(trifluoromethyl)pyrimidin-2-yl]-1-[(1-ethyl-1H-pyrazol-4-yl)methyl]-4-methyl-1,3-dihydro-2H-imidazol-2-one | 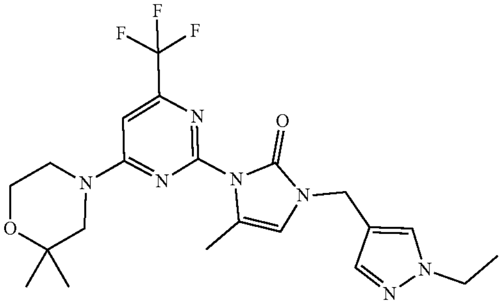 [SMILES: CCn1cc(Cn2cc(C)n(-c3nc(N4CCOC(C)(C)C4)cc(C(F)(F)F)n3)c2=O)cn1] | | 466.3 |

TABLE 1-continued

| Example No. | IUPAC Name | Structure | Salt | MS |
|---|---|---|---|---|
| 135 | 3-[4-(2,2-dimethylmorpholin-4-yl)-6-(trifluoromethyl)pyrimidin-2-yl]-4-methyl-1-{[1-(propan-2-yl)-1H-pyrazol-4-yl]methyl}-1,3-dihydro-2H-imidazol-2-one | 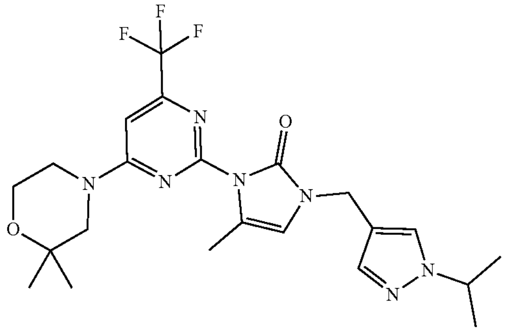 [SMILES: Cc1cn(Cc2cnn(C(C)C)c2)c(=O)n1-c1nc(N2CCOC(C)(C)C2)cc(C(F)(F)F)n1] | | 480.3 |
| 136 | 2-[5-(2,2-dimethylmorpholin-4-yl)-2-fluoro-3-(trifluoromethyl)phenyl]-5-ethyl-4-[(1-ethyl-1H-pyrazol-4-yl)methyl]-2,4-dihydro-3H-1,2,4-triazol-3-one | 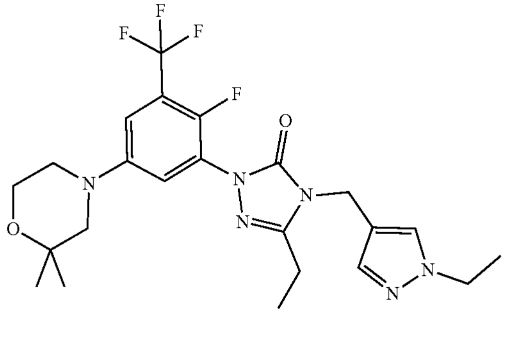 [SMILES: CCc1nn(-c2cc(N3CCOC(C)(C)C3)cc(C(F)(F)F)c2F)c(=O)n1Cc1cnn(CC)c1] | | 497.3 |
| 137 | 3-[3-bromo-5-(2,2-dimethylmorpholin-4-yl)phenyl]-1-[(1-ethyl-1H-pyrazol-4-y)methyl]-4-methyl-1,3-dihydro-2H-imidazol-2-one | 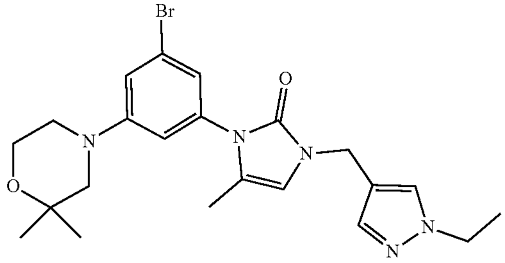 [SMILES: CCn1cc(Cn2cc(C)n(-c3cc(Br)cc(N4CCOC(C)(C)C4)c3)c2=O)cn1] | | 474.1 |
| 138 | 2-[5-(4,4-difluoropiperidin-1-yl)-2-fluoro-3-(trifluoromethyl)phenyl]-5-ethyl-4-[(1-ethyl-1H-pyrazol-4-yl)methyl]-2,4-dihydro-3H-1,2,4-triazol-3-one | 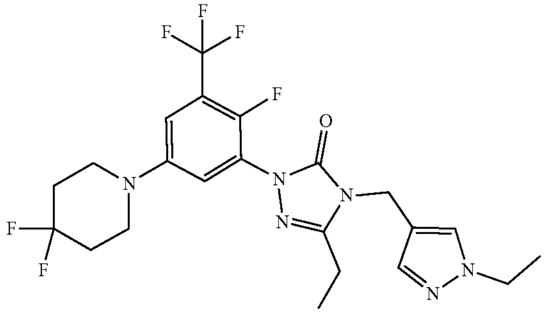 [SMILES: CCc1nn(-c2cc(N3CCC(F)(F)CC3)cc(C(F)(F)F)c2F)c(=O)n1Cc1cnn(CC)c1] | | 503.3 |
| 139 | 1-{3-chloro-2-fluoro-5-[(2R)-2-methylmorpholin-4-yl]phenyl}-3-[(1-ethyl-1H-pyrazol-4-yl)methyl]-4-methyl-1,3-dihydro-2H-imidazol-2-one | 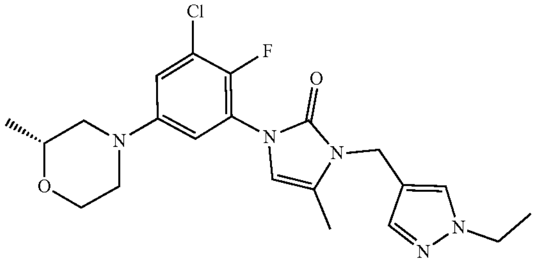 [SMILES: CCn1cc(Cn2c(C)cn(-c3cc(N4CCO[C@H](C)C4)cc(Cl)c3F)c2=O)cn1] | | 434.2 |

TABLE 1-continued

| Example No. | IUPAC Name | Structure | Salt | MS |
|---|---|---|---|---|
| 140 | 1-{3-cyclopropyl-2-fluoro-5-[(2R)-2-methylmorpholin-4-yl]phenyl}-3-[(1-ethyl-1H-pyrazol-4-yl)methyl]-4-methyl-1,3-dihydro-2H-imidazol-2-one | 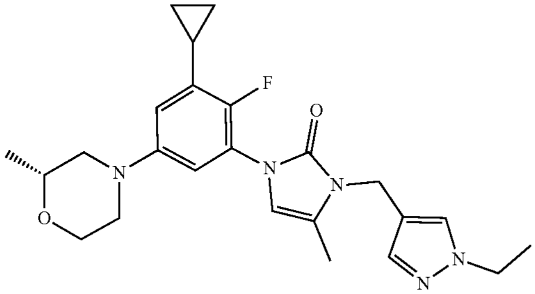 [SMILES: CCn1cc(Cn2c(C)cn(-c3cc(N4CCO[C@H](C)C4)cc(C4CC4)c3F)c2=O)cn1] | | 440.3 |
| 141 | 2-[6-(4,4-difluoropiperidin-1-yl)-4-(trifluoromethyl)pyridin-2-yl-4-[(1-ethyl-1H-pyrazol-4-yl)methyl]-5-methyl-2,4-dihydro-3H-1,2,4-triazol-3-one | 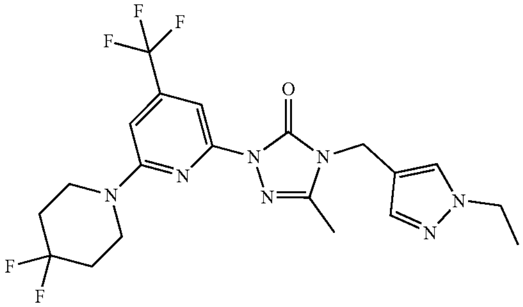 [SMILES: CCn1cc(Cn2c(C)nn(-c3cc(C(F)(F)F)cc(N4CCC(F)(F)CC4)n3)c2=O)cn1] | | 472.2 |
| 142 | 2-[6-(4,4-difluoropiperidin-1-yl)-4-(trifluoromethyl)pyridin-2-yl]-5-methyl-4-{[1-(propan-2-yl)-1H-pyrazol-4-yl]methyl}-2,4-dihydro-3H-1,2,4-triazol-3-one | 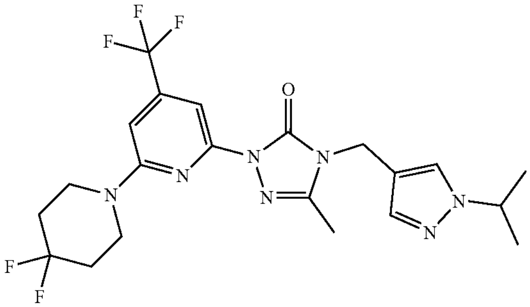 [SMILES: Cc1nn(-c2cc(C(F)(F)F)cc(N3CCC(F)(F)CC3)n2)c(=O)n1Cc1cnn(C(C)C)c1] | | 486.2 |
| 143 | 1-{3-(2,2-difluorocyclopropyl)-2-fluoro-5-[(2R)-2-methylmorpholin-4-yl]phenyl}-3-[(1-ethyl-1H-pyrazol-4-yl)methyl]-4-(trifluoromethyl)-1,3-dihydro-2H-imidazol-2-one | 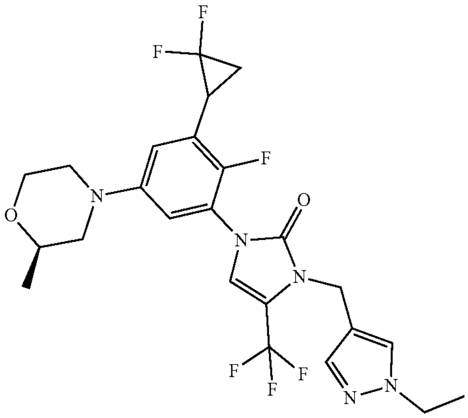 [SMILES: CCn1cc(Cn2c(C(F)(F)F)cn(-c3cc(N4CCO[C@H](C)C4)cc(C4CC4(F)F)c3F)c2=O)cn1] | | 530.2 |

TABLE 1-continued

| Example No. | IUPAC Name | Structure | Salt | MS |
|---|---|---|---|---|
| 144 | 1-[5-(2,2-difluorocyclopropyl)-4,4'-difluoro[1,1'-biphenyl]-3-yl]-3-[(1-ethyl-1H-pyrazol-4-yl)methyl]-1,3-dihydro-2H-imidazol-2-one | 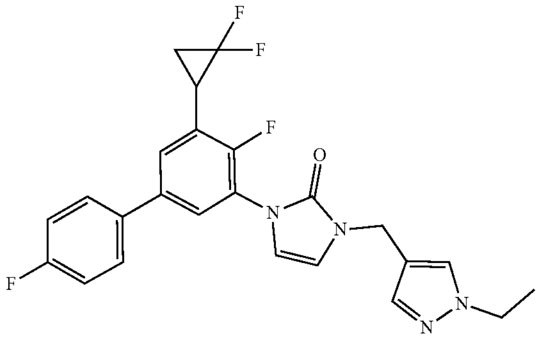 [SMILES: CCn1cc(Cn2ccn(-c3cc(-c4ccc(F)cc4)cc(C4CC4(F)F)c3F)c2=O)cn1] | | 457.2 |
| 145 | 1-[5-(2,2-difluorocyclopropyl)-4,4'-difluoro[1,1'-biphenyl]-3-yl]-3-[(1-ethyl-1H-pyrazol-4-yl)methyl]-1,3-dihydro-2H-imidazol-2-one | 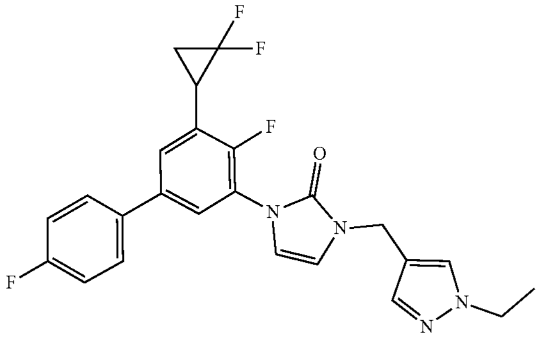 [SMILES: CCn1cc(Cn2ccn(-c3cc(-c4ccc(F)cc4)cc(C4CC4(F)F)c3F)c2=O)cn1] | | 457.2 |
| 146 | 1-[3-bromo-5-(2,2-dimethylmorpholin-4-yl)-2-fluorophenyl]-3-[(1-ethyl-1H-pyrazol-4-yl)methyl]-1,3-dihydro-2H-imidazol-2-one | 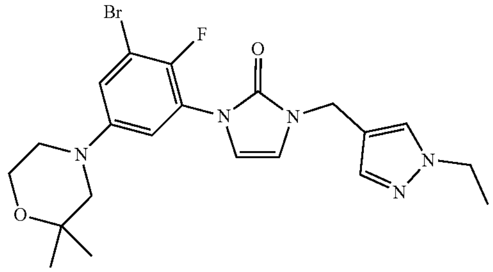 [SMILES: CCn1cc(Cn2ccn(-c3cc(N4CCOC(C)(C)C4)cc(Br)c3F)c2=O)cn1] | | 478.1 |
| 147 | 3-[3-cyclopropyl-5-(2,2-dimethylmorpholin-4-yl)phenyl]-1-[(1-ethyl-1H-pyrazol-4-yl)methyl]-4-methyl-1,3-dihydro-2H-imidazol-2-one | 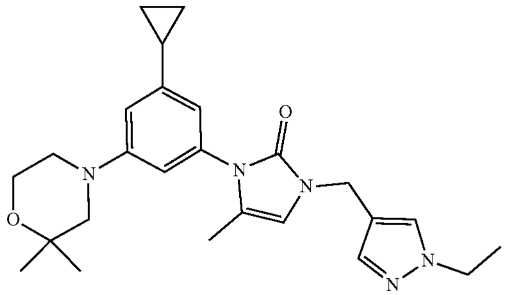 [SMILES: CCn1cc(Cn2cc(C)n(-c3cc(C4CC4)cc(N4CCOC(C)(C)C4)c3)c2=O)cn1] | | 436.3 |

TABLE 1-continued

| Example No. | IUPAC Name | Structure | Salt | MS |
|---|---|---|---|---|
| 148 | 4-methyl-3-[6-{[(2S)-oxolan-2-yl]methoxy}-4-(trifluoromethyl)pyridin-2-yl]-1-{[1-(propan-2-yl)-1H-pyrazol-4-yl]methyl}-1,3-dihydro-2H-imidazol-2-one | 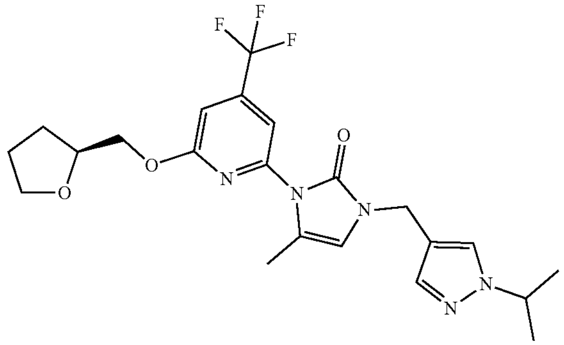 [SMILES: Cc1cn(Cc2cnn(C(C)C)c2)c(=O)n1-c1cc(C(F)(F)F)cc(OC[C@@H]2CCCO2)n1] | | 466.2 |
| 149 | 1-[(1-ethyl-1H-pyrazol-4-yl)methyl]-3-{5-fluoro-6-[(2R)-2-methylmorpholin-4-yl]-4-(trifluoromethyl)pyridin-2-yl}-4-methyl-1,3-dihydro-2H-imidazol-2-one | 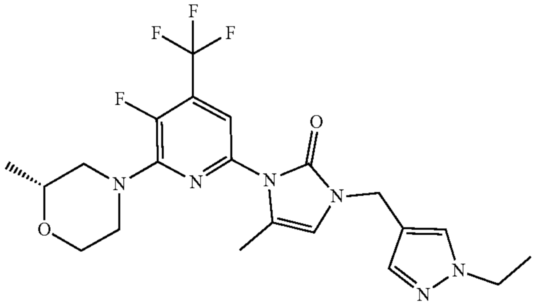 [SMILES: CCn1cc(Cn2cc(C)n(-c3cc(C(F)(F)F)c(F)c(N4CCO[C@H](C)C4)n3)c2=O)cn1] | | 469.3 |
| 150 | 1-[(1-ethyl-1H-pyrazol-4-yl)methyl]-3-{5-fluoro-6-[(2R)-2-methylmorpholin-4-yl]-4-(trifluoromethyl)pyridin-2-yl}-4,5-dimethyl-1,3-dihydro-2H-imidazol-2-one | 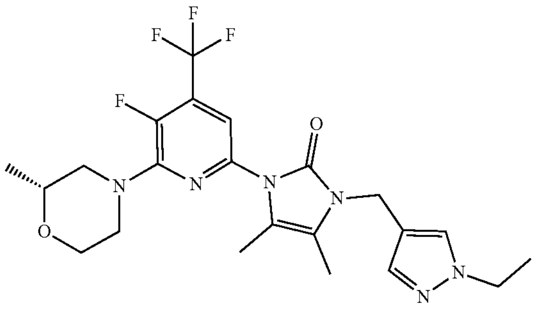 [SMILES: CCn1cc(Cn2c(C)c(C)n(-c3cc(C(F)(F)F)c(F)c(N4CCO[C@H](C)C4)n3)c2=O)cn1] | | 483.3 |
| 151 | 2-{5-[(3,3-difluorocyclobutyl)methoxy]-2-fluoro-3-(trifluoromethyl)phenyl}-4-[(1-ethyl-1H-pyrazol-4-yl)methyl]-2,4-dihydro-3H-1,2,4-triazol-3-one | 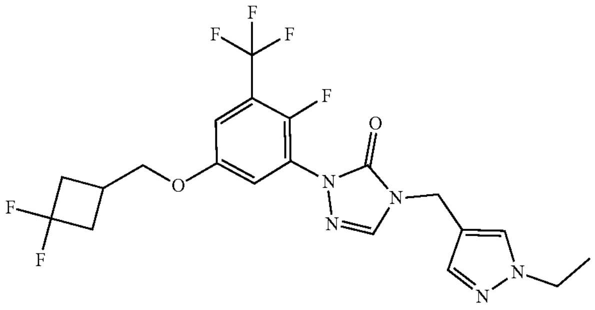 [SMILES: CCn1cc(Cn2cnn(-c3cc(OCC4CC(F)(F)C4)cc(C(F)(F)F)c3F)c2=O)cn1] | | 476.2 |

TABLE 1-continued

| Example No. | IUPAC Name | Structure | Salt | MS |
|---|---|---|---|---|
| 152 | 1-[3,5-bis(4,4-difluoropiperidin-1-yl)-2-fluorophenyl]-3-[(1-ethyl-1H-pyrazol-4-yl)methyl]-1,3-dihydro-2H-imidazol-2-one | 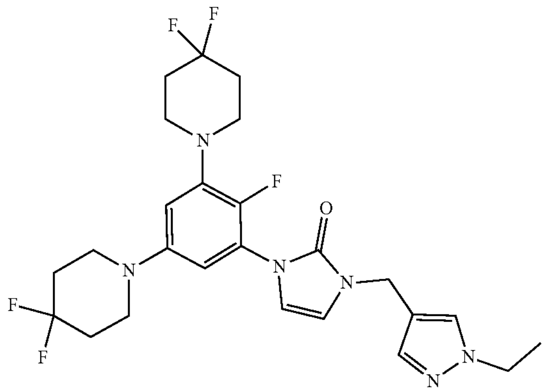 [SMILES: CCn1cc(Cn2ccn(-c3cc(N4CCC(F)(F)CC4)cc(N4CCC(F)(F)CC4)c3F)c2=O)cn1] | | 525.3 |
| 153 | 1-[(1-ethyl-1H-pyrazol-4-yl)methyl]-3-{2-fluoro-5-[(2R)-2-methylmorpholin-4-yl]-3-(trifluoromethoxy)phenyl}-1,3-dihydro-2H-imidazol-2-one | 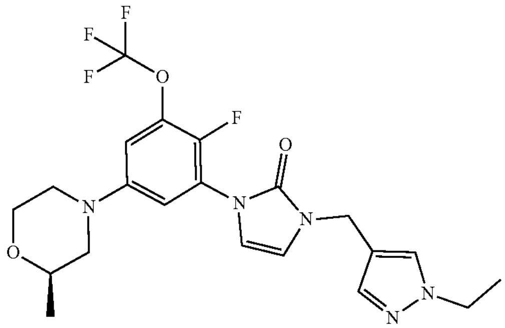 [SMILES: CCn1cc(Cn2ccn(-c3cc(N4CCO[C@H](C)C4)cc(OC(F)(F)F)c3F)c2=O)cn1] | | 470.2 |
| 154 | 2-[6-(4,4-difluoropiperidin-1-yl)-5-fluoro-4-(trifluoromethyl)pyridin-2-yl]-4-[(1-ethyl-1H-pyrazol-4-yl)methyl]-5-methyl-2,4-dihydro-3H-1,2,4-triazol-3-one | 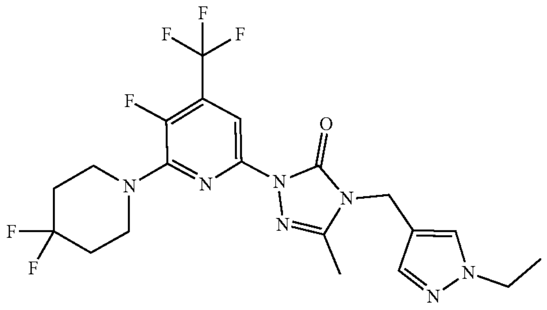 [SMILES: CCn1cc(Cn2c(C)nn(-c3cc(C(F)(F)F)c(F)c(N4CCC(F)(F)CC4)n3)c2=O)cn1] | | 490.2 |
| 155 | 5-chloro-4-[(1-ethyl-1H-pyrazol-4-yl)methyl]-2-{2-fluoro-5-[(2R)-2-methylmorpholin-4-yl]-3-(trifluoromethyl)phenyl}-2,4-dihydro-3H-1,2,4-triazol-3-one | 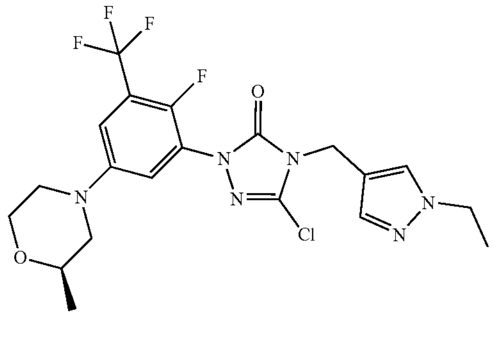 [SMILES: CCn1cc(Cn2c(Cl)nn(-c3cc(N4CCO[C@H](C)C4)cc(C(F)(F)F)c3F)c2=O)cn1] | | 489.2 |

TABLE 1-continued

| Example No. | IUPAC Name | Structure | Salt | MS |
|---|---|---|---|---|
| 156 | 1-[3-(2,2-difluorocyclopropyl)-5-(4,4-difluoropiperidin-1-yl)-2-fluorophenyl]-3-[(1-ethyl-1H-pyrazol-4-yl)methyl]-1,3-dihydro-2H-imidazol-2-one | 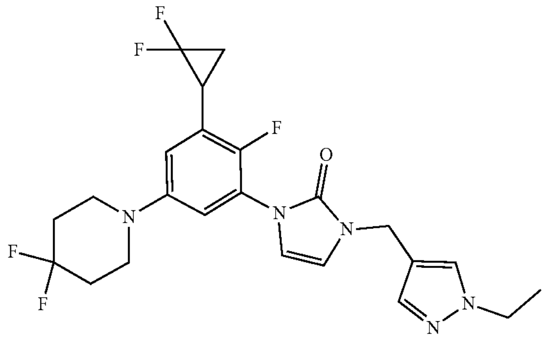 [SMILES: CCn1cc(Cn2ccn(-c3cc(N4CCC(F)(F)CC4)cc(C4CC4(F)F)c3F)c2=O)cn1] | | 482.3 |
| 157 | 4-ethyl-1-[(1-ethyl-1H-pyrazol-4-yl)methyl]-3-{6-[(2R)-2-methylmorpholin-4-yl]-4-(trifluoromethyl)pyridin-2-yl}-1,3-dihydro-2H-imidazol-2-one | 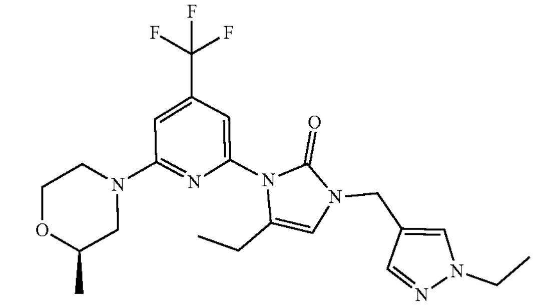 [SMILES: CCc1cn(Cc2cnn(CC)c2)c(=O)n1-c1cc(C(F)(F)F)cc(N2CCO[C@H](C)C2)n1] | | 465.3 |
| 158 | 1-[3-(2,2-difluorocyclopropyl)-5-(4,4-difluoropiperidin-1-yl)-2-fluorophenyl]-3-[(1-ethyl-1H-pyrazol-4-yl)methyl]-1,3-dihydro-2H-imidazol-2-one | 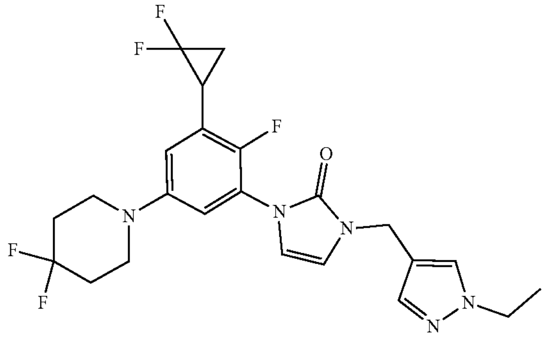 [SMILES: CCn1cc(Cn2ccn(-c3cc(N4CCC(F)(F)CC4)cc(C4CC4(F)F)c3F)c2=O)cn1] | | 482.2 |
| 159 | 2-{2-fluoro-5-[(2R)-2-methylmorpholin-4-yl]-3-(trifluoromethoxy)phenyl}-5-methyl-4-{[1-(propan-2-yl)-1H-pyrazol-4-yl]methyl}-2,4-dihydro-3H-1,2,4-triazol-3-one | 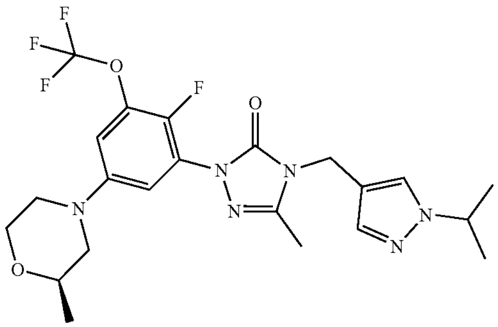 [SMILES: Cc1nn(-c2cc(N3CCO[C@H](C)C3)cc(OC(F)(F)F)c2F)c(=O)n1Cc1cnn(C(C)C)c1] | | 499.2 |

TABLE 1-continued

| Example No. | IUPAC Name | Structure | Salt | MS |
|---|---|---|---|---|
| 160 | 3-{3-cyclopropyl-4-fluoro-5-[(2R)-2-methylmorpholin-4-yl]phenyl}-1-[(1-ethyl-1H-pyrazol-4-yl)methyl]-4-methyl-1,3-dihydro-2H-imidazol-2-one | 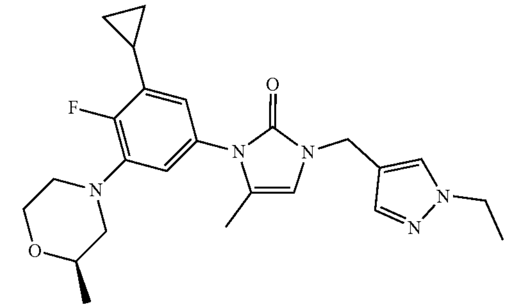 [SMILES: CCn1cc(Cn2cc(C)n(-c3cc(C4CC4)c(F)c(N4CCO[C@H](C)C4)c3)c2=O)cn1] | | 440.3 |
| 161 | 2-[5-(4,4-difluoropiperidin-1-yl)-2-methyl-3-(trifluoromethyl)phenyl]-4-[(1-ethyl-1H-pyrazol-4-yl)methyl]-5-methyl-2,4-dihydro-3H-1,2,4-triazol-3-one | 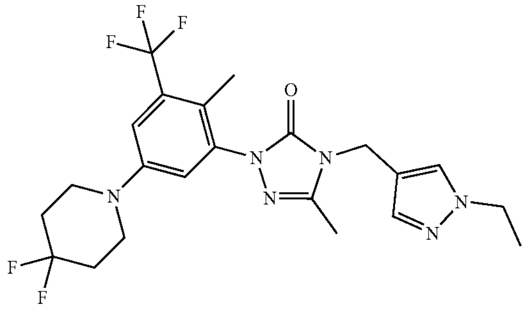 [SMILES: CCn1cc(Cn2c(C)nn(-c3cc(N4CCC(F)(F)CC4)cc(C(F)(F)F)c3C)c2=O)cn1] | | 485.2 |
| 162 | 1-{4-cyclopropyl-6-[(2R)-2-methylmorpholin-4-yl]pyridin-2-yl}-3-[(1-ethyl-1H-pyrazol-4-yl)methyl]-4,5-dimethyl-1,3-dihydro-2H-imidazol-2-one | 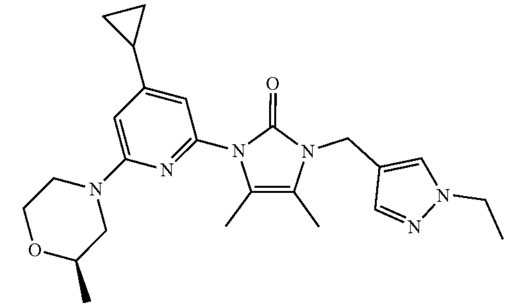 [SMILES: CCn1cc(Cn2c(C)c(C)n(-c3cc(C4CC4)cc(N4CCO[C@H](C)C4)n3)c2=O)cn1] | | 437.3 |
| 163 | 1-[(1-ethyl-1H-pyrazol-4-yl)methyl]-4,5-dimethyl-3-{6-[(2R)-2-methylmorpholin-4-yl]pyridin-2-yl}-1,3-dihydro-2H-imidazol-2-one | 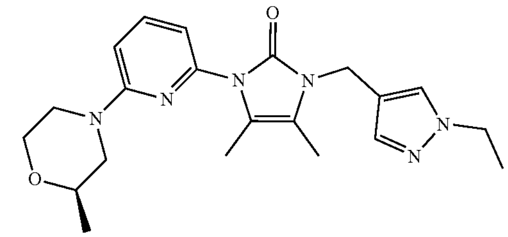 [SMILES: CCn1cc(Cn2c(C)c(C)n(-c3cccc(N4CCO[C@H](C)C4)n3)c2=O)cn1] | | 397.3 |
| 164 | 1-[3-cyclopropyl-5-(2,2-dimethylmorpholin-4-yl)-2-fluorophenyl]-3-[(1-ethyl-1H-pyrazol-4-yl)methyl]-4-methyl-1,3-dihydro-2H-imidazol-2-one | 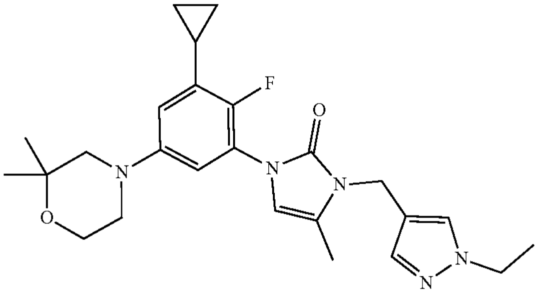 [SMILES: CCn1cc(Cn2c(C)cn(-c3cc(N4CCOC(C)(C)C4)cc(C4CC4)c3F)c2=O)cn1] | | 454.3 |

TABLE 1-continued

| Example No. | IUPAC Name | Structure | Salt | MS |
|---|---|---|---|---|
| 165 | 1-[3-cyclopropyl-5-(4,4-difluoropiperidin-1-yl)-2-fluorophenyl]-3-[(1-ethyl-1H-pyrazol-4-yl)methyl]-4-methyl-1,3-dihydro-2H-imidazol-2-one | 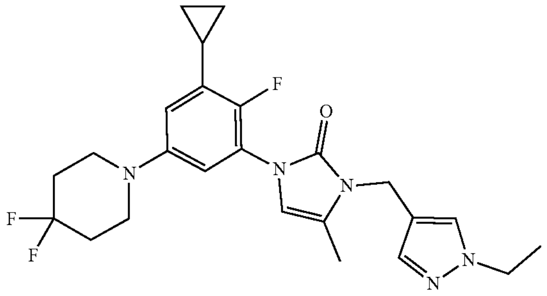 [SMILES: CCn1cc(Cn2c(C)cn(-c3cc(N4CCC(F)(F)CC4)cc(C4CC4)c3F)c2=O)cn1] | | 460.2 |
| 166 | 1-[3-chloro-5-(2,2-dimethylmorpholin-4-yl)-2-fluorophenyl]-3-[(1-ethyl-1H-pyrazol-4-yl)methyl]-4-methyl-1,3-dihydro-2H-imidazol-2-one | 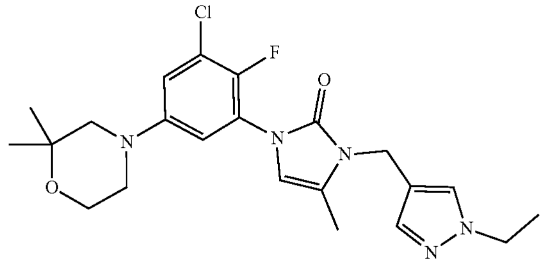 [SMILES: CCn1cc(Cn2c(C)cn(-c3cc(N4CCOC(C)(C)C4)cc(Cl)c3F)c2=O)cn1] | | 448.2 |
| 167 | 1-[3-chloro-5-(4,4-difluoropiperidin-1-yl)-2-fluorophenyl]-3-[(1-ethyl-1H-pyrazol-4-yl)methyl]-4-methyl-1,3-dihydro-2H-imidazol-2-one | 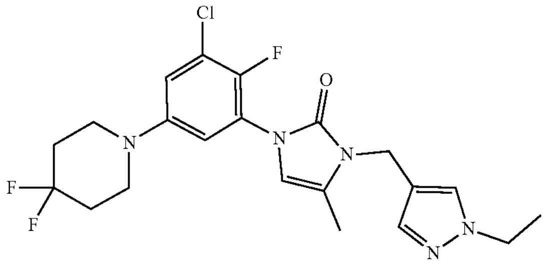 [SMILES: CCn1cc(Cn2c(C)cn(-c3cc(N4CCC(F)(F)CC4)cc(Cl)c3F)c2=O)cn1] | | 454.2 |

Test Example 1

Measurement of the Inhibition Rate of the Amount of $IP_1$ in 30 μM of the Compound of Example 2 in GPR139-Expressed CHO Cells Changes in the amount of $IP_1$ in GPR139-expressed CHO cells were measured in order to evaluate the activity of the compound via GPR139. GPR139 is a Gq-coupled receptor which varies intracellular calcium (Liu C et al., Mol Pharmacol. 2015 November; 88(5):911-25), so the amount of $IP_1$, which is a stable metabolite of the second messenger $IP_3$, changes due to activity regulation of GPR139. GPR139 is considered to be structurally active when expressed recombinantly in mammal cells, so a compound having a GPR139 receptor inverse agonist action is expected to reduce the amount of $IP_1$ production.

The measurement of $IP_1$ was made using an IP-ONE HTFR assay kit (cis-bio) and CHO-TREx (Life Technologies) cells stably transfected with GPR139. The CHO-TREx cells expressed human GPR139 with a tetracycline-inducing element. The cells were cultured in a medium containing F12K and 10% tetracycline-free FBS, and the expression of human GPR139 was induced over the course of 17 hours under conditions of 37° C. and 5% $CO_2$ in the presence of 2 μg/mL of doxycycline (Clontech, 631311) in the growth medium on the day before assay. On the day of the test, after the cells were washed with 10 mL of PBS, the cells were detached with TrypLE Express (Life Technologies) and centrifuged at 1,000 rpm to form pellets, and a cell suspension was then prepared using a stimulation buffer (cis-bio, included in the IP-ONE HTRF assay kit).

The compound was diluted with the stimulation buffer, and 4 μL was added to a 384-well white assay plate (Greiner). The cell suspension was added so that there were 2000 cells per well, and the assay plate was left to stand for 40 minutes at 37° C. Equal amounts of IP1-d2 and Ab-Crp solutions (both available from cis-bio, included in the IP-ONE HTRF assay kit) prepared with a lysis buffer (cis-bio, included in the IP-ONE HTRF assay kit) were mixed, and 4 μL was added to the assay plate and left to stand for one hour at room temperature. After the fluorescence strengths of two wavelengths were measured by the HTRF settings of Envision (PerkinElmer), the value of Ratio={(Signal 665 nm)/(Signal 615 nm)}×10000 was calculated. When the vehicle was set to 0% and the value at which the $IP_1$ concentration is 0 was set to 100%, the inhibition rate of the amount of IP in 30 μM of the compound of Example 2 was 84%.

The compound of Example 2 inhibited the amount of $IP_1$, which is a stable metabolite of the second messenger $IP_3$ in the downstream of signal transmission in GPR139, in GPR139-expressed CHO cells. That is, the compound of Example 2 exhibits GPR139 receptor inverse agonist action.

Test Example 2

Measurement of the Inhibition Rate of the Amount of $IP_1$ in GPR139-Expressed CHO Cells (Inverse Agonist Assay)

The activities of the compounds of Examples 1 and 3 to 167 were expressed as relative values in Table 2 by measuring the inhibition rate of the amount of $IP_1$ with the same method as in Test Example 1 and defining the inhibition rate of the amount of $IP_1$ of Example Compound 2 in Test Example 1 as 100/6.

TABLE 2

| Example No. | Inhibition Rate at 30 μM |
|---|---|
| 1 | 99% |
| 2 | 100% |
| 3 | 101% |
| 4 | 102% |
| 5 | 99% |
| 6 | 102% |
| 7 | 102% |
| 8 | 101% |
| 9 | 102% |
| 10 | 100% |
| 11 | 98% |
| 12 | 98% |
| 13 | 101% |
| 14 | 99% |
| 15 | 101% |
| 16 | 100% |
| 17 | 99% |
| 18 | 101% |
| 19 | 100% |
| 20 | 99% |
| 21 | 99% |
| 22 | 100% |
| 23 | 100% |
| 24 | 100% |
| 25 | 100% |
| 26 | 100% |
| 27 | 99% |
| 28 | 99% |
| 29 | 99% |
| 30 | 99% |
| 31 | 100% |
| 32 | 98% |
| 33 | 100% |
| 34 | 100% |
| 35 | 99% |
| 36 | 101% |
| 37 | 99% |
| 38 | 99% |
| 39 | 99% |
| 40 | 101% |
| 41 | 101% |
| 42 | 99% |
| 43 | 100% |
| 44 | 100% |
| 45 | 101% |
| 46 | 100% |
| 47 | 101% |
| 48 | 101% |
| 49 | 102% |
| 50 | 102% |
| 51 | 102% |
| 52 | 99% |
| 53 | 101% |
| 54 | 101% |
| 55 | 101% |
| 56 | 98% |
| 57 | 101% |
| 58 | 98% |
| 59 | 102% |
| 60 | 101% |
| 61 | 102% |
| 62 | 99% |
| 63 | 100% |
| 64 | 98% |
| 65 | 98% |
| 66 | 99% |
| 67 | 98% |
| 68 | 98% |

TABLE 2-continued

| Example No. | Inhibition Rate at 30 μM |
|---|---|
| 69 | 95% |
| 70 | 100% |
| 71 | 98% |
| 72 | 99% |
| 73 | 99% |
| 74 | 98% |
| 75 | 99% |
| 76 | 97% |
| 77 | 100% |
| 78 | 99% |
| 79 | 98% |
| 80 | 99% |
| 81 | 98% |
| 82 | 100% |
| 83 | 99% |
| 84 | 99% |
| 85 | 97% |
| 86 | 101% |
| 87 | 98% |
| 88 | 99% |
| 89 | 101% |
| 90 | 99% |
| 91 | 100% |
| 92 | 99% |
| 93 | 99% |
| 94 | 99% |
| 95 | 100% |
| 96 | 101% |
| 97 | 102% |
| 98 | 99% |
| 99 | 101% |
| 100 | 99% |
| 101 | 99% |
| 102 | 105% |
| 103 | 103% |
| 104 | 104% |
| 105 | 103% |
| 106 | 102% |
| 107 | 104% |
| 108 | 102% |
| 109 | 101% |
| 110 | 101% |
| 111 | 105% |
| 112 | 100% |
| 113 | 103% |
| 114 | 103% |
| 115 | 103% |
| 116 | 101% |
| 117 | 100% |
| 118 | 100% |
| 119 | 101% |
| 120 | 102% |
| 121 | 101% |
| 122 | 103% |
| 123 | 102% |
| 124 | 103% |
| 125 | 101% |
| 126 | 100% |
| 127 | 99% |
| 128 | 101% |
| 129 | 100% |
| 130 | 100% |
| 131 | 96% |
| 132 | 99% |
| 133 | 99% |
| 134 | 98% |
| 135 | 102% |
| 136 | 100% |
| 137 | 98% |
| 138 | 100% |
| 139 | 98% |
| 140 | 98% |
| 141 | 101% |
| 142 | 100% |
| 143 | 101% |
| 144 | 101% |
| 145 | 102% |

TABLE 2-continued

| Example No. | Inhibition Rate at 30 μM |
|---|---|
| 146 | 103% |
| 147 | 100% |
| 148 | 101% |
| 149 | 101% |
| 150 | 101% |
| 151 | 98% |
| 152 | 98% |
| 153 | 100% |
| 154 | 98% |
| 155 | 101% |
| 156 | 98% |
| 157 | 101% |
| 158 | 98% |
| 159 | 99% |
| 160 | 98% |
| 161 | 100% |
| 162 | 101% |
| 163 | 96% |
| 164 | 97% |
| 165 | 97% |
| 166 | 98% |
| 167 | 97% |

As shown in Table 2, the compound of the present disclosure inhibited the amount of IP1, which is a stable metabolite of the second messenger IP3 in the downstream of signal transmission in GPR139, in GPR139-expressed CHO cells. That is, the compound of the present disclosure has a GPR139 receptor antagonist action (inverse agonist action).

Formulation Examples

In some embodiments, pharmaceuticals comprising a compound of the present disclosure as an active ingredient can be produced using the following non-limiting example formulations.

TABLE 3

| | |
|---|---|
| (1) Compound obtained in Example 1 | 10 mg |
| (2) Lactose | 90 mg |
| (3) Microcrystalline cellulose | 70 mg |
| (4) Magnesium stearate | 10 mg |
| One capsule | 180 mg |

After the total amounts of (1), (2), and (3) and 5 mg of (4) are mixed, and granulated, the remaining 5 mg of (4) is added, and the entire substance mixture is sealed in a gelatin capsule.

TABLE 4

| | |
|---|---|
| (1) Compound obtained in Example 1 | 10 mg |
| (2) Lactose | 35 mg |
| (3) Corn starch | 150 mg |
| (4) Microcrystalline cellulose | 30 mg |
| (5) Magnesium stearate | 5 mg |
| One tablet | 230 mg |

After the total amounts of (1), (2) and (3), 20 mg of (4), and 2.5 mg of (5) are mixed and granulated, the remaining 10 mg of (4) and 2.5 mg of (5) are added to the granules and pressure-molded to form a tablet.

What is claimed is:

1. A compound of Formula (I):

(I)

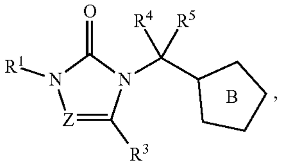

or a pharmaceutically acceptable salt thereof, wherein:

$R^1$ is a group represented by:

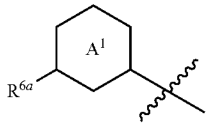

or

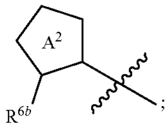

;

ring $A^1$ is chosen from 6-membered aromatic rings optionally further substituted with 1 to 3 substituents independently chosen from:
- (a) halogen atoms;
- (b) $C_{1-6}$ alkyl groups optionally substituted with 1 to 3 substituents independently chosen from;
  - (i) halogen atoms; and
  - (ii) a hydroxy group;
- (c) optionally halogenated $C_{1-6}$ alkoxy groups;
- (d) $C_{3-10}$ cycloalkyl groups optionally substituted with 1 to 3 halogen atoms;
- (e) $C_{2-6}$ alkenyl groups; and
- (f) 3- to 14-membered non-aromatic heterocyclic groups optionally substituted with 1 to 3 halogen atoms;

ring $A^2$ is chosen from 5-membered monocyclic aromatic heterocyclic rings optionally further substituted with 1 to 3 optionally halogenated $C_{1-6}$ alkyl groups;

Z is C—$R^2$ or N;

$R^2$ and $R^3$ are each independently chosen from a hydrogen atom, halogen atoms, and optionally halogenated $C_{1-6}$ alkyl groups;

$R^4$ and $R^5$ are each independently chosen from a hydrogen atom and $C_{1-6}$ alkyl groups;

$R^{6a}$ is chosen from:
- (1) $C_{3-10}$ cycloalkyl groups optionally substituted with 1 to 3 halogen atoms;
- (2) $C_{6-14}$ aryl groups optionally substituted with 1 to 3 halogen atoms;
- (3) 3- to 14-membered non-aromatic heterocyclic groups optionally substituted with 1 to 3 substituents independently chosen from:
  - (a) halogen atoms; and
  - (b) optionally halogenated $C_{1-6}$ alkyl groups;
- (4) 5- to 14-membered aromatic heterocyclic groups optionally substituted with 1 to 3 $C_{1-6}$ alkyl groups;
- (5) mono- or di-$C_{1-6}$ alkylamino groups optionally substituted with 1 to 3 $C_{3-10}$ cycloalkyl groups optionally substituted with 1 to 3 halogen atoms;
- (6) N—$C_{1-6}$ alkyl-N-3- to 14-membered non-aromatic heterocyclic amino groups;
- (7) $C_{1-6}$ alkoxy groups optionally substituted with 1 to 3 substituents independently chosen from:

(a) $C_{1-6}$ alkoxy groups;
(b) $C_{3-10}$ cycloalkyl groups; and
(c) 3- to 14-membered non-aromatic heterocyclic groups;

(8) $C_{6-14}$ aryloxy groups optionally substituted with 1 to 3 halogen atoms; and
(9) 3- to 14-membered non-aromatic heterocyclic oxy groups;

$R^{6b}$ is chosen from $C_{1-6}$ alkyl groups optionally substituted with 1 to 3 $C_{3-10}$ cycloalkyl groups; and ring B is chosen from 5-membered monocyclic aromatic heterocyclic rings optionally further substituted with 1 to 3 $C_{1-6}$ alkyl groups, provided that the compound or pharmaceutically acceptable salt is not 1-(3-chlorophenyl)-3-[(5-phenyl-1,3,4-oxadiazole-2-yl) methyl]1,3-dihydro-2H-imidazole-2-one or a salt thereof.

2. The compound or pharmaceutically acceptable salt according to claim 1, wherein $R^1$ is a group represented by:

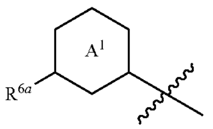
, wherein:

ring $A^1$ is chosen from:

(1) benzene rings optionally further substituted with 1 to 3 substituents independently chosen from:
(a) halogen atoms;
(b) $C_{1-6}$ alkyl groups optionally substituted with 1 to 3 substituents independently chosen from (i) halogen atoms; and (ii) a hydroxy group;
(c) optionally halogenated $C_{1-6}$ alkoxy groups;
(d) $C_{3-6}$ cycloalkyl groups optionally substituted with 1 to 3 halogen atoms;
(e) $C_{2-6}$ alkenyl groups; and
(f) piperidyl groups optionally substituted with 1 to 3 halogen atoms;

(2) pyridine rings optionally further substituted with 1 to 3 substituents independently chosen from:
(a) halogen atoms;
(b) $C_{1-6}$ alkyl groups optionally substituted with 1 to 3 halogen atoms;
(c) optionally halogenated $C_{1-6}$ alkoxy groups; and
(d) $C_{3-6}$ cycloalkyl groups; and (3) pyrimidine rings optionally further substituted with 1 or 2 $C_{1-6}$ alkyl groups optionally substituted with 1 to 3 halogen atoms; and $R^{6a}$ is chosen from:

(1) $C_{3-6}$ cycloalkyl groups optionally substituted with 1 to 3 halogen atoms;
(2) phenyl groups optionally substituted with 1 to 3 halogen atoms;
(3) morpholinyl groups optionally substituted with 1 to 3 substituents independently chosen from:
(a) halogen atoms; and
(b) $C_{1-6}$ alkyl groups optionally substituted with 1 to 3 halogen atoms;
(4) piperidyl groups optionally substituted with 1 to 3 halogen atoms;
(5) pyrrolidinyl groups optionally substituted with 1 to 3 halogen atoms;
(6) a 4-oxa-7-azaspiro[2.5]octyl group;
(7) imidazolyl groups optionally substituted with 1 to 3 $C_{1-6}$ alkyl groups;
(8) mono- or di-$C_{1-6}$ alkylamino groups optionally substituted with 1 to 3 $C_{3-6}$ cycloalkyl groups optionally substituted with 1 to 3 halogen atoms;
(9) N—$C_{1-6}$ alkyl-N-tetrahydropyranylamino groups;
(10) $C_{1-6}$ alkoxy groups optionally substituted with 1 to 3 substituents independently chosen from:
(a) $C_{1-6}$ alkoxy groups;
(b) $C_{3-6}$ cycloalkyl groups;
(c) an oxetanyl group; and
(d) a tetrahydrofuryl group;
(11) phenoxy groups optionally substituted with 1 to 3 halogen; and
(12) a tetrahydropyranyloxy group.

3. The compound or pharmaceutically acceptable salt according to claim 1, wherein the group represented by:

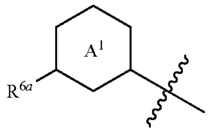

is a group represented by:

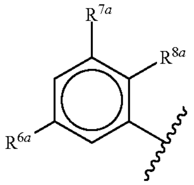
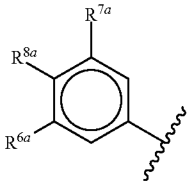
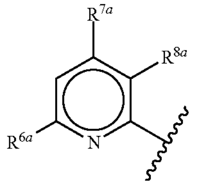
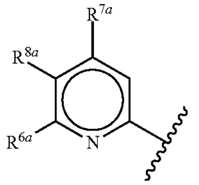
or
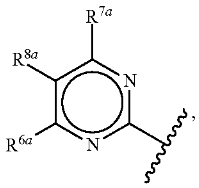
, wherein:

$R^{7a}$ is chosen from:
(a) a hydrogen atom;
(b) halogen atoms;
(c) $C_{1-6}$ alkyl groups optionally substituted with 1 to 3 substituents independently chosen from (i) halogen atoms; and (ii) a hydroxy group;
(d) optionally halogenated $C_{1-6}$ alkoxy groups;
(e) $C_{3-10}$ cycloalkyl groups optionally substituted with 1 to 3 halogen atoms;
(f) $C_{2-6}$ alkenyl groups; and
(g) 3- to 14-membered non-aromatic heterocyclic groups optionally substituted with 1 to 3 halogen atoms; and $R^{8a}$ is chosen from:
(a) a hydrogen atom;

(b) halogen atoms; and (c) $C_{1-6}$ alkyl groups.

4. The compound or pharmaceutically acceptable salt according to claim 1, wherein the group represented by:

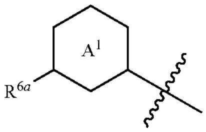

is a group represented by:

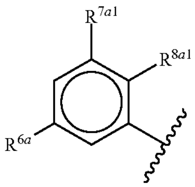

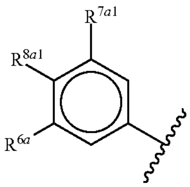

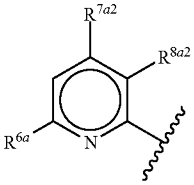

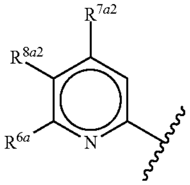

or

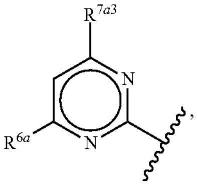

, wherein:

$R^{7a1}$ is chosen from:

(a) halogen atoms;

(b) $C_{1-6}$ alkyl groups optionally substituted with 1 to 3 substituents independently chosen from halogen atoms and a hydroxy group;

(c) optionally halogenated $C_{1-6}$ alkoxy groups;

(d) $C_{3-6}$ cycloalkyl groups optionally substituted with 1 to 3 halogen atoms;

(e) $C_{2-6}$ alkenyl groups; and (f) piperidyl groups optionally substituted with 1 to 3 halogen atoms;

$R^{7a2}$ is chosen from:

(a) a hydrogen atom;

(b) $C_{1-6}$ alkyl groups optionally substituted with 1 to 3 halogen atoms;

(c) optionally halogenated $C_{1-6}$ alkoxy groups; and (d) $C_{3-6}$ cycloalkyl groups;

$R^{7a3}$ is chosen from $C_{1-6}$ alkyl groups optionally substituted with 1 to 3 halogen atoms;

$R^{8a1}$ is chosen from:

(a) a hydrogen atom;

(b) halogen atoms; and (c) $C_{1-6}$ alkyl groups; and $R^{8a2}$ is chosen from:

(a) a hydrogen atom;

(b) halogen atoms; and (c) $C_{1-6}$ alkyl groups.

5. The compound or pharmaceutically acceptable salt according to claim 1, wherein the group represented by:

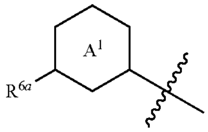

is a group represented by:

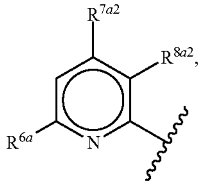

wherein:

$R^{7a2}$ is chosen from $C_{1-6}$ alkyl groups substituted with 1 to 3 halogen atoms; and $R^{8a2}$ is chosen from a hydrogen atom and halogen atoms.

6. The compound or pharmaceutically acceptable salt according to claim 1, wherein the group represented by:

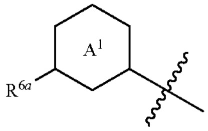

is a group represented by:

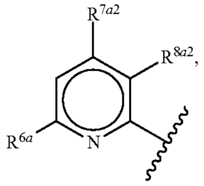

wherein:

$R^{7a2}$ is chosen from $C_{1-6}$ alkyl groups substituted with 1 to 3 halogen atoms; and $R^{8a2}$ is a hydrogen atom.

7. The compound or pharmaceutically acceptable salt according to claim 1, wherein $R^1$ is a group represented by:

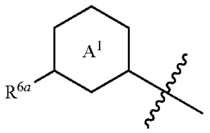

, wherein:

ring $A^1$ is chosen from pyridine rings optionally further substituted with 1 or 2 substituents independently chosen from:

(a) halogen atoms; and (b) $C_{1-6}$ alkyl groups substituted with 1 to 3 halogen atoms; and $R^{6a}$ is chosen from morpholinyl groups optionally substituted with 1 to 3 $C_{1-6}$ alkyl groups.

8. The compound or pharmaceutically acceptable salt according to claim 1, wherein $R^1$ is a group represented by:

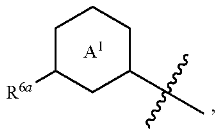

wherein:

ring $A^1$ is chosen from pyridine rings further substituted with one $C_{1-6}$ alkyl group substituted with 1 to 3 halogen atoms; and $R^{6a}$ is chosen from morpholinyl groups substituted with one $C_{1-6}$ alkyl group.

9. The compound or pharmaceutically acceptable salt according to claim 1, wherein:

ring $A^2$ is chosen from pyrazole rings optionally further substituted with 1 to 3 $C_{1-6}$ alkyl groups optionally substituted with 1 to 3 halogen atoms.

10. The compound or pharmaceutically acceptable salt according to claim 1, wherein the group represented by:

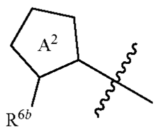

is a group represented by:

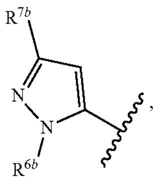

wherein:

$R^{6b}$ is chosen from $C_{1-6}$ alkyl groups optionally substituted with 1 to 3 $C_{3-10}$ cycloalkyl groups; and $R^{7b}$ is chosen from $C_{1-6}$ alkyl groups optionally substituted with 1 to 3 halogen atoms.

11. The compound or pharmaceutically acceptable salt according to claim 1, wherein ring B is chosen from pyrazole rings optionally further substituted with 1 to 3 $C_{1-6}$ alkyl groups.

12. The compound or pharmaceutically acceptable salt according to claim 1, wherein ring B is chosen from pyrazole rings further substituted with one $C_{1-6}$ alkyl group.

13. The compound or pharmaceutically acceptable salt according to claim 1, wherein ring B is:

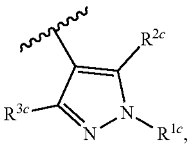

wherein:

$R^{1c}$ is chosen from a hydrogen atom and $C_{1-6}$ alkyl groups; and $R^{2c}$ and $R^{3c}$ are each independently chosen from a hydrogen atom and $C_{1-6}$ alkyl groups.

14. The compound or pharmaceutically acceptable salt according to claim 1, wherein ring B is:

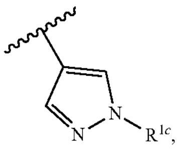

wherein $R^{1c}$ is chosen from $C_{1-6}$ alkyl groups.

15. The compound or pharmaceutically acceptable salt according to claim 1, wherein:

Z is C—$R^2$; and $R^2$ is chosen from a hydrogen atom and optionally halogenated $C_{1-6}$ alkyl groups.

16. The compound or pharmaceutically acceptable salt according to claim 1, wherein:

Z is C—$R^2$; and $R^2$ is chosen from a hydrogen atom and $C_{1-3}$ alkyl groups.

17. The compound or pharmaceutically acceptable salt according to claim 1, wherein:

Z is C—$R^2$; and $R^2$ is chosen from $C_{1-3}$ alkyl groups.

18. The compound or pharmaceutically acceptable salt according to claim 1, wherein Z is N.

19. The compound or pharmaceutically acceptable salt according to claim 1, wherein $R^3$ is chosen from a hydrogen atom and $C_{1-3}$ alkyl groups.

20. The compound or pharmaceutically acceptable salt according to claim 1, wherein $R^3$ is chosen from $C_{1-3}$ alkyl groups.

21. The compound or pharmaceutically acceptable salt according to claim 1, wherein:

$R^4$ is chosen from a hydrogen atom and $C_{1-6}$ alkyl groups; and $R^5$ is a hydrogen atom.

22. The compound or pharmaceutically acceptable salt according to claim 1, wherein $R^4$ and $R^5$ are both hydrogen atoms.

23. A compound chosen from:

1-[(1-ethyl-1H-pyrazol-4-yl) methyl]-3-[4'-fluoro-5-(trifluoromethyl) [1,1'-biphenyl]-3-yl]-1,3-dihydro-2H-imidazol-2-one;

1-[(1-ethyl-1H-pyrazol-4-yl) methyl]-3-{2-fluoro-5-[(2R)-2-methylmorpholin-4-yl]-3-(trifluoromethyl) phenyl}-1,3-dihydro-2H-imidazol-2-one;

1-[(1-ethyl-1H-pyrazol-4-yl) methyl]-3-[4'-fluoro-5-(trifluoromethyl) [1,1'-biphenyl]-3-yl]-4-methyl-1,3-dihydro-2H-imidazol-2-one;

1-[(1-ethyl-1H-pyrazol-4-yl) methyl]-3-{2-fluoro-5-[(2R)-2-methylmorpholin-4-yl]-3-(trifluoromethyl) phenyl}-4-methyl-1,3-dihydro-2H-imidazol-2-one;

1-[(1-ethyl-1H-pyrazol-4-yl) methyl]-3-[3-(4-fluorophenoxy)-5-(trifluoromethyl) phenyl]-4-methyl-1,3-dihydro-2H-imidazol-2-one;

1-[(1-ethyl-1H-pyrazol-4-yl) methyl]-4-methyl-3-{3-[(oxan-4-yl) oxy]-5-(trifluoromethyl) phenyl}-1,3-dihydro-2H-imidazol-2-one;

3-{3-[(3,3-difluorocyclobutyl) methoxy]-5-(trifluoromethyl) phenyl}-1-[(1-ethyl-1H-pyrazol-4-yl) methyl]-4-methyl-1,3-dihydro-2H-imidazol-2-one;

1-[(1-ethyl-1H-pyrazol-4-yl) methyl]-3-{2-methyl-5-[(2R)-2-methylmorpholin-4-yl]-3-(trifluoromethyl) phenyl}-1,3-dihydro-2H-imidazol-2-one;

1-[1-(1-ethyl-1H-pyrazol-4-yl) ethyl]-3-{2-fluoro-5-[(2R)-2-methylmorpholin-4-yl]-3-(trifluoromethyl) phenyl}-1,3-dihydro-2H-imidazol-2-one;

1-[(1-ethyl-1H-pyrazol-4-yl) methyl]-3-{2-fluoro-5-[methyl(oxan-4-yl) amino]-3-(trifluoromethyl) phenyl}-1,3-dihydro-2H-imidazol-2-one;

1-[(1-ethyl-1H-pyrazol-4-yl) methyl]-3-{2-fluoro-5-[(2S)-2-methylmorpholin-4-yl]-3-(trifluoromethyl) phenyl}-1,3-dihydro-2H-imidazol-2-one;

1-[5-(2,2-dimethylmorpholin-4-yl)-2-fluoro-3-(trifluoromethyl) phenyl]-3-[(1-ethyl-1H-pyrazol-4-yl) methyl]-1,3-dihydro-2H-imidazol-2-one;

1-[(1-ethyl-5-methyl-1H-pyrazol-4-yl) methyl]-3-{2-fluoro-5-[(2R)-2-methylmorpholin-4-yl]-3-(trifluoromethyl) phenyl}-1,3-dihydro-2H-imidazol-2-one;

1-[(1-ethyl-1H-pyrazol-4-yl) methyl]-4-methyl-3-{3-[(2R)-2-methylmorpholin-4-yl]-5-(trifluoromethyl) phenyl}-1,3-dihydro-2H-imidazol-2-one;

1-{2-chloro-5-[(2R)-2-methylmorpholin-4-yl]-3-(trifluoromethyl) phenyl}-3-[(1-ethyl-1H-pyrazol-4-yl) methyl]-1,3-dihydro-2H-imidazol-2-one;

1-[(1-ethyl-1H-pyrazol-4-yl) methyl]-4,5-dimethyl-3-{3-[(2R)-2-methylmorpholin-4-yl]-5-(trifluoromethyl) phenyl}-1,3-dihydro-2H-imidazol-2-one;

3-[3-(cyclopropylmethoxy)-5-(trifluoromethyl) phenyl]-1-[(1-ethyl-1H-pyrazol-4-yl) methyl]-4-methyl-1,3-dihydro-2H-imidazol-2-one;

1-[(1-ethyl-1H-pyrazol-4-yl) methyl]-4-methyl-3-{6-[(2R)-2-methylmorpholin-4-yl]-4-(trifluoromethyl) pyridin-2-yl}-1,3-dihydro-2H-imidazol-2-one;

3-[3-(4,4-difluoropiperidin-1-yl)-5-(trifluoromethyl) phenyl]-1-[(1-ethyl-1H-pyrazol-4-yl) methyl]-4-methyl-1,3-dihydro-2H-imidazol-2-one;

3-{3-[2-(difluoromethyl) morpholin-4-yl]-5-(trifluoromethyl) phenyl}-1-[(1-ethyl-1H-pyrazol-4-yl) methyl]-4-methyl-1,3-dihydro-2H-imidazol-2-one;

1-[(1-ethyl-1H-pyrazol-4-yl) methyl]-4-methyl-3-[3-(4-methyl-1H-imidazol-1-yl)-5-(trifluoromethyl) phenyl]-1,3-dihydro-2H-imidazol-2-one;

3-{3-[(2,2-difluorocyclopropyl) methoxy]-5-(trifluoromethyl) phenyl}-1-[(1-ethyl-1H-pyrazol-4-yl) methyl]-4-methyl-1,3-dihydro-2H-imidazol-2-one;

3-{3-[(2R,6S)-2,6-dimethylmorpholin-4-yl]-5-(trifluoromethyl) phenyl}-1-[(1-ethyl-1H-pyrazol-4-yl) methyl]-4-methyl-1,3-dihydro-2H-imidazol-2-one;

3-[3-(3,3-difluoropyrrolidin-1-yl)-5-(trifluoromethyl) phenyl]-1-[(1-ethyl-1H-pyrazol-4-yl) methyl]-4-methyl-1,3-dihydro-2H-imidazol-2-one;

3-[(1-ethyl-1H-pyrazol-4-yl) methyl]-1-{2-fluoro-5-[(2R)-2-methylmorpholin-4-yl]-3-(trifluoromethyl) phenyl}-4-methyl-1,3-dihydro-2H-imidazol-2-one;

1-[(1-ethyl-1H-pyrazol-4-yl) methyl]-3-{3-fluoro-6-[(2R)-2-methylmorpholin-4-yl]-4-(trifluoromethyl) pyridin-2-yl}-1,3-dihydro-2H-imidazol-2-one;

4-[(1-ethyl-1H-pyrazol-4-yl) methyl]-2-{2-fluoro-5-[(2R)-2-methylmorpholin-4-yl]-3-(trifluoromethyl) phenyl}-2,4-dihydro-3H-1,2,4-triazol-3-one;

1-[(1-ethyl-1H-pyrazol-4-yl) methyl]-4-methyl-3-{3-[(2S)-2-methylmorpholin-4-yl]-5-(trifluoromethyl) phenyl}-1,3-dihydro-2H-imidazol-2-one;

3-[3-(2,2-dimethylmorpholin-4-yl)-5-(trifluoromethyl) phenyl]-1-[(1-ethyl-1H-pyrazol-4-yl) methyl]-4-methyl-1,3-dihydro-2H-imidazol-2-one;

3-[(1-ethyl-1H-pyrazol-4-yl) methyl]-1-{3-fluoro-6-[(2R)-2-methylmorpholin-4-yl]-4-(trifluoromethyl) pyridin-2-yl}-4-methyl-1,3-dihydro-2H-imidazol-2-one;

1-{5-[(2R,6S)-2,6-dimethylmorpholin-4-yl]-2-fluoro-3-(trifluoromethyl) phenyl}-3-[(1-ethyl-1H-pyrazol-4-yl) methyl]-1,3-dihydro-2H-imidazol-2-one;

1-{3-chloro-2-fluoro-5-[(2R)-2-methylmorpholin-4-yl] phenyl}-3-[(1-ethyl-1H-pyrazol-4-yl) methyl]-1,3-dihydro-2H-imidazol-2-one;

3-[3-(4,4-difluorocyclohexyl)-5-(trifluoromethyl) phenyl]-1-[(1-ethyl-1H-pyrazol-4-yl) methyl]-4-methyl-1,3-dihydro-2H-imidazol-2-one;

1-{5-[(2R,6R)-2,6-dimethylmorpholin-4-yl]-2-fluoro-3-(trifluoromethyl) phenyl}-3-[(1-ethyl-1H-pyrazol-4-yl) methyl]-1,3-dihydro-2H-imidazol-2-one;

1-{2-fluoro-5-[(2R)-2-methylmorpholin-4-yl]-3-(trifluoromethyl) phenyl}-3-{[1-(propan-2-yl)-1H-pyrazol-4-yl]methyl}-1,3-dihydro-2H-imidazol-2-one;

1-[5-(4,4-difluoropiperidin-1-yl)-2-fluoro-3-(trifluoromethyl) phenyl]-3-[(1-ethyl-1H-pyrazol-4-yl) methyl]-1,3-dihydro-2H-imidazol-2-one;

1-[5-(3,3-difluoropiperidin-1-yl)-2-fluoro-3-(trifluoromethyl) phenyl]-3-[(1-ethyl-1H-pyrazol-4-yl) methyl]-1,3-dihydro-2H-imidazol-2-one;

1-[(1-ethyl-1H-pyrazol-4-yl) methyl]-4-methyl-3-{3-[methyl(oxan-4-yl) amino]-5-(trifluoromethyl) phenyl}-1,3-dihydro-2H-imidazol-2-one;

1-[5-(3,3-difluoropyrrolidin-1-yl)-2-fluoro-3-(trifluoromethyl) phenyl]-3-[(1-ethyl-1H-pyrazol-4-yl) methyl]-1,3-dihydro-2H-imidazol-2-one;

1-[5-(2,2-difluoromorpholin-4-yl)-2-fluoro-3-(trifluoromethyl) phenyl]-3-[(1-ethyl-1H-pyrazol-4-yl) methyl]-1,3-dihydro-2H-imidazol-2-one;

3-[3-(2,2-difluoromorpholin-4-yl)-5-(trifluoromethyl) phenyl]-1-[(1-ethyl-1H-pyrazol-4-yl) methyl]-4-methyl-1,3-dihydro-2H-imidazol-2-one;

1-[(1-ethyl-1H-pyrazol-4-yl) methyl]-3-{3-methyl-6-[(2R)-2-methylmorpholin-4-yl]-4-(trifluoromethyl) pyridin-2-yl}-1,3-dihydro-2H-imidazol-2-one;

1-[(1-ethyl-1H-pyrazol-4-yl) methyl]-3-[2-fluoro-5-(4-oxa-7-azaspiro[2.5]octan-7-yl)-3-(trifluoromethyl) phenyl]-1,3-dihydro-2H-imidazol-2-one;

1-{3-cyclopropyl-2-fluoro-5-[(2R)-2-methylmorpholin-4-yl]phenyl}-3-[(1-ethyl-1H-pyrazol-4-yl) methyl]-1,3-dihydro-2H-imidazol-2-one;

3-[(1-ethyl-1H-pyrazol-4-yl) methyl]-4-methyl-1-{3-methyl-6-[(2R)-2-methylmorpholin-4-yl]-4-(trifluoromethyl) pyridin-2-yl}-1,3-dihydro-2H-imidazol-2-one;

1-{3-(2,2-difluoroethoxy)-5-[(2R)-2-methylmorpholin-4-yl]phenyl}-3-[(1-ethyl-1H-pyrazol-4-yl) methyl]-4,5-dimethyl-1,3-dihydro-2H-imidazol-2-one;

1-[(1-ethyl-1H-pyrazol-4-yl) methyl]-4,5-dimethyl-3-{3-[(2R)-2-methylmorpholin-4-yl]-5-(2,2,2-trifluoroethoxy) phenyl}-1,3-dihydro-2H-imidazol-2-one;

1-[(1-ethyl-1H-pyrazol-4-yl) methyl]-3-[3-(methoxymethoxy)-5-(trifluoromethyl) phenyl]-4-methyl-1,3-dihydro-2H-imidazol-2-one;

1-[(1-ethyl-1H-pyrazol-4-yl) methyl]-4-methyl-3-{3-[(oxetan-2-yl) methoxy]-5-(trifluoromethyl) phenyl}-1,3-dihydro-2H-imidazol-2-one;

1-[(1-ethyl-1H-pyrazol-4-yl) methyl]-3-{3-[(1-fluorocyclobutyl) methoxy]-5-(trifluoromethyl) phenyl}-4-methyl-1,3-dihydro-2H-imidazol-2-one;

3-[(1-ethyl-1H-pyrazol-4-yl) methyl]-1-{2-fluoro-5-[methyl(oxan-4-yl) amino]-3-(trifluoromethyl) phenyl}-4-methyl-1,3-dihydro-2H-imidazol-2-one;

1-[5-(2,2-difluoromorpholin-4-yl)-2-fluoro-3-(trifluoromethyl) phenyl]-3-[(1-ethyl-1H-pyrazol-4-yl) methyl]-4-methyl-1,3-dihydro-2H-imidazol-2-one;

3-[(1-ethyl-1H-pyrazol-4-yl) methyl]-1-{2-fluoro-5-[(2R)-2-methylmorpholin-4-yl]-3-(2,2,2-trifluoroethoxy) phenyl}-4-methyl-1,3-dihydro-2H-imidazol-2-one;

1-[(1-ethyl-1H-pyrazol-4-yl) methyl]-3-{3-[(1-fluorocyclopropyl) methoxy]-5-(trifluoromethyl) phenyl}-4-methyl-1,3-dihydro-2H-imidazol-2-one;

1-{2-chloro-5-[(2R)-2-methylmorpholin-4-yl]-3-(trifluoromethyl) phenyl}-3-[(1-ethyl-1H-pyrazol-4-yl) methyl]-4-methyl-1,3-dihydro-2H-imidazol-2-one;

1-{2-chloro-5-[methyl(oxan-4-yl) amino]-3-(trifluoromethyl) phenyl}-3-[(1-ethyl-1H-pyrazol-4-yl) methyl]-4-methyl-1,3-dihydro-2H-imidazol-2-one;

1-[(1-ethyl-1H-pyrazol-4-yl) methyl]-3-{3-fluoro-6-[(2R)-2-methylmorpholin-4-yl]-4-(trifluoromethyl) pyridin-2-yl}-4,5-dimethyl-1,3-dihydro-2H-imidazol-2-one;

1-[(1-ethyl-1H-pyrazol-4-yl) methyl]-4,5-dimethyl-3-{6-[(2R)-2-methylmorpholin-4-yl]-4-(trifluoromethyl) pyridin-2-yl}-1,3-dihydro-2H-imidazol-2-one;

1-{2-fluoro-5-[methyl(oxan-4-yl) amino]-3-(trifluoromethyl) phenyl}-3-{[1-(propan-2-yl)-1H-pyrazol-4-yl] methyl}-1,3-dihydro-2H-imidazol-2-one;

3-[(1-ethyl-1H-pyrazol-4-yl) methyl]-4-methyl-1-{2-methyl-5-[(2R)-2-methylmorpholin-4-yl]-3-(trifluoromethyl) phenyl}-1,3-dihydro-2H-imidazol-2-one;

1-[3-(2,2-difluoromorpholin-4-yl)-5-(trifluoromethyl) phenyl]-3-[(1-ethyl-1H-pyrazol-4-yl) methyl]-4,5-dimethyl-1,3-dihydro-2H-imidazol-2-one;

1-{3-fluoro-6-[(2R)-2-methylmorpholin-4-yl]-4-(trifluoromethyl) pyridin-2-yl}-4-methyl-3-{[1-(propan-2-yl)-1H-pyrazol-4-yl]methyl}-1,3-dihydro-2H-imidazol-2-one;

3-{3-bromo-5-[(3,3-difluorocyclobutyl) methoxy]phenyl}-1-[(1-ethyl-1H-pyrazol-4-yl) methyl]-4-methyl-1,3-dihydro-2H-imidazol-2-one;

1-[(1-ethyl-1H-pyrazol-4-yl) methyl]-4-methyl-3-[3-{[(2S)-oxolan-2-yl]methoxy}-5-(trifluoromethyl) phenyl]-1,3-dihydro-2H-imidazol-2-one;

3-{3-cyclopropyl-5-[(3,3-difluorocyclobutyl) methoxy] phenyl}-1-[(1-ethyl-1H-pyrazol-4-yl) methyl]-4-methyl-1,3-dihydro-2H-imidazol-2-one;

3-{3-[(3,3-difluorocyclobutyl) methoxy]-5-(difluoromethyl) phenyl}-1-[(1-ethyl-1H-pyrazol-4-yl) methyl]-4-methyl-1,3-dihydro-2H-imidazol-2-one;

1-{2-chloro-5-[(3,3-difluorocyclobutyl) methoxy]-3-(difluoromethyl) phenyl}-3-[(1-ethyl-1H-pyrazol-4-yl) methyl]-1,3-dihydro-2H-imidazol-2-one;

1-[5-(2,2-difluoromorpholin-4-yl)-2-fluoro-3-(trifluoromethyl) phenyl]-3-[(1-ethyl-1H-pyrazol-4-yl) methyl]-4,5-dimethyl-1,3-dihydro-2H-imidazol-2-one;

3-{3-(2,2-difluoroethoxy)-5-[(2R)-2-methylmorpholin-4-yl]phenyl}-1-[(1-ethyl-1H-pyrazol-4-yl) methyl]-4-methyl-1,3-dihydro-2H-imidazol-2-one;

1-[(1-ethyl-1H-pyrazol-4-yl) methyl]-4-methyl-3-{3-[(2R)-2-methylmorpholin-4-yl]-5-(2,2,2-trifluoroethoxy) phenyl}-1,3-dihydro-2H-imidazol-2-one;

1-[(1-ethyl-1H-pyrazol-4-yl) methyl]-4,5-dimethyl-3-{3-[methyl(oxan-4-yl) amino]-5-(2,2,2-trifluoroethoxy) phenyl}-1,3-dihydro-2H-imidazol-2-one;

1-{3-ethenyl-2-fluoro-5-[(2R)-2-methylmorpholin-4-yl] phenyl}-3-[(1-ethyl-1H-pyrazol-4-yl) methyl]-1,3-dihydro-2H-imidazol-2-one;

1-{3-fluoro-6-[(2R)-2-methylmorpholin-4-yl]-4-(trifluoromethyl) pyridin-2-yl}-3-{[1-(propan-2-yl)-1H-pyrazol-4-yl]methyl}-1,3-dihydro-2H-imidazol-2-one;

1-{3-(difluoromethyl)-5-[methyl(oxan-4-yl) amino]phenyl}-4,5-dimethyl-3-{[1-(propan-2-yl)-1H-pyrazol-4-yl]methyl}-1,3-dihydro-2H-imidazol-2-one;

3-[1-(2-cyclobutylethyl)-3-(trifluoromethyl)-1H-pyrazol-5-yl]-1-[(1-ethyl-1H-pyrazol-4-yl) methyl]-4-methyl-1,3-dihydro-2H-imidazol-2-one;

1-{3-(2,2-difluorocyclopropyl)-2-fluoro-5-[(2R)-2-methylmorpholin-4-yl]phenyl}-3-[(1-ethyl-1H-pyrazol-4-yl) methyl]-1,3-dihydro-2H-imidazol-2-one;

1-[3-(difluoromethyl)-5-(2,2-dimethylmorpholin-4-yl)-2-fluorophenyl]-4-methyl-3-{[1-(propan-2-yl)-1H-pyrazol-4-yl]methyl}-1,3-dihydro-2H-imidazol-2-one;

1-{3-ethyl-2-fluoro-5-[(2R)-2-methylmorpholin-4-yl] phenyl}-3-[(1-ethyl-1H-pyrazol-4-yl) methyl]-1,3-dihydro-2H-imidazol-2-one;

1-{3-ethyl-2-fluoro-5-[(2R)-2-methylmorpholin-4-yl] phenyl}-3-[(1-ethyl-1H-pyrazol-4-yl) methyl]-4-methyl-1,3-dihydro-2H-imidazol-2-one;

3-{2-chloro-5-[(2R)-2-methylmorpholin-4-yl]-3-(trifluoromethyl) phenyl}-1-[(1-ethyl-1H-pyrazol-4-yl) methyl]-4-methyl-1,3-dihydro-2H-imidazol-2-one;

1-{3-chloro-6-[methyl(oxan-4-yl) amino]-4-(trifluoromethyl) pyridin-2-yl}-3-[(1-ethyl-1H-pyrazol-4-yl) methyl]-4-methyl-1,3-dihydro-2H-imidazol-2-one;

1-{3-chloro-6-[(2R)-2-methylmorpholin-4-yl]-4-(trifluoromethyl) pyridin-2-yl}-3-[(1-ethyl-1H-pyrazol-4-yl) methyl]-4-methyl-1,3-dihydro-2H-imidazol-2-one;

1-{3-chloro-6-[(2R)-2-methylmorpholin-4-yl]-4-(trifluoromethyl) pyridin-2-yl}-4-methyl-3-{[1-(propan-2-yl)-1H-pyrazol-4-yl]methyl}-1,3-dihydro-2H-imidazol-2-one;

1-[(1-ethyl-1H-pyrazol-4-yl) methyl]-4-methyl-3-{6-[methyl(oxan-4-yl) amino]-4-(trifluoromethyl) pyridin-2-yl}-1,3-dihydro-2H-imidazol-2-one;

1-{2-fluoro-3-methyl-5-[(2R)-2-methylmorpholin-4-yl] phenyl}-4-methyl-3-{[1-(propan-2-yl)-1H-pyrazol-4-yl]methyl}-1,3-dihydro-2H-imidazol-2-one;

1-[(1-ethyl-1H-pyrazol-4-yl) methyl]-4-methyl-3-{3-[methyl(oxan-4-yl) amino]-5-(2,2,2-trifluoroethoxy) phenyl}-1,3-dihydro-2H-imidazol-2-one;

3-{3-bromo-5-[(2R)-2-methylmorpholin-4-yl]phenyl}-1-[(1-ethyl-1H-pyrazol-4-yl) methyl]-4-methyl-1,3-dihydro-2H-imidazol-2-one;

2-{2-fluoro-5-[(2S)-2-methylmorpholin-4-yl]-3-(trifluoromethyl) phenyl}-5-methyl-4-{[1-(propan-2-yl)-1H-pyrazol-4-yl]methyl}-2,4-dihydro-3H-1,2,4-triazol-3-one;

2-{2-fluoro-5-[(2R)-2-methylmorpholin-4-yl]-3-(trifluoromethyl) phenyl}-5-methyl-4-{[1-(propan-2-yl)-1H-pyrazol-4-yl]methyl}-2,4-dihydro-3H-1,2,4-triazol-3-one;

2-{2-fluoro-5-[methyl(oxan-4-yl) amino]-3-(trifluoromethyl) phenyl}-5-methyl-4 {[1-(propan-2-yl)-1H-pyrazol-4-yl]methyl}-2,4-dihydro-3H-1,2,4-triazol-3-one;

2-[5-(2,2-dimethylmorpholin-4-yl)-2-fluoro-3-(trifluoromethyl) phenyl]-5-methyl-4-{[1-(propan-2-yl)-1H-pyrazol-4-yl]methyl}-2,4-dihydro-3H-1,2,4-triazol-3-one;

2-[5-(3,3-difluoropyrrolidin-1-yl)-2-fluoro-3-(trifluoromethyl) phenyl]-5-methyl-4-{[1-(propan-2-yl)-1H-pyrazol-4-yl]methyl}-2,4-dihydro-3H-1,2,4-triazol-3-one;

4-[(1-ethyl-1H-pyrazol-4-yl) methyl]-2-{2-fluoro-5-[methyl(oxan-4-yl) amino]-3-(trifluoromethyl) phenyl}-5-methyl-2,4-dihydro-3H-1,2,4-triazol-3-one;

2-[5-(2,2-dimethylmorpholin-4-yl)-2-fluoro-3-(trifluoromethyl) phenyl]-4-[(1-ethyl-1H-pyrazol-4-yl) methyl]-5-methyl-2,4-dihydro-3H-1,2,4-triazol-3-one;

2-[5-(4,4-difluoropiperidin-1-yl)-2-fluoro-3-(trifluoromethyl) phenyl]-4-[(1-ethyl-1H-pyrazol-4-yl) methyl]-5-methyl-2,4-dihydro-3H-1,2,4-triazol-3-one;

1-{3-(difluoromethyl)-2-fluoro-5-[(2R)-2-methylmorpholin-4-yl]phenyl}-4-methyl-3-{[1-(propan-2-yl)-1H-pyrazol-4-yl]methyl}-1,3-dihydro-2H-imidazol-2-one;

1-[1-(2-cyclobutylethyl)-3-(trifluoromethyl)-1H-pyrazol-5-yl]-3-[(1-ethyl-1H-pyrazol-4-yl) methyl]-4-methyl-1,3-dihydro-2H-imidazol-2-one;

1-[(1-ethyl-1H-pyrazol-4-yl) methyl]-4,5-dimethyl-3-[3-{[(2S)-oxolan-2-yl]methoxy}-5-(trifluoromethyl) phenyl]-1,3-dihydro-2H-imidazol-2-one;

4-methyl-3-[3-{[(2S)-oxolan-2-yl]methoxy}-5-(trifluoromethyl) phenyl]-1-{[1-(propan-2-yl)-1H-pyrazol-4-yl]methyl}-1,3-dihydro-2H-imidazol-2-one;

1-{6-[(2R)-2-methylmorpholin-4-yl]-4-(trifluoromethyl) pyridin-2-yl}-3-{[1-(propan-2-yl)-1H-pyrazol-4-yl] methyl}-1,3-dihydro-2H-imidazol-2-one;

4-methyl-3-{6-[(2R)-2-methylmorpholin-4-yl]-4-(trifluoromethyl) pyridin-2-yl}-1-{[1-(propan-2-yl)-1H-pyrazol-4-yl]methyl}-1,3-dihydro-2H-imidazol-2-one;

3-{3-cyclopropyl-5-[(2R)-2-methylmorpholin-4-yl]phenyl}-1-[(1-ethyl-1H-pyrazol-4-yl) methyl]-4-methyl-1,3-dihydro-2H-imidazol-2-one;

1-[(1-ethyl-1H-pyrazol-4-yl) methyl]-4-methyl-3-{6-[(2R)-2-methylmorpholin-4-yl]-4-(2,2,2-trifluoroethoxy) pyridin-2-yl}-1,3-dihydro-2H-imidazol-2-one;

1-[(1-ethyl-1H-pyrazol-4-yl) methyl]-4-methyl-3-{6-[(oxolan-2-yl) methoxy]-4-(trifluoromethyl) pyridin-2-yl}-1,3-dihydro-2H-imidazol-2-one;

1-[(1-ethyl-1H-pyrazol-4-yl) methyl]-3-[2-fluoro-5-{[(2S)-oxolan-2-yl]methoxy}-3-(trifluoromethyl) phenyl]-4-methyl-1,3-dihydro-2H-imidazol-2-one;

1-[(1-ethyl-1H-pyrazol-4-yl) methyl]-3-[6-{[(1-fluorocyclobutyl) methyl]amino}-4-(trifluoromethyl) pyridin-2-yl]-4-methyl-1,3-dihydro-2H-imidazol-2-one;

3-[6-(2,2-difluoromorpholin-4-yl)-4-(trifluoromethyl) pyridin-2-yl]-1-[(1-ethyl-1H-pyrazol-4-yl) methyl]-4-methyl-1,3-dihydro-2H-imidazol-2-one;

1-[6-(2,2-dimethylmorpholin-4-yl)-3-fluoro-4-(trifluoromethyl) pyridin-2-yl]-3-[(1-ethyl-1H-pyrazol-4-yl) methyl]-1,3-dihydro-2H-imidazol-2-one;

1-[(1-ethyl-1H-pyrazol-4-yl) methyl]-3-{2-fluoro-3-(2-hydroxypropan-2-yl)-5-[methyl(oxan-4-yl) amino] phenyl}-1,3-dihydro-2H-imidazol-2-one;

1-[(1-ethyl-1H-pyrazol-4-yl) methyl]-4,5-dimethyl-3-[6-{[(2R)-oxolan-2-yl]methoxy}-4-(trifluoromethyl) pyridin-2-yl]-1,3-dihydro-2H-imidazol-2-one;

1-[(1-ethyl-1H-pyrazol-4-yl) methyl]-4,5-dimethyl-3-[6-{[(2S)-oxolan-2-yl]methoxy}-4-(trifluoromethyl) pyridin-2-yl]-1,3-dihydro-2H-imidazol-2-one;

1-[(1-ethyl-1H-pyrazol-4-yl) methyl]-3-{2-fluoro-5-[(oxan-4-yl) oxy]-3-(trifluoromethyl) phenyl}-1,3-dihydro-2H-imidazol-2-one;

3-[(1-ethyl-1H-pyrazol-4-yl) methyl]-1-{2-fluoro-5-[(oxan-4-yl) oxy]-3-(trifluoromethyl) phenyl}-4-methyl-1,3-dihydro-2H-imidazol-2-one;

1-[(1-ethyl-1H-pyrazol-4-yl) methyl]-3-[2-fluoro-5-{[(2S)-oxolan-2-yl]methoxy}-3-(trifluoromethyl) phenyl]-1,3-dihydro-2H-imidazol-2-one;

1-{2-fluoro-5-[(oxan-4-yl) oxy]-3-(trifluoromethyl) phenyl}-4-methyl-3-{[1-(propan-2-yl)-1H-pyrazol-4-yl] methyl}-1,3-dihydro-2H-imidazol-2-one;

1-[6-(2,2-dimethylmorpholin-4-yl)-3-methyl-4-(trifluoromethyl) pyridin-2-yl]-3-[(1-ethyl-1H-pyrazol-4-yl) methyl]-4-methyl-1,3-dihydro-2H-imidazol-2-one;

1-[(1-ethyl-1H-pyrazol-4-yl) methyl]-3-[3-fluoro-6-{[(1-fluorocyclobutyl) methyl]amino}-4-(trifluoromethyl) pyridin-2-yl]-1,3-dihydro-2H-imidazol-2-one;

1-[(1-ethyl-1H-pyrazol-4-yl) methyl]-3-{2-fluoro-3-(2-fluoropropan-2-yl)-5-[methyl(oxan-4-yl) amino]phenyl}-1,3-dihydro-2H-imidazol-2-one;

1-[6-(2,2-difluoromorpholin-4-yl)-3-fluoro-4-(trifluoromethyl) pyridin-2-yl]-3-[(1-ethyl-1H-pyrazol-4-yl) methyl]-1,3-dihydro-2H-imidazol-2-one;

1-[(1-ethyl-1H-pyrazol-4-yl) methyl]-4-methyl-3-{4-[(2R)-2-methylmorpholin-4-yl]-6-(trifluoromethyl) pyrimidin-2-yl}-1,3-dihydro-2H-imidazol-2-one;

3-[6-(2,2-dimethylmorpholin-4-yl)-4-(trifluoromethyl) pyridin-2-yl]-1-[(1-ethyl-1H-pyrazol-4-yl) methyl]-4-methyl-1,3-dihydro-2H-imidazol-2-one;

3-{4-cyclopropyl-6-[(2R)-2-methylmorpholin-4-yl]pyridin-2-yl}-4-methyl-1-{[1-(propan-2-yl)-1H-pyrazol-4-yl]methyl}-1,3-dihydro-2H-imidazol-2-one;

3-[(1-ethyl-1H-pyrazol-4-yl) methyl]-1-{3-fluoro-6-[(2R)-2-methylmorpholin-4-yl]-4-(trifluoromethyl) pyridin-2-yl}-4-(trifluoromethyl)-1,3-dihydro-2H-imidazol-2-one;

4-methyl-3-{6-[methyl(oxan-4-yl) amino]-4-(trifluoromethyl) pyridin-2-yl}-1-{[1-(propan-2-yl)-1H-pyrazol-4-yl]methyl}-1,3-dihydro-2H-imidazol-2-one;

4-methyl-1-{6-[(2R)-2-methylmorpholin-4-yl]-4-(trifluoromethyl) pyridin-2-yl}-3-{[1-(propan-2-yl)-1H-pyrazol-4-yl]methyl}-1,3-dihydro-2H-imidazol-2-one;

3-[4-cyclopropyl-6-(2,2-dimethylmorpholin-4-yl) pyridin-2-yl]-4-methyl-1 {[1-(propan-2-yl)-1H-pyrazol-4-yl]methyl}-1,3-dihydro-2H-imidazol-2-one;

1-[5-(2,2-difluorocyclopropyl)-4,4'-difluoro[1,1'-biphenyl]-3-yl]-3-[(1-ethyl-1H-pyrazol-4-yl) methyl]-1,3-dihydro-2H-imidazol-2-one;

1-[6-(2,2-dimethylmorpholin-4-yl)-3-fluoro-4-(trifluoromethyl) pyridin-2-yl]-3-{[1-(propan-2-yl)-1H-pyrazol-4-yl]methyl}-1,3-dihydro-2H-imidazol-2-one;

1-[3-fluoro-6-{[(1-fluorocyclobutyl) methyl]amino}-4-(trifluoromethyl) pyridin-2-yl]-3-{[1-(propan-2-yl)-1H-pyrazol-4-yl]methyl}-1,3-dihydro-2H-imidazol-2-one;

3-[4-(2,2-dimethylmorpholin-4-yl)-6-(trifluoromethyl) pyrimidin-2-yl]-1-[(1-ethyl-1H-pyrazol-4-yl) methyl]-4-methyl-1,3-dihydro-2H-imidazol-2-one;

3-[4-(2,2-dimethylmorpholin-4-yl)-6-(trifluoromethyl) pyrimidin-2-yl]-4-methyl-1-{[1-(propan-2-yl)-1H-pyrazol-4-yl]methyl}-1,3-dihydro-2H-imidazol-2-one;

2-[5-(2,2-dimethylmorpholin-4-yl)-2-fluoro-3-(trifluoromethyl) phenyl]-5-ethyl-4-[(1-ethyl-1H-pyrazol-4-yl) methyl]-2,4-dihydro-3H-1,2,4-triazol-3-one;

3-[3-bromo-5-(2,2-dimethylmorpholin-4-yl) phenyl]-1-[(1-ethyl-1H-pyrazol-4-yl) methyl]-4-methyl-1,3-dihydro-2H-imidazol-2-one;

2-[5-(4,4-difluoropiperidin-1-yl)-2-fluoro-3-(trifluoromethyl) phenyl]-5-ethyl-4-[(1-ethyl-1H-pyrazol-4-yl) methyl]-2,4-dihydro-3H-1,2,4-triazol-3-one;

1-{3-chloro-2-fluoro-5-[(2R)-2-methylmorpholin-4-yl] phenyl}-3-[(1-ethyl-1H-pyrazol-4-yl) methyl]-4-methyl-1,3-dihydro-2H-imidazol-2-one;

1-{3-cyclopropyl-2-fluoro-5-[(2R)-2-methylmorpholin-4-yl]phenyl}-3-[(1-ethyl-1H-pyrazol-4-yl) methyl]-4-methyl-1,3-dihydro-2H-imidazol-2-one;

2-[6-(4,4-difluoropiperidin-1-yl)-4-(trifluoromethyl) pyridin-2-yl]-4-[(1-ethyl-1H-pyrazol-4-yl) methyl]-5-methyl-2,4-dihydro-3H-1,2,4-triazol-3-one;

2-[6-(4,4-difluoropiperidin-1-yl)-4-(trifluoromethyl) pyridin-2-yl]-5-methyl-4-{[1-(propan-2-yl)-1H-pyrazol-4-yl]methyl}-2,4-dihydro-3H-1,2,4-triazol-3-one;

1-{3-(2,2-difluorocyclopropyl)-2-fluoro-5-[(2R)-2-methylmorpholin-4-yl]phenyl}-3-[(1-ethyl-1H-pyrazol-4-yl) methyl]-4-(trifluoromethyl)-1,3-dihydro-2H-imidazol-2-one;

1-[3-bromo-5-(2,2-dimethylmorpholin-4-yl)-2-fluorophenyl]-3-[(1-ethyl-1H-pyrazol-4-yl) methyl]-1,3-dihydro-2H-imidazol-2-one;

3-[3-cyclopropyl-5-(2,2-dimethylmorpholin-4-yl) phenyl]-1-[(1-ethyl-1H-pyrazol-4-yl) methyl]-4-methyl-1,3-dihydro-2H-imidazol-2-one;

4-methyl-3-[6-{[(2S)-oxolan-2-yl]methoxy}-4-(trifluoromethyl) pyridin-2-yl]-1-{[1-(propan-2-yl)-1H-pyrazol-4-yl]methyl}-1,3-dihydro-2H-imidazol-2-one;

1-[(1-ethyl-1H-pyrazol-4-yl) methyl]-3-{5-fluoro-6-[(2R)-2-methylmorpholin-4-yl]-4-(trifluoromethyl) pyridin-2-yl}-4-methyl-1,3-dihydro-2H-imidazol-2-one;

1-[(1-ethyl-1H-pyrazol-4-yl) methyl]-3-{5-fluoro-6-[(2R)-2-methylmorpholin-4-yl]-4-(trifluoromethyl) pyridin-2-yl}-4,5-dimethyl-1,3-dihydro-2H-imidazol-2-one;

2-{5-[(3,3-difluorocyclobutyl) methoxy]-2-fluoro-3-(trifluoromethyl) phenyl}-4-[(1-ethyl-1H-pyrazol-4-yl) methyl]-2,4-dihydro-3H-1,2,4-triazol-3-one;

1-[3,5-bis(4,4-difluoropiperidin-1-yl)-2-fluorophenyl]-3-[(1-ethyl-1H-pyrazol-4-yl) methyl]-1,3-dihydro-2H-imidazol-2-one;

1-[(1-ethyl-1H-pyrazol-4-yl) methyl]-3-{2-fluoro-5-[(2R)-2-methylmorpholin-4-yl]-3-(trifluoromethoxy) phenyl}-1,3-dihydro-2H-imidazol-2-one;

2-[6-(4,4-difluoropiperidin-1-yl)-5-fluoro-4-(trifluoromethyl) pyridin-2-yl]-4-[(1-ethyl-1H-pyrazol-4-yl) methyl]-5-methyl-2,4-dihydro-3H-1,2,4-triazol-3-one;

5-chloro-4-[(1-ethyl-1H-pyrazol-4-yl) methyl]-2-{2-fluoro-5-[(2R)-2-methylmorpholin-4-yl]-3-(trifluoromethyl) phenyl}-2,4-dihydro-3H-1,2,4-triazol-3-one;

1-[3-(2,2-difluorocyclopropyl)-5-(4,4-difluoropiperidin-1-yl)-2-fluorophenyl]-3-[(1-ethyl-1H-pyrazol-4-yl) methyl]-1,3-dihydro-2H-imidazol-2-one;

4-ethyl-1-[(1-ethyl-1H-pyrazol-4-yl) methyl]-3-{6-[(2R)-2-methylmorpholin-4-yl]-4-(trifluoromethyl) pyridin-2-yl}-1,3-dihydro-2H-imidazol-2-one;

2-{2-fluoro-5-[(2R)-2-methylmorpholin-4-yl]-3-(trifluoromethoxy) phenyl}-5-methyl-4-{[1-(propan-2-yl)-1H-pyrazol-4-yl]methyl}-2,4-dihydro-3H-1,2,4-triazol-3-one;

3-{3-cyclopropyl-4-fluoro-5-[(2R)-2-methylmorpholin-4-yl]phenyl}-1-[(1-ethyl-1H-pyrazol-4-yl) methyl]-4-methyl-1,3-dihydro-2H-imidazol-2-one;

2-[5-(4,4-difluoropiperidin-1-yl)-2-methyl-3-(trifluoromethyl) phenyl]-4-[(1-ethyl-1H-pyrazol-4-yl) methyl]-5-methyl-2,4-dihydro-3H-1,2,4-triazol-3-one;

1-{4-cyclopropyl-6-[(2R)-2-methylmorpholin-4-yl]pyridin-2-yl}-3-[(1-ethyl-1H-pyrazol-4-yl) methyl]-4,5-dimethyl-1,3-dihydro-2H-imidazol-2-one;

1-[(1-ethyl-1H-pyrazol-4-yl) methyl]-4,5-dimethyl-3-{6-[(2R)-2-methylmorpholin-4-yl]pyridin-2-yl}-1,3-dihydro-2H-imidazol-2-one;

1-[3-cyclopropyl-5-(2,2-dimethylmorpholin-4-yl)-2-fluorophenyl]-3-[(1-ethyl-1H-pyrazol-4-yl) methyl]-4-methyl-1,3-dihydro-2H-imidazol-2-one;

1-[3-cyclopropyl-5-(4,4-difluoropiperidin-1-yl)-2-fluorophenyl]-3-[(1-ethyl-1H-pyrazol-4-yl) methyl]-4-methyl-1,3-dihydro-2H-imidazol-2-one;

1-[3-chloro-5-(2,2-dimethylmorpholin-4-yl)-2-fluorophenyl]-3-[(1-ethyl-1H-pyrazol-4-yl) methyl]-4-methyl-1,3-dihydro-2H-imidazol-2-one; and 1-[3-chloro-5-(4,4-difluoropiperidin-1-yl)-2-fluorophenyl]-3-[(1-ethyl-1H-pyrazol-4-yl) methyl]-4-methyl-1,3-dihydro-2H-imidazol-2-one, or a pharmaceutically acceptable salt thereof.

24. A pharmaceutical composition comprising:

at least one compound or pharmaceutically acceptable salt according to claim 1; and at least one pharmaceutically acceptable carrier.

25. A method of treating or preventing a disease in a mammal in need thereof, the method comprising administering to the mammal at least one compound according to claim 1.

26. The method according to claim 25, wherein the disease is chosen from depression, Alzheimer's disease, schizophrenia, drug addiction, sleep disorders, pain, and attention deficit hyperactivity disorder.

27. The method according to claim 25, wherein the mammal is a human.

28. The method according to claim 25, further comprising administering to the mammal at least one combination drug.

29. The compound or pharmaceutically acceptable salt according to claim 1, which is 1-[(1-ethyl-1H-pyrazol-4-yl) methyl]-4,5-dimethyl-3-{6-[(2R)-2-methylmorpholin-4-yl]-4-(trifluoromethyl) pyridin-2-yl}-1,3-dihydro-2H-imidazol-2-one or a pharmaceutically acceptable salt thereof.

30. The method according to claim 25, wherein the disease is depression.

31. The method according to claim 25, wherein the disease is schizophrenia.

* * * * *